(12) United States Patent
Vendeville et al.

(10) Patent No.: US 11,957,683 B2
(45) Date of Patent: Apr. 16, 2024

(54) BICYCLIC COMPOUNDS

(71) Applicant: Aligos Therapeutics, Inc., South San Francisco, CA (US)

(72) Inventors: Sandrine Vendeville, Brussels (BE); Pierre Jean-Marie Bernard Raboisson, Wavre (BE); David McGowan, Brussels (BE); Yannick Debing, Bilzen (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/807,057

(22) Filed: Jun. 15, 2022

(65) Prior Publication Data
US 2023/0051483 A1    Feb. 16, 2023

Related U.S. Application Data

(60) Provisional application No. 63/269,017, filed on Mar. 8, 2022, provisional application No. 63/264,496, filed on Nov. 23, 2021, provisional application No. 63/264,434, filed on Nov. 22, 2021, provisional application No. 63/212,369, filed on Jun. 18, 2021.

(51) Int. Cl.

| | | |
|---|---|---|
| *A61K 31/522* | (2006.01) | |
| *A61K 31/513* | (2006.01) | |
| *A61K 31/519* | (2006.01) | |
| *A61K 31/675* | (2006.01) | |
| *A61K 31/7072* | (2006.01) | |
| *A61K 31/7088* | (2006.01) | |
| *A61K 38/21* | (2006.01) | |
| *A61P 31/14* | (2006.01) | |
| *C07D 471/04* | (2006.01) | |
| *C07D 519/00* | (2006.01) | |

(52) U.S. Cl.
CPC .......... *A61K 31/519* (2013.01); *A61K 31/513* (2013.01); *A61K 31/522* (2013.01); *A61K 31/675* (2013.01); *A61K 31/7072* (2013.01); *A61K 31/7088* (2013.01); *A61K 38/212* (2013.01); *A61P 31/14* (2018.01); *C07D 471/04* (2013.01); *C07D 519/00* (2013.01)

(58) Field of Classification Search
CPC ............................ C07D 471/04; C07D 519/00
See application file for complete search history.

(56) References Cited

U.S. PATENT DOCUMENTS

| | | |
|---|---|---|
| 6,414,157 B1 | 7/2002 | Lubisch et al. |
| 6,657,063 B1 | 12/2003 | Dow |
| 2005/0054645 A1 | 3/2005 | Miyazaki et al. |
| 2005/0165025 A1 | 7/2005 | Leonardi et al. |
| 2010/0093771 A1 | 4/2010 | Nakamura et al. |
| 2020/0147124 A1 | 5/2020 | Beigelman et al. |
| 2021/0403461 A1 | 12/2021 | Iwata et al. |
| 2022/0119385 A1 | 4/2022 | Vendeville et al. |

FOREIGN PATENT DOCUMENTS

| | | |
|---|---|---|
| CN | 109956930 | 7/2019 |
| CN | 111039942 | 4/2020 |
| DE | 19747063 | 4/1999 |
| WO | WO 99/02990 | 1/1999 |
| WO | WO 2001/089570 | 11/2001 |
| WO | WO 2005/016927 | 2/2005 |
| WO | WO 2008/038768 | 4/2008 |
| WO | WO 2008/130581 | 10/2008 |
| WO | WO 2022/053010 | 7/2018 |
| WO | WO 2019/022061 | 1/2019 |
| WO | WO 2020/182990 | 9/2020 |
| WO | WO 2021/178885 | 9/2021 |
| WO | WO 2022/087011 | 3/2022 |

OTHER PUBLICATIONS

"IUPAC-IUB Commission on Biochemical Nomenclature Abbreviated Nomenclature of Synthetic Polypeptides (Polymerized Amino Acids) Revised Recommendations (1971)" *Biochemistry.* (1972) 11(5):942-944.
Liang, "Hepatitis B: The Virus and Disease" Hepatology (2009) 49(S5):S13-S21.
International Search Report and Written Opinion dated Aug. 12, 2022 for PCT Application No. PCT/US2022/033585, filed Jun. 15, 2022.
Second Written Opinion dated May 12, 2023 for PCT Application No. PCT/US2022/033585, filed Jun. 15, 2022.
International Preliminary Report on Patentability dated Sep. 27, 2023 for PCT Application No. PCT/US2022/033585, filed Jun. 15, 2022.

*Primary Examiner* — Alicia L Otton
(74) *Attorney, Agent, or Firm* — Knobbe, Martens, Olson & Bear

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

46 Claims, No Drawings
Specification includes a Sequence Listing.

BICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/212,369, filed Jun. 18, 2021, 63/264,434, filed Nov. 22, 2021, 63/264,496, filed Nov. 23, 2021 and 63/269,017, filed Mar. 8, 2022.

REFERENCE TO SEQUENCE LISTING

The present application is filed with a Sequence Listing in Electronic format. The Sequence Listing is provided as a file entitled ALIG069.txt, created Jun. 15, 2022, which is approximately 4 kb in size. The information in the electronic format of the sequence listing is incorporated herein by reference in its entirety.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroalkyl, hydroxy, alkoxyalkyl, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine, a di-substituted amine, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH (an unsubstituted $C_{1-4}$ alkyl), —O-(an unsubstituted $C_{1-4}$ alkyl)-N (an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g., 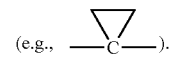).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). In some instances, a haloalkoxy can be —OR, wherein R is a $C_{1-4}$ alkyl substituted by 1, 2 or 3 halogens. Such groups include but are not limited to, chloromethoxy, fluoromethoxy, difluoromethoxy, trifluoro-2-ethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$_A$" in which R$_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$_A$, wherein R$_A$ can be an unsubstituted C$_{1-6}$ alkyl or an unsubstituted or a substituted benzyl.

A "di-substituted amine" refers to a "—NR$_A$R$_B$" in which R$_A$ and R$_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents are not specified (e.g., haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

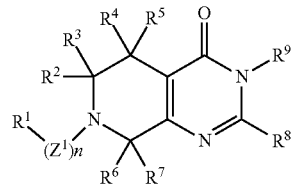

(I)

wherein: n can be 0 or 1; $Z^1$ can be —C(=O)— or —NH—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an optionally substituted $C_{1-4}$ alkyl, an optionally substituted $C_{2-4}$ alkenyl, an optionally substituted $C_{2-4}$ alkynyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be —$NR^{10A}R^{10B}$ or an optionally substituted $C_{2-12}$ alkynyl, wherein the $C_{2-12}$ alkynyl is optionally substituted with one or more substituents selected from amino, —NH—C(=O) (an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 membered monocyclic heterocyclyl, an optionally substituted aryl and an optionally substituted 5-6 membered monocyclic heteroaryl; $R^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted $C_{1-4}$ alkyl, a cyano-substituted $C_{1-4}$ alkyl, an unsubstituted $C_{1-4}$ haloalkyl, an unsubstituted $C_{1-4}$ alkoxy, a hydroxy-substituted $C_{1-4}$ alkoxy, an optionally substituted monocyclic $C_{3-6}$ cycloalkyl, an optionally substituted monocyclic heteroaryl, an optionally substituted monocyclic heterocyclyl, amino, a mono-substituted amine, a di-substituted amine and —C(=O)$NHR^{11}$; $R^{10A}$ can be hydrogen, an unsubstituted $C_{1-6}$ alkyl, a monocyclic $C_{3-6}$ cycloalkyl optionally substituted with one or two halogens, an optionally substituted 5-6 membered monocyclic heteroaryl, an optionally substituted 4-6 membered monocyclic heterocyclyl or an optionally substituted monocyclic $C_{3-6}$ cycloalkyl($C_{1-4}$ alkyl); $R^{10B}$ can be selected from an optionally substituted $C_{2-8}$ alkenyl, an optionally substituted $C_{2-8}$ alkynyl, an optionally substituted aryl, an optionally substituted aryl($C_{1-4}$ alkyl), an optionally substituted heteroaryl ($C_{1-4}$ alkyl) and an optionally substituted heterocyclyl($C_{1-4}$ alkyl), wherein the $C_{2-8}$ alkenyl and the $C_{2-8}$ alkynyl is optionally substituted with one or more substituents selected from amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and an unsubstituted 4-6 membered monocyclic heterocyclyl; and $R^{11}$ can be hydrogen, an unsubstituted $C_{1-6}$ alkyl, an optionally substituted $C_{2-6}$ alkenyl, an optionally substituted $C_{1-6}$ alkynyl or an optionally substituted monocyclic $C_{3-6}$ cycloalkyl.

As provided herein, various groups can be attached to the piperidinyl ring of the ring structure of Formula (I). In some embodiments, n can be 1; $Z^1$ can be —C(=O)—; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In other embodiments, n can be 1; $Z^1$ can be —NH—C(=O)—; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). As shown below, when $Z^1$ is —C(=O)— or —NH—C(=O)—, Formula (I) can be Formula (Ia) or (Ib), or a pharmaceutically acceptable salt thereof, respectively.

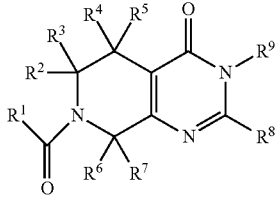

(Ia)

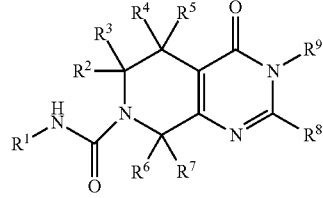

(Ib)

Various cyclic moieties can be present for $R^1$. In some embodiments, $R^1$ can be a carbocyclic moiety, for example an optionally substituted aryl. For example, $R^1$ can be an optionally substituted phenyl. In some embodiments, $R^1$ can be an unsubstituted phenyl. In other embodiments, $R^1$ can be a substituted phenyl. When $R^1$ is a substituted phenyl, the phenyl can be mono-substituted. The mono-substituted phenyl can be a para-substituted phenyl, a meta-substituted phenyl or an ortho-substituted phenyl. The substituted phenyl can be substituted by multiple moieties, such as 2, 3 or more than 3 times. For example, the substituted phenyl of $R^1$ can be di-substituted (such as a meta- and para-substituted phenyl). When more than one moiety is present, the moieties can be the same or different moieties can be different.

As described herein, $R^1$ can be a cyclic moiety, including a cyclic moiety that can include one or more heteroatoms in the ring(s). In some embodiments, $R^1$ can be an optionally substituted heteroaryl. The heteroaryl can be monocyclic or bicyclic. In some embodiments, $R^1$ can be an unsubstituted or a substituted monocyclic heteroaryl. For example, $R^1$ can be a 5-membered or 6-membered monocyclic heteroaryl. In other embodiments, $R^1$ can be an unsubstituted or a substituted bicyclic heteroaryl. The bicyclic heteroaryl can be a 9-membered or 10-membered heteroaryl. The heteroaryl can include one or more heteroatoms (such as 1, 2 or 3), such as N (nitrogen), O (oxygen) and/or S (sulfur). In some embodiments, $R^1$ can be an optionally substituted heterocyclyl. The heterocyclyl can be a monocyclic heterocyclyl or a bicyclic heterocyclyl. In some embodiments, $R^1$ can be an unsubstituted or a substituted monocyclic heterocyclyl, such as a 5-membered or 6-membered monocyclic heterocyclyl. In other embodiments, $R^1$ can be an unsubstituted or a substituted bicyclic heterocyclyl, including a 9-membered or 10-membered heterocyclyl. The number and types of heteroatoms that can be present in a heterocyclyl can vary. As an example, 1, 2, 3 or more than 3 heteroatoms, such as N (nitrogen), O (oxygen) and/or S (sulfur), can be present in a heterocyclyl of $R^1$.

In some embodiments, $R^1$ can be selected from an unsubstituted or a substituted [5,5] bicyclic heteroaryl, an unsubstituted or a substituted [5,6] bicyclic heteroaryl, an unsubstituted or a substituted [6,5] bicyclic heteroaryl, an unsubstituted or a substituted [6,6] bicyclic heteroaryl, an unsubstituted or a substituted [5,5] bicyclic heterocyclyl, an unsubstituted or a substituted [5,6] bicyclic heterocyclyl, an unsubstituted or a substituted [6,5] bicyclic heterocyclyl and an unsubstituted or a substituted [6,6] bicyclic heterocyclyl. In some embodiments, $R^1$ can be a nitrogen-containing, bicyclic heteroaryl. In other embodiments, $R^1$ can be a nitrogen-containing, bicyclic heterocyclyl. In some embodiments, $R^1$ can have the general structure

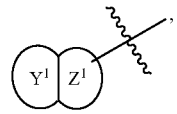

wherein Ring $Z^1$ indicates the point of attachment to the remaining portion of Formula (I); and wherein Ring $Y^1$ and Ring $Z^1$ can be independently selected from phenyl, furan, furazan, thiophene, phthalazine, pyrrole, oxazole, 1,2,3-oxadiazole, 1,2,4-oxadiazole, thiazole, 1,2,3-thiadiazole, 1,2,4-thiadiazole, imidazole, pyrazole, isoxazole, isothiazole, triazole, thiadiazole, tetrazole, pyridine, pyridazine, pyrimidine, pyrazine, 1,2,3-triazine, 1,2,4-triazine, 1,2,3,4-tetrazine, 2H-1,2-oxazine, hexahydro-1,3,5-triazine, imidazoline, imidazolidine, isoxazoline, isoxazolidine, oxazoline, oxazolidine, thiazoline, thiazolidine, morpholine, piperidine, piperazine, pyrrolidine, pyrazoline, pyrazolidine and thiamorpholine, wherein Ring $Y^1$ and Ring $Z^1$ can be each optionally substituted. In some embodiments, Ring $Y^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In some embodiments, Ring $Z^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In other embodiments, Ring $Z^1$ can be selected from an optionally substituted furan, an optionally substituted thiophene, an optionally substituted pyrrole, an optionally substituted oxazole, an optionally substituted thiazole, an optionally substituted imidazole, an optionally substituted pyrazole, an optionally substituted isoxazole and an optionally substituted isothiazole.

Various cyclic groups can be attached via a $C_{1-4}$ alkyl linker for $R^1$. In some embodiments, $R^1$ can be an optionally substituted aryl($C_{1-4}$ alkyl). An exemplary optionally substituted aryl($C_{1-4}$ alkyl) is an optionally substituted benzyl. In other embodiments, $R^1$ can be an optionally substituted heteroaryl($C_{1-4}$ alkyl). In still other embodiments, $R^1$ can be an optionally substituted heterocyclyl($C_{1-4}$ alkyl). Examples of heteroaryls and heterocyclyls are described herein and include those of the previous paragraph. As described herein, the linker can include 1 to 4 carbons. In some embodiments, the $C_{1-4}$ alkyl linker for $R^1$ can be —$CH_2$—, —$CH_2CH_2$—, —$CH_2CH_2CH_2$— or —$CH_2CH_2CH_2CH_2$—. Further as described herein lower alkylene linker ($C_{1-4}$ alkyl linker) for $R^1$ can be substituted. Examples of substituents that can be present on a substituted lower alkylene linker ($C_{1-4}$ alkyl linker) for aryl($C_{1-4}$ alkyl), heteroaryl($C_{1-4}$ alkyl) and heterocyclyl($C_{1-4}$ alkyl) include an unsubstituted $C_{1-4}$ haloalkyl (such as $CF_3$).

As described herein, $R^1$ can be substituted. A variety of substituents can substitute the $R^1$ groups described herein. In some embodiments, $R^1$ can be substituted with one or more substituents (for example, 1, 2 or 3) independently selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{2-6}$ alkenyl (for example, ethenyl, propenyl and butenyl), an unsubstituted $C_{2-6}$ alkynyl (for example, ethynyl, propynyl and butynyl), an unsubstituted or a substituted monocyclic $C_{3-6}$ cycloalkyl (such as cyclopropyl, cyclobutyl, cyclopentyl and cyclohexyl, including halo-substituted versions of each of the aforementioned examples), an unsubstituted $C_{1-6}$ haloalkyl (such as —$CHF_2$, —$CH_2F$, —$CF_3$, —$CHClF$, —$CH_2Cl$, —$CHCl_2$, —$CCl_3$, —$CH_2CHF_2$, —$CH_2CH_2F$, —$CH_2CF_3$, —$CH_2CHClF$, —$CH_2CH_2Cl$, —$CH_2CHCl_2$, —$CH_2CCl_3$, —$CH(CH_3)CF_3$, —$CH(CH_3)CHF_2$, —$C(CH_3)_2CF_3$ and —$C(CH_3)_2CHF_2$), an unsubstituted $C_{1-6}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-6}$ haloalkoxy (for example, —$OCHF_2$, —$OCH_2F$, —$OCF_3$, —$OCHClF$, —$OCH_2Cl$, —$OCHCl_2$, —$OCCl_3$, —$OCH_2CHF_2$, —$OCH_2CH_2F$, —$OCH_2CF_3$, —$OCH_2CHClF$, —$OCH_2CH_2Cl$, —$OCH_2CHCl_2$, —$OCH_2CCl_3$, —$OCH(CH_3)CF_3$, —$OCH(CH_3)CHF_2$, —$OC(CH_3)_2CF_3$, —$OC(CH_3)_2CHF_2$, —O(halo-substituted cyclopropyl) and —O(halo-substituted cyclobutyl)), an unsubstituted acyl (for example, —C(=O)—$C_{1-4}$ alkyl), an unsubstituted C-amido (such as —C(=O)$NH_2$ and —C(=O)NH—$C_{1-4}$ alkyl), an unsubstituted sulfonyl (such as —S(=O)$_2$—$C_{1-4}$ alkyl), an unsubstituted amino, a mono-substituted amine (for example, an mono-alkyl substituted amine) and a di-substituted amine (such as a di-alkyl substituted amine). In some embodiments, $R^1$ can be substituted with one or more substituents (such as 1, 2 or 3) independently selected from halogen (such as F, Cl and/or Br), cyano, an unsubstituted $C_{1-6}$ alkyl (such as methyl) and an unsubstituted $C_{2-6}$ alkynyl (for example, ethynyl).

The number of substituents present on a substituted $R^1$ group can vary. In some embodiments, $R^1$ is substituted with 1 substituent. In other embodiments, $R^1$ is substituted with 2 substituents. In still other embodiments, $R^1$ is substituted with 3 substituents.

Exemplary $R^1$ groups include, but are not limited to, the following:

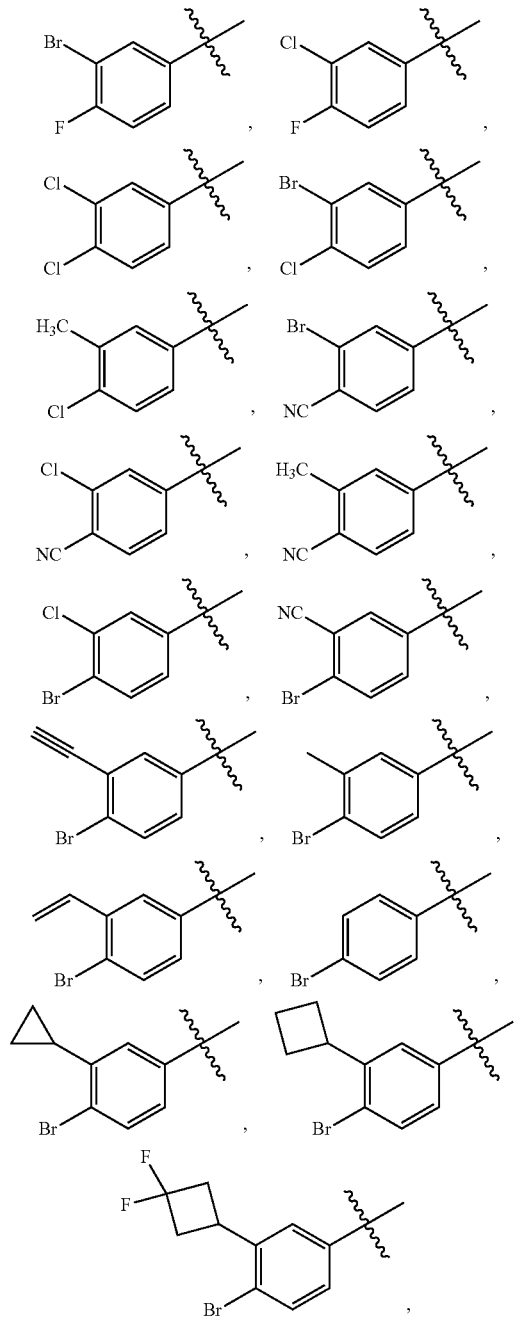

-continued

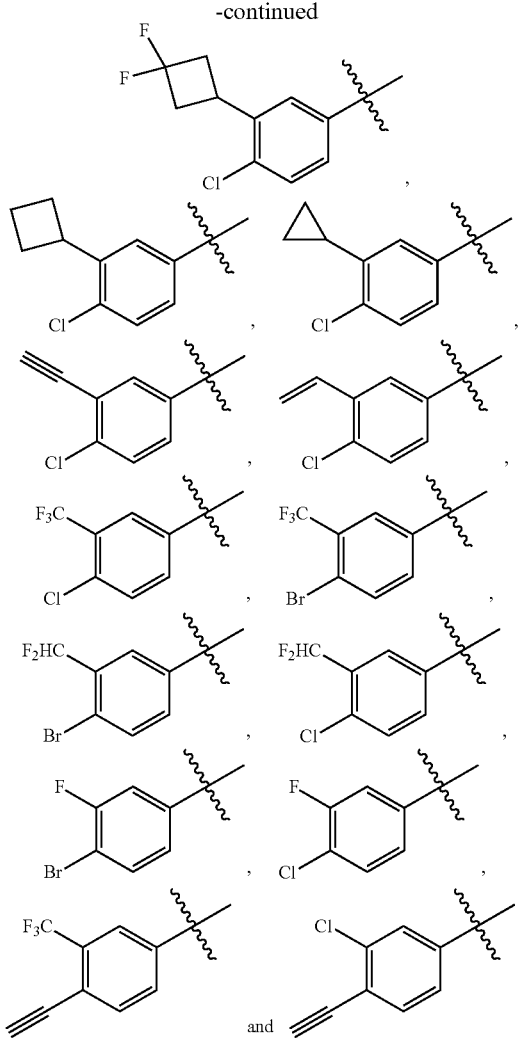

In addition to the groups described herein that can be attached to the piperazine ring of the tetracyclic ring structure of Formula (I), the piperidinyl ring can be further unsubstituted or substituted. In some embodiments, $R^2$ can be hydrogen. In other embodiments, $R^2$ can be an optionally substituted $C_{1-4}$ alkyl. In some embodiments, $R^2$ can be an unsubstituted $C_{1-4}$ alkyl. For example, $R^2$ can be methyl, ethyl, n-propyl, iso-propyl, n-butyl, iso-butyl, sec-butyl and tert-butyl. In other embodiments, $R^2$ can be a substituted $C_{1-4}$ alkyl, such as a $C_{1-4}$ alkyl substituted with a moiety selected form hydroxy, cyano and an unsubstituted $C_{1-4}$ alkoxy. Exemplary substituted $C_{1-4}$ alkyls for $R^2$ include, but are not limited to, —CH$_2$OH, —CH$_2$OCH$_3$ and —CH$_2$CN. In some embodiments, $R^2$ can be an optionally substituted $C_{2-4}$ alkenyl. In other embodiments, $R^2$ can be an optionally substituted $C_{2-4}$ alkynyl. In still other embodiments, $R^2$ can be an unsubstituted $C_{1-4}$ haloalkyl. Suitable unsubstituted $C_{1-4}$ haloalkyls are described herein, and include —CHF$_2$, —CH$_2$F, —CF$_3$, —CH$_2$Cl, —CHCl$_2$ and —CCl$_3$. In yet still other embodiments, $R^2$ can be an optionally substituted monocyclic $C_{3-6}$ cycloalkyl. Examples of monocyclic $C_{3-6}$ cycloalkyls include, but are not limited to, cyclopropyl, cyclobutyl, cyclopentyl and cyclohexyl, wherein each of the aforementioned can be unsubstituted or substituted. In some embodiments, $R^2$ can be an optionally substituted aryl (such as an optionally phenyl), an optionally substituted heteroaryl (such as an optionally substituted monocyclic heteroaryl) or an optionally substituted heterocyclyl (for example, an optionally substituted monocyclic heterocyclyl). The heteroaryl and heterocyclyl can include 3, 4, 5 or 6 ring(s) atoms. In other embodiments, $R^2$ can be an optionally substituted aryl($C_{1-4}$ alkyl), an optionally substituted heteroaryl($C_{1-4}$ alkyl) or an optionally substituted heterocyclyl ($C_{1-4}$ alkyl).

In some embodiments, $R^3$ can be hydrogen. In other embodiments, $R^3$ can be an unsubstituted $C_{1-4}$ alkyl. In other embodiments, $R^3$ can be an optionally substituted $C_{1-4}$ alkyl. In some embodiments, $R^3$ can be an unsubstituted $C_{1-4}$ alkyl. In other embodiments, $R^3$ can be a substituted $C_{1-4}$ alkyl, such as a $C_{1-4}$ alkyl substituted with a moiety selected form hydroxy, cyano and an unsubstituted $C_{1-4}$ alkoxy. In some embodiments, $R^3$ can be an optionally substituted $C_{2-4}$ alkenyl. In other embodiments, $R^3$ can be an optionally substituted $C_{2-4}$ alkynyl. In still other embodiments, $R^3$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^2$. In yet still other embodiments, $R^3$ can be an optionally substituted monocyclic $C_{3-6}$ cycloalkyl, such as those described herein with respect to $R^2$. When $R^3$ is a monocyclic $C_{3-6}$ cycloalkyl, the $C_{3-6}$ cycloalkyl can be unsubstituted or substituted. In some embodiments, $R^3$ can be an optionally substituted aryl, an optionally substituted heteroaryl or an optionally substituted heterocyclyl. In some embodiments, $R^3$ can be an optionally substituted aryl($C_{1-4}$ alkyl), an optionally substituted heteroaryl($C_{1-4}$ alkyl) or an optionally substituted heterocyclyl($C_{1-4}$ alkyl). For example, $R^3$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^4$ can be hydrogen. In other embodiments, $R^4$ can be an unsubstituted $C_{1-4}$ alkyl, such as those described herein. In still other embodiments, $R^4$ can be an unsubstituted $C_{1-4}$ haloalkyl, for example, —CHF$_2$, —CH$_2$F, —CF$_3$, —CH$_2$Cl, —CHCl$_2$ and —CCl$_3$. In yet still other embodiments, $R^4$ can be an optionally substituted aryl, an optionally substituted heteroaryl or an optionally substituted heterocyclyl. In some embodiments, $R^4$ can be an optionally substituted aryl($C_{1-4}$ alkyl), an optionally substituted heteroaryl($C_{1-4}$ alkyl) or an optionally substituted heterocyclyl($C_{1-4}$ alkyl). In other embodiments, $R^4$ can be an optionally substituted phenyl, an optionally substituted monocyclic heteroaryl or an optionally substituted monocyclic heterocyclyl.

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. For example, $R^5$ can be methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$. In yet still other embodiments, $R^5$ can be an optionally substituted aryl, an optionally substituted heteroaryl or an optionally substituted heterocyclyl. In some embodiments, $R^5$ can be an optionally substituted aryl($C_{1-4}$ alkyl), an optionally substituted heteroaryl($C_{1-4}$ alkyl) or an optionally substituted heterocyclyl($C_{1-4}$ alkyl). Exemplary $R^5$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^6$ can be hydrogen. In other embodiments, $R^6$ can be an unsubstituted $C_{1-4}$ alkyl. In still other embodiments, $R^6$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —$CHF_2$, —$CH_2F$, —$CF_3$, —$CH_2Cl$, —$CHCl_2$ and —$CCl_3$.

In some embodiments, $R^7$ can be hydrogen. In other embodiments, $R^7$ can be an unsubstituted $C_{1-4}$ alkyl, such as methyl, ethyl, n-propyl, iso-propyl, n-butyl, iso-butyl, sec-butyl or tert-butyl. In still other embodiments, $R^7$ can be an unsubstituted $C_{1-4}$ haloalkyl, for example, —$CHF_2$, —$CH_2F$, —$CF_3$, —$CH_2Cl$, —$CHCl_2$ and —$CCl_3$.

In some embodiments, $R^2$, $R^3$, $R^4$, $R^5$, $R^6$ and $R^7$ can be each hydrogen. In other embodiments, at least one of $R^2$, $R^3$, $R^4$, $R^5$, $R^6$ and $R^7$ can be a non-hydrogen group, such as those described herein in the previous paragraphs. When at one of $R^2$, $R^3$, $R^4$, $R^5$, $R^6$ and $R^7$ is a non-hydrogen group, at least one of $R^2$, $R^3$, $R^4$, $R^5$, $R^6$ and $R^7$ can be an unsubstituted $C_{1-4}$ alkyl (for example, methyl) or an optionally substituted monocyclic $C_{3-6}$ cycloalkyl (such as an unsubstituted or a substituted cyclopropyl). In some embodiments, $R^3$, $R^4$, $R^5$, $R^6$ and $R^7$ can be each hydrogen; and $R^2$ can be an unsubstituted $C_{1-4}$ alkyl (such as methyl) or an optionally substituted monocyclic $C_{3-6}$ cycloalkyl (such as an unsubstituted or a substituted cyclopropyl). When at least one of $R^2$, $R^3$, $R^4$, $R^5$, $R^6$ and $R^7$ is a non-hydrogen group, a stereocenter may be formed. In some embodiments, the stereocenter that is formed can be in the (R)-configuration. In other embodiments, the stereocenter that is formed can be in the (S)-configuration.

An $R^8$ substituent can be an amine, such as an amine having the general formula —$NR^{10A}R^{10B}$. In some embodiments, $R^{10A}$ can be hydrogen. In other embodiments, $R^{10A}$ can be an unsubstituted $C_{1-6}$ alkyl, such as methyl, ethyl, n-propyl, iso-propyl, n-butyl, iso-butyl, sec-butyl, tert-butyl, pentyl (straight-chained and branched) and hexyl (straight-chained and branched). In still other embodiments, $R^{10A}$ can be a monocyclic $C_{3-6}$ cycloalkyl optionally substituted with one or two halogens. For example, $R^{10A}$ can be a monocyclic $C_{3-6}$ cycloalkyl that is substituted with 1 or 2 fluoros. In some embodiments, $R^{10A}$ can be an unsubstituted $C_{3-6}$ cycloalkyl. In other embodiments, $R^{10A}$ can be an optionally substituted 5-6-membered monocyclic heteroaryl. In still other embodiments, $R^{10A}$ can be an optionally substituted 4-6 membered monocyclic heterocyclyl. As an example, $R^{10A}$ can be an optionally substituted 4-6 membered monocyclic heterocyclyl that includes 1-3 heteroatoms selected from O (oxygen), S (sulfur) and N (nitrogen). In some embodiments, $R^{10A}$ can be azetidine, oxetane or thietane, wherein each of the aforementioned can be unsubstituted or substituted. Examples of groups that can be present on a substituted 4-6 membered monocyclic heterocyclyl are fluoro, chloro, methyl, ethyl and an unsubstituted $C_{1-4}$ haloalkyl (such as $CF_3$, $CHF_2$ and $CH_2F$). In other embodiments, $R^{10A}$ can be an optionally substituted monocyclic $C_{3-6}$ cycloalkyl($C_{1-4}$ alkyl). Exemplary monocyclic $C_{3-6}$ cycloalkyl($C_{1-4}$ alkyl) moieties include, but are not limited to, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$— and cyclohexyl-$CH_2CH_2$—.

For $R^{10B}$, $R^{10B}$ can be an optionally substituted $C_{2-8}$ alkenyl, an optionally substituted $C_{2-8}$ alkynyl, an optionally substituted aryl, an optionally substituted aryl($C_{1-4}$ alkyl), an optionally substituted heteroaryl($C_{1-4}$ alkyl) and an optionally substituted heterocyclyl($C_{1-4}$ alkyl). In some embodiments, $R^{10B}$ can be an unsubstituted $C_{2-8}$ alkenyl. In other embodiments, $R^{10B}$ can be a $C_{2-8}$ alkenyl substituted with amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and/or an unsubstituted 4-6 membered monocyclic heterocyclyl. In still other embodiments, $R^{10B}$ can be an unsubstituted $C_{2-8}$ alkynyl. In yet still other embodiments, $R^{10B}$ can be a substituted $C_{2-8}$ alkynyl substituted with amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and/or an unsubstituted 4-6 membered monocyclic heterocyclyl.

A variety of groups can be present on a substituted $C_{2-8}$ alkenyl and a substituted $C_{2-8}$ alkynyl. In some embodiments, the substituted $C_{2-8}$ alkenyl and/or the substituted $C_{2-8}$ alkynyl can be substituted with amino, hydroxy and/or an unsubstituted $C_{1-4}$ alkoxy. Examples of unsubstituted $C_{1-4}$ alkoxys include methoxy, ethoxy, n-propoxy, iso-propoxy, n-butoxy, iso-butoxy, sec-butoxy and tert-butoxy. In some embodiments, the substituted $C_{2-8}$ alkenyl and/or the substituted $C_{2-8}$ alkynyl can be substituted with an unsubstituted $C_{1-4}$ haloalkyl, such as —$CF_3$, —$CHF_2$, —$CH_2F$, —$CCl_3$, —$CHCl_2$ and —$CH_2Cl$.

When the $C_{2-8}$ alkenyl and/or the $C_{2-8}$ alkynyl is substituted with an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and/or an unsubstituted 4-6 membered monocyclic heterocyclyl, the unsubstituted $C_{3-4}$ monocyclic cycloalkyl, the fluoro-substituted $C_{3-4}$ monocyclic cycloalkyl, the hydroxy-substituted $C_{3-4}$ monocyclic cycloalkyl and/or the unsubstituted 4-6 membered monocyclic heterocyclyl can replace a single hydrogen of the $C_{2-8}$ alkenyl and/or the $C_{2-8}$ alkynyl. In other instances, the unsubstituted $C_{3-4}$ monocyclic cycloalkyl, the fluoro-substituted $C_{3-4}$ monocyclic cycloalkyl, the hydroxy-substituted $C_{3-4}$ monocyclic cycloalkyl and/or the unsubstituted 4-6 membered monocyclic heterocyclyl can replace two hydrogen of the $C_{2-8}$ alkenyl and/or the $C_{2-8}$ alkynyl such that the unsubstituted $C_{3-4}$ monocyclic cycloalkyl, the fluoro-substituted $C_{3-4}$ monocyclic cycloalkyl, the hydroxy-substituted $C_{3-4}$ monocyclic cycloalkyl and/or the unsubstituted 4-6 membered monocyclic heterocyclyl is connected to the $C_{2-8}$ alkenyl and/or the $C_{2-8}$ alkynyl in a spiro-fashion. In some embodiments, the $C_{3-4}$ monocyclic cycloalkyl substituted on the $C_{2-8}$ alkenyl and/or the $C_{2-8}$ alkynyl can be cyclopropyl. In other embodiments, the $C_{3-4}$ monocyclic cycloalkyl substituted on the $C_{2-8}$ alkenyl and/or the $C_{2-8}$ alkynyl can be cyclobutyl. In some embodiments, the unsubstituted 4-6 membered monocyclic heterocyclyl substituted on the $C_{2-8}$ alkenyl and/or the $C_{2-8}$ alkynyl can be azetidine, oxetane or thietane.

Examples of $R^{10B}$ being an optionally substituted $C_{2-8}$ alkenyl or an optionally substituted $C_{2-8}$ alkynyl include:

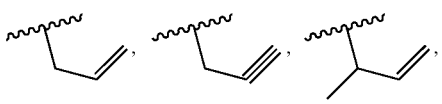

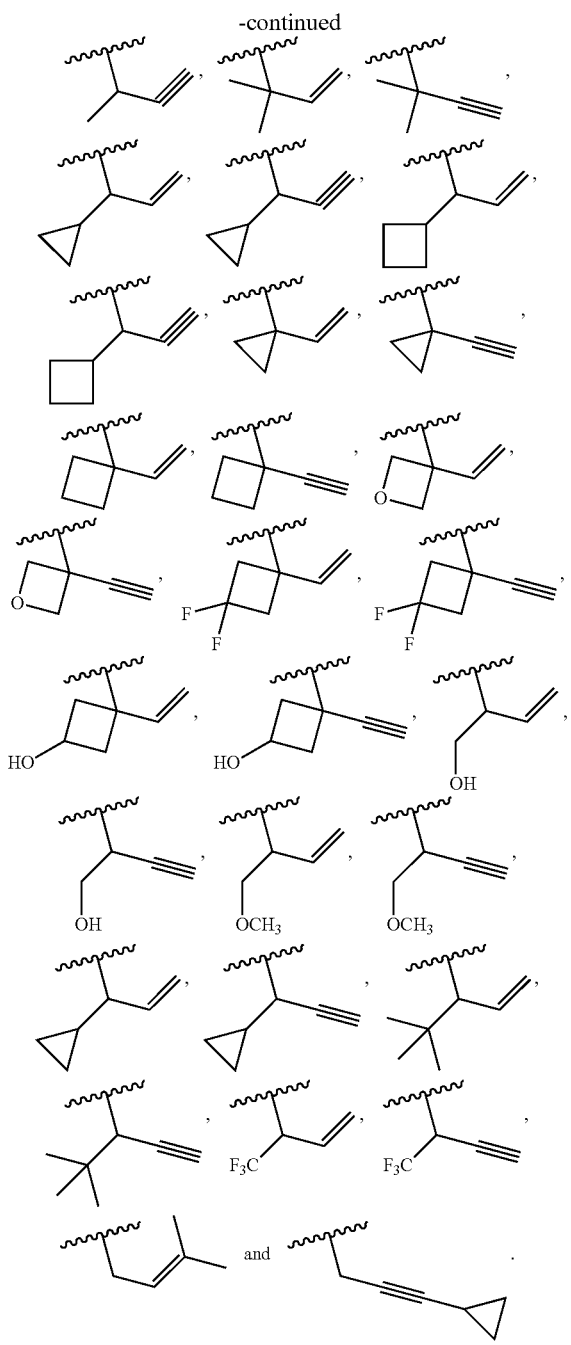

As provided herein, $R^{10B}$ can include a cyclic moiety. an optionally substituted aryl, an optionally substituted aryl($C_{1-4}$ alkyl), an optionally substituted heteroaryl($C_{1-4}$ alkyl) and an optionally substituted heterocyclyl($C_{1-4}$ alkyl). In some embodiments, $R^{10B}$ can be an optionally substituted aryl, such as an optionally substituted phenyl or an optionally substituted naphthyl. In still other embodiments, $R^{10B}$ can be an optionally substituted aryl($C_{1-4}$ alkyl), such as an optionally substituted benzyl. In yet still other embodiments, $R^{10B}$ can be an optionally substituted heteroaryl($C_{1-4}$ alkyl). In some embodiments, $R^{10B}$ can be an optionally substituted heterocyclyl($C_{1-4}$ alkyl). The heteroaryl and heterocyclyl that can be attached via a $C_{1-4}$ alkyl linker for $R^{10B}$ can be monocyclic or bicyclic. Examples of a heteroaryl that can be attached via $C_{1-4}$ alkyl linker are a 5- to 6-membered monocyclic heteroaryl that includes 1-5 heteroatoms selected from N (nitrogen), O (oxygen) and S (sulfur) and a 9- to 10-membered bicyclic heteroaryl that includes 1-5 heteroatoms selected from N (nitrogen), O (oxygen) and S (sulfur). When $R^{10B}$ can be an optionally substituted heterocyclyl($C_{1-4}$ alkyl), in some embodiments, $R^{10B}$ can be an optionally substituted monocyclic 5- to 6-membered heterocyclyl or an optionally substituted bicyclic 9- to 10-membered heterocyclyl, wherein the heterocyclyl can include 1 or more heteroatoms selected from O (oxygen), S (sulfur) and N (nitrogen). The bicyclic heteroaryls and bicyclic heterocyclyls for $R^{10B}$ can be fused wherein the rings are connected via two adjacent ring atoms or spiro-cyclic wherein the rings are connected via 1 ring atom.

As described herein, the $C_{1-4}$ alkyl of the optionally substituted aryl($C_{1-4}$ alkyl), the optionally substituted heteroaryl($C_{1-4}$ alkyl) and the optionally substituted heterocyclyl($C_{1-4}$ alkyl) for $R^{10B}$ can be optionally substituted with an unsubstituted $C_{1-3}$ alkyl (for example, methyl, ethyl, n-propyl and isopropyl) or an unsubstituted $C_{3-4}$ monocyclic cycloalkyl (such as cyclopropyl and cyclobutyl). Further, the aryl of an aryl($C_{1-4}$ alkyl), the heteroaryl of a heteroaryl($C_{1-4}$ alkyl) and the heterocyclyl of a heterocyclyl($C_{1-4}$ alkyl) can be unsubstituted or substituted. For example, the aryl of an aryl($C_{1-4}$ alkyl), the heteroaryl of a heteroaryl($C_{1-4}$ alkyl) and the heterocyclyl of a heterocyclyl($C_{1-4}$ alkyl) can be substituted with one or more moieties (for example, 1, 2 or 3) selected from halogen, an unsubstituted a $C_{2-5}$ alkenyl, a substituted a $C_{2-5}$ alkenyl, an unsubstituted a $C_{2-5}$ alkynyl, a substituted a $C_{2-5}$ alkynyl, an unsubstituted monocyclic heteroaryl (for example, a 5- to 6-membered monocyclic heteroaryl containing 1-3 heteroatoms selected from O (oxygen), S (sulfur) and N (nitrogen)) and a substituted monocyclic heteroaryl (for example, a 5- to 6-membered monocyclic heteroaryl containing 1-3 heteroatoms selected from O (oxygen), S (sulfur) and N (nitrogen)).

In some embodiments, $R^8$ can be —$NR^{10A}R^{10B}$, $R^{10A}$ can be hydrogen; and $R^{10B}$ can be an optionally substituted $C_{2-8}$ alkenyl or an optionally substituted $C_{2-8}$ alkynyl, such as those described herein. In some embodiments, $R^8$ can be —$NR^{10A}R^{10B}$; $R^{10A}$ can be a monocyclic $C_{3-6}$ cycloalkyl optionally substituted with one or two halogens or an optionally substituted 4-6 membered monocyclic heterocyclyl; and $R^{10B}$ can be an unsubstituted aryl($C_{1-4}$ alkyl) or a substituted aryl($C_{1-4}$ alkyl), such as an unsubstituted benzyl or a substituted benzyl. In other embodiments, $R^8$ can be —$NR^{10A}R^{10B}$; $R^{10A}$ can be an optionally substituted 5-6 membered monocyclic heteroaryl; and $R^{10B}$ can be an unsubstituted aryl($C_{1-4}$ alkyl) or a substituted aryl($C_{1-4}$ alkyl), such as an unsubstituted benzyl or a substituted benzyl. In other embodiments, $R^8$ can be —$NR^{10A}R^{10B}$; $R^{10A}$ can be an optionally substituted monocyclic $C_{3-6}$ cycloalkyl($C_{1-4}$ alkyl); and $R^{10B}$ can be an unsubstituted aryl($C_{1-4}$ alkyl) or a substituted aryl($C_{1-4}$ alkyl). For example, $R^{10A}$ can be an optionally substituted cyclopropyl-$CH_2$—, an optionally substituted cyclobutyl-$CH_2$—, an optionally substituted cyclopentyl-$CH_2$— or an optionally substituted cyclohexyl-$CH_2$—; and $R^{10B}$ can be an unsubstituted benzyl or a substituted benzyl. In some embodiments, $R^8$ can be —$NR^{10A}R^{10B}$; $R^{10A}$ can be an optionally substituted monocyclic $C_{3-6}$ cycloalkyl($C_{1-4}$ alkyl); and $R^{10B}$ can be a substituted aryl. As an example, $R^{10A}$ can be an optionally substituted cyclopropyl-$CH_2$—, an optionally substituted cyclobutyl-$CH_2$—, an optionally substituted cyclopentyl-$CH_2$— or an optionally substituted cyclohexyl-$CH_2$— and $R^{10B}$ can be an optionally substituted phenyl.

In some embodiments, when $R^{10A}$ is an optionally substituted monocyclic $C_{3-6}$ cycloalkyl($C_{1-4}$ alkyl), then $R^{10B}$ cannot be an unsubstituted $C_{2-8}$ alkenyl. In some embodiments, $R^{10A}$ cannot be an optionally substituted monocyclic $C_{3-6}$ cycloalkyl($C_{1-4}$ alkyl), such as unsubstituted cyclopropyl-CH$_2$— or substituted cyclopropyl-CH$_2$—.

In some embodiments, $R^8$ can be an unsubstituted $C_{2-12}$ alkynyl. In other embodiments, $R^8$ can be a substituted $C_{2-12}$ alkynyl substituted with one or more substituents (such as 1, 2 or 3) selected from amino, —NH—C(=O) (an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 membered monocyclic heterocyclyl, an optionally substituted aryl and an optionally substituted 5-6 membered monocyclic heteroaryl. In some embodiments, $R^8$ can be an unsubstituted or a substituted phenyl. In other embodiments, $R^8$ can be an unsubstituted or a substituted 5-6 membered monocyclic heteroaryl. For example, $R^8$ can be a 5-6 membered monocyclic heteroaryl that includes 1, 2 or 3 heteroatoms independently selected from N (nitrogen), O (oxygen) and S (sulfur). In other embodiments, $R^8$ can be an unsubstituted 4-6 membered monocyclic heterocyclyl, such as an unsubstituted 4-6 membered monocyclic heterocyclyl that includes 1, 2 or 3 heteroatoms independently selected from N (nitrogen), O (oxygen) and S (sulfur). In some embodiments, when $R^8$ is a substituted aryl or a substituted 5-6 membered monocyclic heteroaryl, then the aryl and/or the heteroaryl can be substituted one or more times (1, 2, 3 or 4 times) with a moiety independently selected from halogen (such as F, Cl or Br) and an unsubstituted $C_{1-3}$ alkyl (for example, methyl, ethyl, n-propyl and isopropyl). Exemplary $R^8$ moieties include, but are not limited to,

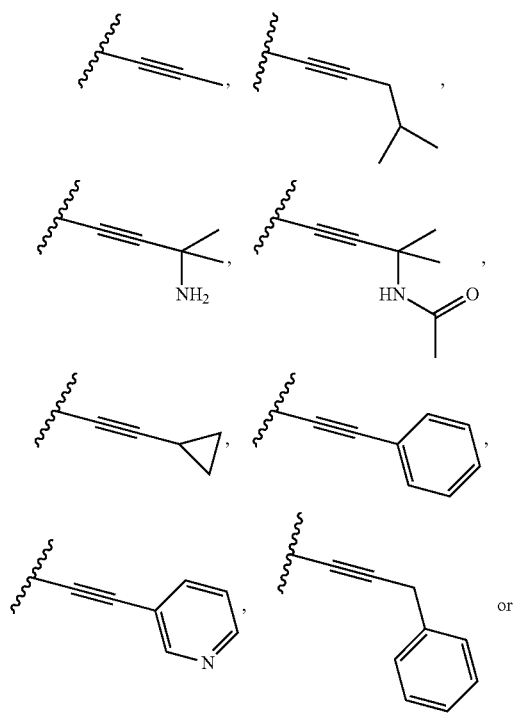

As provided herein, $R^9$ can be a cyclic moiety that can be substituted. For example, in some embodiments, $R^9$ can be a substituted phenyl. $R^9$ can also be a heteroaryl (monocyclic or fused-bicyclic heteroaryl). The heteroaryl can have one or more heteroatoms present, for example, 1, 2 or 3 heteroatoms. Exemplary heteroatoms include, but are not limited to, N (nitrogen), O (oxygen) and S (sulfur). The size of the heteroaryl can vary. In some embodiments, $R^9$ can be a substituted monocyclic heteroaryl. The monocyclic heteroaryl can be a 5- or 6-membered heteroaryl. In other embodiments, $R^9$ can be a substituted fused-bicyclic heteroaryl. The number of ring atoms of the fused-bicyclic heteroaryl can be 9 or 10 such that $R^9$ can be a substituted fused-bicyclic 9- or 10-membered heteroaryl. Examples of suitable heteroaryls for $R^9$ include pyrazole, imidazole, pyridine, pyrimidine, pyrazine, pyridazine, indazole, benzo[d]imidazole and imidazo[4,5-b]pyridine. In some embodiments, $R^9$ can be selected from:

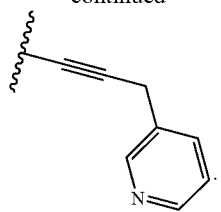

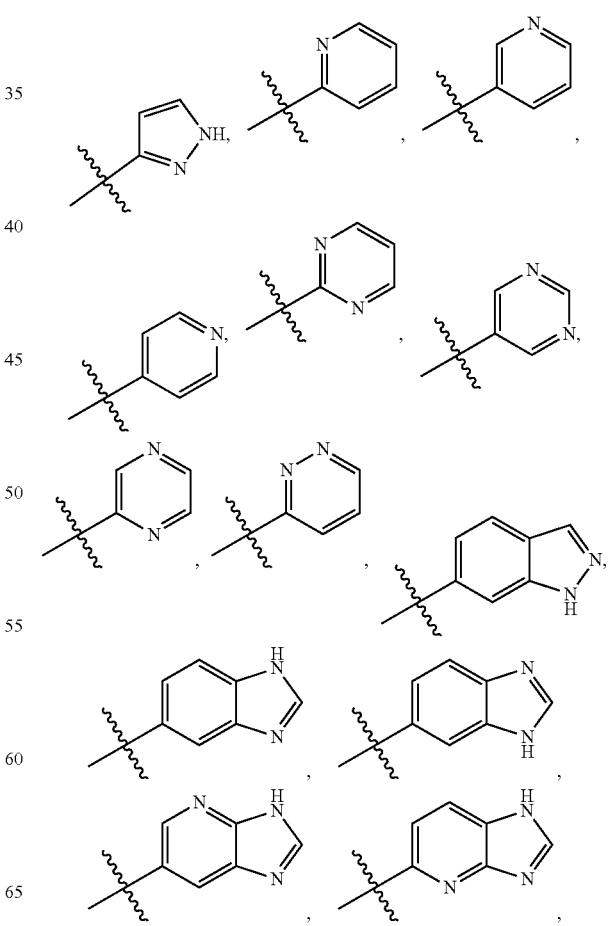

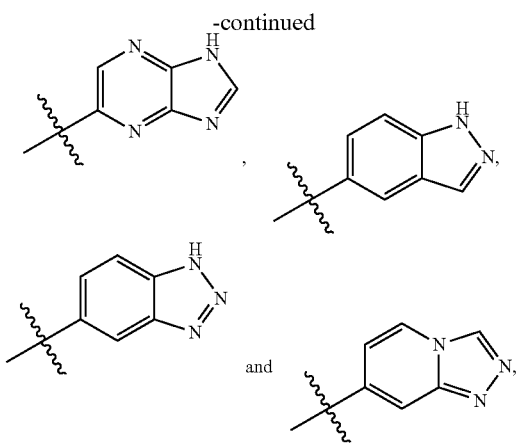

wherein each of the aforementioned can be unsubstituted or substituted as described herein.

As provided herein, $R^9$ can be substituted. Exemplary substituent(s) that can be present on $R^9$ include halogen (such as F, Cl or Br), an unsubstituted $C_{1-4}$ alkyl, a cyano-substituted $C_{1-4}$ alkyl, an unsubstituted $C_{1-4}$ haloalkyl, an unsubstituted $C_{1-4}$ alkoxy, a hydroxy-substituted $C_{1-4}$ alkoxy, an optionally substituted monocyclic $C_{3-6}$ cycloalkyl (such as cyclopropyl, cyclobutyl, cyclopentyl and cyclohexyl), an optionally substituted monocyclic heteroaryl, an optionally substituted monocyclic heterocyclyl, amino, a mono-substituted amine, a di-substituted amine and —C(=O)NHR$^{11}$. Examples of unsubstituted $C_{1-4}$ alkyls and an unsubstituted $C_{1-4}$ alkoxys include the following: methyl, ethyl, n-propyl, isopropyl, n-butyl, sec-butyl, iso-butyl, tert-butyl, methoxy, ethoxy, n-propoxy, isopropoxy, n-butoxy, sec-butoxy, iso-butoxy and tert-butoxy. Exemplary unsubstituted $C_{1-4}$ haloalkyls include —CHF$_2$, —CH$_2$F, —CF$_3$, —CH$_2$Cl, —CHCl$_2$, —CCl$_3$, —CH$_2$CF$_3$, —CH$_2$CHF$_2$, —CH$_2$CCl$_3$ and —CH$_2$CHCl$_2$. A non-limiting list of cyano-substituted $C_{1-4}$ alkyls include —CH$_2$CN, —CH$_2$CH$_2$CN, —CH$_2$CH(CH$_3$)CN and —CH$_2$C(CH$_3$)$_2$CN. Examples of hydroxy-substituted $C_{1-4}$ alkoxy include —OCH$_2$CH$_2$OH, —OCH$_2$CH(CH$_3$)OH and —OCH$_2$C(CH$_3$)$_2$OH.

An $R^9$ group described herein, can be substituted with an unsubstituted or a substituted monocyclic heteroaryl, such as a 5- or 6-membered monocyclic heteroaryl that includes one or more heteroatoms (such as 1, 2 or 3) selected from O (oxygen), S (sulfur) and N (nitrogen). Suitable monocyclic heteroaryls that can be present on $R^9$ are described herein, and include pyrazole, imidazole, pyridine, pyrimidine, pyrazine, pyridazine, pyridazine, pyridazine, 1,2,3-trizole and 1,2,4-triazole. In some embodiments, an unsubstituted or a substituted heterocyclyl (such as a 5- or 6-membered heterocyclyl) can be substituted on an $R^9$ group described herein. The heteroatoms present in an unsubstituted or a substituted heterocyclyl that can be substituted on an $R^9$ group described herein can vary, and include O (oxygen), S (sulfur) and N (nitrogen). Exemplary unsubstituted or a substituted heterocyclyls that can be present on an $R^9$ group described herein include morpholine, piperidine, piperazine, pyrrolidine, 1,2,4-oxadiazol-5(2H)-one, 1,2,4-oxadiazol-5(4H)-one, 2,4-dihydro-3H-1,2,4-triazol-3-one, azetidine and oxetane. The substituted heteroaryls and/or substituted heterocyclyls that can be substituted on an $R^9$ group described herein can be substituted with one or more moieties (for example, 1, 2 or 3 moieties) such as those described herein for "optionally substituted." In some embodiments, the substituted heteroaryls and/or substituted heterocyclyls that can be substituted on an $R^9$ group described herein can be substituted with halogen, amino, an unsubstituted $C_{1-4}$ alkyl, an unsubstituted $C_{1-4}$ haloalkyl (for example, CF$_3$, CHF$_2$, CH$_2$F) and/or an unsubstituted $C_{1-4}$ alkoxy. Suitable halogens, unsubstituted $C_{1-4}$ alkyls, unsubstituted $C_{1-4}$ haloalkyls and/or unsubstituted $C_{1-4}$ alkoxys are described herein, such as those described in this paragraph.

As provided herein, amino, a mono-substituted amine, a di-substituted amine and/or —C(=O)NHR$^{11}$ can be substituted on an $R^9$ group described herein. The mono-substituted amine can have the general formula —NH (an unsubstituted $C_{1-4}$ alkyl), and the di-substituted amine can have the general formula —N(an unsubstituted $C_{1-4}$ alkyl)$_2$. In some embodiment, an $R^9$ group described herein can be substituted with —C(=O)NHR$^{11}$, wherein R$^{11}$ can be hydrogen, an unsubstituted $C_{1-6}$ alkyl (such as methyl, ethyl, n-propyl, isopropyl, n-butyl, sec-butyl, iso-butyl, tert-butyl, pentyl (straight-chained or branched) and hexyl (straight-chained or branched), an optionally substituted $C_{2-6}$ alkenyl (for example, ethenyl and propenyl), an optionally substituted $C_{1-6}$ alkynyl (such as ethynyl and propynyl) or an optionally substituted monocyclic $C_{3-6}$ cycloalkyl. The optionally substituted monocyclic $C_{3-6}$ cycloalkyl for R$^{11}$ can be an unsubstituted monocyclic $C_{3-6}$ cycloalkyl, a halo-substituted monocyclic $C_{3-6}$ cycloalkyl or an unsubstituted $C_{1-4}$ alkyl-substituted monocyclic $C_{3-6}$ cycloalkyl.

In some embodiments, to a compound of Formula (I), or a pharmaceutically acceptable salt thereof, can be where n can be 0 or 1; $Z^1$ can be —C(=O)— or —NH—C(=O)—; R$^1$ can be selected from an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^2$ and R$^3$ can be independently selected from hydrogen, an optionally substituted $C_{1-4}$ alkyl, an optionally substituted $C_{2-4}$ alkenyl, an optionally substituted $C_{2-4}$ alkynyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^4$ and R$^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^6$ and R$^7$ can be independently selected from hydrogen, an unsubstituted $C_{1-4}$ alkyl and an unsubstituted $C_{1-4}$ haloalkyl; R$^8$ can be —NR$^{10A}$R$^{10B}$; R$^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted $C_{1-4}$ alkyl, an unsubstituted $C_{1-4}$ haloalkyl, an unsubstituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{11}$; R$^{10A}$ can be hydrogen, an unsubstituted $C_{1-6}$ alkyl, a monocyclic $C_{3-6}$ cycloalkyl optionally substituted with one or two halogens, an optionally substituted 5-6 member monocyclic heteroaryl, an optionally substituted 4-6 member monocyclic heterocyclyl or an optionally substituted monocyclic $C_{3-6}$ cycloalkyl($C_{1-4}$ alkyl); $R^{10B}$ can be selected from an optionally substituted $C_{2-6}$ alkenyl, an optionally substituted $C_{2-6}$ alkynyl, an optionally substituted aryl, an optionally substituted aryl($C_{1-4}$ alkyl), an optionally substituted heteroaryl($C_{1-4}$ alkyl) and an optionally substituted heterocyclyl($C_{1-4}$ alkyl), wherein the $C_{2-6}$ alkenyl and the $C_{2-6}$ alkynyl is optionally substituted with hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl or an unsubstituted 4-6 member monocyclic heterocyclyl; and $R^{11}$ can be hydrogen, an unsubstituted $C_{1-6}$ alkyl, an optionally substituted $C_{2-6}$ alkenyl, an optionally substituted $C_{1-6}$ alkynyl or an optionally substituted monocyclic $C_{3-6}$ cycloalkyl.

In some embodiments, to a compound of Formula (I), or a pharmaceutically acceptable salt thereof, can be where n can be 0 or 1; $Z^1$ can be —C(=O)— or —NH—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an optionally substituted $C_{1-4}$ alkyl, an optionally substituted $C_{2-4}$ alkenyl, an optionally substituted $C_{2-4}$ alkynyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be —NR$^{10A}$R$^{10B}$ or an optionally substituted $C_{2-12}$ alkynyl, wherein the $C_{2-12}$ alkynyl is optionally substituted with one or more substituents selected from amino, —NH—C(=O) (an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 member monocyclic heterocyclyl, an optionally substituted aryl and an optionally substituted 5-6 member monocyclic heteroaryl; $R^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted $C_{1-4}$ alkyl, an unsubstituted $C_{1-4}$ haloalkyl, an unsubstituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{11}$; $R^{10A}$ can be hydrogen, an unsubstituted $C_{1-6}$ alkyl, a monocyclic $C_{3-6}$ cycloalkyl optionally substituted with one or two halogens, an optionally substituted 5-6 member monocyclic heteroaryl, an optionally substituted 4-6 member monocyclic heterocyclyl or an optionally substituted monocyclic $C_{3-6}$ cycloalkyl($C_{1-4}$ alkyl); $R^{10B}$ can be selected from an optionally substituted $C_{2-8}$ alkenyl, an optionally substituted $C_{2-8}$ alkynyl, an optionally substituted aryl, an optionally substituted aryl ($C_{1-4}$ alkyl), an optionally substituted heteroaryl($C_{1-4}$ alkyl) and an optionally substituted heterocyclyl($C_{1-4}$ alkyl), wherein the $C_{2-8}$ alkenyl and the $C_{2-8}$ alkynyl is optionally substituted with one or more substituents selected from amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl or an unsubstituted 4-6 member monocyclic heterocyclyl; and $R^{11}$ can be hydrogen, an unsubstituted $C_{1-6}$ alkyl, an optionally substituted $C_{2-6}$ alkenyl, an optionally substituted $C_{1-6}$ alkynyl and an optionally substituted monocyclic $C_{3-6}$ cycloalkyl.

In some embodiments, to a compound of Formula (I), or a pharmaceutically acceptable salt thereof, can be where n can be 0 or 1; $Z^1$ can be —C(=O)— or —NH—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an optionally substituted $C_{1-4}$ alkyl, an optionally substituted $C_{2-4}$ alkenyl, an optionally substituted $C_{2-4}$ alkynyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be —NR$^{10A}$R$^{10B}$ or an optionally substituted $C_{2-12}$ alkynyl, wherein the $C_{2-12}$ alkynyl is optionally substituted with one or more substituents selected from amino, —NH—C(=O) (an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 membered monocyclic heterocyclyl, an optionally substituted aryl and an optionally substituted 5-6 membered monocyclic heteroaryl; $R^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted $C_{1-4}$ alkyl, an unsubstituted $C_{1-4}$ haloalkyl, an unsubstituted $C_{1-4}$ alkoxy, a hydroxy-substituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{11}$; $R^{10A}$ can be hydrogen, an unsubstituted $C_{1-6}$ alkyl, a monocyclic $C_{3-6}$ cycloalkyl optionally substituted with one or two halogens, an optionally substituted 5-6 membered monocyclic heteroaryl, an optionally substituted 4-6 membered monocyclic heterocyclyl or an optionally substituted monocyclic $C_{3-6}$ cycloalkyl($C_{1-4}$ alkyl); $R^{10B}$ can be selected from an optionally substituted $C_{2-8}$ alkenyl, an optionally substituted $C_{2-8}$ alkynyl, an optionally substituted aryl, an optionally substituted aryl(C$_{1-4}$ alkyl), an optionally substituted heteroaryl(C$_{1-4}$ alkyl) and an optionally substituted heterocyclyl(C$_{1-4}$ alkyl), wherein the C$_{2-8}$ alkenyl and the C$_{2-8}$ alkynyl is optionally substituted with one or more substituents selected from amino, hydroxy, an unsubstituted C$_{1-4}$ alkoxy, an unsubstituted C$_{1-4}$ haloalkyl, an unsubstituted C$_{3-4}$ monocyclic cycloalkyl, a fluoro-substituted C$_{3-4}$ monocyclic cycloalkyl, a hydroxy-substituted C$_{3-4}$ monocyclic cycloalkyl or an unsubstituted 4-6 membered monocyclic heterocyclyl; and R$^{11}$ can be hydrogen, an unsubstituted C$_{1-6}$ alkyl, an optionally substituted C$_{2-6}$ alkenyl, an optionally substituted C$_{1-6}$ alkynyl and an optionally substituted monocyclic C$_{3-6}$ cycloalkyl.

In some embodiments, to a compound of Formula (I), or a pharmaceutically acceptable salt thereof, can be where n can be 1; Z$^1$ is —C(═O)—; R$^1$ can be

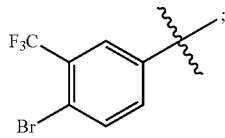

R$^2$ can be selected from hydrogen, an unsubstituted C$_{1-4}$ alkyl, an unsubstituted C$_{2-4}$ alkenyl, an unsubstituted C$_{2-4}$ alkynyl and an unsubstituted C$_{1-4}$ haloalkyl; R$^3$, R$^4$, R$^5$, R$^6$ and R$^7$ can each be hydrogen; R$^8$ can be —NHR$^{10B}$ or an optionally substituted C$_{2-12}$ alkynyl, wherein the C$_{2-12}$ alkynyl is optionally substituted with one or more substituents (such as 1, 2 or 3 substituents) selected from amino, —NH—C(═O) (an unsubstituted C$_{1-4}$ alkyl), hydroxy, an unsubstituted C$_{1-4}$ alkoxy, an unsubstituted C$_{1-4}$ haloalkyl, an unsubstituted C$_{3-4}$ monocyclic cycloalkyl, a fluoro-substituted C$_{3-4}$ monocyclic cycloalkyl, a hydroxy-substituted C$_{3-4}$ monocyclic cycloalkyl, an unsubstituted 4-6 membered monocyclic heterocyclyl, an optionally substituted aryl and an optionally substituted 5-6 membered monocyclic heteroaryl; R$^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents (such as 1, 2 or 3 substituents) selected from halogen, an unsubstituted C$_{1-4}$ alkyl, an unsubstituted C$_{1-4}$ haloalkyl, an unsubstituted C$_{1-4}$ alkoxy, a hydroxy-substituted C$_{1-4}$ alkoxy, an optionally substituted monocyclic C$_{3-6}$ cycloalkyl, an optionally substituted monocyclic heteroaryl, an optionally substituted monocyclic heterocyclyl, amino, a mono-substituted amine, a di-substituted amine and —C(═O)NHR$^{11}$; R$^{10B}$ can be selected from an optionally substituted C$_{2-8}$ alkenyl and an optionally substituted C$_{2-8}$ alkynyl, wherein the C$_{2-8}$ alkenyl and the C$_{2-8}$ alkynyl is optionally substituted with one or more substituents (for example, 1, 2 or 3 substituents) selected from amino, hydroxy, an unsubstituted C$_{1-4}$ alkoxy, an unsubstituted C$_{1-4}$ haloalkyl, an unsubstituted C$_{3-4}$ monocyclic cycloalkyl, a fluoro-substituted C$_{3-4}$ monocyclic cycloalkyl, a hydroxy-substituted C$_{3-4}$ monocyclic cycloalkyl and an unsubstituted 4-6 membered monocyclic heterocyclyl; and R$^{11}$ can be hydrogen, an unsubstituted C$_{1-6}$ alkyl, an optionally substituted C$_{2-6}$ alkenyl, an optionally substituted C$_{1-6}$ alkynyl or an optionally substituted monocyclic C$_{3-6}$ cycloalkyl.

In some embodiments, a compound of Formula (I), or a pharmaceutically acceptable salt thereof, can be where n can be 1; Z$^1$ is —C(═O)—; R$^1$ can be

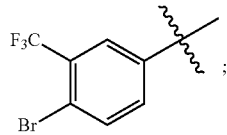 [SMILES: *c1ccc(Br)c(C(F)(F)F)c1]

R$^2$ can be an unsubstituted C$_{1-4}$ alkyl (such as methyl); R$^3$, R$^4$, R$^5$, R$^6$ and R$^7$ can each be hydrogen; R$^8$ can be —NHR$^{10B}$; R$^9$ can be a substituted phenyl, wherein the phenyl is substituted with —C(═O)NHR$^{11}$; R$^{10B}$ can be an unsubstituted C$_{2-8}$ alkenyl; and R$^{11}$ can be an unsubstituted C$_{1-6}$ alkyl (for example, methyl). In some embodiments, a compound of Formula (I), or a pharmaceutically acceptable salt thereof, can be where n can be 1; Z$^1$ is —C(═O)—; R$^1$ can be

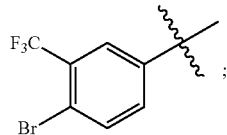 [SMILES: *c1ccc(Br)c(C(F)(F)F)c1]

R$^2$ can be an unsubstituted C$_{1-4}$ alkyl (such as methyl); R$^3$, R$^4$, R$^5$, R$^6$ and R$^7$ can each be hydrogen; R$^8$ can be —NHR$^{10B}$; R$^9$ can be a substituted phenyl, wherein the phenyl is substituted with —C(═O)NHR$^{11}$; R$^{10B}$ can be an unsubstituted C$_{2-8}$ alkynyl; and R$^{11}$ can be an unsubstituted C$_{1-6}$ alkyl (for example, methyl). In some embodiments, a compound of Formula (I), or a pharmaceutically acceptable salt thereof, can be where n can be 1; Z$^1$ is —C(═O)—; R$^1$ can be

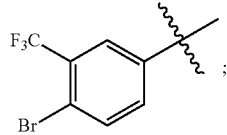 [SMILES: *c1ccc(Br)c(C(F)(F)F)c1]

R$^2$ can be an unsubstituted C$_{1-4}$ alkyl (such as methyl); R$^3$, R$^4$, R$^5$, R$^6$ and R$^7$ can each be hydrogen; R$^8$ can be —NHR$^{10B}$; R$^9$ can be a substituted phenyl, wherein the phenyl is substituted with an optionally substituted monocyclic heteroaryl; and R$^{10B}$ can be an unsubstituted C$_{2-8}$ alkenyl or an unsubstituted C$_{2-8}$ alkynyl. In some embodiments, a compound of Formula (I), or a pharmaceutically acceptable salt thereof, can be where n can be 1; Z$^1$ is —C(═O)—; R$^1$ can be

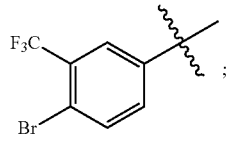 [SMILES: *c1ccc(Br)c(C(F)(F)F)c1]

R$^2$ can be an unsubstituted C$_{1-4}$ alkyl (such as methyl); R$^3$, R$^4$, R$^5$, R$^6$ and R$^7$ can each be hydrogen; an optionally substituted C$_{2-12}$ alkynyl, wherein the C$_{2-12}$ alkynyl is optionally substituted with one or more substituents (such as 1, 2 or 3 substituents) selected from amino, —NH—C(═O) (an unsubstituted C$_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 membered monocyclic heterocyclyl, an optionally substituted aryl and an optionally substituted 5-6 membered monocyclic heteroaryl; $R^9$ can be a substituted phenyl, wherein the phenyl is substituted with —C(=O)NHR$^{11}$; $R^{10B}$ can be an unsubstituted $C_{2-8}$ alkynyl; and $R^{11}$ can be an unsubstituted $C_{1-6}$ alkyl (for example, methyl).

Examples of compounds of Formula (I), including pharmaceutically acceptable salts thereof, include:

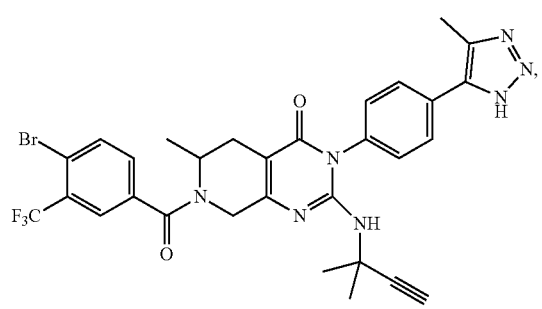

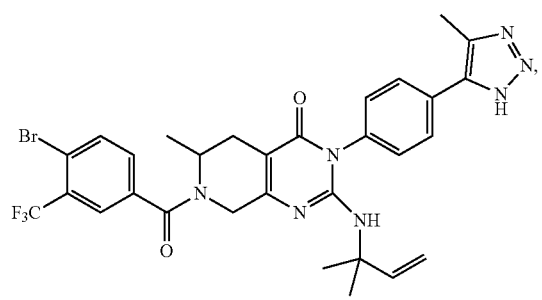

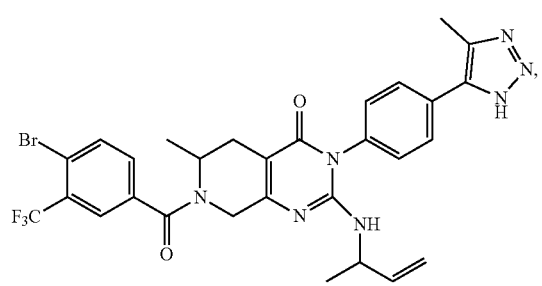

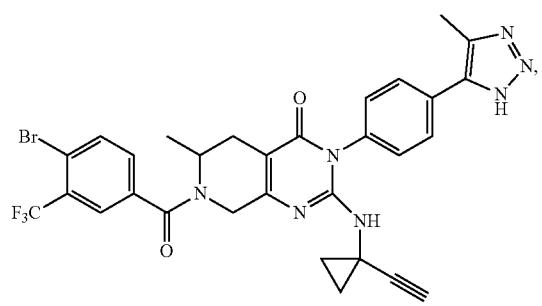

-continued

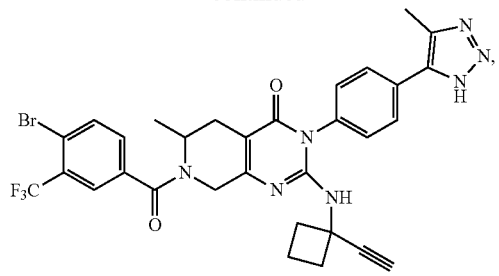

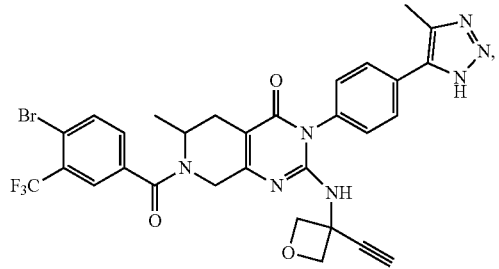

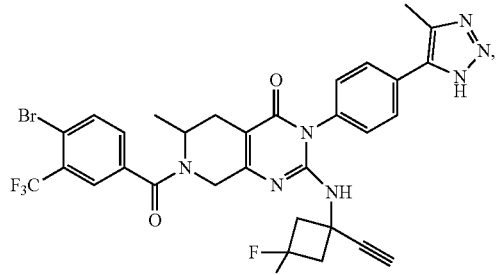

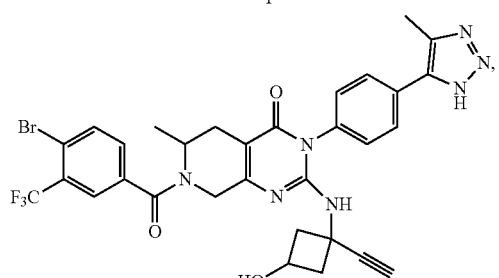

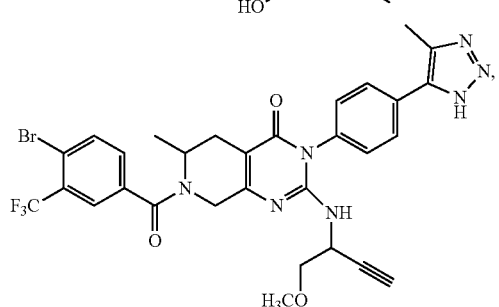

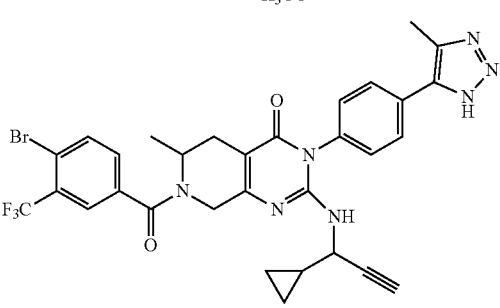

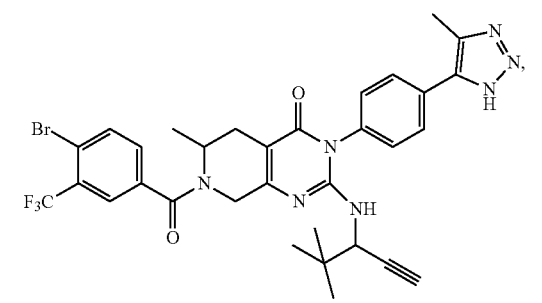
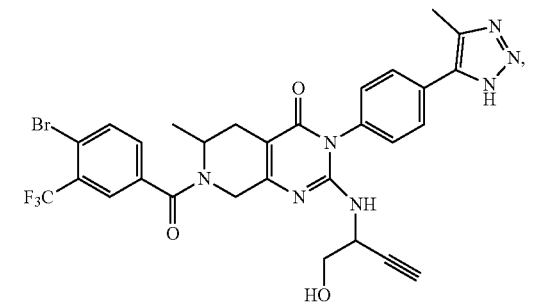
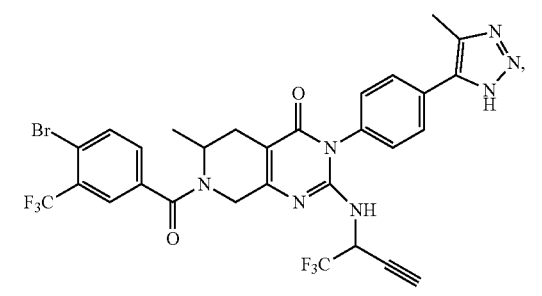
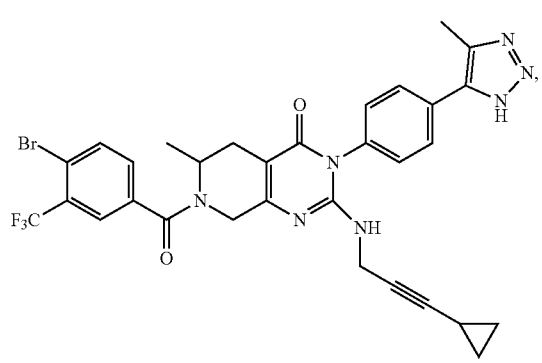
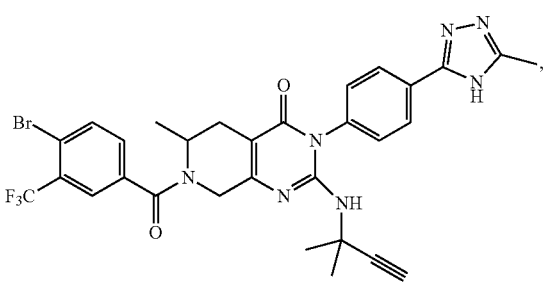
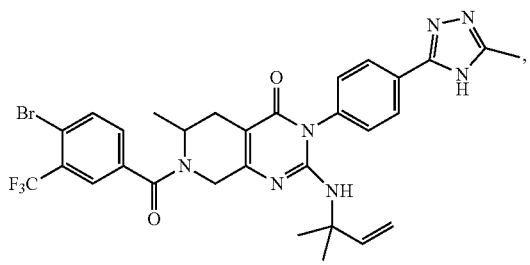
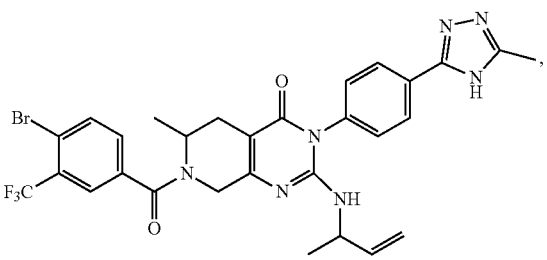
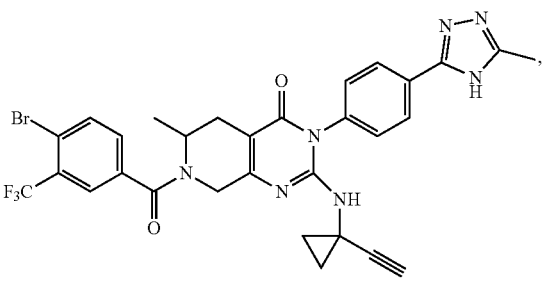
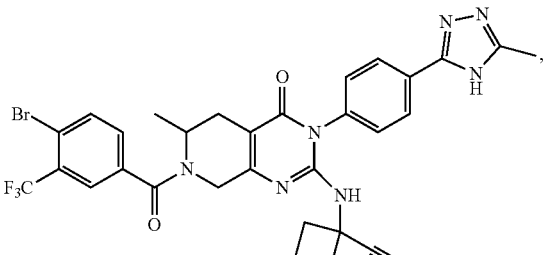
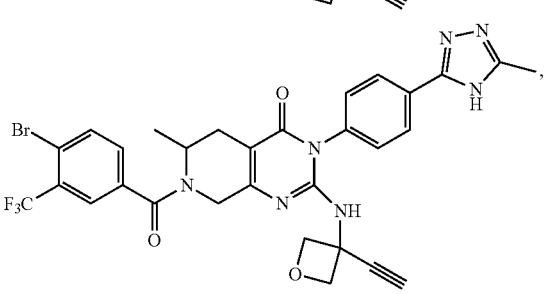
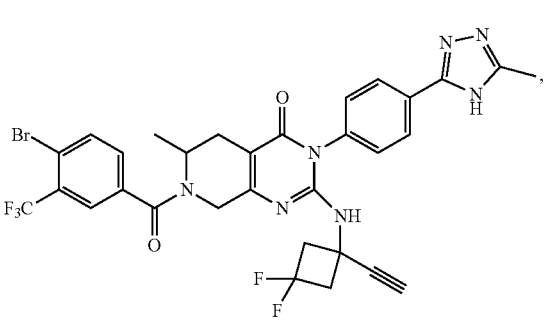

-continued
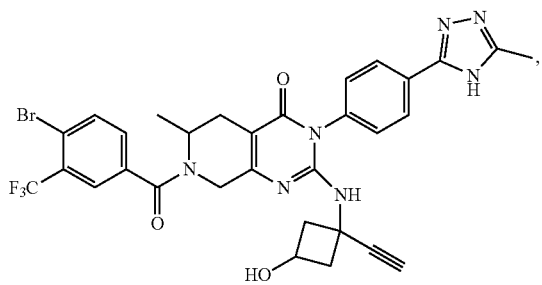
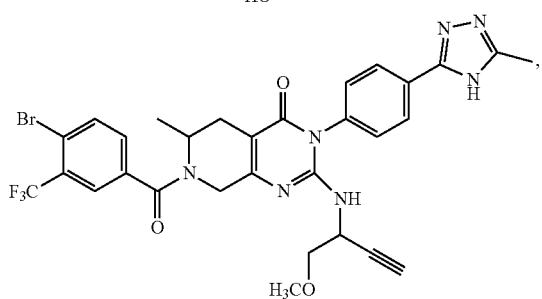
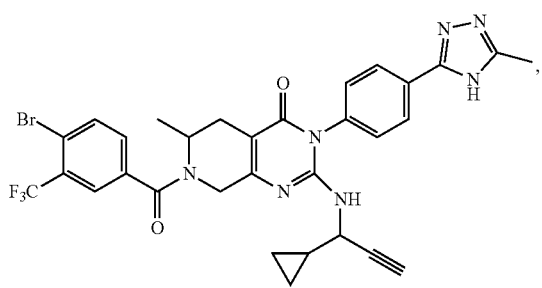
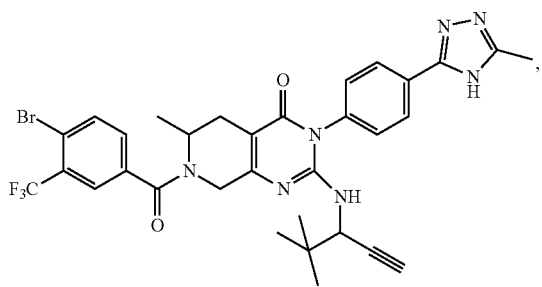
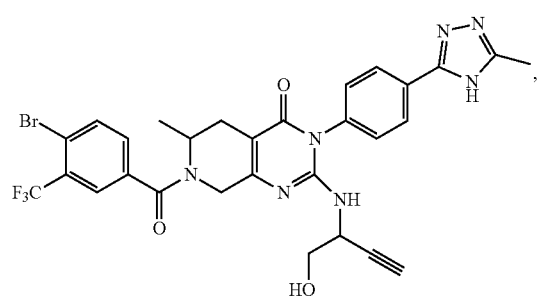
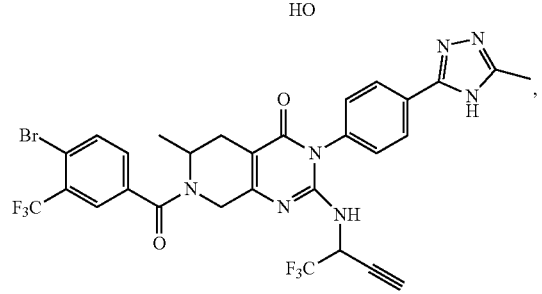
-continued
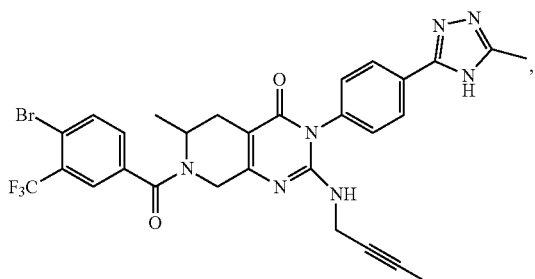
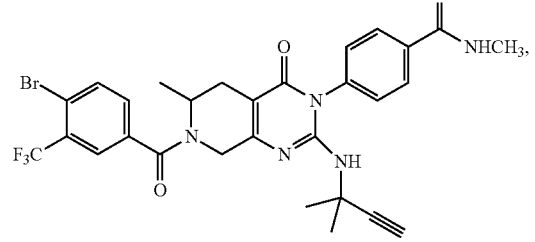
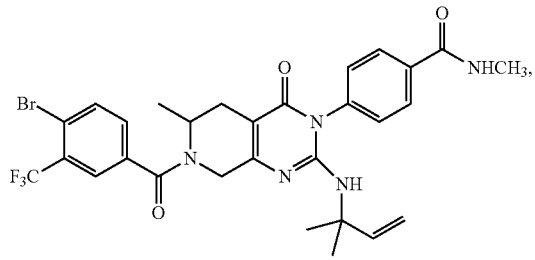
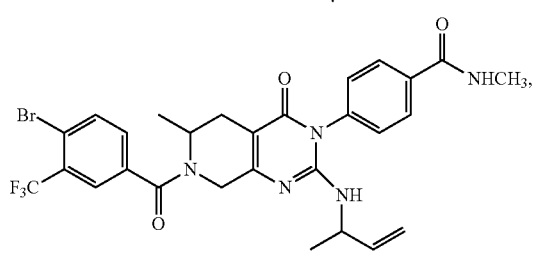
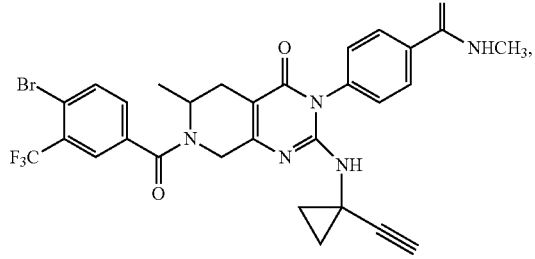
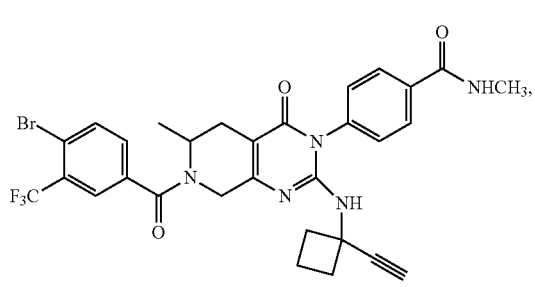

35
-continued
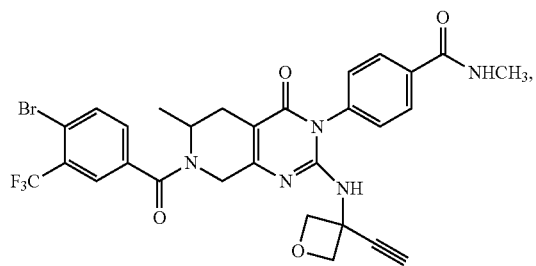
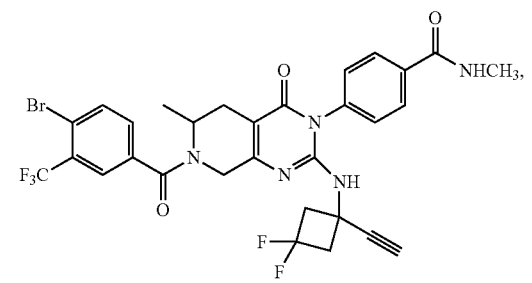
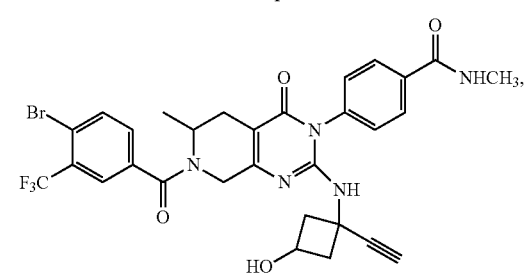
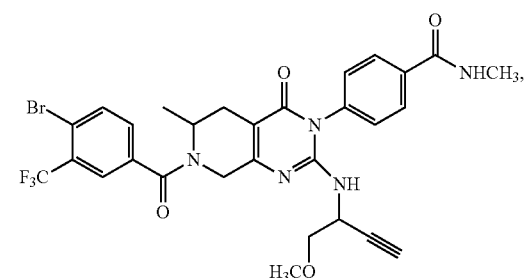
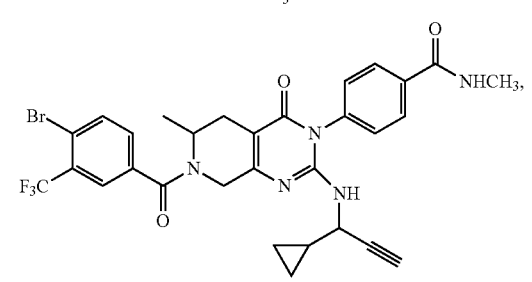
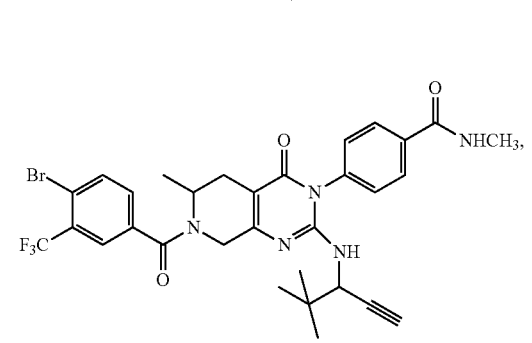
36
-continued
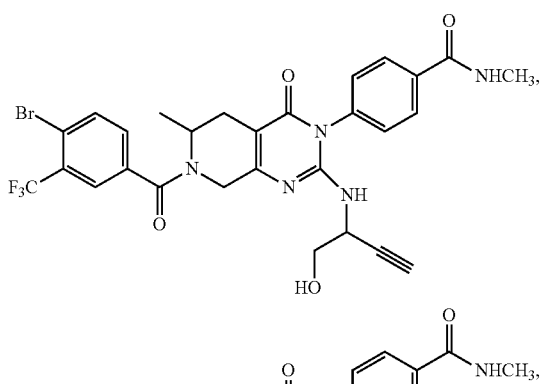
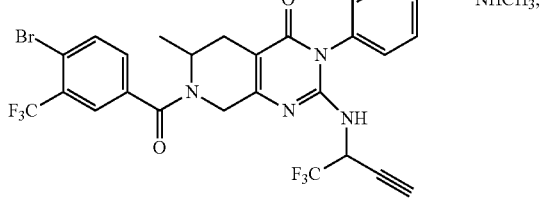
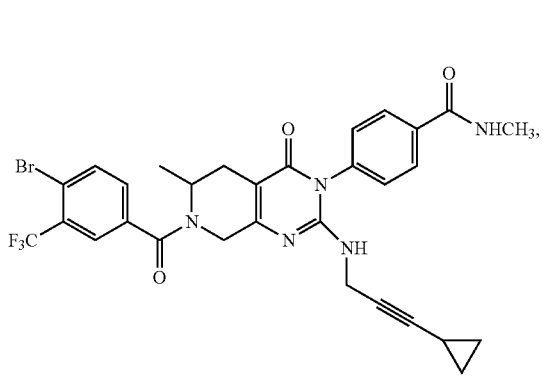
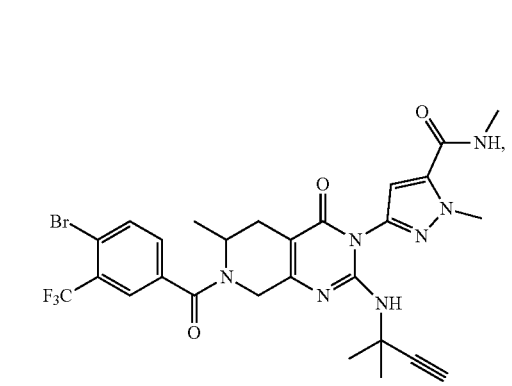
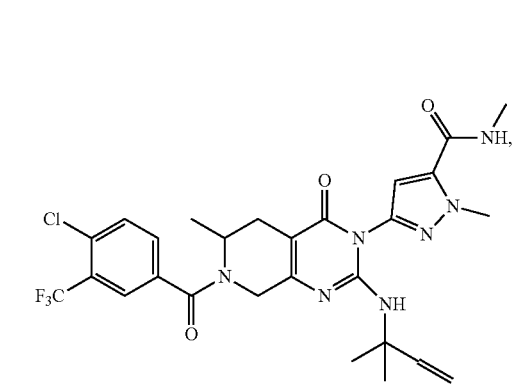

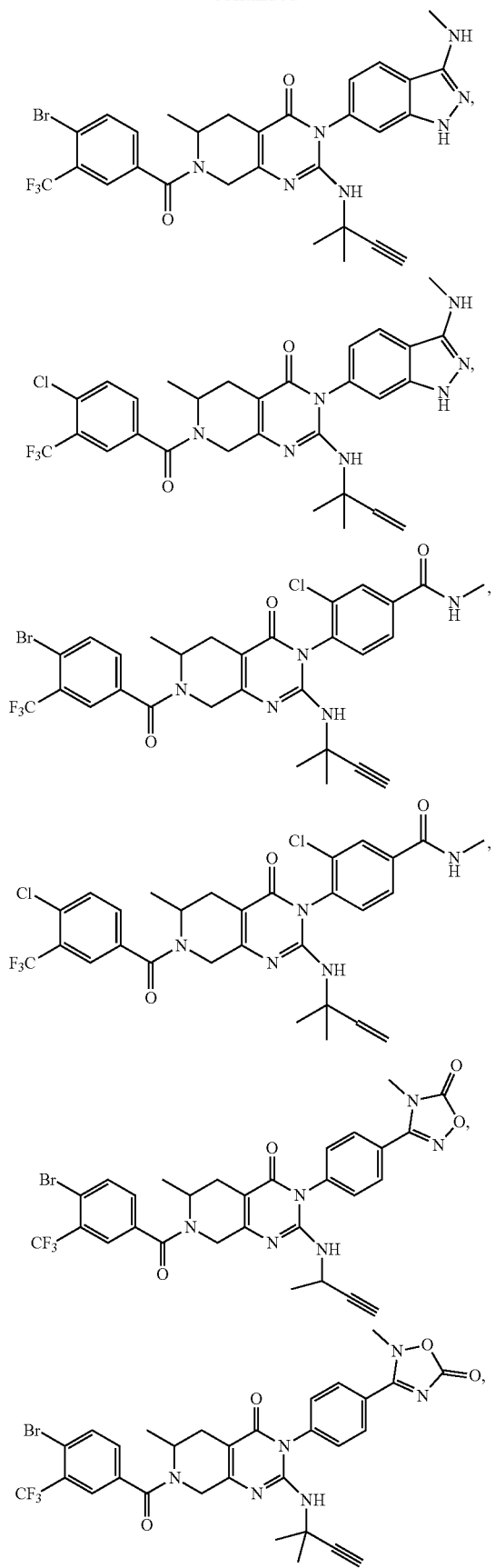
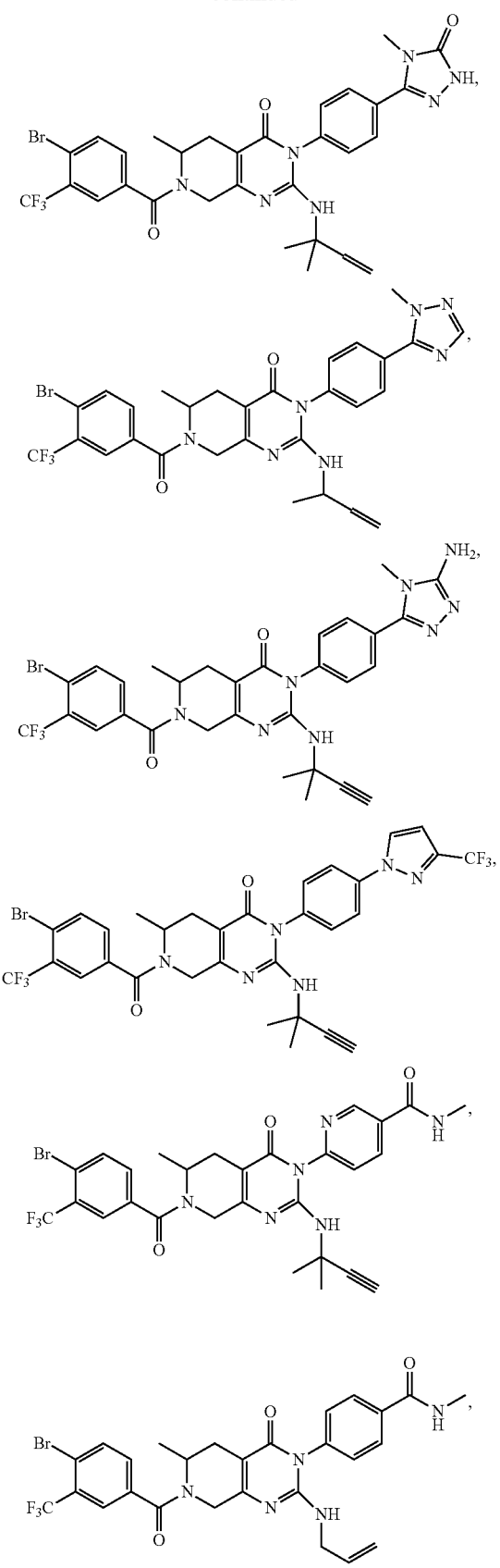

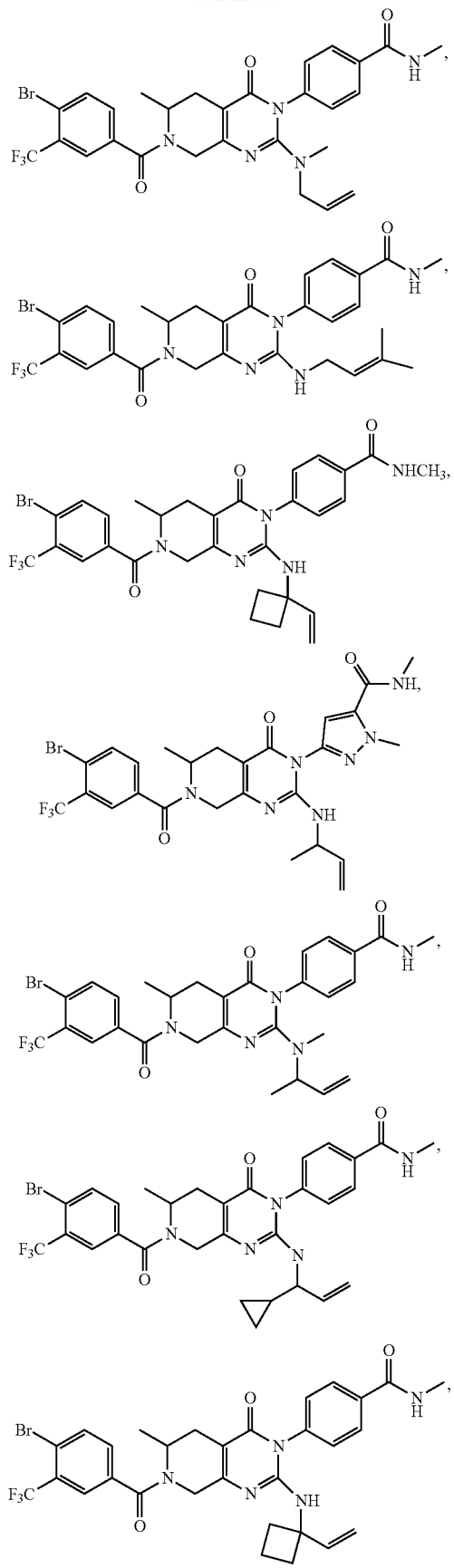
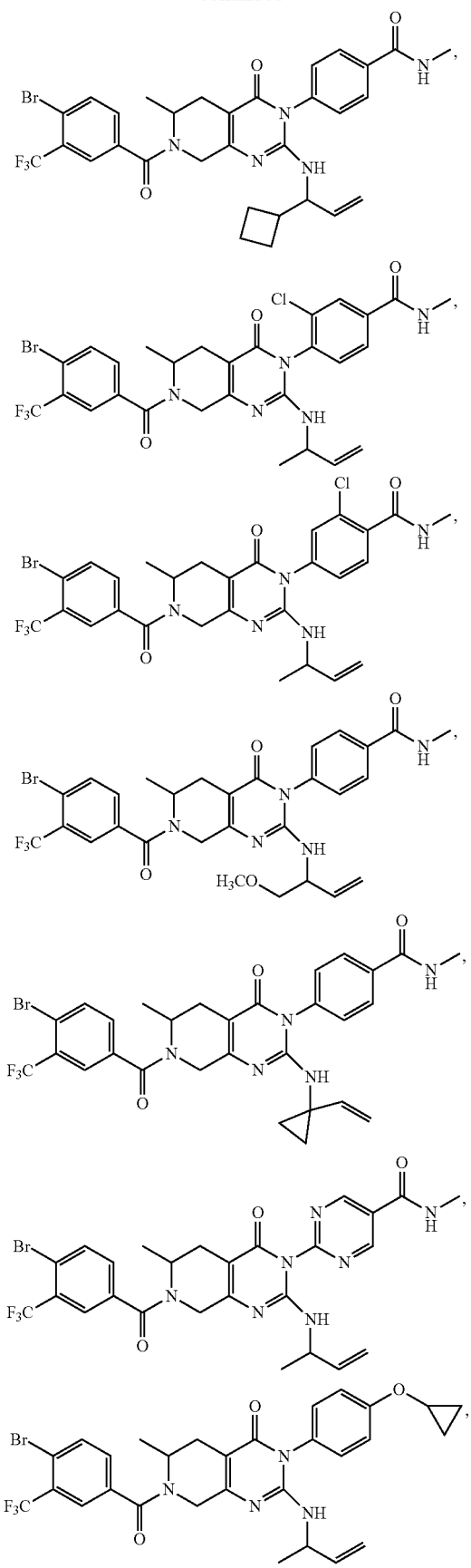

41
-continued
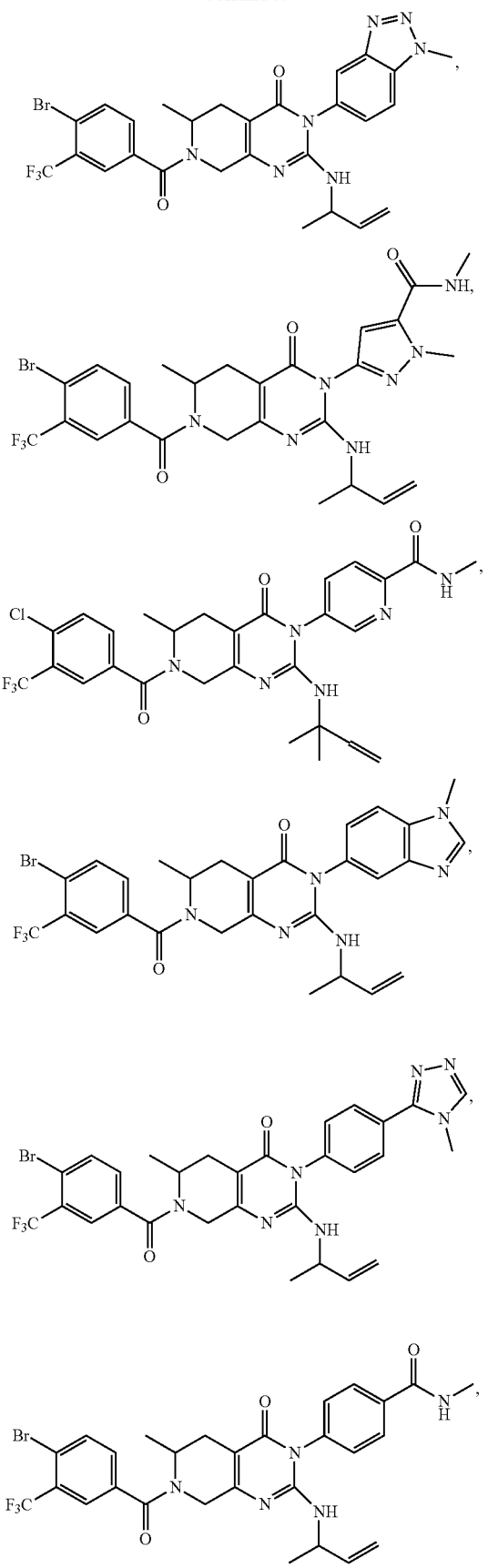
42
-continued
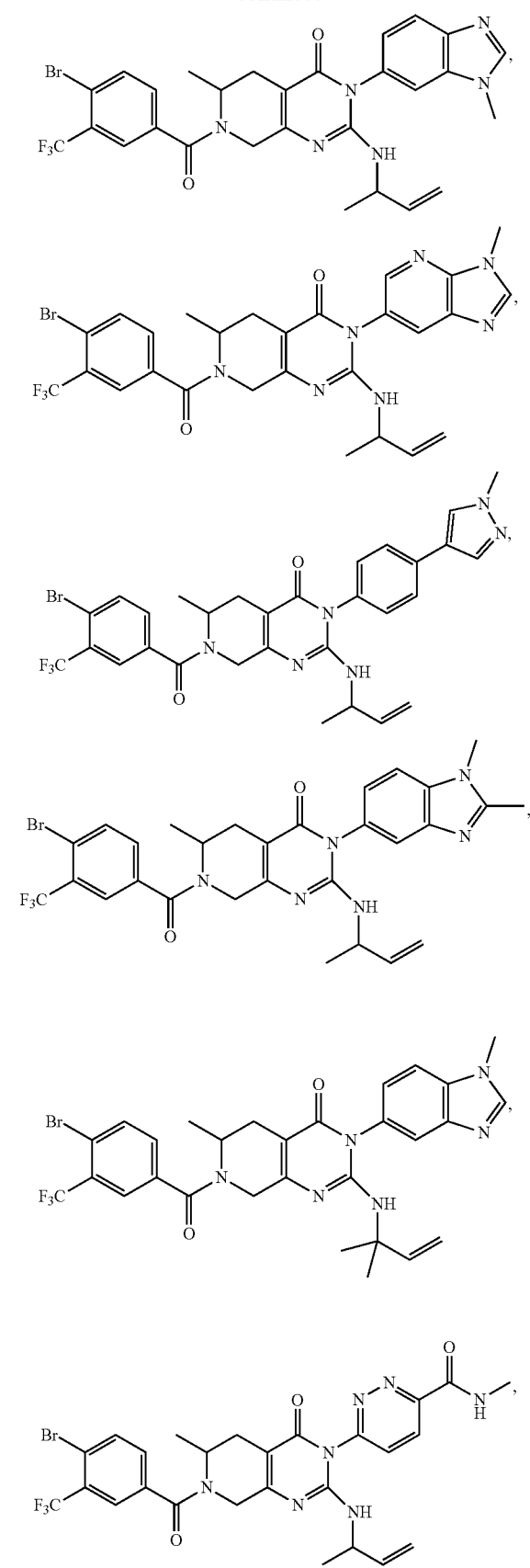

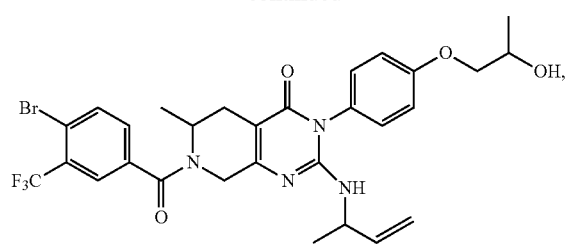
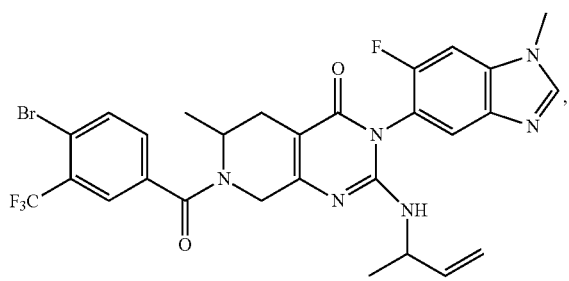
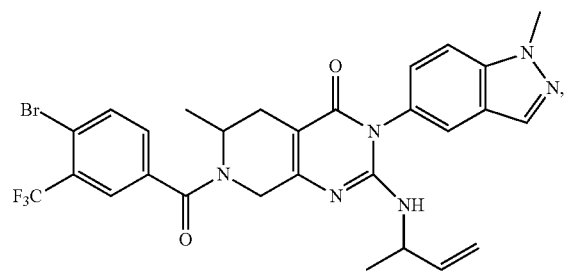
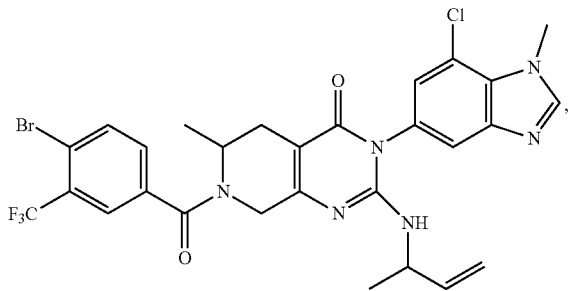
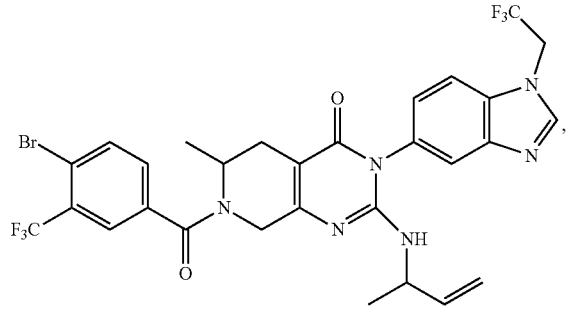
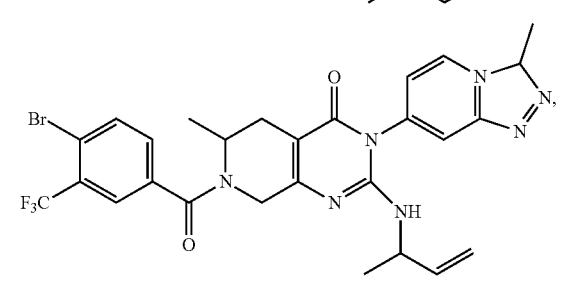
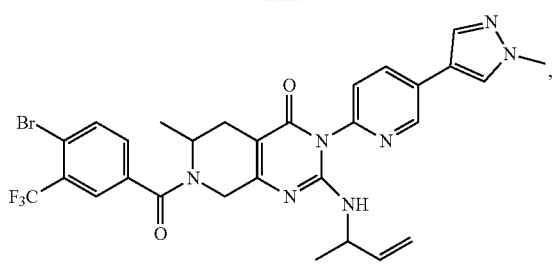
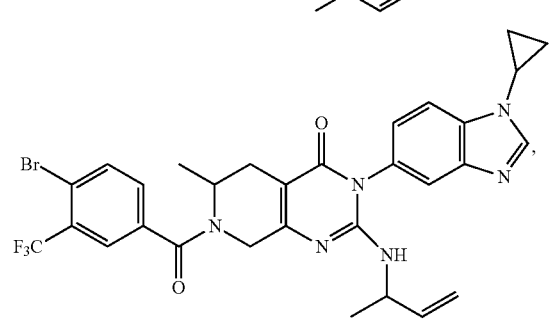
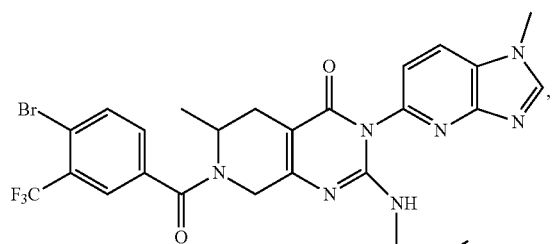
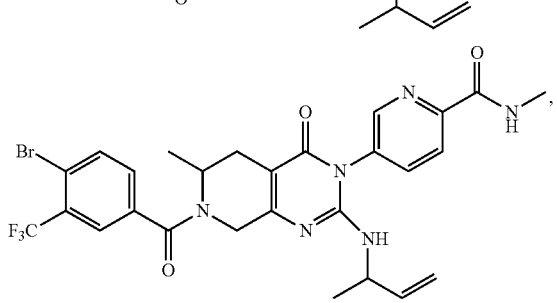
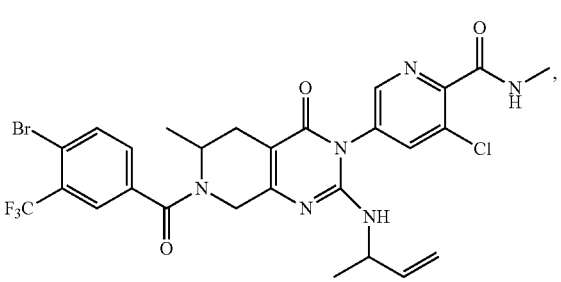
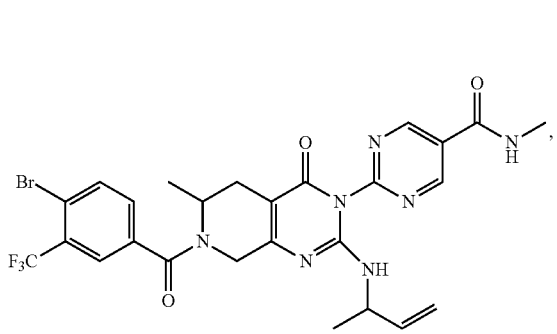

-continued
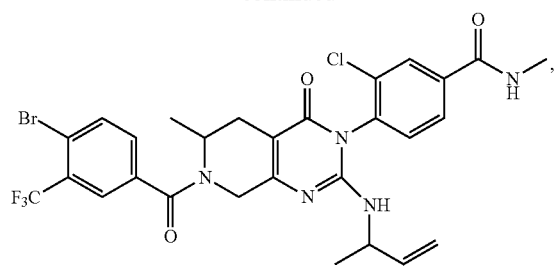
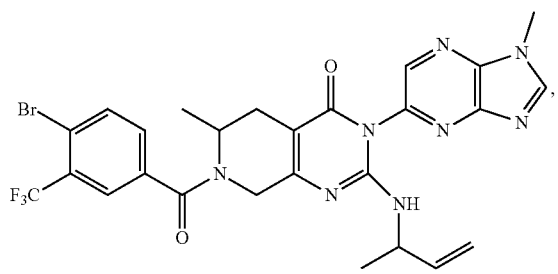
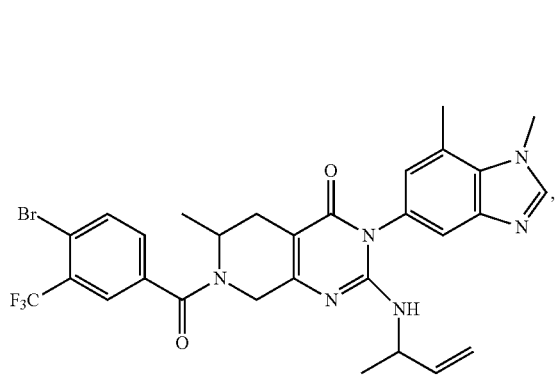
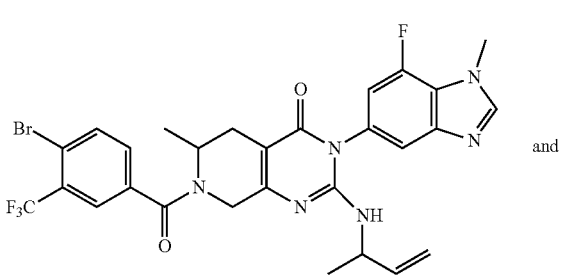
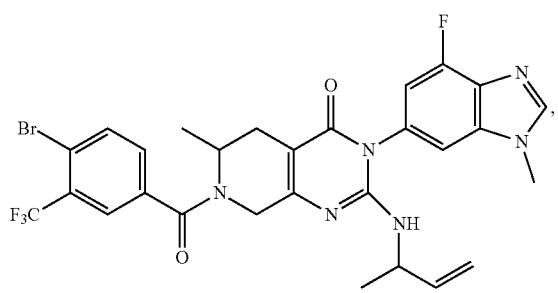
or a pharmaceutically acceptable salt of any of the foregoing.
Additional examples of compounds of Formula (I), including pharmaceutically acceptable salts thereof, include:
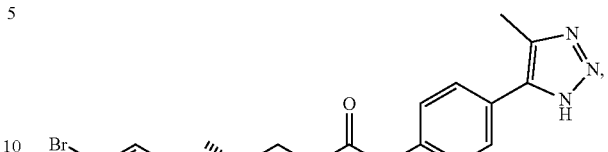
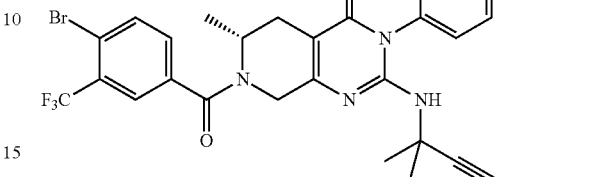
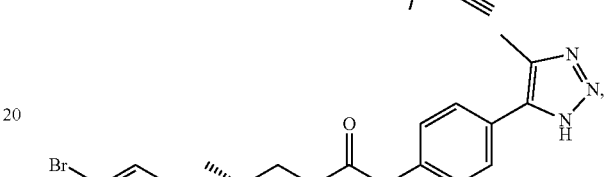
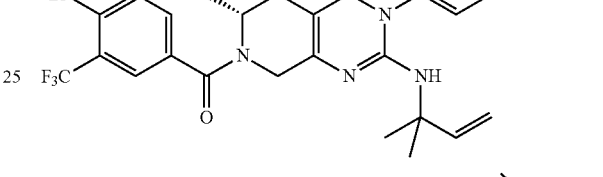
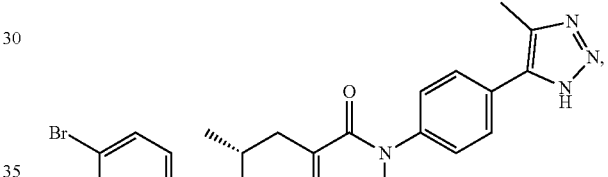
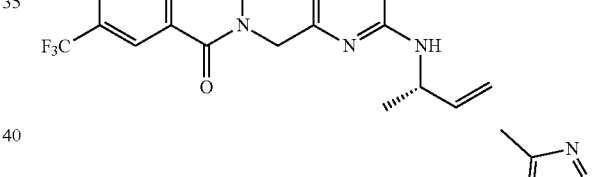
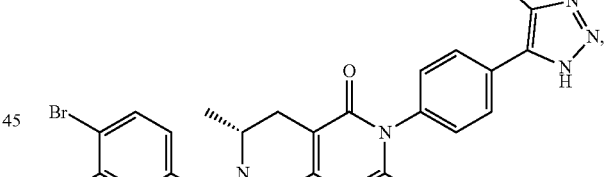
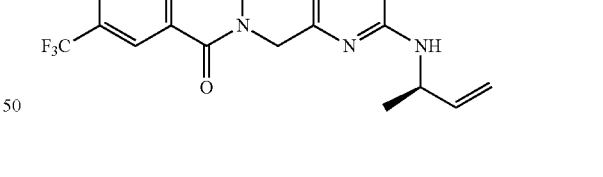
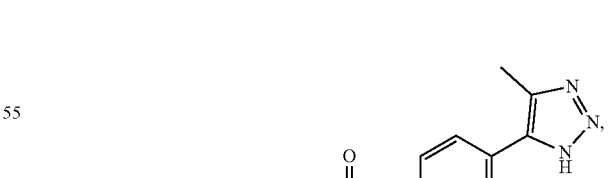
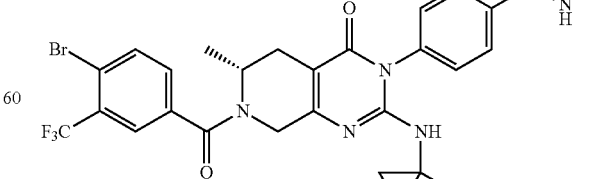

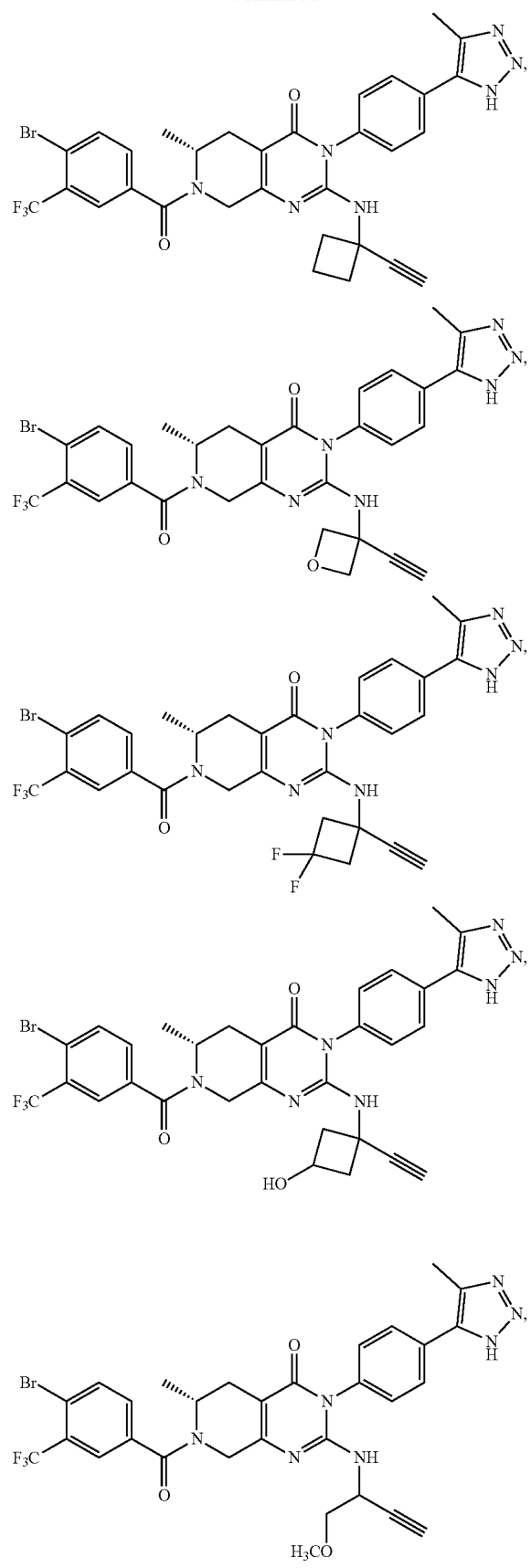
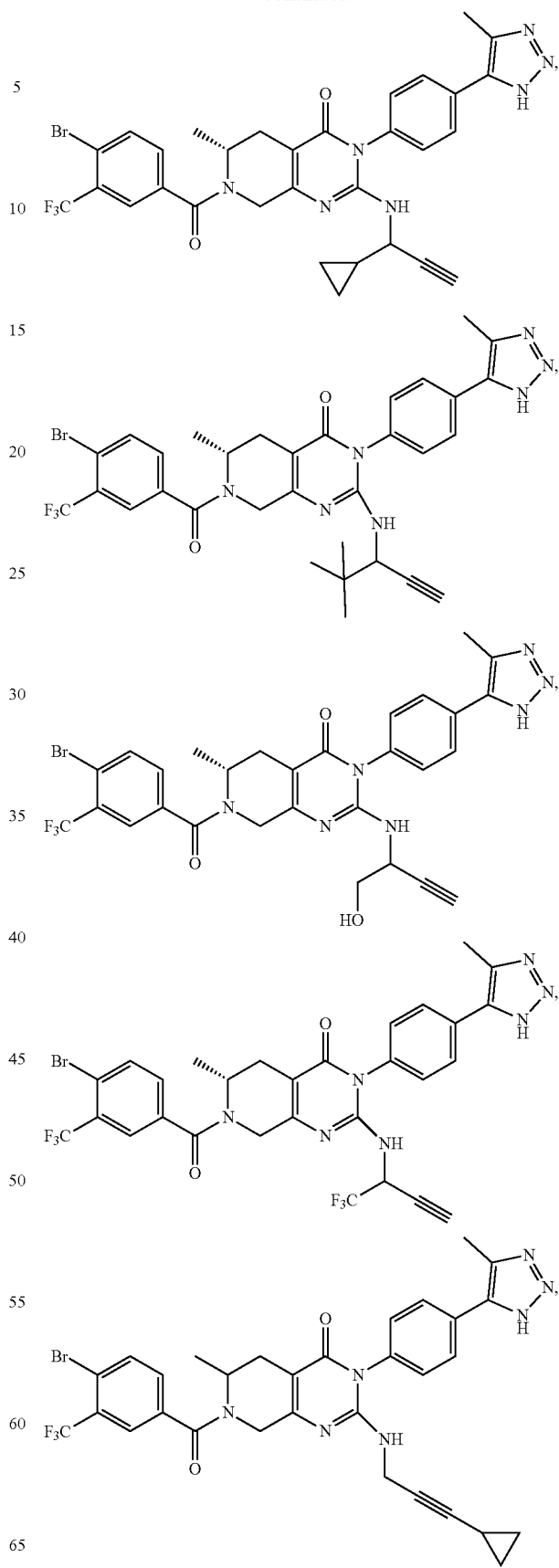

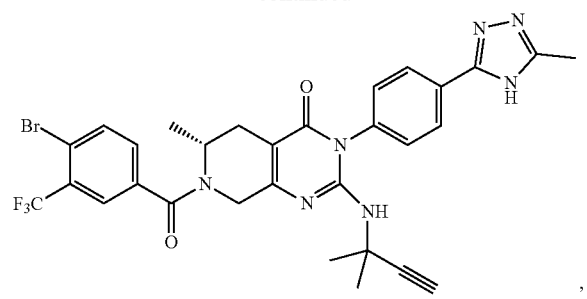
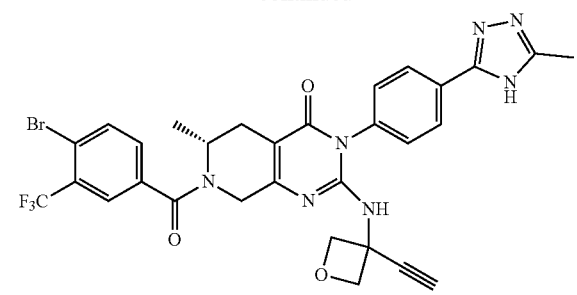

51
-continued
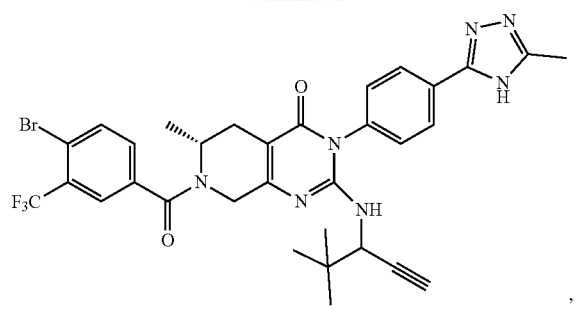
52
-continued
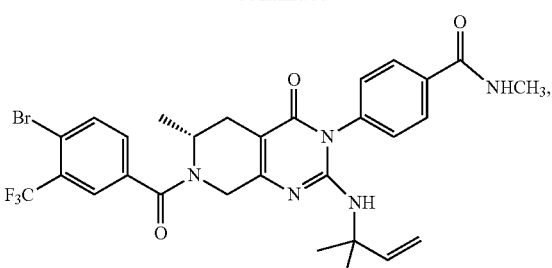
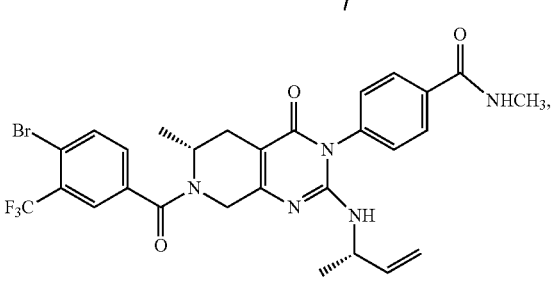
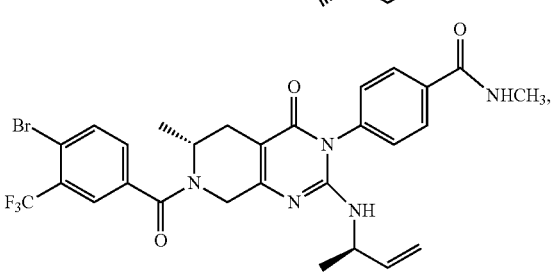
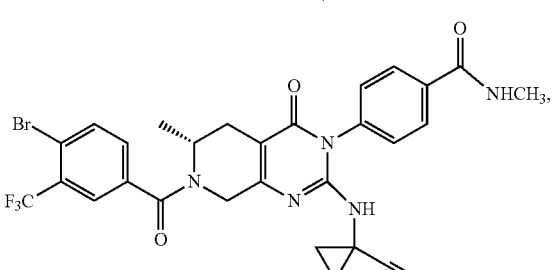
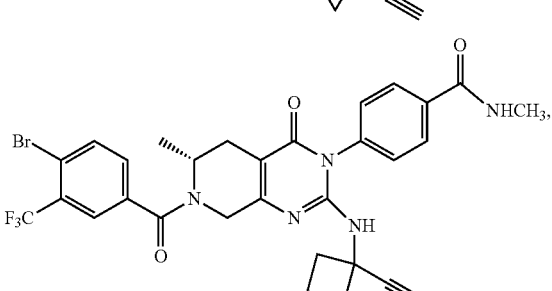
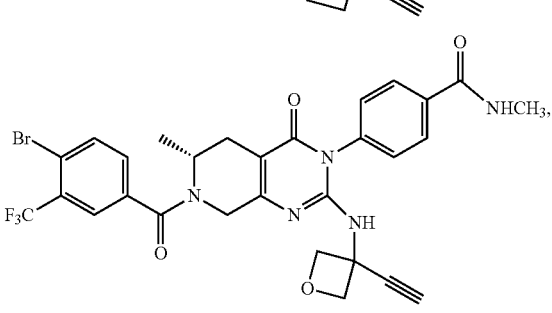

-continued

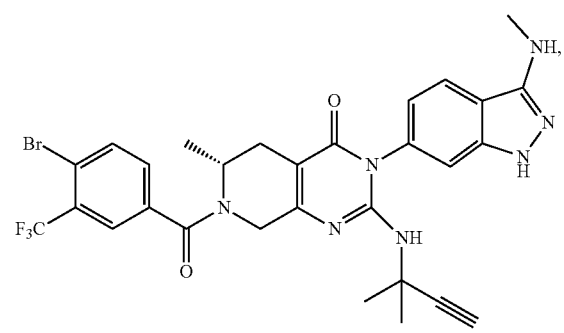
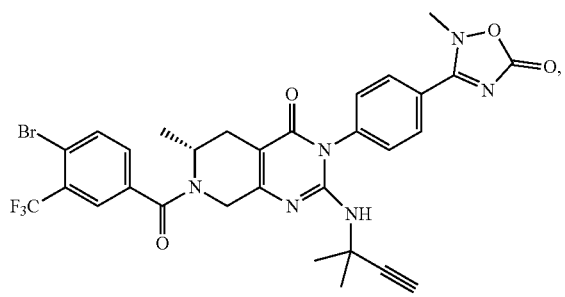
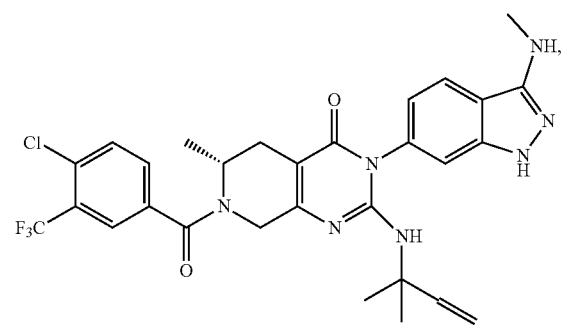
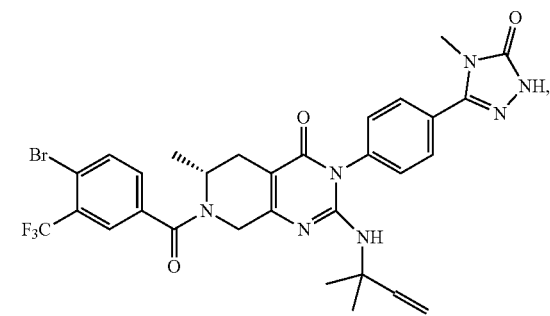
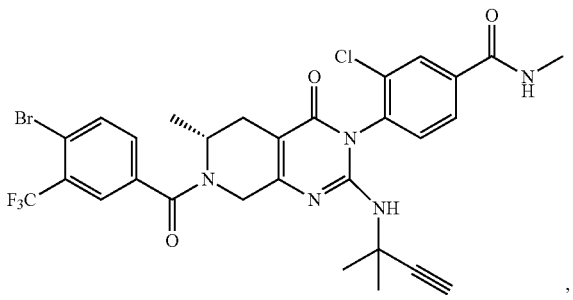
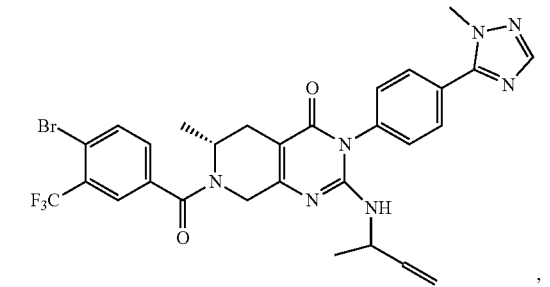
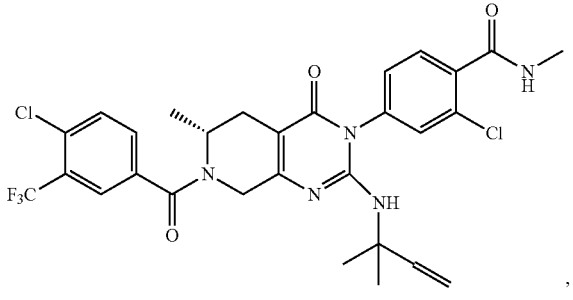
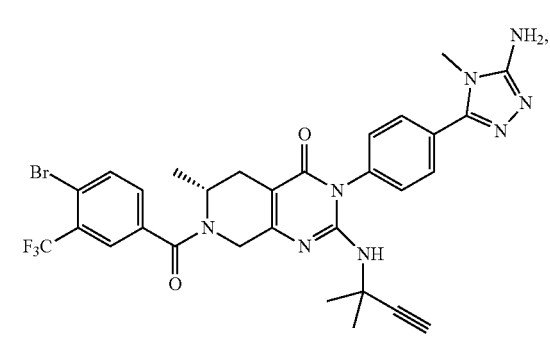
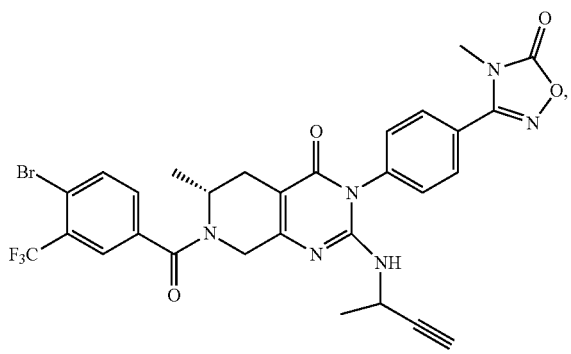
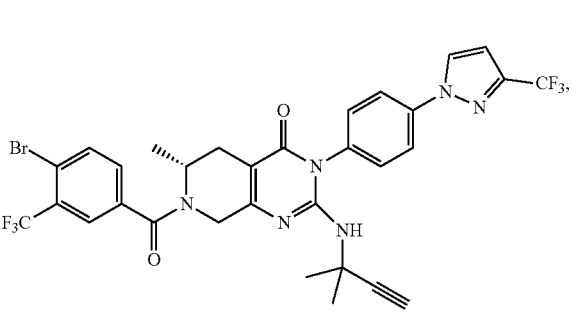

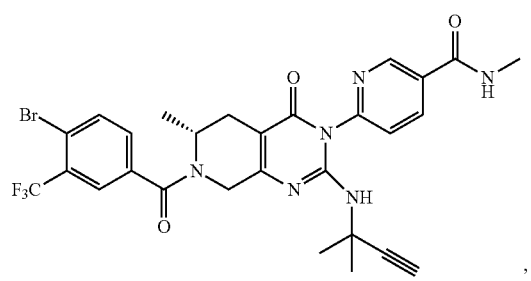
,
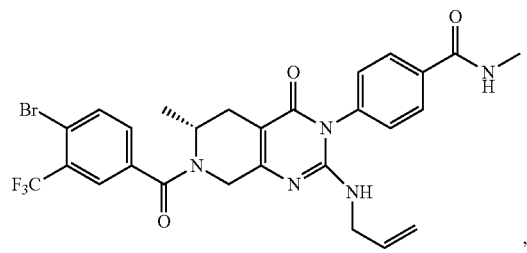
,
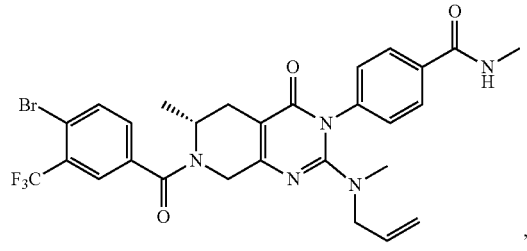
,
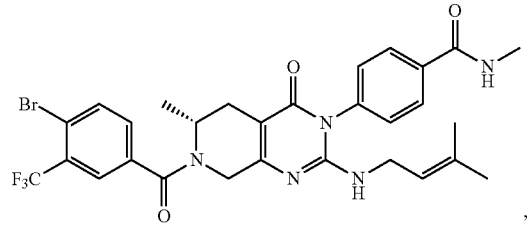
,
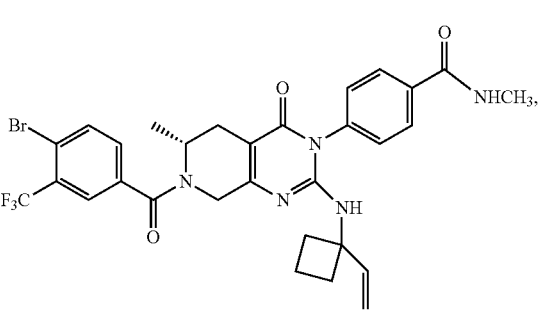
,
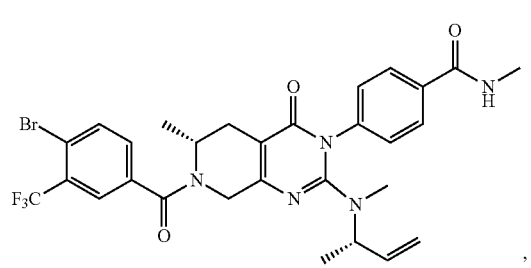
,
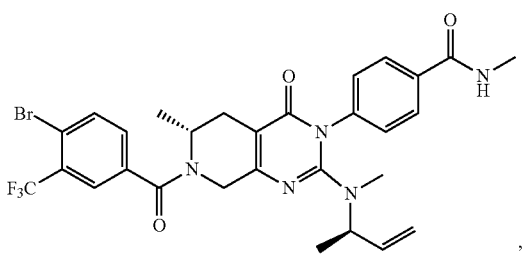
,
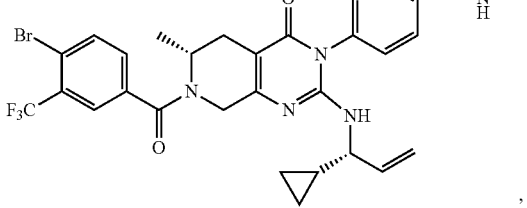
,
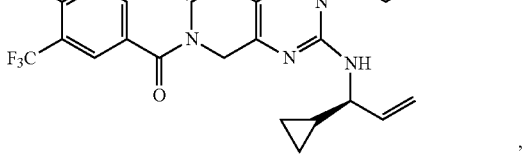
,
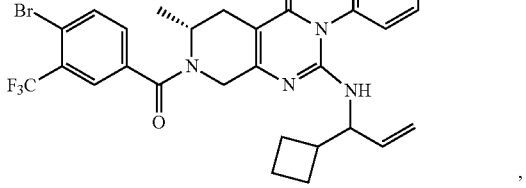
,
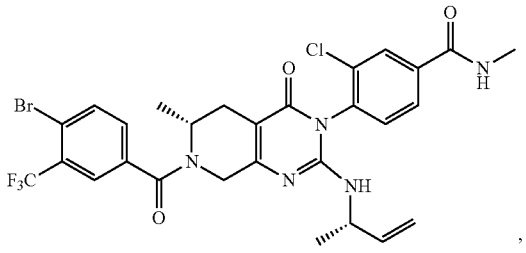
,
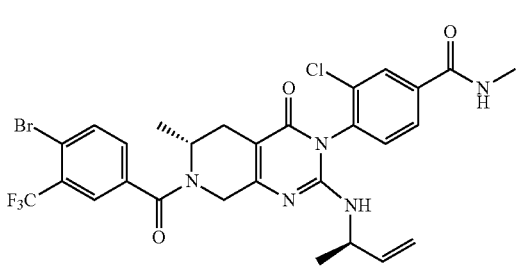
,

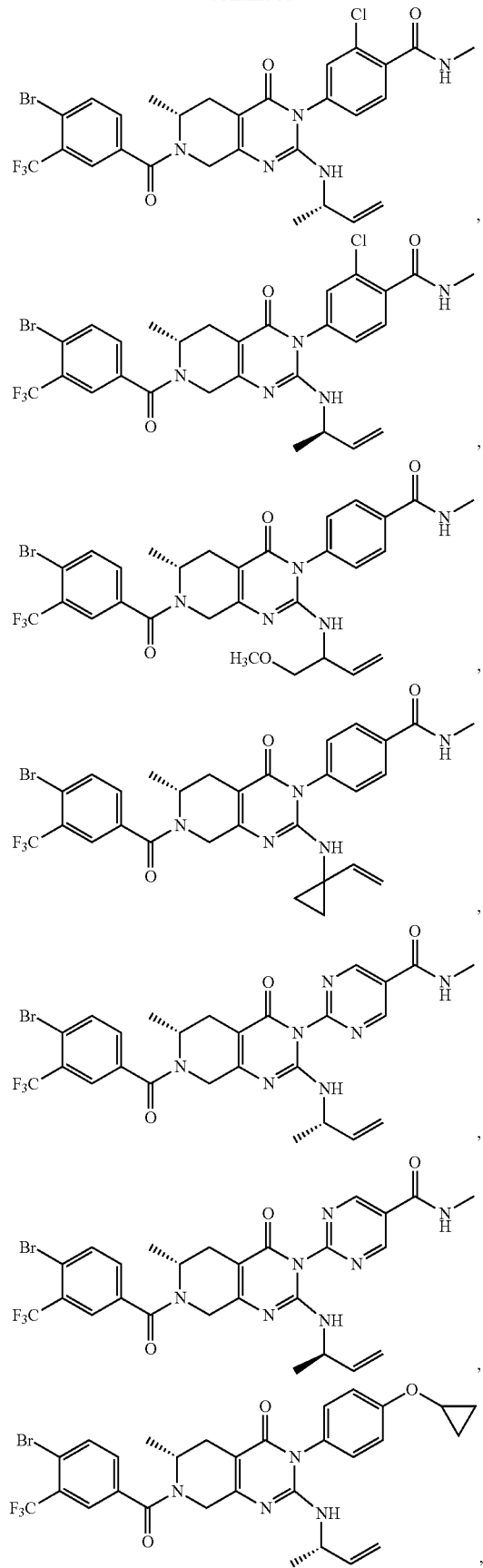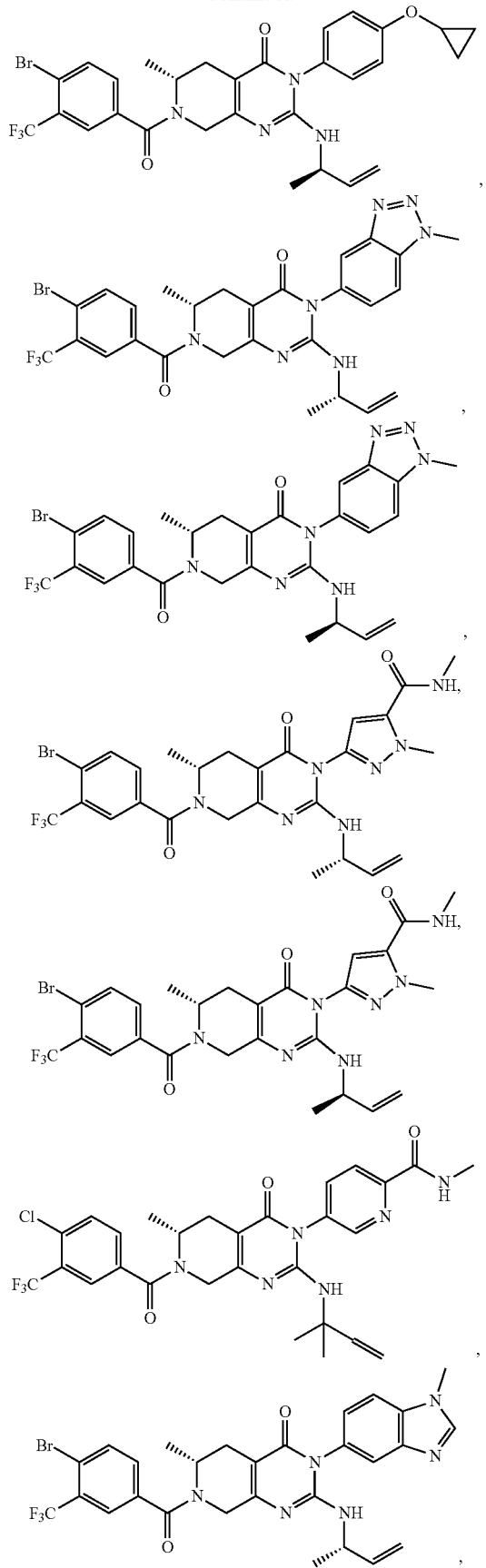

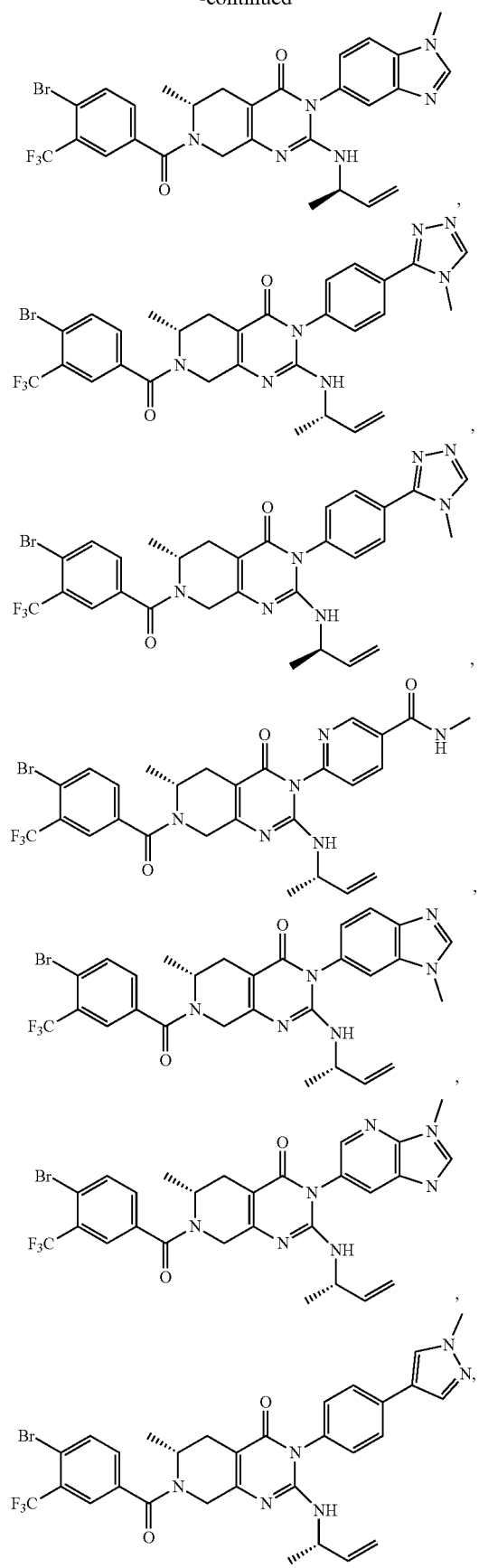
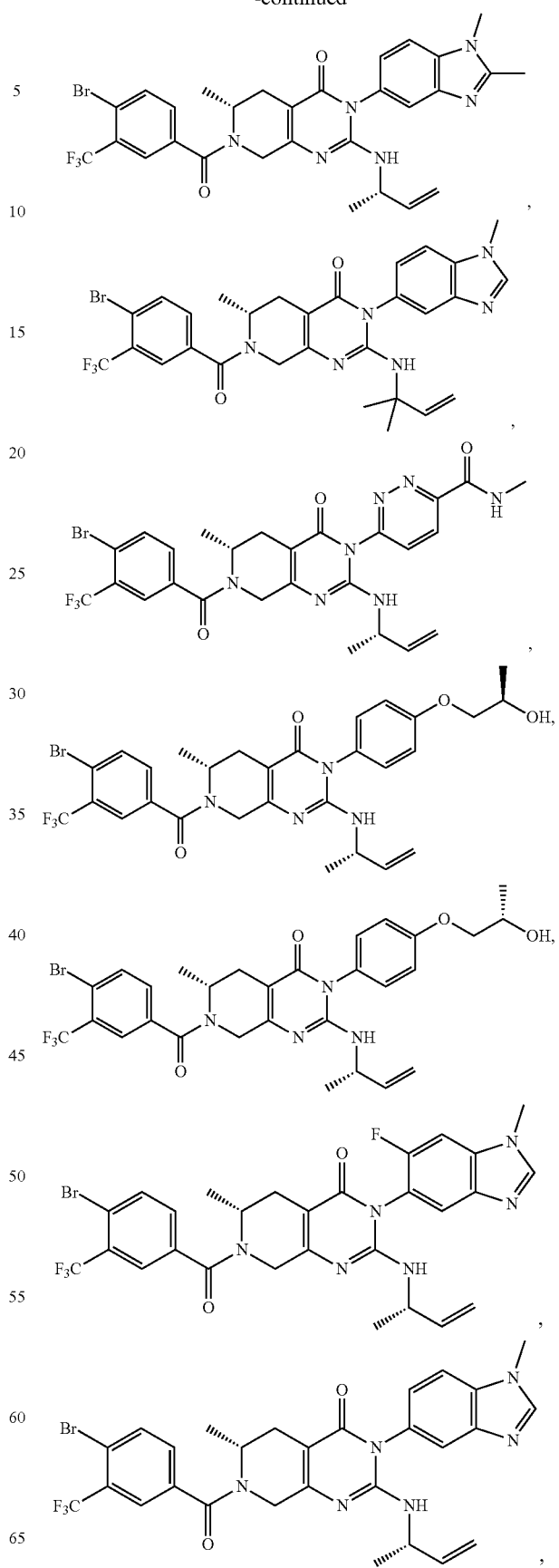

63
-continued
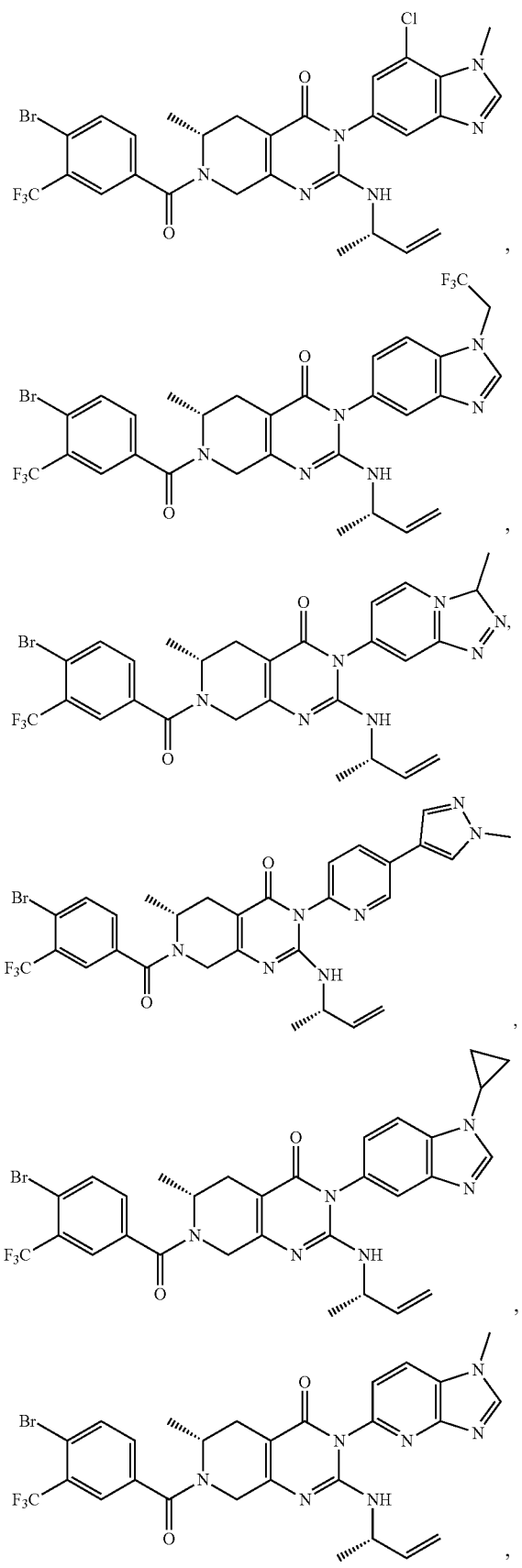
64
-continued
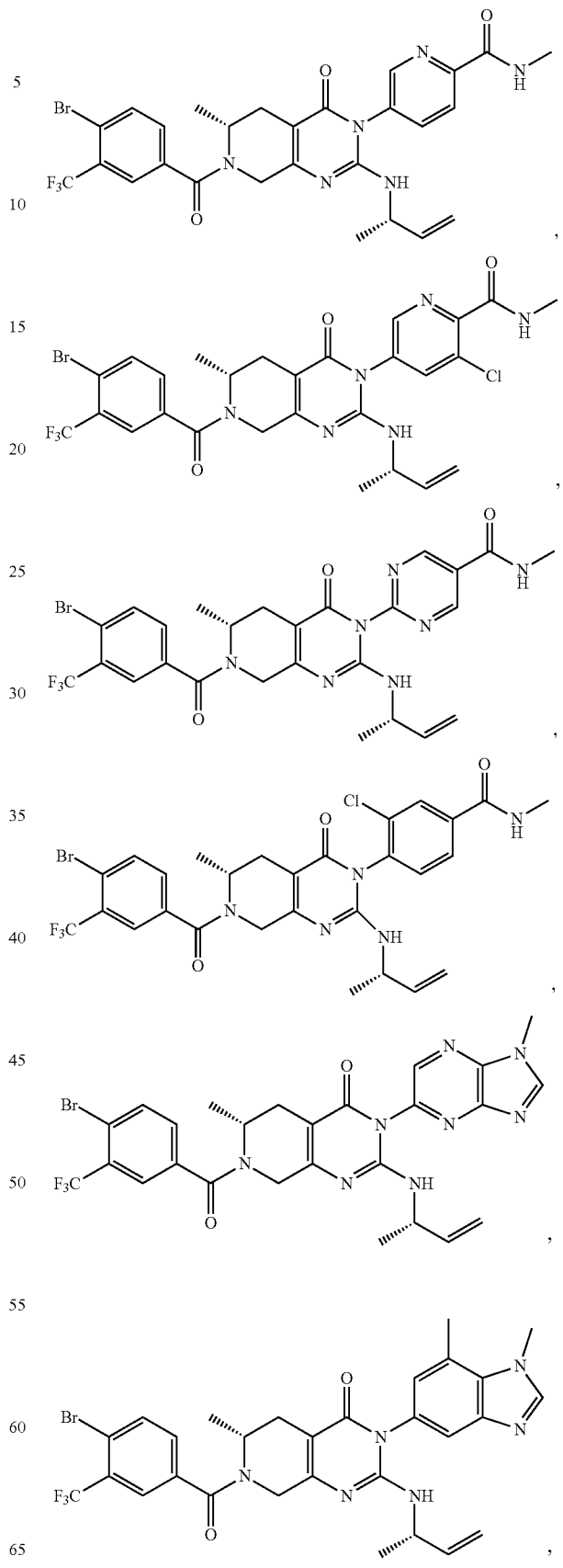

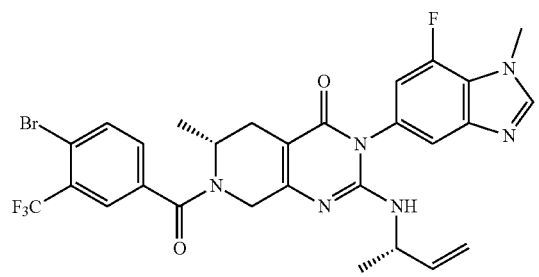
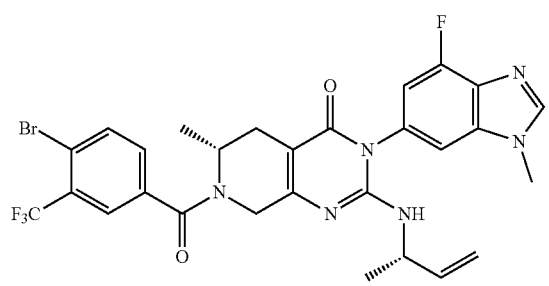
or a pharmaceutically acceptable salt of any of the foregoing.
Additional examples of compounds of Formula (I), including pharmaceutically acceptable salts thereof, include:
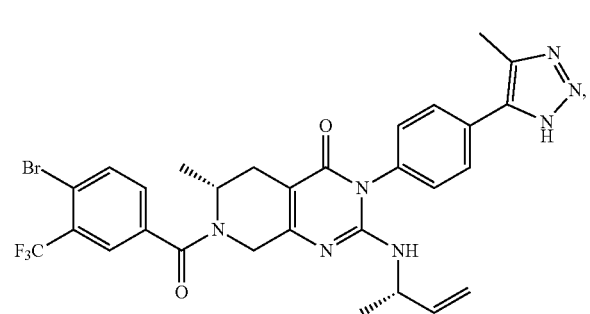
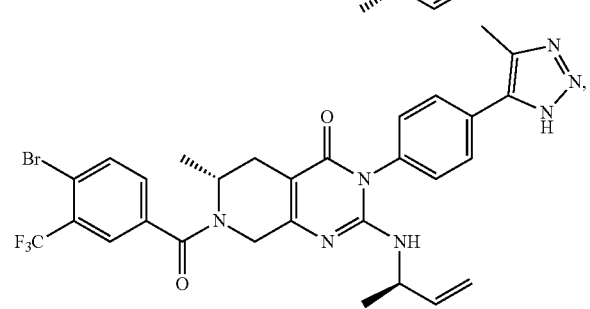
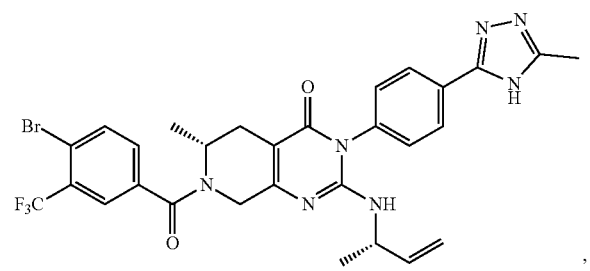
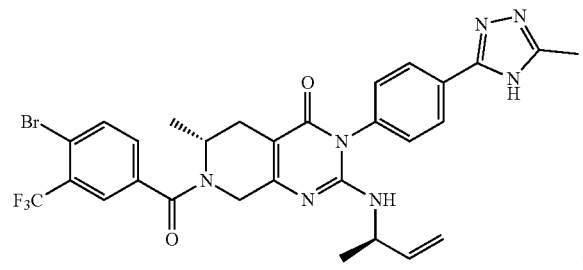
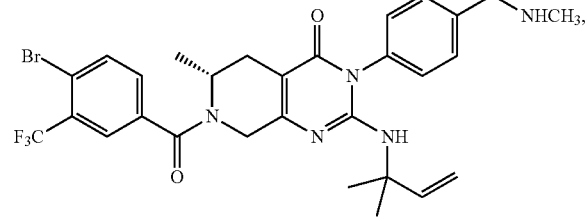
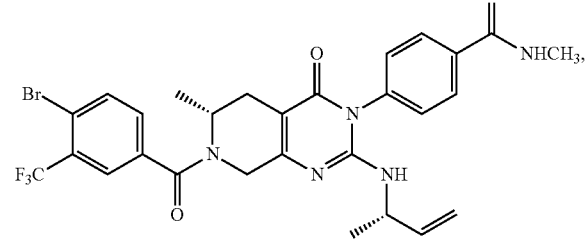
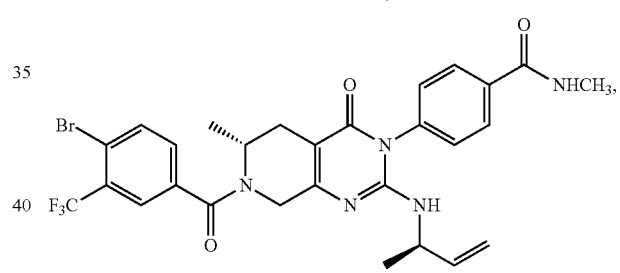
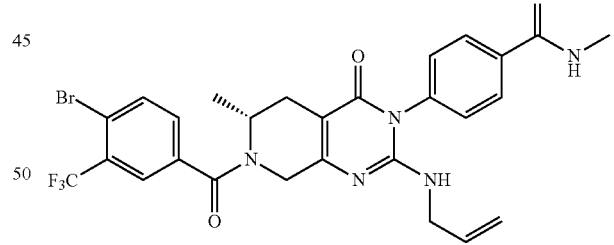
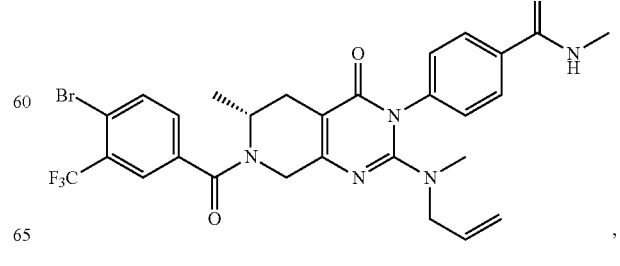

67
-continued
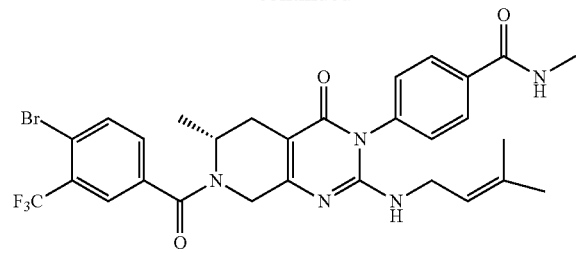
,
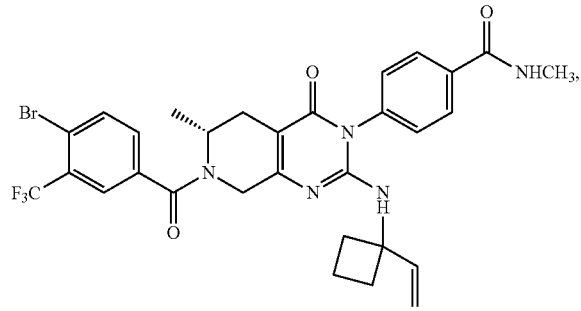
,
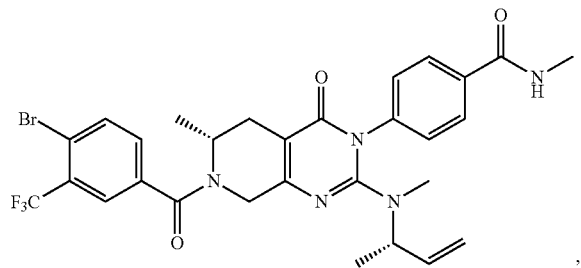
,
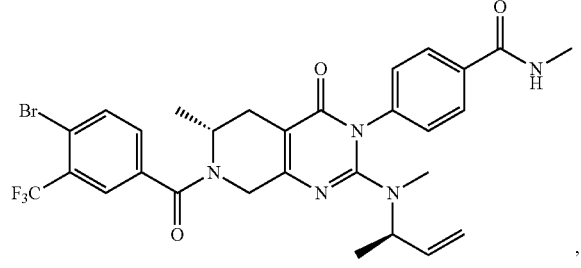
,
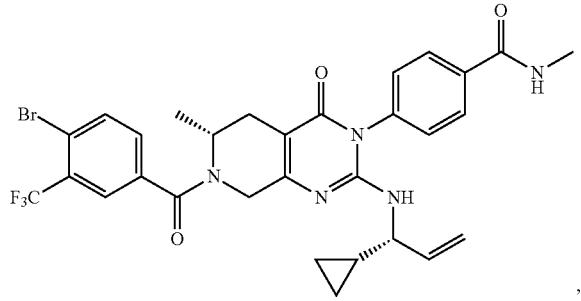
,
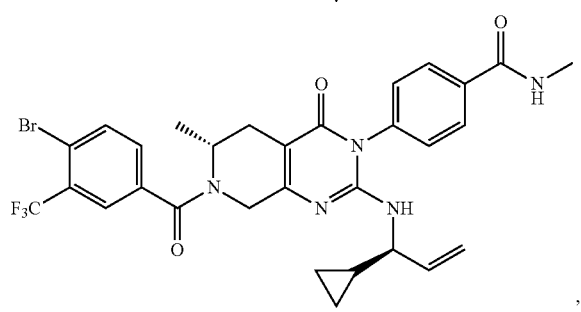
,
68
-continued
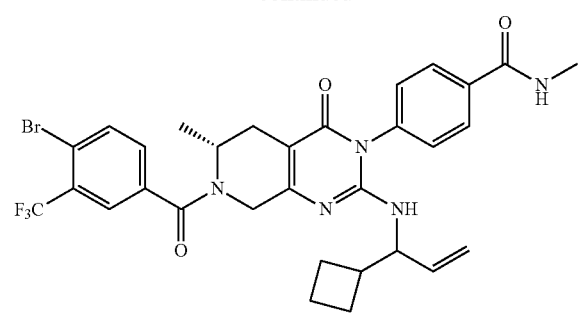
,
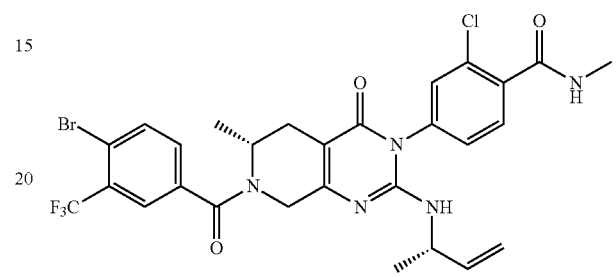
,
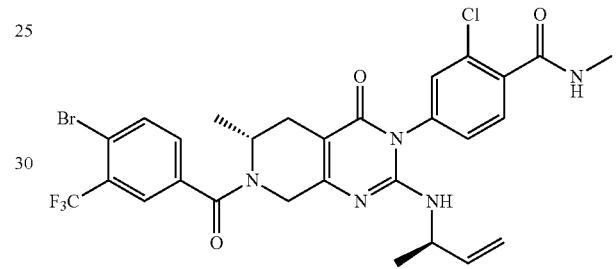
,
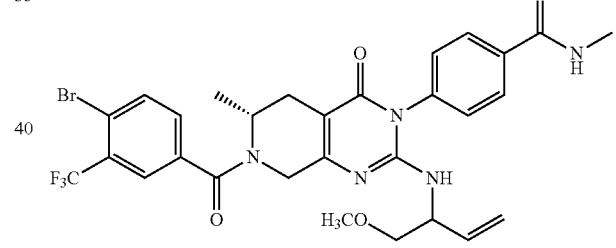
,
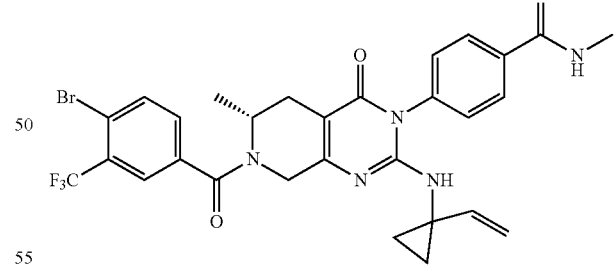
,
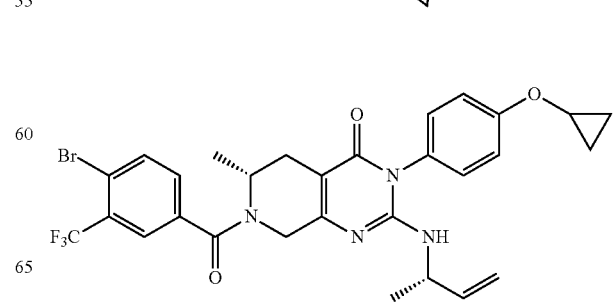
, 69
-continued
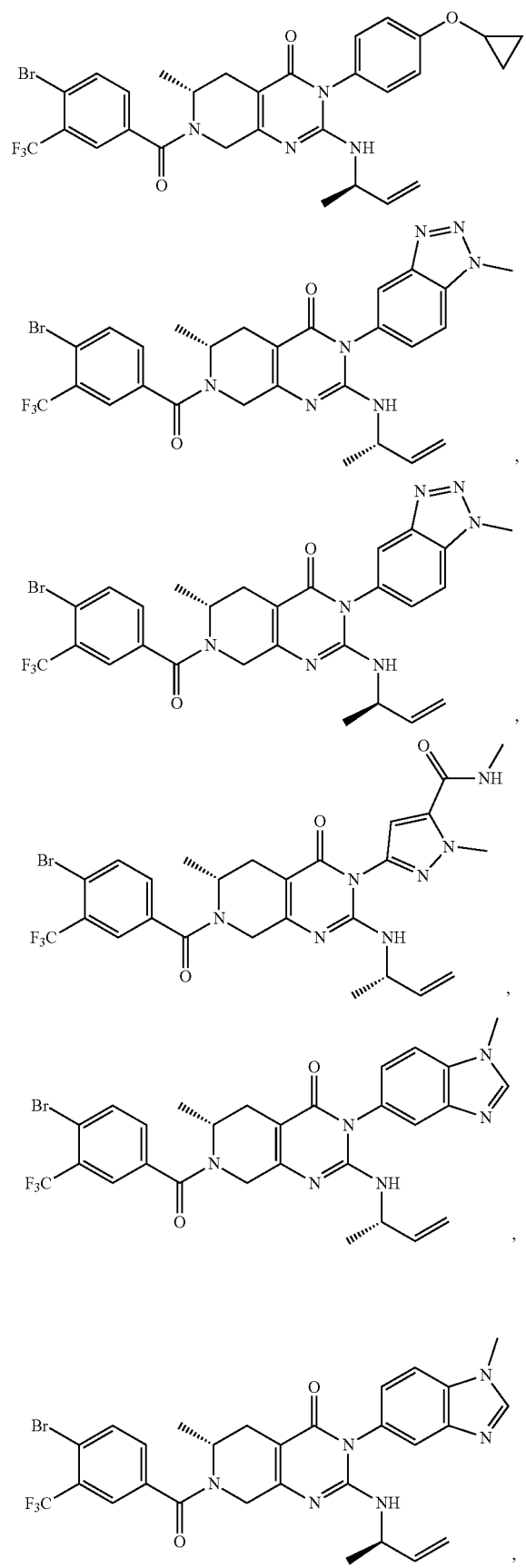
70
-continued
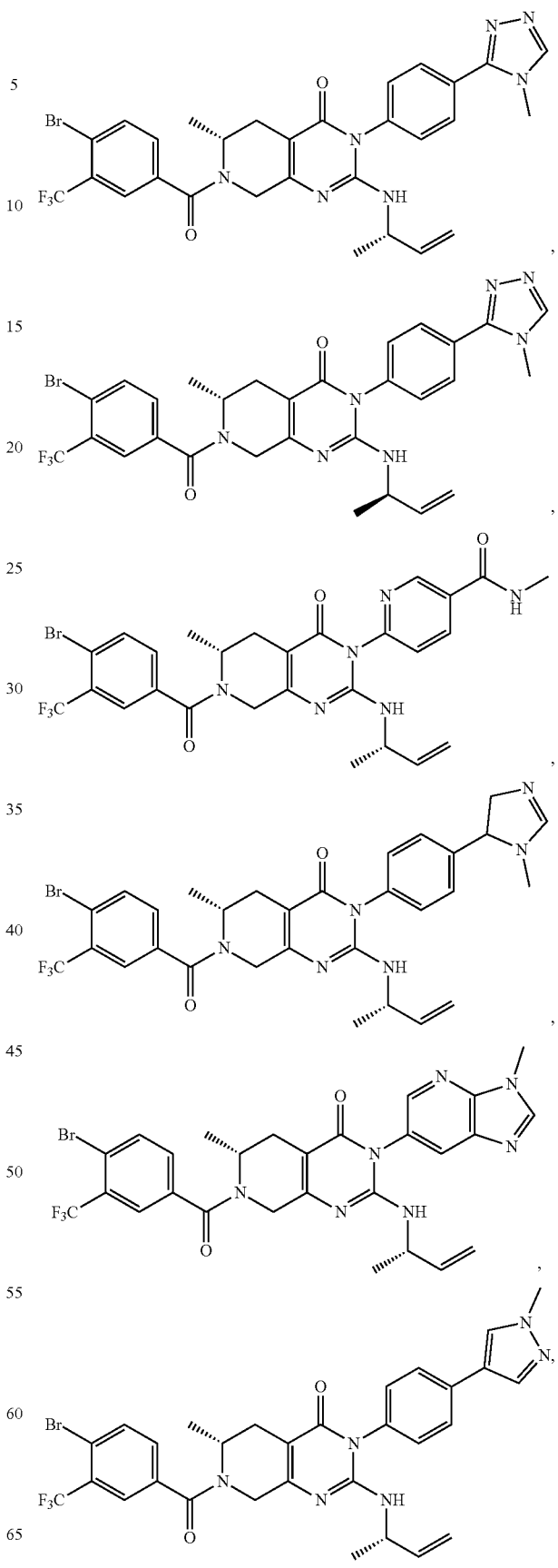

71
-continued
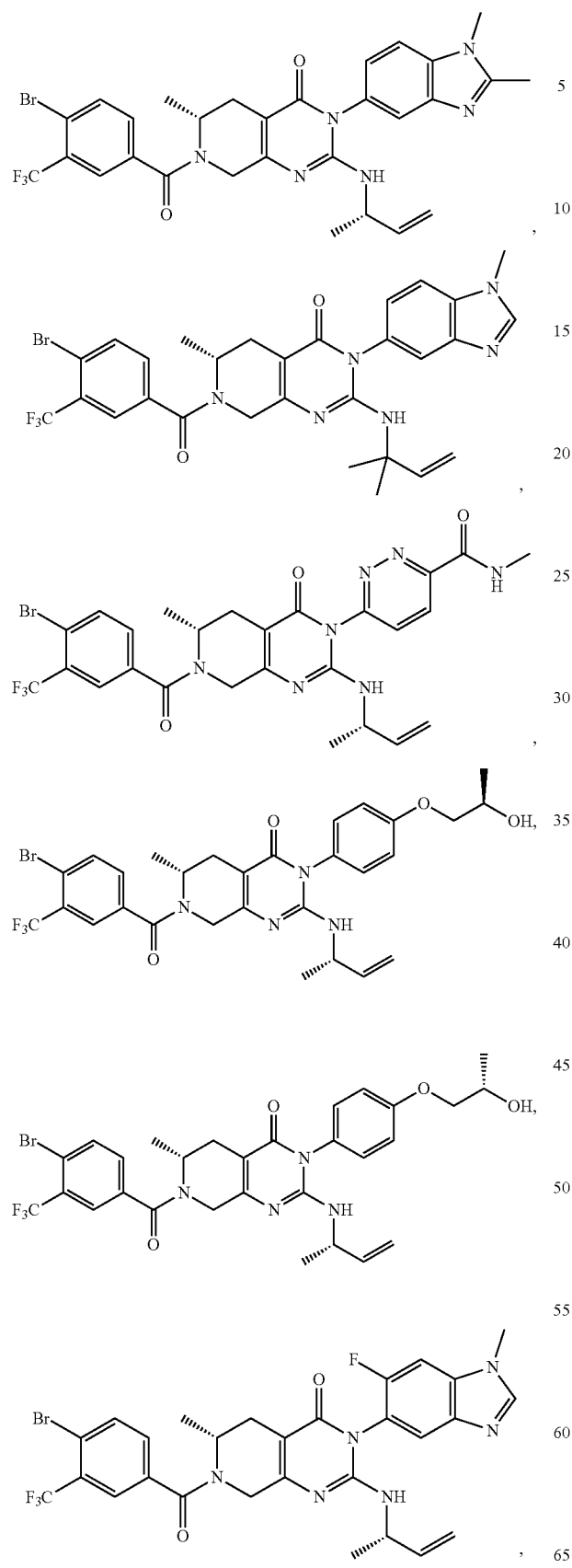
72
-continued
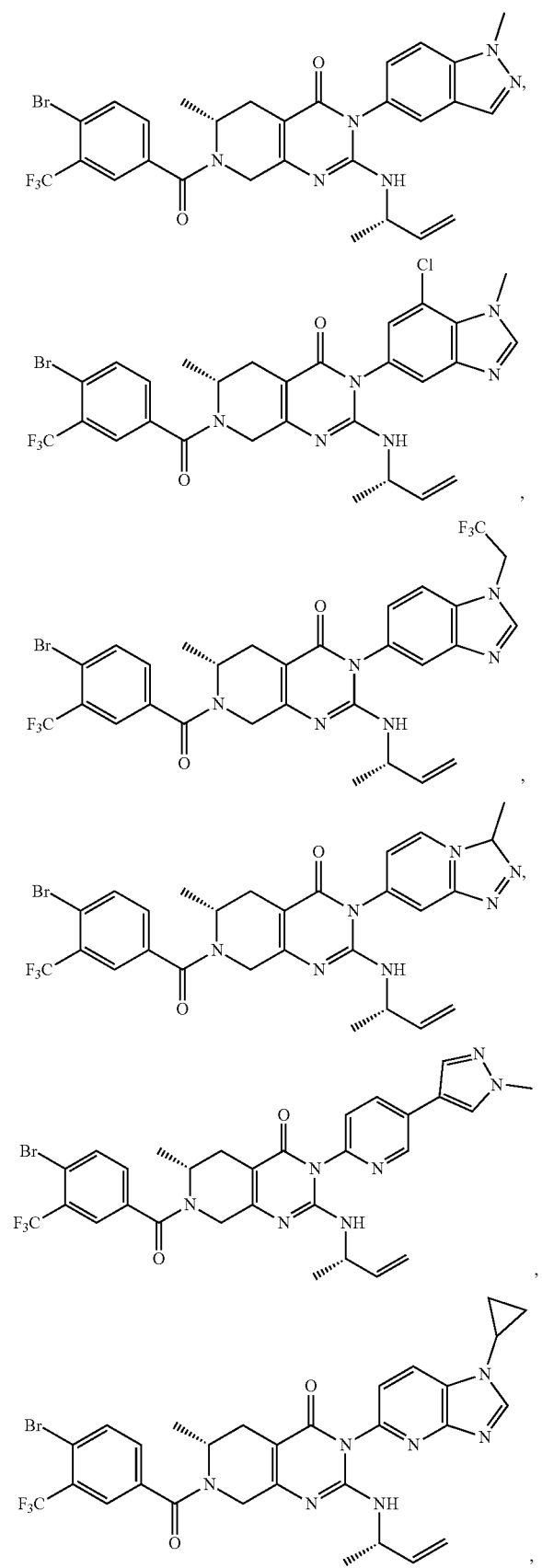

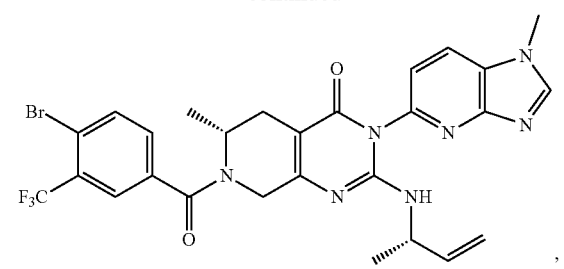
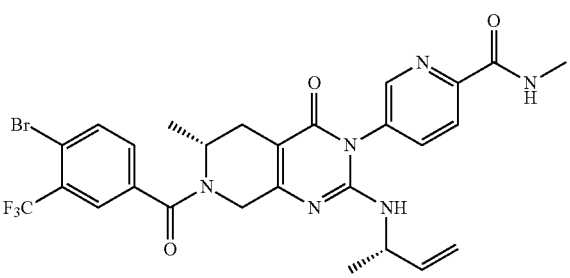
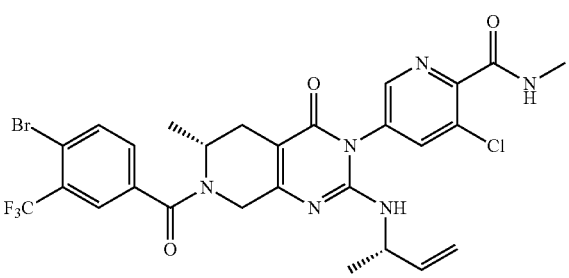
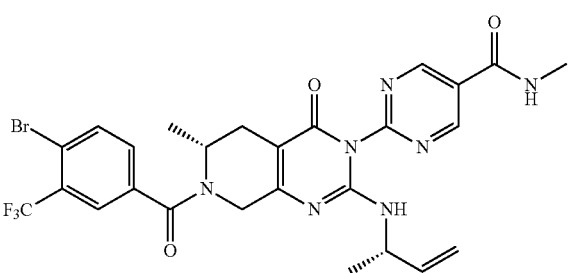
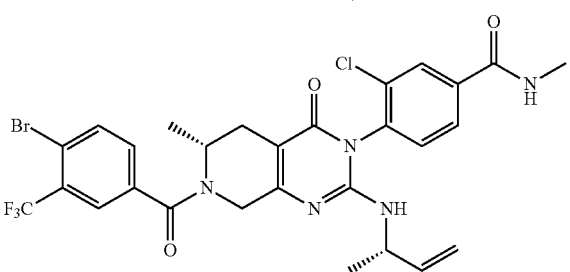
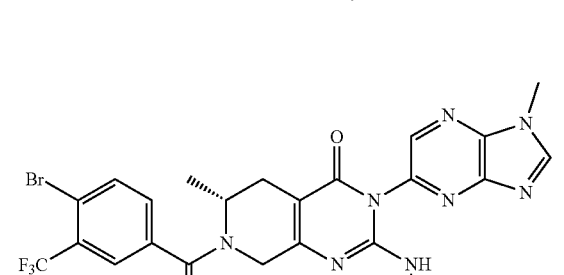
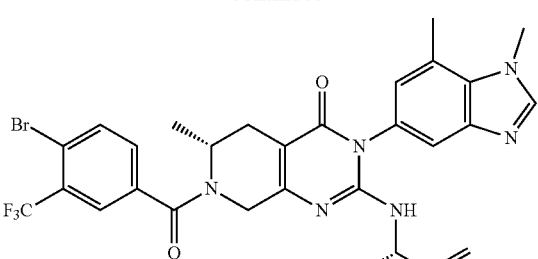
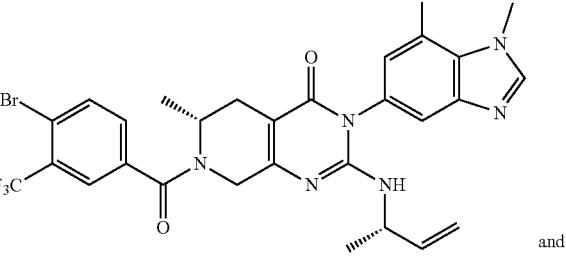
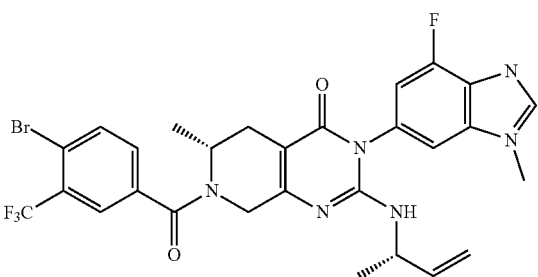
or a pharmaceutically acceptable salt of any of the foregoing.
Further examples of compounds of Formula (I), including pharmaceutically acceptable salts thereof, include:
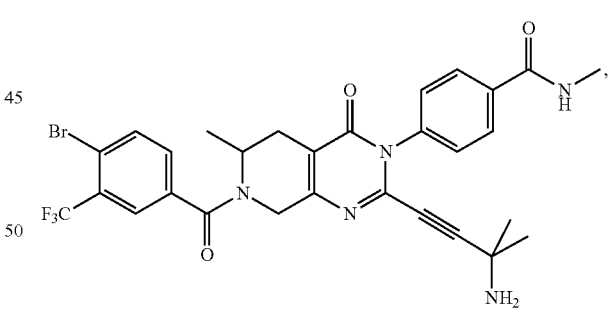
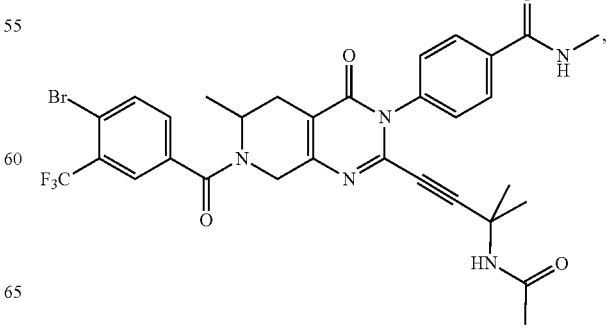

75
-continued
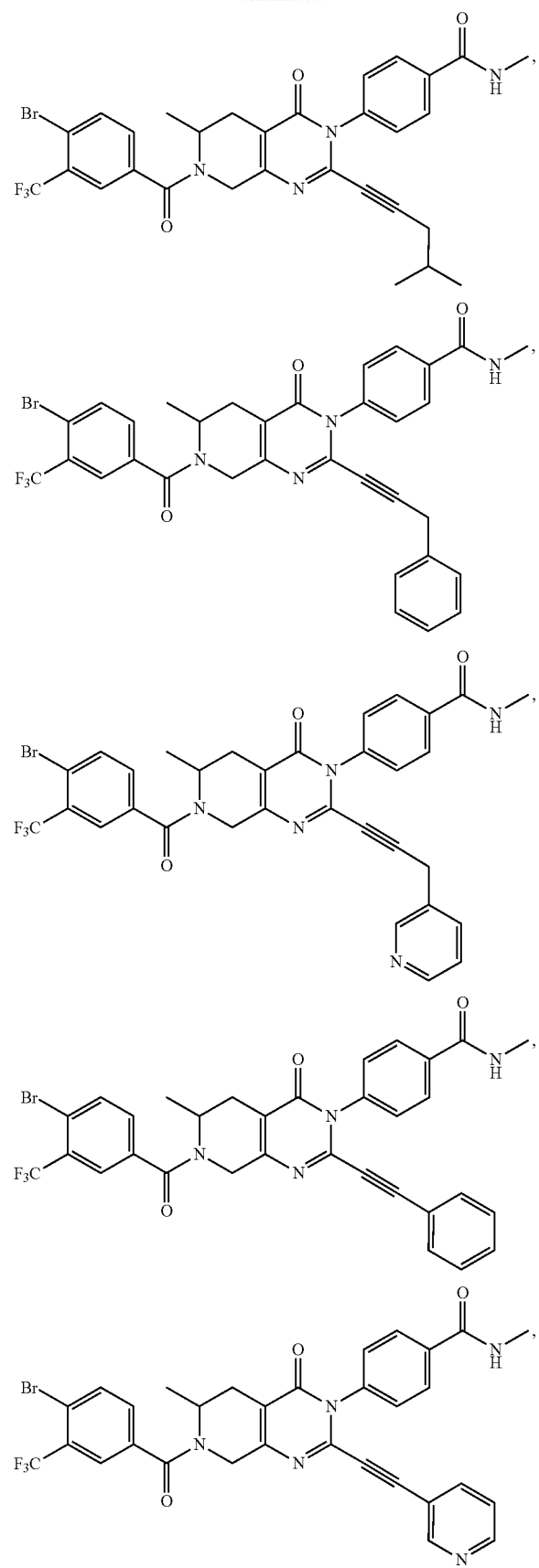
76
-continued
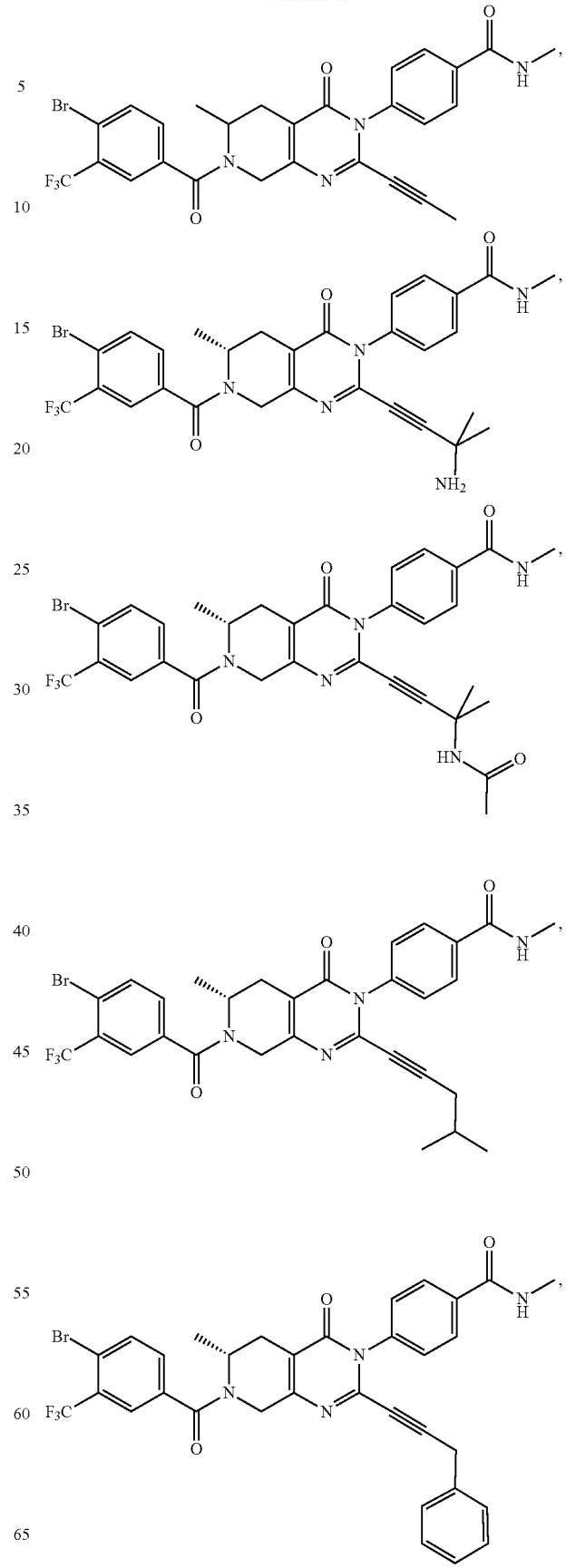

-continued

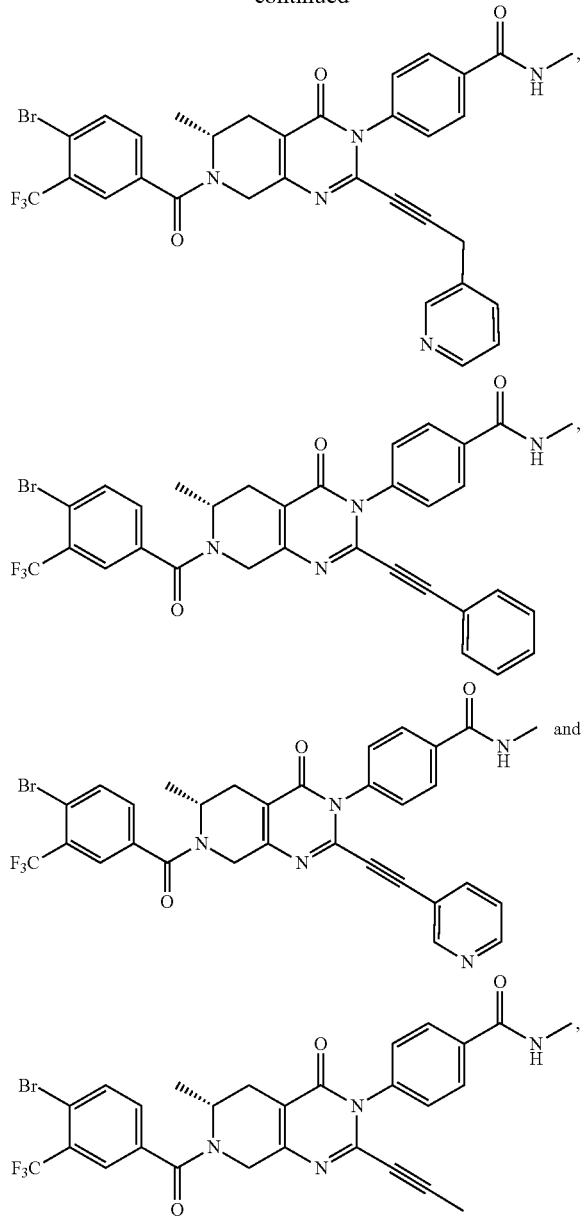

or a pharmaceutically acceptable salt of any of the foregoing.

Provided herein is the following compound

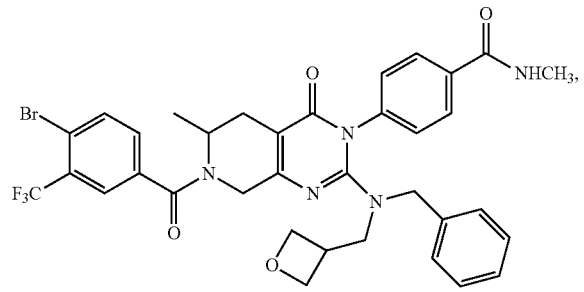 [SMILES: CNC(=O)c1ccc(-n2c(N(Cc3ccccc3)CC3COC3)nc3c(c2=O)CC(C)N(C(=O)c2ccc(Br)c(C(F)(F)F)c2)C3)cc1]

or a pharmaceutically acceptable salt of thereof.

In some embodiments, when n is 1, then $Z^1$ cannot be —C(=O)—. In other embodiments, when n is 1, then $Z^1$ cannot be —NH—C(=O)—. In some embodiments, $R^8$ cannot be —NR$^{10A}$R$^{10B}$, wherein R$^{10A}$ is a monocyclic $C_{3-6}$ cycloalkyl optionally substituted with one or two halogens, an optionally substituted 5-6 membered monocyclic heteroaryl or an optionally substituted 4-6 membered monocyclic heterocyclyl; and R$^{10B}$ is an unsubstituted $C_{1-6}$ alkyl. In other embodiments, $R^8$ cannot be —NR$^{10A}$R$^{10B}$, wherein R$^{10A}$ is hydrogen or an unsubstituted $C_{1-6}$ alkyl (including an unsubstituted $C_{1-4}$ alkyl) and R$^{10B}$ is an optionally substituted aryl, an optionally substituted aryl($C_{1-4}$ alkyl), an optionally substituted heteroaryl($C_{1-4}$ alkyl) or an optionally substituted heterocyclyl($C_{1-4}$ alkyl). In still other embodiments, $R^8$ cannot be —NR$^{10A}$R$^{10B}$, wherein R$^{10A}$ is a monocyclic $C_{3-6}$ cycloalkyl optionally substituted with one or two halogens, an optionally substituted 4-6 membered monocyclic heterocyclyl or an unsubstituted monocyclic $C_{3-6}$ cycloalkyl($C_{1-4}$ alkyl); and R$^{10B}$ is an unsubstituted phenyl, an unsubstituted —CH$_2$-phenyl and an optionally substituted heteroaryl($C_{1-4}$ alkyl) (such as an unsubstituted or a substituted monocyclic heteroaryl($C_{1-4}$ alkyl) including an unsubstituted or a substituted monocyclic heteroaryl-CH$_2$—). In some embodiments, $R^9$ can be substituted with a substituted heterocyclyl (such as a 5- to 6-membered monocyclic heterocyclyl), wherein the heterocyclyl can be substituted with one or more moieties (such as 1, 2 or 3) independently selected from halogen, an unsubstituted $C_{1-4}$ alkyl, unsubstituted $C_{1-4}$ haloalkyl and an unsubstituted $C_{1-4}$ alkoxy. In some embodiments, when $R^8$ is —NR$^{10A}$R$^{10B}$, then R$^{10B}$ is not —CH$_2$-(phenyl substituted with methoxy). In some embodiments, $R^1$ cannot be selected from

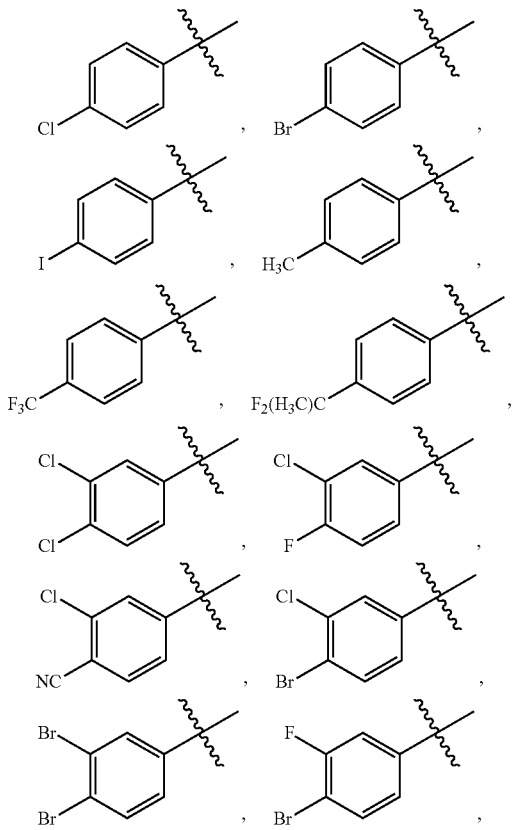

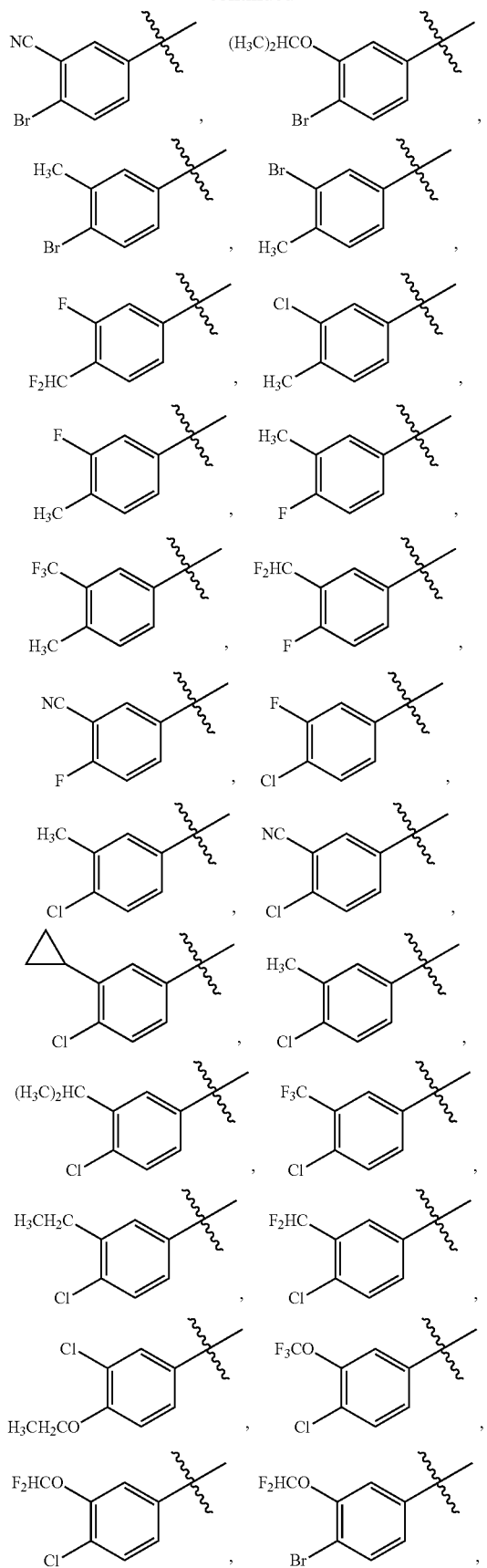
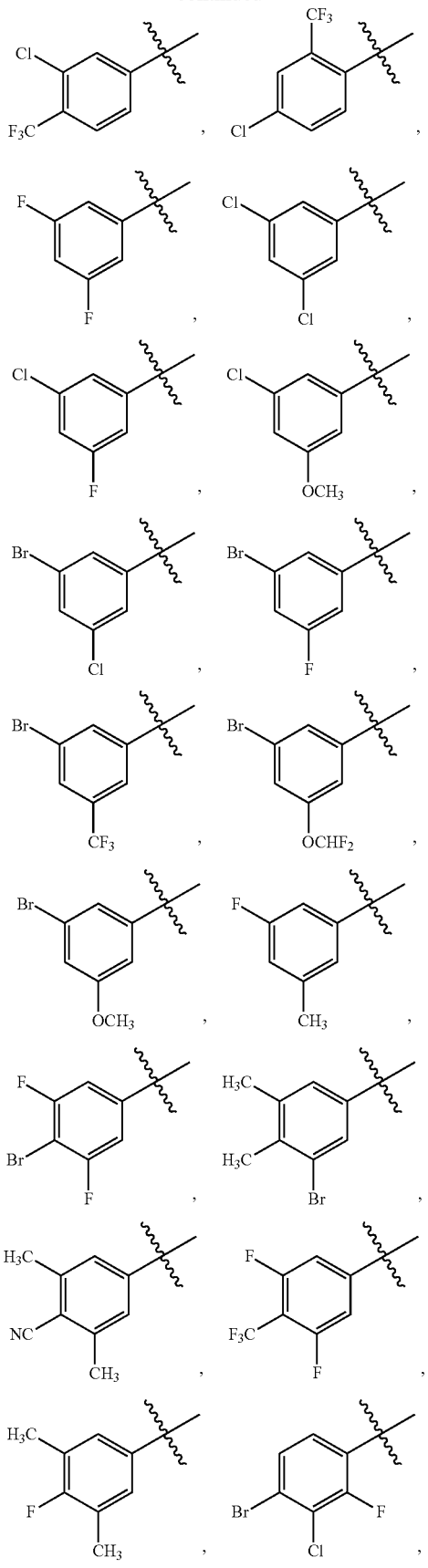

-continued pyrrole, pyrazole, pyridine, thiophene, benzofuran, benzoxazole, benzothiazole, indole, indazole, indoline, indolizine, benzoimidazole, 2,3-dihydrobenzofuran, imidazo[1,2-a]pyridine, imidazo[1,5-a]pyridine, [1,2,4]triazolo[1,5-a]pyridine, isoquinoline, quinoxaline, chromane, pyrrolo[3,2-b]pyridine, pyrrolo[3,2-c]pyridine, thieno[3,2-b]pyrrole, thieno[2,3-c]pyridine, isoindolin-1-one, 1,3-dihydro-2H-benzo[d]imidazol-2-one, benzo[b]thiophene 1,1-dioxide, 1H-benzo[d][1,2,3]triazole and pyrazolo[1,5-a]pyridine, such as when $R^8$ is —$NR^{10A}R^{10B}$. In some embodiments, $R^1$ cannot be

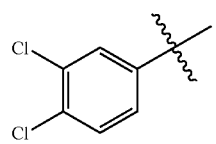 [SMILES: *c1ccc(Cl)c(Cl)c1]

when $R^8$ is —$NHR^{10B}$ and $R^{10B}$ is an optionally substituted $C_{2-8}$ alkenyl or an optionally substituted $C_{2-8}$ alkynyl, wherein the $C_{2-8}$ alkenyl and the $C_{2-8}$ alkynyl is optionally substituted with one or more substituents selected from amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and an unsubstituted 4-6 membered monocyclic heterocyclyl. In some embodiments, a compound of Formula (I), or a pharmaceutically acceptable salt thereof, cannot be a compound disclosed in WO 2020/182990. In some embodiments, a compound of Formula (I), or a pharmaceutically acceptable salt thereof, cannot be

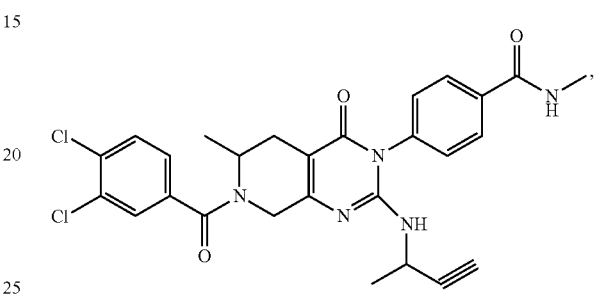

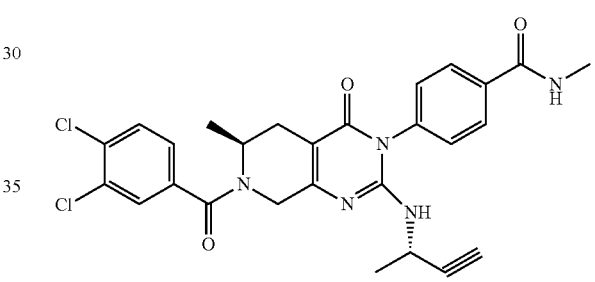

and/or Compound C302 from WO 2020/182990

( 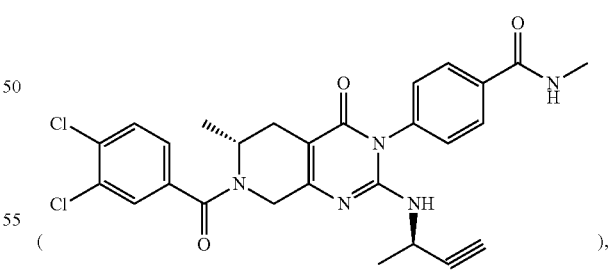 ), including pharmaceutically acceptable salts of any of the foregoing. In some embodiments, a compound of Formula (I), or a pharmaceutically acceptable salt thereof, cannot be a compound disclosed in U.S. 2022/0119385 A1. For example, a compound of a compound of Formula (I), or a pharmaceutically acceptable salt thereof, cannot be

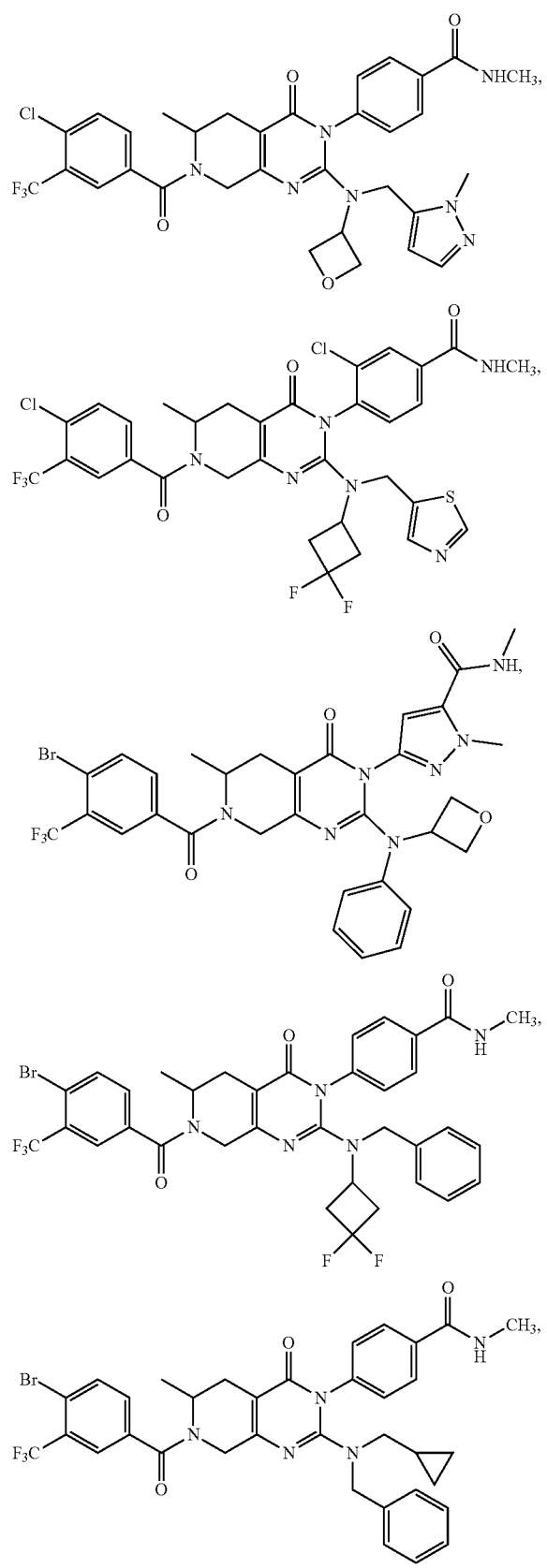
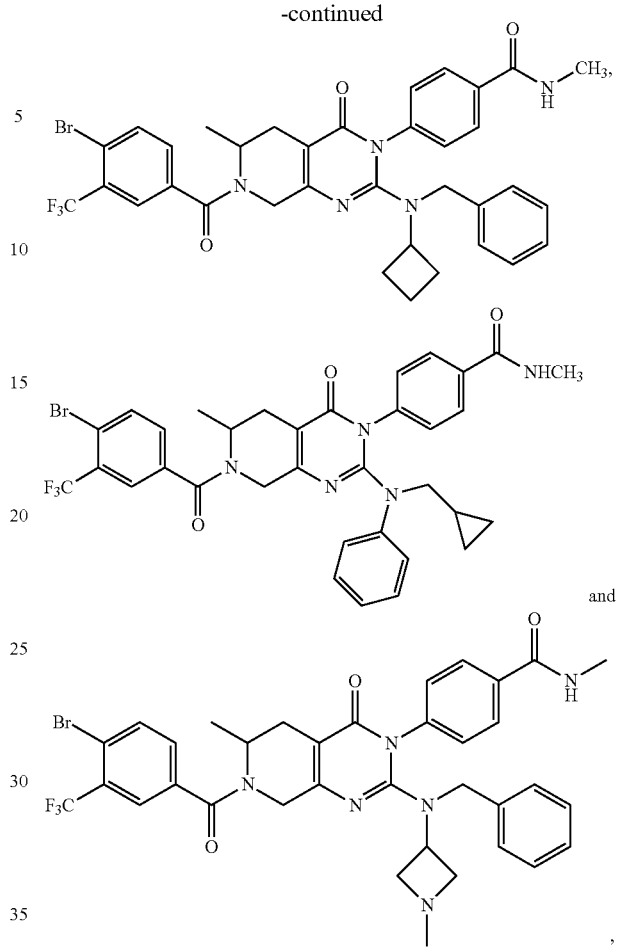

including pharmaceutically acceptable salts of any of the foregoing.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

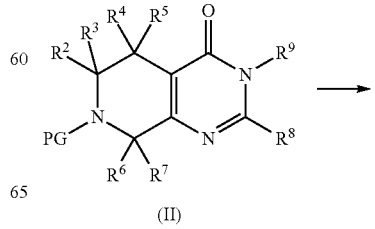

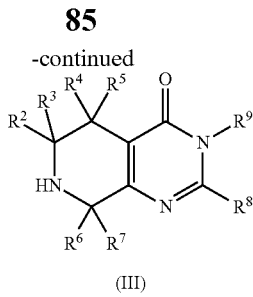

(III)

Compounds of Formula (I) can be prepared from an intermediate of Formula (II), in which PG represents an amino protecting group such as Boc. The PG group can be cleaved from a compound of Formula (II) using methods known in the art. For example, when PG represents a Boc group, PG can be cleaved using acidic conditions, for example, in the presence of HCl in a suitable solvent (such as 1,4-dioxane) or in the presence of copper triflate. The coupling of the intermediate of Formula (III) with a suitable agent can afford a compound of Formula (I), along with pharmaceutically acceptable salts thereof. As an example, compounds of Formula (I), along with pharmaceutically acceptable salts thereof, wherein $Z^1$ represents —NH—C(=O)— and n=1, can be obtained by reacting a compound of Formula (III) with a phenyl carbamate of general formula $R^1$—NH—C(=O)—O-phenyl or with an isocyanate of general formula $R^1$—N=C=O, in the presence of a suitable base in a suitable solvent. An example of a suitable base is triethylamine, and an example of suitable solvent is acetonitrile.

Other compounds of Formula (I), along with pharmaceutically acceptable salts thereof, wherein $Z^1$ represents —C(=O)— and n=1, can be obtained by reacting a compound of Formula (III) with an acyl chloride of general formula $R^1$—C(=O)—Cl in the presence of a base in a suitable solvent. Additional compounds of Formula (I) and pharmaceutically acceptable salts thereof, wherein $Z^1$ represents —C(=O)— and n=1, can be obtained by reacting compound of Formula (III) with a carboxylic acid of general formula $R^1$—C(=O)—OH in the presence of an amide coupling agent (such as HATU) in a suitable solvent. Further compounds of Formula (I), along with pharmaceutically acceptable salts thereof, can be prepared from a compound of Formula (III) using methods known in the art.

Scheme 2

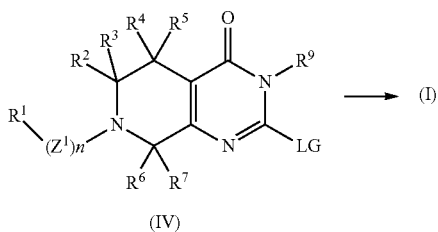

(IV)

Compounds of Formula (I), including pharmaceutically acceptable salts thereof, can also be prepared from an intermediate of Formula (IV), in which LG represents a leaving group (such as sulfhydryl, methylsulfoxide or halo, in particular chloro or bromo). A compound of Formula (I) in which $R^8$ represents —$NR^{10A}R^{10B}$ can be prepared from a compound of Formula (IV) in which LG represents methylsulfoxide by reacting an amine of Formula $HNR^{10A}R^{10B}$, in the presence of a base (such as diisopropylethylamine (DIPEA) or sodium bicarbonate) in a suitable solvent (such as 1,4-dioxane or acetonitrile), optionally in the presence of a catalyst (for example, DMAP). A compound of Formula (I) in which $R^8$ represents —$NR^{10A}R^{10B}$ can be prepared from a compound of Formula (IV) in which LG represents chloro by reacting an amine of Formula $HNR^{10A}R^{10B}$, in the presence of a base (for example, triethylamine, sodium bicarbonate or DIPEA) in a suitable solvent (such as acetonitrile, n-butanol or dioxane), optionally in the presence of a catalyst, such as DMAP.

Scheme 3

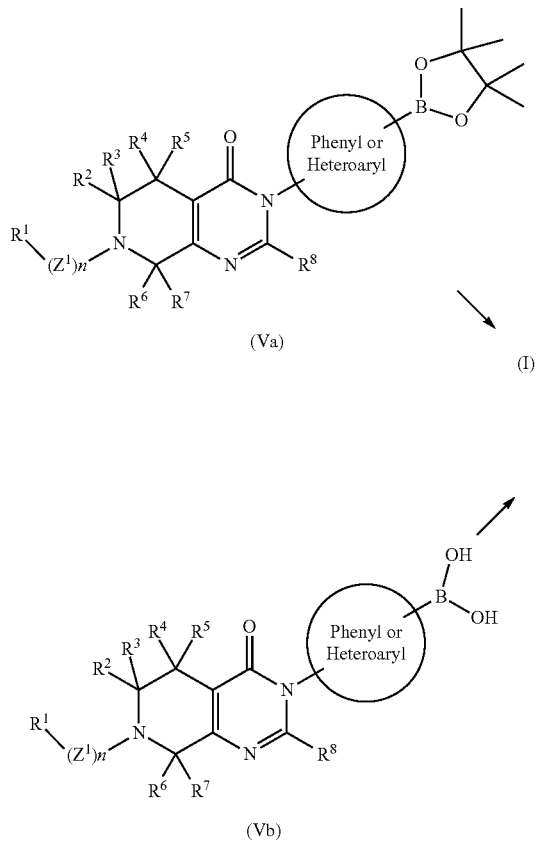

A compound of Formula (I), along with pharmaceutically acceptable salts thereof, in which $R^9$ represents a phenyl or a heteroaryl substituted with an optionally substituted heteroaryl, can be prepared from an intermediate of Formula (Va) and an optionally substituted bromoheteroaryl using a palladium catalyst (such as Pd(PPh$_3$)$_4$) in the presence of a base (for example, Cs$_2$CO$_3$) in a suitable solvent(s) (such as 1,4-dioxane/H$_2$O). The optionally substituted bromoheteroaryl can also be replaced in a similar reaction using an optionally substituted iodoheteroaryl. The boronic ester intermediate of Formula (Va) can be replaced with a boronic acid of Formula (Vb) using similar reaction conditions to afford a compound of Formula (I), or a pharmaceutically acceptable salt thereof.

Scheme 4

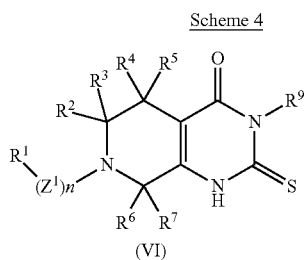

Compounds of Formula (I) in which $R^8$ represents $-NR^{10A}R^{10B}$ can be prepared from an intermediate of Formula (VI) and an amine of general formula $HNR^{10A}R^{10B}$, in the presence of tert-Butyl hydroperoxide (TBHP) in a suitable solvent (such as acetonitrile).

Scheme 5

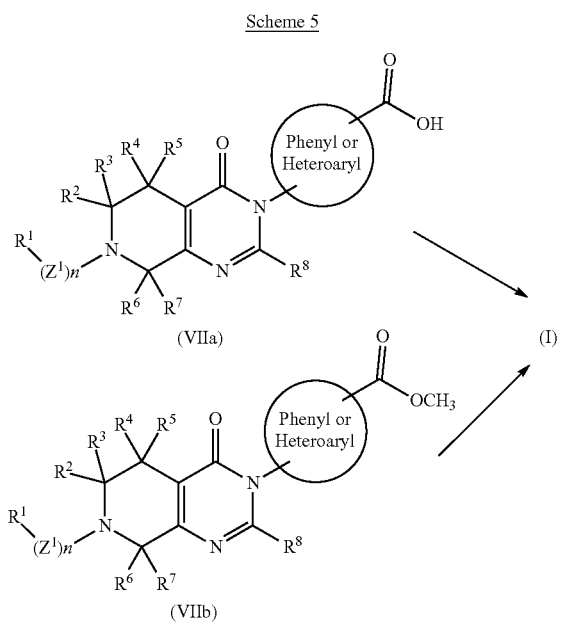

Compounds of Formula (I), including pharmaceutically acceptable salts thereof, in which $R^9$ represents a phenyl substituted with $-C(=O)NHR^{11}$ or $R^9$ represents an heteroaryl substituted with $-C(=O)NHR^{11}$ can be prepared from an acid intermediate of general formula (VIIa) and an amine of Formula $NH_2$-$R^{11}$, using a peptide coupling agent (such as CDI) in the presence of a base (for example, DBU) in a suitable solvent, such as acetonitrile or DMF. Compounds of Formula (I), along with pharmaceutically acceptable salts thereof, in which $R^9$ represents a phenyl substituted with $-C(=O)NHR^{11}$ or $R^9$ represents an heteroaryl substituted with $-C(=O)NHR^{11}$ can be prepared from an ester intermediate of Formula (VIIb) and an amine of general formula $NH_2$-$R^{11}$ in a suitable solvent (such as acetonitrile).

Scheme 6

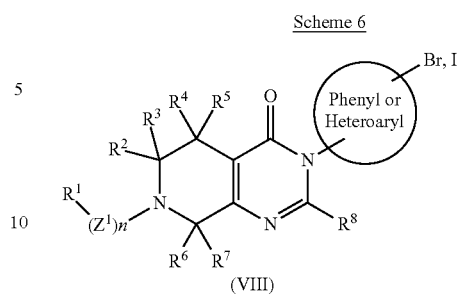

Compounds of Formula (I), or a pharmaceutically acceptable salt thereof, in which $R^9$ represents a phenyl or an heteroaryl substituted with a mono-substituted amine, can be prepared from an intermediate of Formula (VIII) and a mono-substituted amine, using a catalyst (for example, XantPhos Pd G3) in the presence of a base (such as $Cs_2CO_3$) in a suitable solvent (such as 1,4-dioxane). Compounds of Formula (I) in which $R^9$ represents a phenyl or an heteroaryl substituted with a di-substituted amine, can be prepared from an intermediate of Formula (VIII) and an di-substituted amine, using a catalyst (such as XantPhos Pd G3) in the presence of a base, such as $Cs_2CO_3$, in a suitable solvent (for example, 1,4-dioxane). Compounds of Formula (I), including pharmaceutically acceptable salts thereof, in which $R^9$ represents a phenyl or an heteroaryl substituted with a di-substituted amine, can be prepared from an intermediate of Formula (VIII) and an di-substituted amine, using a catalyst (such as copper(I) iodide (CuI) and a ligand such as 4,7-dimethoxy-1,10-phenanthroline) in the presence of a base. such as $K_3PO_4$, in a suitable solvent (for example, ethanol). Compounds of Formula (I), or a pharmaceutically acceptable salt thereof, in which $R^9$ represents a phenyl or an heteroaryl substituted with an optionally substituted monocyclic heteroaryl, can be prepared from an intermediate of Formula (VIII) and a boronic acid or boronic ester (for example, an optionally substituted monocyclic 4,4,5,5-tetramethyl-1,3,2-dioxaborolan-2-yl heteroaryl) using a catalyst, such as $Pd(PPh_3)_4$, in the presence of a base (such as $Cs_2CO_3$) in a suitable solvents, such as 1,4-dioxane/$H_2O$.

Scheme 7

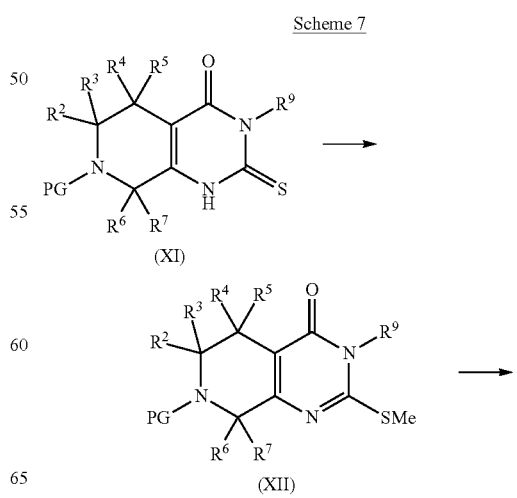

-continued

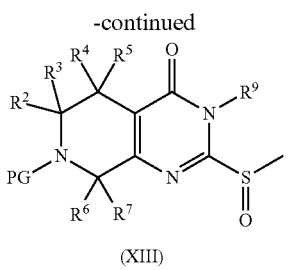

(XIII)

Scheme 9

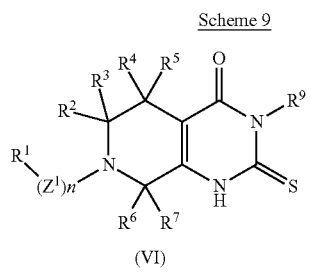

(VI)

Intermediate of Formula (II) in which $R^8$ represents —$NR^{10A}R^{10B}$ can be prepared from a compound of Formula (XI) using methyl iodide or methyl bromide, in the presence of a base, such as DBU, in a suitable solvent, such as DMF, to afford an intermediate of Formula (XII). Oxidation of an intermediate of Formula (XII) to a sulfoxide intermediate of Formula (XIII) can be achieved by a treatment with an oxidative agent (such as m-CPBA) in the presence of $MgSO_4$ and NaOAc in a suitable solvent (such as dichloromethane). Treatment of intermediate of Formula (XIII) with an amine of general formula $HNR^{10A}R^{10B}$ in the presence of a base (such as DIPEA) in the presence of a catalyst (for example, DMAP) in a suitable solvent (such as 1,4-dioxane) can afford an intermediate of Formula (II) in which $R^8$ represents —$NR^{10A}R^{10B}$.

Intermediates of Formula (IV) in which the leaving group LG represents a chloro can be prepared from an intermediate of Formula (VI) using thiophosgene in a suitable solvent (such as 1,4-dioxane).

Scheme 10

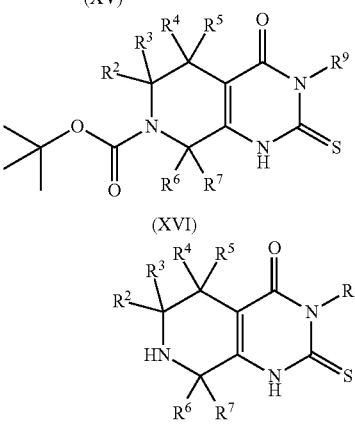

(XV)

(XVI)

(XVII)

Scheme 8

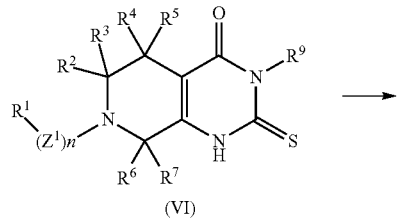

(VI)

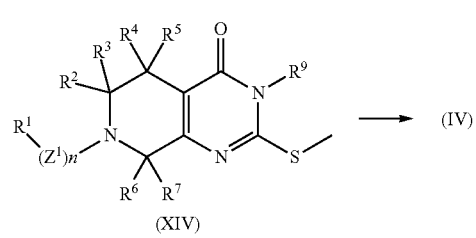

(XIV)

Intermediates of Formula (IV) in which the leaving group LG represents a methylsulfoxide can be prepared from an intermediate of Formula (VI) using methyl iodide or methyl bromide, in the presence of a base (for example, DBU) in a suitable solvent, such as DMF, to afford an intermediate of Formula (XIV). Oxidation of an intermediate of Formula (XIV) to a sulfoxide intermediate of Formula (IV) can be achieved using an oxidative agent, such as m-CPBA, in the presence of $MgSO_4$ and NaOAc in a suitable solvent, such as dichloromethane.

Intermediate of Formula (VI) can be prepared from an intermediate of Formula (XV) in the presence of a strong base, such as NaH, in a suitable solvent (for example, THF or 2-methylTHF) followed by the subsequent addition of an isothiocyanate of general formula $R^9$—NCS to afford an intermediate of Formula (XVI). The Boc group of an intermediate of Formula (XVI) can be obtained in the presence of an acid (such as HCl or TFA) in a suitable solvent (for example, 1,4-dioxane) to afford an intermediate of Formula (XVII). Intermediates of Formula (VI) can be prepared from an intermediate of Formula (XVII) following several conditions known to those skilled in the art. For example, compounds of Formula (XVII), wherein $Z^1$ represents —NH—C(=O)— and n=1, can be obtained by reacting a compound of Formula (XVII) with a phenyl carbamate of general formula $R^1$—NH—C(=O)—O— phenyl or with an isocyanate of general formula $R^1$—N=C=O, in the presence of a suitable base in a suitable solvent. An example of a suitable base is triethylamine, and an example of suitable solvent is acetonitrile or dichloromethane.

Further compounds of Formula (VI) wherein $Z^1$ represents —C(=O)— and n=1, can be obtained by reacting a compound of Formula (XVII) with an acyl chloride of general formula $R^1$—C(=O)—Cl in the presence of a base in a suitable solvent, including those bases and solvents described herein and/or known to those skilled in the art. Compounds of Formula (VI), wherein $Z^1$ represents —C(=O)— and n=1, can be obtained by reacting compound of Formula (XVII) with a carboxylic acid of general formula $R^1$—C(=O)—OH in the presence of an amide coupling agent (such as HATU) in a suitable solvent. Additional compounds of Formula (VI) can be prepared from a compound of Formula (XVII) using methods known in the art.

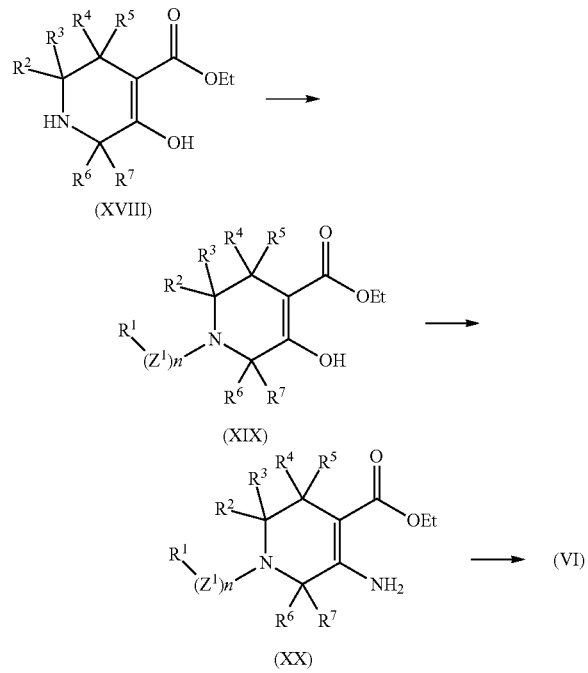

Scheme 11

An intermediate of Formula (VI) can be prepared from an intermediate of Formula (XVIII) following other conditions known in the art, similar to the conditions used to convert an intermediate of Formula (XVII) to an intermediate for Formula (VI). For example, intermediates of Formula (XIX) wherein $Z^1$ represents —C(=O)— and n=1, can be obtained by reacting a compound of Formula (XVIII) with an acyl chloride of general formula $R^1$—C(=O)—Cl in the presence of a base in a suitable solvent. Additional compounds of Formula (XIX), wherein $Z^1$ represents —C(=O)— and n=1, can be obtained by reacting compound of Formula (XVIII) with a carboxylic acid of general formula $R^1$—C(=O)—OH in the presence of an amide coupling agent (such as HATU) in a suitable solvent. Suitable solvents are known to those skilled in the art and/or described herein.

Intermediates of Formula (XX) can be prepared from an intermediate of Formula (XI) in the presence of ammonium acetate, in a suitable solvent (such as ethanol). Intermediate of Formula (VI) can be prepared from an intermediate of Formula (XX) in the presence of a strong base (for example, NaH) in a suitable solvent (such as THF or 2-methylTHF) followed by the addition of an isothiocyanate of general formula $R^9$—NCS. An intermediate of Formula (XX) can be treated with thiophosgene/NMM in a suitable solvent, such as dichloromethane, to afford an intermediate isothiocyanate, which can be converted to an intermediate of Formula (VI) by using an amine of general formula $NH_2$-$R^9$, in the presence of a base, such as triethylamine, in a suitable solvent (such as acetonitrile).

Scheme 12

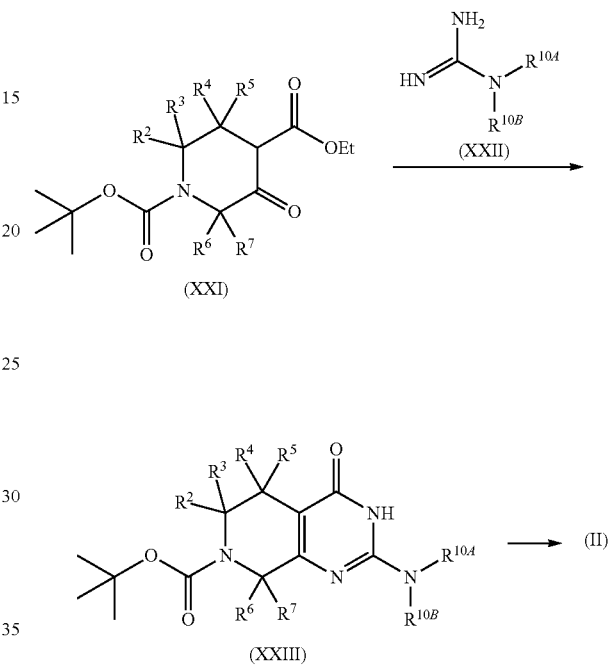

Intermediates of Formula (II) in which $R^8$ represents —$NR^{10A}R^{10B}$ and the protecting group PG represents Boc, can be prepared from an intermediate of Formula (XXI) using a guanidine derivative of Formula (XXII), in the presence of a base, such as DBU, in a suitable solvent (such as acetonitrile) to afford an intermediate of Formula (XXIII). An intermediate of Formula (XXIII) can be converted in the intermediate of Formula (II) using methods known in the art. As an example, an intermediate of formula (XXIII) can be reacted with an aryl or heteroaryl boronic acid of general formula $R^9$—$B(OH)_2$, in the presence of TMEDA and $Cu(OAc)_2$ to afford an intermediate of Formula (II) in which $R^9$ represents a substituted phenyl, a substituted monocyclic heteroaryl or a substituted fused-bicyclic heteroaryl.

Scheme 13

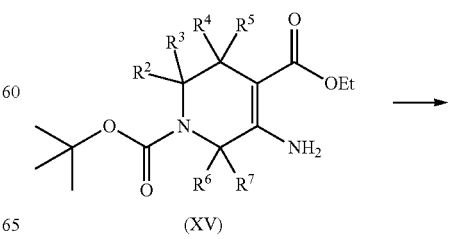

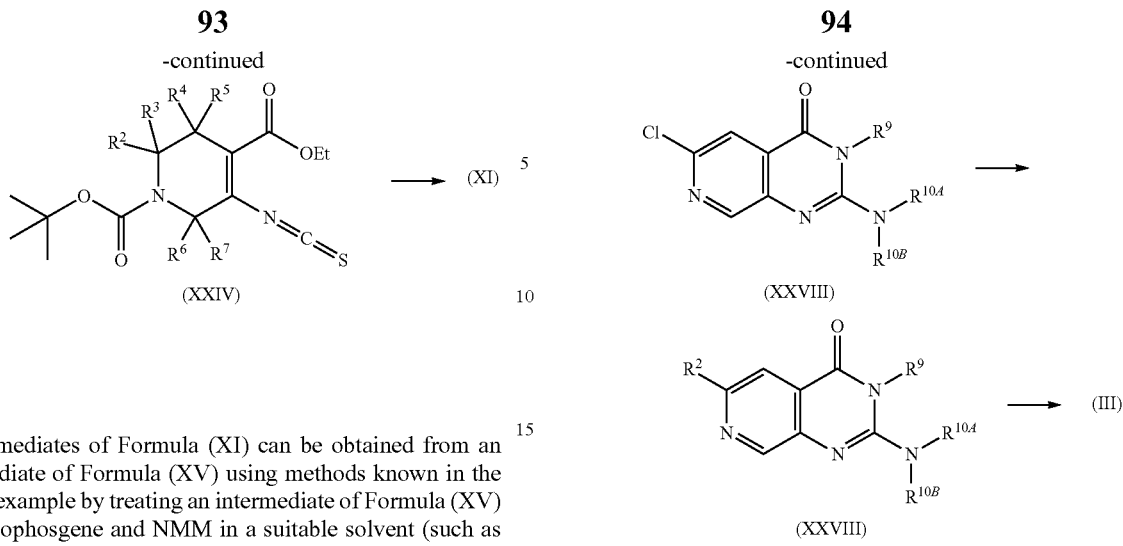

Intermediates of Formula (XI) can be obtained from an intermediate of Formula (XV) using methods known in the art, for example by treating an intermediate of Formula (XV) with thiophosgene and NMM in a suitable solvent (such as dichloromethane). Treatment of an intermediate of Formula (XXIV) with an amine of general formula $R^9$—$NH_2$ affords an intermediate of Formula (XI) in which PG represents a Boc group.

Scheme 14

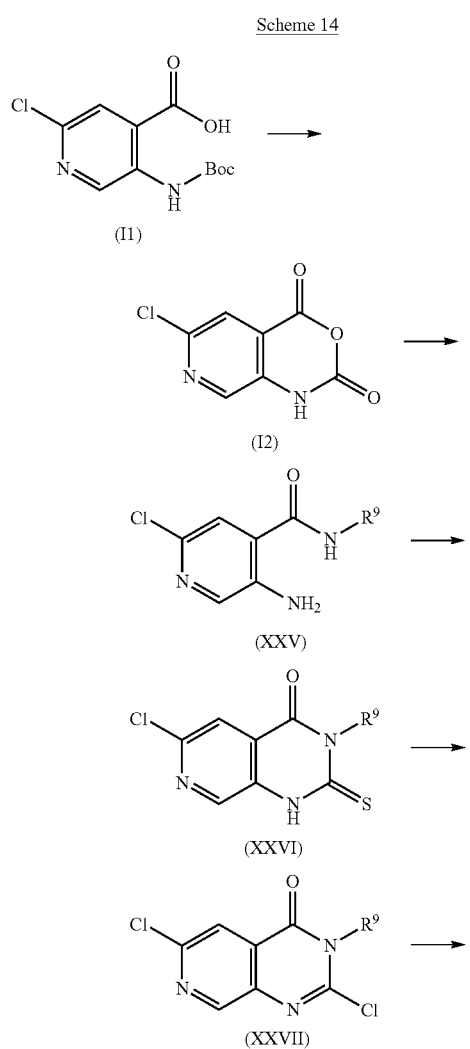

Intermediates of Formula (III) in which $R^3$, $R^4$, $R^5$, $R^6$ and $R^7$ each represent hydrogen, and in which $R^8$ represents —$NR^{10A}R^{10B}$, can be prepared from a chloro-N-Boc-aminopyridinecarboxylic acid intermediate of Formula (I1) using a base (such as triethylamine) in the presence of 2-chloro-N-methylpyridinium iodide in a suitable solvent (for example, acetonitrile) to afford an intermediate of Formula (I2). An intermediate of Formula (I2) can be converted to an intermediate of Formula (XXV) using an amine of general formula $R^9$—$NH_2$, in a suitable solvent (for example, acetic acid). Reaction of an intermediate of Formula (XXV) with thiocarbonyldiimidazole in DMF can afford the thio intermediate of Formula (XXVI), which can be converted in an intermediate of Formula (XXVII) using thiophosgene in a suitable solvent (such as 1,4-dioxane). Treatment of an intermediate of Formula (XXVII) with an amine of general formula $NR^{10A}R^{10B}$ can afford an intermediate of Formula (XXVIII). An intermediate of Formula (XXVIII) can be reacted with an organometallic derivative (such as a tin derivative of general formula $R^2$—$Sn(n-Bu)_3$). An intermediate of Formula (XXVIII) can be converted to an intermediate of Formula (III) in which $R^3$, $R^4$, $R^5$, $R^6$ and $R^7$ each can be hydrogen, and in which $R^8$ represents —$NR^{10A}R^{10B}$, by hydrogenation using $H_2$ in the presence of a catalyst (such as Pt/C) in a mixture of solvents (for example, acetic acid/THF/ethanol). In the instance where $R^2$ can be an unsaturated group, such as an alkene, the $R^2$ can be converted to another $R^2$ group, such as an alkyl, by hydrogenation.

Scheme 15

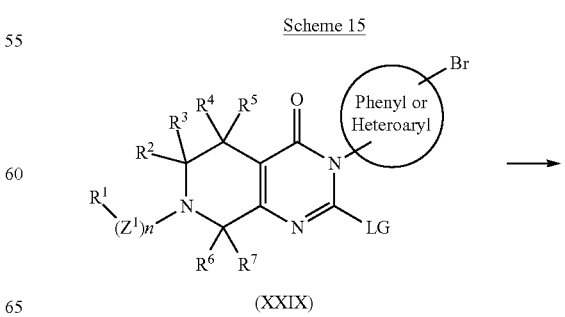

-continued

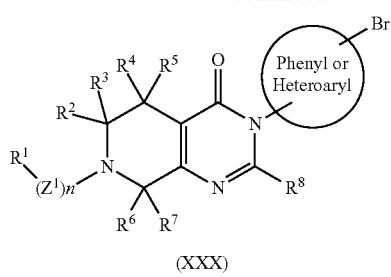

(XXX)

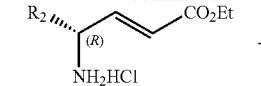

(XXXIV)

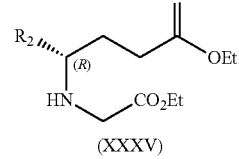

(XXXV)

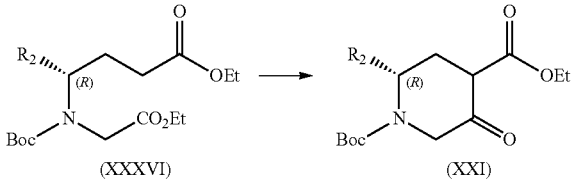

(XXXVI)            (XXI)

Intermediates of Formula (Va), in which R⁸ represents —NR$^{10A}$R$^{10B}$, can be prepared from an intermediate of Formula (XXIX), in which LG represents a leaving group (such as sulfhydryl, methylsulfoxide or halo, in particular chloro of bromo). Intermediates of Formula (XXIX) can be reacted with an amine of general formula HNR$^{10A}$R$^{10B}$, in the presence of a base (for example, triethylamine) in a suitable solvent, such as acetonitrile, to afford an intermediate of Formula (XXX). The conversion of a bromo intermediate of Formula (XXX) to a boronic ester intermediate of Formula (Va) can be achieved using bis(pinacolato) diboron in the presence of a catalyst (such as Pd(dppf)Cl$_2$) in the presence of a base, such as KOAc, in a suitable solvent (for example, 1,4-dioxane).

Scheme 16

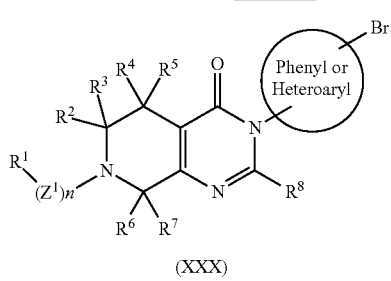

(XXX)

Intermediates of Formula (Vb) can be prepared from an intermediate of Formula (XXX) using bis(pinacolato)diboron, in the presence of a base (such as potassium acetate and 1,1'-bis(diphenylphosphino)ferrocene-palladium(II)dichloride dichloromethane complex) in a suitable solvent, such as 1,4-dioxane, to obtain an intermediate of Formula (Vb).

Scheme 17

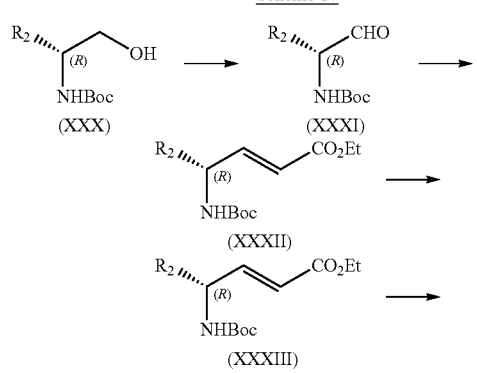

An alternative approach towards the chiral synthesis of compounds of Formula (XXI) is provided in Scheme 17. Oxidation of a chiral, boc-protected aminoalcohol of Formula (XXX), for example, via Swern oxidation, leads to aldehydes of Formula (XXXI). Subsequent formation of an unsaturated ester, for example, via the Wittig reaction (compounds of Formula (XXXII)), and then reduction of the resultant double bond (e.g., Pd/C) can afford compounds of Formula (XXXIII). Deprotection of the boc group and alkylation with ethyl 2-bromoacetate can provide compounds of Formula (XXXV). Boc protection of compounds of Formula (XXXV) followed by Dieckmann condensation can provide to compounds of Formula (XXI).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure.

Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction <$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT > twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139 and REP 2165. Exemplary siRNA's that can be used in combination with a compound, or pharmaceutically acceptable salt thereof, provide herein include those described in WO 2021/178885, which is hereby incorporated by reference for the purpose of describing the siRNA compounds provided therein, such as a siRNA selected from SEQ. ID. NO. 1-617 and SEQ. ID. NO. 618.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Table of Abbreviations

| Abbreviation | Meaning |
| --- | --- |
| h | hour |
| * | single diasteromer, absolute stereochemistry unknown |
| rt | room temperature |
| EA | ethyl acetate |
| CyH | cyclohexane |
| PE | petroleum ether |
| DIPEA | diisopropylethylamine |
| SFC | Supercritical Fluid Chromatography |

Example 1

Compound 1

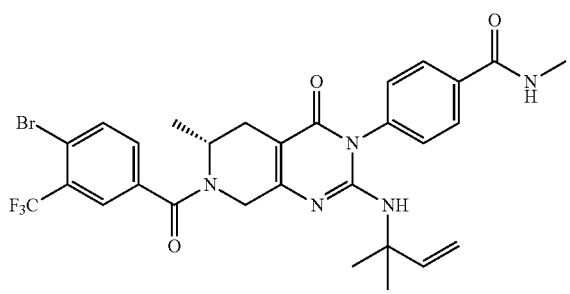 [SMILES: C=CC(C)(C)Nc1nc2c(c(=O)n1-c1ccc(C(=O)NC)cc1)C[C@@H](C)N(C(=O)c1ccc(Br)c(C(F)(F)F)c1)C2]

To a solution of oxalyl dichloride (181 g, 1.43 mol) in $CH_2Cl_2$ (1.5 L) at −65° C. was added DMSO (111 mL) in $CH_2Cl_2$ (500 mL). After stirring for 1 h, t-butyl (R)-(1-hydroxypropan-2-yl)carbamate (250 g, 1.43 mol) in $CH_2Cl_2$ (500 mL) was added dropwise. After stirring for 2 h, $Et_3N$ (144 g, 1.43 mol, 198 mL) was added dropwise. The mixture was gradually warmed to 25° C. and then stirred at 25° C. for 4 h. The reaction was quenched by the addition of $NH_4Cl$ (sat., aq., 2.5 L), and then extracted with $CH_2Cl_2$ (2×2.5 L). The combined organic layers were dried over $Na_2SO_4$, the solids were removed by filtration and the filtrate was concentrated under reduced pressure to give the crude product as a colorless oil, t-butyl (R)-(1-oxopropan-2-yl)carbamate (450 g, 2.60 mol, 91% yield) which was used in the next step without further purification.

To a solution of t-butyl (R)-(1-oxopropan-2-yl)carbamate (225 g, 1.30 mol) in $CH_2Cl_2$ (2.25 L) was added (carbethoxymethylene)triphenylphosphorane (429 g, 1.23 mol). The mixture was stirred at 25° C. for 12 h. The mixture was concentrated under reduced pressure to give the crude product that was purified by silica gel column chromatography (PE:EA=15:1 to 5:1) to afford ethyl (R)-4-((t-butoxycarbonyl)amino)pent-2-enoate (500 g, 2.06 mol, 79.1% yield) as a colorless oil. $^1$HNMR (400 MHz, $CDCl_3$) δ 6.86 (dd, J=15.76, 4.88 Hz, 1H) 5.89 (dd, J=15.70, 1.56 Hz, 1H) 4.58 (br s, 1H) 4.39 (br s, 1H) 4.18 (q, J=7.13 Hz, 2H) 1.44 (s, 9H) 1.24-1.29 (m, 6H).

To a solution of ethyl (R)-4-((t-butoxycarbonyl)amino)pent-2-enoate (125 g, 513 mmol) in $CH_3OH$ (1.25 L) was added 10% Pd/C (6.00 g) and $Pd(OH)_2$ (6.06 g) under $N_2$. The suspension was degassed under vacuum and purged with $H_2$ (1.04 g, 514 mmol) several times. The mixture was stirred under $H_2$ (50 psi) at 50° C. for 12 h. The solids were removed by filtration under $N_2$, and the filtrate was evaporated to dryness to afford ethyl (R)-4-((t-butoxycarbonyl)amino)pentanoate (480 g, 1.96 mol, 95% yield) as a colorless oil. $^1$HNMR (400 MHz, $CDCl_3$) δ 4.29-4.45 (m, 1H) 4.13 (q, J=7.13 Hz, 2H) 3.57-3.75 (m, 1H) 2.35 (t, J=7.69 Hz, 2H) 1.66-1.84 (m, 3H) 1.43 (s, 9H) 1.25 (t, J=7.13 Hz, 3H) 1.14 (d, J=6.50 Hz, 3H).

To a solution of ethyl (R)-4-((t-butoxycarbonyl)amino)pentanoate (480 g, 1.96 mol) in HCl/EA (4M, 2.5 L). The mixture was stirred at 25° C. for 2 h. The mixture was concentrated under reduced pressure to give ethyl (R)-4-aminopentanoate HCl (450 g, crude) as a yellow oil that was used directly in the next step without purification.

To mixture of ethyl (R)-4-aminopentanoate HCl (225 g, 1.24 mol) in THF (4 L) and $H_2O$ (1 L), was added $K_2CO_3$ (427 g, 3.10 mol) at 25° C. After addition, the yellow solution was stirred at 25° C. for 30 min. A solution of ethyl 2-bromoacetate (206 g, 1.24 mol, 137 mL) dropwise at 25° C. over 30 min. The yellow solution was stirred at 25° C. for 11 h. The crude product, ethyl (R)-4-((2-ethoxy-2-oxoethyl)amino)pentanoate (400 g, 1.73 mol, 70% yield), was obtained as a colorless oil that used in the next step without work up or purification.

A solution of $(Boc)_2O$ (189 g, 865 mmol, 199 mL) was added dropwise into ethyl (R)-4-((2-ethoxy-2-oxoethyl)amino)pentanoate (200 g, 865 mmol) over 30 min. The yellow solution was stirred for 6 h at 25° C., and then pumped onto a filter. The filter cake was washed with EA (1 L), and the filtrate was collected. To the filtrate was added $H_2O$ (3 L). The mixture was extracted with EA (2×5 L). The combined organic layers were washed with brine (2 L) and dried over $Na_2SO_4$. The solids were removed by filtration. The filtrate was concentrated under reduced pressure to give the crude product, ethyl (R)-4-((t-butoxycarbonyl)(2-ethoxy-2-oxoethyl)amino)pentanoate (400 g, 1.21 mol, 70% yield), as a yellow oil, which used in the next step without purification. ¹HNMR (400 MHz, CDCl₃) δ 4.06-4.22 (m, 4H) 3.54-3.93 (m, 2H) 2.26-2.55 (m, 2H) 1.71 (qd, J=7.48, 3.69 Hz, 2H) 1.45-1.55 (m, 6H) 1.42 (s, 4H) 1.22-1.35 (m, 6H).

To a mixture of ethyl (R)-4-((t-butoxycarbonyl)(2-ethoxy-2-oxoethyl)amino)pentanoate (200 g, 603 mmol) in THF (2 L) was added t-BuOK (135 g, 1.21 mol) at 0° C. under N₂. The yellow mixture was stirred at 25° C. for 12 h under N₂. The reaction was quenched by the addition of aq. citric acid (250 g in 3 L of H₂O) at below 10° C. The mixture was extracted with EA (3×2.5 L). The combined organic layers were washed with brine (2 L×1) and dried over Na₂SO₄. The solids were removed by filtration, and the filtrate was concentrated under reduced pressure. The residue was purified by silica column chromatography (PE: EA=15:1 to 10:1) to afford 1-(t-butyl) 4-ethyl 5-oxo-2-(R)-methyl-3,6-dihydropyridine-1,4(2H)-dicarboxylate (210 g, 736 mmol, 61% yield) as a yellow oil. ¹H NMR (400 MHz, CDCl₃) δ 12.06 (s, 1H) 4.54 (br s, 1H) 4.33 (br d, J=19.39 Hz, 1H) 4.23 (dtt, J=10.62, 7.07, 7.07, 3.63, 3.63 Hz, 2H) 3.64 (br d, J=19.26 Hz, 1H) 2.45-2.55 (m, 1H) 2.18 (d, J=15.63 Hz, 1H) 1.47 (s, 9H) 1.31 (t, J=7.13 Hz, 3H) 1.11 (d, J=6.88 Hz, 3H).

To a solution of 1-(t-butyl) 4-ethyl 5-oxo-2-(R)-methyl-3,6-dihydropyridine-1,4(2H)-dicarboxylate (210 g, 736 mmol) in EA (1 L) was added a solution of HCl:EA (4 M, 2 L) dropwise at 25° C. The mixture was stirred at 25° C. for 3 h, and then concentrated under reduced pressure. The crude product was triturated with EA (500 mL) at 25° C. for 30 min to afford ethyl (R)-5-hydroxy-2-methyl-1,2,3,6-tetrahydropyridine-4-carboxylate HCl (140 g, 631 mmol, 86% yield, 100% purity) as a white solid. ¹H NMR (400 MHz, Methanol-d₄) δ 4.29 (q, J=6.96 Hz, 2H) 3.92-4.01 (m, 1H) 3.77-3.87 (m, 1H) 3.42-3.54 (m, 1H) 2.66-2.76 (m, 1H) 2.23-2.39 (m, 1H) 1.43 (d, J=6.50 Hz, 3H) 1.32 (t, J=7.07 Hz, 3H).

A solution of ethyl (R)-5-hydroxy-2-methyl-1,2,3,6-tetrahydropyridine-4-carboxylate HCl (115 g, 519 mmol), in DMF (1 L) was cooled to 0° C. DIPEA (268 g, 2.08 mol, 361 mL), and T₃P (495 g, 778 mmol, 463 mL, 50% purity) were added. The mixture was stirred at 25° C. for 12 h. The reaction was quenched by the addition water 2 L at 25° C. The mixture was diluted with EA (1.5 L) and extracted with EA (3×1 L). The combined organic layers were washed with brine 500 mL and dried over Na₂SO₄. The solids were removed by filtration, and the filtrate was concentrated under reduced pressure. The residue was purified by silica gel chromatography (0 to 10% EA:PE gradient) to afford ethyl (R)-1-(4-bromo-3-(trifluoromethyl)benzoyl)-5-hydroxy-2-methyl-1,2,3,6-tetrahydropyridine-4-carboxylate (130 g, 259 mmol, 50% yield, 87% purity) as a yellow oil. ¹H NMR (CDCl₃ 400 MHz), δ 12.10 (br s, 1H) 7.80 (d, J=8.13 Hz, 1H) 7.74 (d, J=1.88 Hz, 1H) 7.42 (dd, J=8.13, 1.88 Hz, 1H) 4.64-5.30 (m, 1H) 4.19-4.34 (m, 2H) 4.08-4.17 (m, 1H) 3.81 (br dd, J=12.13, 2.75 Hz, 1H) 2.58 (br d, J=14.76 Hz, 1H) 2.24 (br d, J=16.01 Hz, 1H) 1.32 (t, J=7.13 Hz, 3H) 1.25 (br t, J=3.13 Hz, 3H).

To a solution of ethyl (R)-1-(4-bromo-3-(trifluoromethyl)benzoyl)-5-hydroxy-2-methyl-1,2,3,6-tetrahydropyridine-4-carboxylate (90.0 g, 206 mmol) in ethanol (900 mL) was added NH₄OAc (79.5 g, 1.03 mol). The mixture was stirred at 60° C. for 2 h. The mixture was concentrated under reduced pressure, diluted with water (200 mL) and extracted with EA (3×200 mL). The combined organic layers were washed with brine (200 mL) and dried over Na₂SO₄. The solids were removed by filtration, and the filtrate was concentrated under reduced pressure. The residue was purified by silica gel chromatography (0 to 50% EA:PE gradient) to afford ethyl (R)-5-amino-1-(4-bromo-3-(trifluoromethyl)benzoyl)-2-methyl-1,2,3,6-tetrahydropyridine-4-carboxylate (55.0 g, 125 mmol, 61% yield, 99% purity) as a yellow solid. ¹H-NMR (DMSO-d₆, 400 MHz) δ 7.98 (d, J=8.13 Hz, 1H) 7.84 (d, J=1.75 Hz, 1H) 7.63 (dd, J=8.19, 1.56 Hz, 1H) 6.74-7.47 (m, 2H) 4.63-4.91 (m, 1H) 4.00-4.08 (m, 2H) 3.80-3.95 (m, 1H) 3.59-3.75 (m, 1H) 2.45 (br d, J=5.75 Hz, 1H) 2.14 (br d, J=1.25 Hz, 1H) 1.06-1.20 (m, 6H).

To a solution of ethyl (R)-5-amino-1-(4-bromo-3-(trifluoromethyl)benzoyl)-2-methyl-1,2,3,6-tetrahydropyridine-4-carboxylate (100 g, 230 mmol) and NMM (102 g, 1.01 mol, 111 mL) in CH₂Cl₂ (1 L) was added SCCl₂ (55.5 g, 483 mmol, 37.0 mL) at 0° C. The mixture was stirred at 0° C. for 1 h. The reaction was quenched by the addition ice-water (100 mL) at 0° C. The mixture was diluted with CH₂Cl₂ (150 mL) and extracted with CH₂Cl₂ (3×500 mL). The combined organic layers were washed with brine (500 mL) and dried over Na₂SO₄. The solids were removed by filtration, and the solvent of the filtrate was concentrated under reduced pressure. The residue was purified by silica gel chromatography (0 to 20% EA:PE gradient) to afford ethyl (R)-1-(4-bromo-3-(trifluoromethyl)benzoyl)-5-isothiocyanato-2-methyl-1,2,3,6-tetrahydropyridine-4-carboxylate (100 g, 163 mmol, 71% yield, 78% purity) as a yellow oil. ¹H-NMR (CDCl₃, 400 MHz) δ 7.74 (d, J=8.13 Hz, 1H) 7.66 (d, J=1.75 Hz, 1H) 7.34 (dd, J=8.13, 2.00 Hz, 1H) 4.55-5.18 (m, 1H) 4.14-4.26 (m, 3H) 3.67-3.85 (m, 2H) 2.51-2.70 (m, 1H) 2.31-2.47 (m, 1H) 1.29 (t, J=7.13 Hz, 3H) 1.18 (dd, J=7.00, 3.38 Hz, 4H).

To a solution of ethyl (R)-1-(4-bromo-3-(trifluoromethyl)benzoyl)-5-isothiocyanato-2-methyl-1,2,3,6-tetrahydropyridine-4-carboxylate (100 g, 210 mmol) in CH₃CN (1 L) were added 4-amino-N-methylbenzamide (31.5 g, 210 mmol) and Et₃N (53.0 g, 524 mmol, 72.9 mL). The mixture was stirred at 95° C. for 12 h to obtain a yellow suspension. The mixture was concentrated under reduced pressure. The crude product was triturated with EA (500 mL) at 25° C. for 1 h to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 119 mmol, 57% yield, 86% purity) as a white solid. ¹H-NMR (DMSO-d₆, 400 MHz) δ 8.49-8.57 (m, 1H) 8.02 (br d, J=7.63 Hz, 1H) 7.88 (m, 3H) 7.69 (br d, J=7.63 Hz, 1H) 7.29 (d, J=8.88 Hz, 1H) 7.25 (br s, 1H) 5.08-5.27 (m, 1H) 4.18-4.35 (m, 1H) 4.05-4.14 (m, 1H) 2.80 (d, J=4.50 Hz, 3H) 2.53-2.62 (m, 1H) 2.17-2.36 (m, 1H) 1.18-1.20 (m, 3H).

To a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 138 mmol) in dioxane (880 mL) was added SCCl₂ (31.6 g, 275 mmol, 21.1 mL). The mixture was stirred at 100° C. for 2 h and then concentrated under reduced pressure. The residue was purified by silica gel chromatography (0 to 80% EA:PE gradient) to afford 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (49.0 g, 81.5 mmol, 59% yield, 97% purity) as an off-white solid. ¹H-NMR (CD₃OD, 400 MHz) δ 7.94-8.03 (m, 3H) 7.90 (d, J=1.75 Hz, 1H) 7.61-7.68 (m, 1H) 7.42-7.54 (m, 2H) 5.02-5.49 (m, 1H) 4.13-4.56 (m, 2H) 2.95 (s, 3H) 2.72-2.86 (m, 1H) 2.56 (br d, J=17.89 Hz, 1H) 1.24-1.38 (m, 3H).

DIPEA (1.13 mL, 6.85 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (200 mg, 0.34 mmol) and 2-methylbut-3-en-2-amine (292 mg, 3.43 mmol) in anhydrous CH₃CN (3.4 mL) under N₂. The mixture was stirred at 170° C. for 24 h. After cooling to rt, the mixture was diluted with EA, washed with water, HCl 1M and brine (2×) and dried over Na₂SO₄. The solids were removed by filtration, and the filtrate was evaporated to dryness. The crude mixture was purified by chromatography on silica gel (0 to 7% [CH₃OH:NH₄OH (9:1)] in CH₂Cl₂) and by prep-HPLC (25 to 100% CH₃CN in water) to give (R)-4-(7-(4-bromo-3-(trifluoromethyl)benzoyl)-6-methyl-2-((2-methylbut-3-en-2-yl)amino)-4-oxo-5,6,7,8-tetrahydropyrido[3,4-d]pyrimidin-3(4H)-yl)-N-methylbenzamide (91 mg, 42%) as a white solid. $^1$H-NMR (DMSO-d₆, 600 MHz, 80° C.) δ 1.20 (d, J=6.8 Hz, 3H), 1.39 (s, 3H), 1.40 (s, 3H), 2.35 (d, J=16.8 Hz, 1H), 2.58 (dd, J=16.2 Hz, 5.8 Hz, 1H), 2.84 (d, J=4.8 Hz, 3H), 4.01 (d, J=16.8 Hz, 1H), 4.36 (s, 1H), 4.30-4.74 (m, 2H), 4.92 (d, J=7.4 Hz, 1H), 4.94 (s, 1H), 6.04 (dd, J=17.8 Hz, 10.6 Hz, 1H), 7.42 (d, J=8.1 Hz, 2H), 7.66 (d, J=8.1 Hz, 1H), 7.85 (s, 1H), 7.98 (d, J=8.3 Hz, 1H), 8.01 (d, J=8.4 Hz, 2H), 8.35 (br s, 1H) ppm. LC-MS: (C₂₉H₂₉BrF₃N₅O₃) [M+H]⁺: 632/634.

Example 2

Compound 2

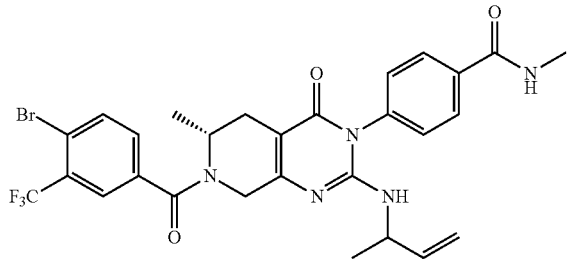 [SMILES: C=CC(C)Nc1nc2c(c(=O)n1-c1ccc(C(=O)NC)cc1)C[C@@H](C)N(C(=O)c1ccc(Br)c(C(F)(F)F)c1)C2]

NEt₃ (0.83 mL, 6 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (500 mg, 0.86 mmol) and but-3-en-2-amine (183 mg, 2.57 mmol) in anhydrous CH₃CN (15 mL) under N₂. The mixture was stirred at 110° C. for 30 h, at which point additional but-3-en-2-amine (183 mg, 2.57 mmol) and NEt₃ (0.83 mL, 6 mmol) were added. The mixture was stirred at 110° C. for 18 h and then evaporated to dryness. The residue was dissolved in EA:isopropanol (85:15), washed with sat. aq. NH₄Cl and brine and dried over Na₂SO₄. The solids were removed by filtration, and the filtrate was evaporated to dryness. The crude mixture was purified by chromatography on silica gel (0 to 10% CH₃OH in CH₂Cl₂) and by SFC (20:80 CH₃OH/CO₂ [0.2% v/v NH₃]) to afford two diastereoisomers of compound 2, 4-((6R)-7-(4-bromo-3-(trifluoromethyl)benzoyl)-2-(but-3-en-2-ylamino)-6-methyl-4-oxo-5,6,7,8-tetrahydropyrido[3,4-d]pyrimidin-3(4H)-yl)-N-methylbenzamide where the first eluting diastereoisomer (2a) was isolated as a white solid (128 mg, 24%). $^1$H-NMR (DMSO-d₆, 600 MHz, 80° C.) δ 1.15 (d, J=7.4 Hz, 3H), 1.21 (d, J=6.8 Hz, 3H), 2.35 (d, J=16.4 Hz, 1H), 2.53-2.60 (m, 1H), 2.84 (d, J=4.8 Hz, 3H), 4.04 (d, J=18.4 Hz, 1H), 4.21-4.70 (m, 3H), 4.93-5.04 (m, 2H), 5.25-5.32 (m, 1H), 5.77-5.86 (m, 1H), 7.36 (d, J=7.5 Hz, 2H), 7.66 (dd, J=8.0 Hz, 1.3 Hz, 1H), 7.84 (d, J=1.2 Hz, 1H), 7.96-8.02 (m, 3H), 8.29-8.35 (m, 1H) ppm. LC-MS: (C₂₈H₂₇BrF₃N₅O₃) 618/620 [M+H]⁺. The second eluting isomer (2b) was isolated as a white solid (137 mg, 26%). $^1$H-NMR (DMSO-d₆, 600 MHz, 80° C.) δ 1.14 (d, J=7.0 Hz, 3H), 1.20 (d, J=7.0 Hz, 3H), 2.35 (d, J=16.6 Hz, 1H), 2.53-2.60 (m, 1H), 2.84 (d, J=4.7 Hz, 3H), 4.03 (d, J=18.7 Hz, 1H), 4.30-4.75 (m, 3H), 4.95-5.05 (m, 2H), 5.28 (d, J=7.3 Hz, 1H), 5.79-5.87 (m, 1H), 7.36 (d, J=7.6 Hz, 2H), 7.65-7.69 (m, 1H), 7.83-7.86 (m, 1H), 7.96-8.02 (m, 3H), 8.29-8.34 (m, 1H) ppm. LC-MS: (C₂₈H₂₇BrF₃N₅O₃) [M+H]⁺: 618/620.

Example 3

Compound 3

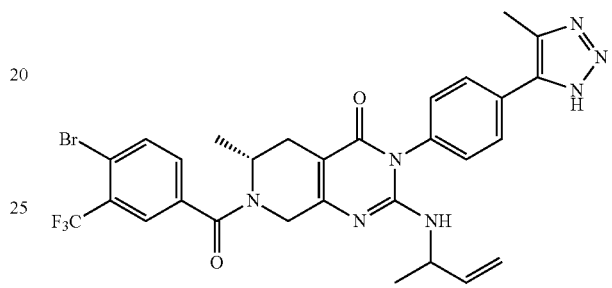

Et₃N (0.73 mL, 5.24 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 g, 2.095 mmol) and 4-{1-[(4-methoxyphenyl)methyl]-4-methyl-1H-1,2,3-triazol-5-yl}aniline (0.62 g, 2.095 mmol) in anhydrous CH₃CN (20 mL) under N₂. The mixture was stirred at 95° C. for 2 h and then evaporated to dryness. The crude mixture was purified by chromatography on silica gel (0 to 5% CH₃OH in CH₂Cl₂) to afford (R)-7-(4-bromo-3-(trifluoromethyl)benzoyl)-3-(4-(1-(4-methoxybenzyl)-4-methyl-1H-1,2,3-triazol-5-yl)phenyl)-6-methyl-2-thioxo-2,3,5,6,7,8-hexahydropyrido[3,4-d]pyrimidin-4(1H)-one (1.14 g, 75%) as a brown solid. LC-MS: (C₃₃H₂₈BrF₃N₆O₃S) [M+H]⁺: 726.

Thiophosgene (0.21 g, 0.14 mL, 1.57 mmol) was added to a solution of (R)-7-(4-bromo-3-(trifluoromethyl)benzoyl)-3-(4-(1-(4-methoxybenzyl)-4-methyl-1H-1,2,3-triazol-5-yl)phenyl)-6-methyl-2-thioxo-2,3,5,6,7,8-hexahydropyrido[3,4-d]pyrimidin-4(1H)-one (1.14 g, 1.57 mmol) in anhydrous dioxane (12 mL) under N₂. The mixture was stirred at rt for 30 min, then at 100° C. for 30 min. The mixture was evaporated to dryness. The crude mixture was purified by chromatography on silica gel (0 to 10% CH₃OH in CH₂Cl₂) to give (R)-7-(4-bromo-3-(trifluoromethyl)benzoyl)-2-chloro-3-(4-(1-(4-methoxybenzyl)-4-methyl-1H-1,2,3-triazol-5-yl)phenyl)-6-methyl-5,6,7,8-tetrahydropyrido[3,4-d]pyrimidin-4(3H)-one (490 mg, 43%) as an orange solid. LC-MS: (C₃₃H₂₇BrClF₃N₆O₃) [M+H]⁺: 729.

NEt₃ (0.65 mL, 4.71 mmol) was added to a solution of (R)-7-(4-bromo-3-(trifluoromethyl)benzoyl)-2-chloro-3-(4-(1-(4-methoxybenzyl)-4-methyl-1H-1,2,3-triazol-5-yl)phenyl)-6-methyl-5,6,7,8-tetrahydropyrido[3,4-d]pyrimidin-4(3H)-one (490 mg, 0.67 mmol) and but-3-en-2-amine (144 mg, 2.019 mmol) in anhydrous CH₃CN (12 mL) under N₂. The mixture was stirred at 110° C. for 5 h and then evaporated to dryness. The residue was dissolved in EA:isopropanol (85:15), washed with sat. aq. NH₄Cl and brine, and dried over Na₂SO₄. The solids were removed by filtration.

The filtrate was evaporated to dryness. The crude mixture was purified by chromatography on silica gel (0 to 10% CH$_3$OH in CH$_2$Cl$_2$) to give (6R)-7-(4-bromo-3-(trifluoromethyl)benzoyl)-2-(but-3-en-2-ylamino)-3-(4-(1-(4-methoxybenzyl)-4-methyl-1H-1,2,3-triazol-5-yl)phenyl)-6-methyl-5,6,7,8-tetrahydropyrido[3,4-d]pyrimidin-4(3H)-one (346 mg, 67%) as an orange oil. LC-MS: (C$_{37}$H$_{35}$BrF$_3$N$_7$O$_3$) [M+H]$^+$: 762.

A solution of (6R)-7-(4-bromo-3-(trifluoromethyl)benzoyl)-2-(but-3-en-2-ylamino)-3-(4-(1-(4-methoxybenzyl)-4-methyl-1H-1,2,3-triazol-5-yl)phenyl)-6-methyl-5,6,7,8-tetrahydropyrido[3,4-d]pyrimidin-4(3H)-one (346 mg, 0.45 mmol) in TFA (6.9 mL) was stirred at 50° C. under N$_2$ for 3 days. The mixture was evaporated to dryness and purified by chromatography on silica gel (0 to 10% CH$_3$OH in CH$_2$Cl$_2$), chiral SFC (40:60 IPA/CO$_2$ [0.2% v/v NH$_3$]) and chiral HPLC (30 to 100% CH$_3$CN in water [0.2% v/v NH$_3$]) to afford two diastereomers of 3, (6R)-7-(4-bromo-3-(trifluoromethyl)benzoyl)-2-(but-3-en-2-ylamino)-6-methyl-3-(4-(4-methyl-1H-1,2,3-triazol-5-yl)phenyl)-5,6,7,8-tetrahydropyrido[3,4-d]pyrimidin-4(3H)-one. The first eluting isomer (3a) was isolated as a white solid (14.5 mg, 5%). $^1$H-NMR (DMSO-d$_6$, 400 MHz, 80° C.) δ 1.17 (d, J=6.7 Hz, 3H), 1.22 (d, J=6.9 Hz, 3H), 2.30-2.40 (m, 1H), 2.48-2.53 (m, 3H), 2.53-2.62 (m, 1H), 4.05 (d, J=18.3 Hz, 1H), 4.24-4.75 (m, 3H), 4.93-5.08 (m, 2H), 5.33 (d, J=8.6 Hz, 1H), 5.78-5.90 (m, 1H), 7.36 (d, J=7.5 Hz, 2H), 7.67 (dd, J=8.3 Hz, 1.7 Hz, 1H), 7.85 (d, J=1.5 Hz, 1H), 7.90 (d, J=8.8 Hz, 2H), 7.98 (d, J=8.3 Hz, 1H) ppm. LC-MS: (C$_{29}$H$_{27}$BrF$_3$N$_7$O$_2$) 642/644 [M+H]$^+$. The second eluting isomer (3b) was isolated as a white solid (32 mg, 11%). $^1$H-NMR (DMSO-d$_6$, 400 MHz, 80° C.) δ 1.16 (d, J=7.0 Hz, 3H), 1.21 (d, J=6.7 Hz, 3H), 2.31-2.40 (m, 1H), 2.47-2.53 (m, 3H), 2.53-2.62 (m, 1H), 4.04 (d, J=18.8 Hz, 1H), 4.29-4.77 (m, 3H), 4.95-5.08 (m, 2H), 5.33 (d, J=8.1 Hz, 1H), 5.79-5.93 (m, 1H), 7.37 (d, J=7.9 Hz, 2H), 7.67 (dd, J=8.3 Hz, 1.6 Hz, 1H), 7.86 (d, J=1.7 Hz, 1H), 7.90 (d, J=8.7 Hz, 2H), 7.99 (d, J=8.0 Hz, 1H) ppm. LC-MS: (C$_{29}$H$_{27}$BrF$_3$N$_7$O$_2$) [M+H]$^+$: 642/644.

Example 4

Compound 4

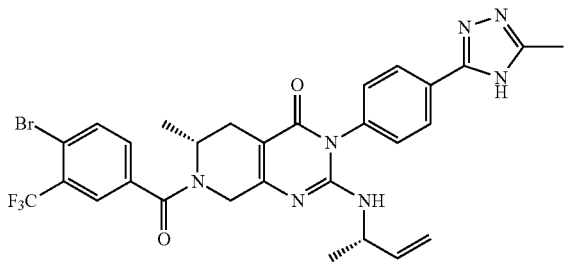 [SMILES: C=C[C@H](C)Nc1nc2c(c(=O)n1-c1ccc(-c3nnc(C)[nH]3)cc1)C[C@@H](C)N(C(=O)c1ccc(Br)c(C(F)(F)F)c1)C2]

NEt$_3$ (0.16 mL, 1.13 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (359 mg, 0.75 mmol) and 4-{4-[(4-methoxyphenyl)methyl]-5-methyl-4H-1,2,4-triazol-3-yl}aniline (266 mg, 0.903 mmol) in anhydrous CH$_3$CN (7.4 mL) under N$_2$. The mixture was stirred at 95° C. for 20 h. The mixture was evaporated to dryness and then purified by chromatography on silica gel (0 to 10% CH$_3$OH in CH$_2$Cl$_2$) to afford (R)-7-(4-bromo-3-(trifluoromethyl)benzoyl)-3-(4-(4-(4-methoxybenzyl)-5-methyl-4H-1,2,4-triazol-3-yl)phenyl)-6-methyl-2-thioxo-2,3,5,6,7,8-hexahydropyrido[3,4-d]pyrimidin-4(1H)-one (368 mg, 67%) as a yellow solid. LC-MS: (C$_{33}$H$_{28}$BrF$_3$N$_6$O$_3$S) [M+H]$^+$: 725/727.

Thiophosgene (0.12 mL, 1.38 mmol) was added to a solution of (R)-7-(4-bromo-3-(trifluoromethyl)benzoyl)-3-(4-(4-(4-methoxybenzyl)-5-methyl-4H-1,2,4-triazol-3-yl)phenyl)-6-methyl-2-thioxo-2,3,5,6,7,8-hexahydropyrido[3,4-d]pyrimidin-4(1H)-one (501 mg, 0.69 mmol) in anhydrous dioxane (5 mL) under N$_2$. The mixture was stirred at 100° C. for 1 h, then evaporated to dryness and purified by chromatography on silica gel (0 to 10% CH$_3$OH in CH$_2$Cl$_2$) to give (R)-7-(4-bromo-3-(trifluoromethyl)benzoyl)-2-chloro-3-(4-(4-(4-methoxybenzyl)-5-methyl-4H-1,2,4-triazol-3-yl)phenyl)-6-methyl-5,6,7,8-tetrahydropyrido[3,4-d]pyrimidin-4(3H)-one (272 mg, 54%) as a yellow oil. LC-MS: (C$_{33}$H$_{27}$BrClF$_3$N$_6$O$_3$) 729 [M+H]$^+$.

DIPEA (0.21 mL, 1.25 mmol) was added to a solution of (R)-7-(4-bromo-3-(trifluoromethyl)benzoyl)-2-chloro-3-(4-(4-(4-methoxybenzyl)-5-methyl-4H-1,2,4-triazol-3-yl)phenyl)-6-methyl-5,6,7,8-tetrahydropyrido[3,4-d]pyrimidin-4(3H)-one (130 mg, 0.18 mmol) and (2S)-but-3-en-2-amine hydrochloride (58 mg, 0.54 mmol) in anhydrous CH$_3$CN (3 mL) under N$_2$. The mixture was stirred at 100° C. for 18 h, and then evaporated to dryness. The residue was dissolved in EA:isopropanol (85:15), washed with sat. aq. NH$_4$Cl and brine and dried over Na$_2$SO$_4$. The solids were removed by filtration, and the filtrate was evaporated to dryness. The crude mixture was purified by flash chromatography on silica gel (0 to 10% CH$_3$OH in CH$_2$Cl$_2$) to give (R)-7-(4-bromo-3-(trifluoromethyl)benzoyl)-2-(((S)-but-3-en-2-yl)amino)-3-(4-(4-(4-methoxybenzyl)-5-methyl-4H-1,2,4-triazol-3-yl)phenyl)-6-methyl-5,6,7,8-tetrahydropyrido[3,4-d]pyrimidin-4(3H)-one (110 mg, 81%) as a beige solid. LC-MS: C$_{37}$H$_{35}$BrF$_3$N$_7$O$_3$ [M+H]$^+$: 762/764.

A solution of (R)-7-(4-bromo-3-(trifluoromethyl)benzoyl)-2-(((S)-but-3-en-2-yl)amino)-3-(4-(4-(4-methoxybenzyl)-5-methyl-4H-1,2,4-triazol-3-yl)phenyl)-6-methyl-5,6,7,8-tetrahydropyrido[3,4-d]pyrimidin-4(3H)-one (110 mg, 0.14 mmol) in TFA (2.2 mL) was stirred at 50° C. under N$_2$ for 24 h. After cooling to rt, the mixture was diluted with CH$_3$CN and evaporated to dryness. The crude mixture was purified by flash chromatography on silica gel (0 to 10% CH$_3$OH in CH$_2$Cl$_2$), followed by prep-HPLC (20 to 100% CH$_3$CN in water [0.2% v/v formic acid]) to give (R)-7-(4-bromo-3-(trifluoromethyl)benzoyl)-2-(((S)-but-3-en-2-yl)amino)-6-methyl-3-(4-(5-methyl-4H-1,2,4-triazol-3-yl)phenyl)-5,6,7,8-tetrahydropyrido[3,4-d]pyrimidin-4(3H)-one (4) (35 mg, 38%) as a white solid. $^1$H-NMR (DMSO-d$_6$, 400 MHz, 80° C.): 1.16 (d, J=7.0 Hz, 3H), 1.21 (d, J=6.7 Hz, 3H), 2.35-2.39 (m, 1H), 2.42 (s, 3H), 2.53-2.61 (m, 1H), 3.99-4.10 (m, 1H), 4.26-4.73 (m, 3H), 4.92-5.06 (m, 2H), 5.34 (d, J=8.3 Hz, 1H), 5.75-5.90 (m, 1H), 7.35 (d, J=7.7 Hz, 2H), 7.67 (dd, J=8.0 Hz, 1.7 Hz, 1H), 7.85 (d, J=1.7 Hz, 1H), 7.98 (d, J=8.2 Hz, 1H), 8.13 (d, J=8.8 Hz, 2H), 13.62 (br s, 1H) ppm. LC-MS: C$_{29}$H$_{27}$BrF$_3$N$_7$O$_2$ [M+H]$^+$: 642/644.

The compounds listed in Table 1 were made using similar procedures as those described for compounds 1 and 2.

TABLE 1

| Entry | Structure | ¹H-NMR | LC-MS [M + H]⁺ |
|---|---|---|---|
| 5 | 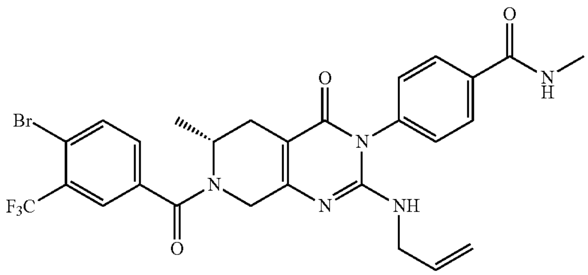 [SMILES: C=CCNc1nc2c(c(=O)n1-c1ccc(C(=O)NC)cc1)C[C@@H](C)N(C(=O)c1ccc(Br)c(C(F)(F)F)c1)C2] | (DMSO-d₆, 400 MHz, 80° C.): 1.20 (d, J = 6.9 Hz, 3H), 2.34 (d, J = 16.4 Hz, 1H), 2.53-2.61 (m, 1H), 2.84 (d, J = 4.9 Hz, 3H), 3.77-3.91 (m, 2H), 4.03 (d, J = 19.5 Hz, 1H), 4.51 (br s, 2H), 4.97-5.11 (m, 2H), 5.76-5.87 (m, 1H), 5.89-5.95 (m, 1H), 7.36 (d, J = 7.5 Hz, 2H), 7.64-7.69 (m, 1H), 7.84-7.86 (m, 1H), 7.95-8.03 (m, 3H), 8.28-8.40 (m, 1H) ppm | 604 |
| 6 | 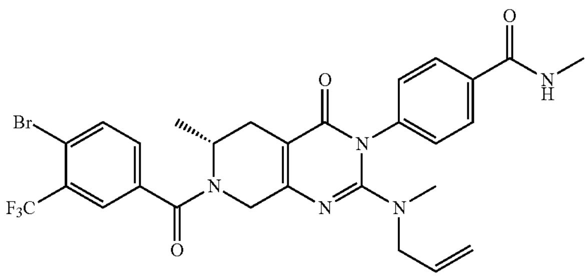 [SMILES: C=CCN(C)c1nc2c(c(=O)n1-c1ccc(C(=O)NC)cc1)C[C@@H](C)N(C(=O)c1ccc(Br)c(C(F)(F)F)c1)C2] | (DMSO-d₆, 400 MHz, 80° C.): 1.21 (d, J = 6.8 Hz, 3H), 2.38 (d, J = 16.6 Hz, 1H), 2.49 (s, 3H), 2.55-2.64 (m, 1H), 2.84 (d, J = 4.7 Hz, 3H), 3.64 (d, J = 6.1 Hz, 2H), 4.10 (d, J = 18.5 Hz, 1H), 4.36-4.77 (m, 2H), 5.02-5.10 (m, 2H), 5.38-5.55 (m, 1H), 7.43 (d, J = 8.4 Hz, 2H), 7.68 (dd, J = 8.1 Hz, 1.6 Hz, 1H), 7.86 (d, J = 1.5 Hz, 1H), 7.94 (d, J = 8.3 Hz, 2H), 8.00 (d, J = 8.3 Hz, 2H), 8.28-8.35 (m, 1H) ppm | 618 |
| 7 | 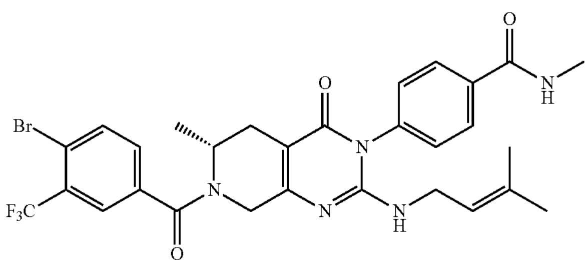 [SMILES: CNC(=O)c1ccc(-n2c(NCC=C(C)C)nc3c(c2=O)C[C@@H](C)N(C(=O)c2ccc(Br)c(C(F)(F)F)c2)C3)cc1] | (DMSO-d₆ 400 MHz, 80° C.): 1.21 (d, J = 6.5 Hz, 3H), 1.60 (s, 3H), 1.63 (s, 3H), 2.31-2.35 (m, 1H), 2.49-2.59 (m, 1H), 2.84 (d, J = 4.7 Hz, 3H), 3.71-3.86 (m, 2H), 4.01-4.05 (m, 1H), 4.48-4.53 (m, 2H), 5.09-5.12 (m, 1H), 5.75-5.78 (m, 1H), 7.33 (d, J = 7.9 Hz, 2H), 7.65-7.67 (m, 1H), 7.85 (d, J = 1.8 Hz, 1H), 7.97-8.00 (m, 3H), 8.31-8.33 (m, 1H) ppm | 632 |
| 8 | 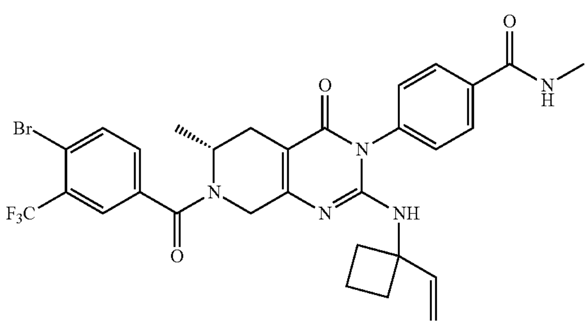 [SMILES: C=CC1(Nc2nc3c(c(=O)n2-c2ccc(C(=O)NC)cc2)C[C@@H](C)N(C(=O)c2ccc(Br)c(C(F)(F)F)c2)C3)CCC1] | (DMSO-d₆, 400 MHz, 80° C.): 1.18 (d, J = 6.5 Hz, 3H), 1.65-1.81 (m, 2H), 2.11-2.28 (m, 4H), 2.29-2.36 (m, 1H), 2.48-2.58 (m, 1H), 2.84 (d, J = 4.8 Hz, 3H), 3.92-3.96 (m, 1H), 4.38-4.56 (m, 2H), 4.99-5.02 (m, 1H), 5.09-5.13 (m, 1H), 5.55 (s, 1H), 6.15-6.23 (m, 1H), 7.38 (d, J = 8.3 Hz, 2H), 7.64-7.66 (m, 1H), 7.84 (d, J = 1.6 Hz, 1H), 7.97-8.00 (m, 3H), 8.31-8.33 (m, 1H) ppm | 644 |
| 10a | 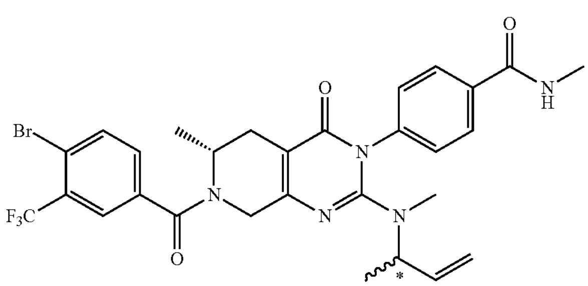 [SMILES: C=CC(C)N(C)c1nc2c(c(=O)n1-c1ccc(C(=O)NC)cc1)C[C@@H](C)N(C(=O)c1ccc(Br)c(C(F)(F)F)c1)C2] | (DMSO-d₆, 400 MHz, 80° C.): 1.00 (d, J = 6.8 Hz, 3H), 1.20 (d, J = 6.8 Hz, 3H), 2.28 (s, 3H), 2.37 (d, J = 17.1 Hz, 1H), 2.54-2.63 (m, 1H), 2.83 (d, J = 4.8 Hz, 3H), 4.09 (d, J = 19.0 Hz, 1H), 4.38-4.80 (m, 3H), 4.98-5.10 (m, 2H), 5.60-5.72 (m, 1H), 7.44 (d, J = 8.0 Hz, 2H), 7.67 (dd, J = 8.1 Hz, 1.7 Hz, 1H), 7.85 (d, J = 1.9 Hz, 1H), 7.92 (d, J = 8.6 Hz, 2H), 7.98 (d, J = 8.3 Hz, 1H), 8.26-8.34 (m, 1H) ppm | 632 |

TABLE 1-continued

| Entry | Structure | ¹H-NMR | LC-MS [M + H]⁺ |
|---|---|---|---|
| 10b | 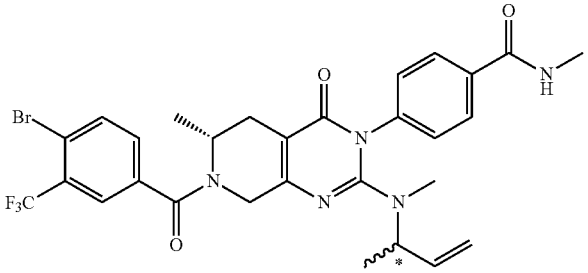 [SMILES: C=CC(C)N(C)c1nc2c(c(=O)n1-c1ccc(C(=O)NC)cc1)C[C@@H](C)N(C(=O)c1ccc(Br)c(C(F)(F)F)c1)C2] | (DMSO-d₆, 400 MHz, 80° C.): 1.00 (d, J = 6.8 Hz, 3H), 1.20 (d, J = 6.8 Hz, 3H), 2.28 (s, 3H), 2.37 (d, J = 17.1 Hz, 1H), 2.54-2.63 (m, 1H), 2.83 (d, J = 4.8 Hz, 3H), 4.09 (d, J = 19.0 Hz, 1H), 4.38-4.80 (m, 3H), 4.98-5.10 (m, 2H), 5.60-5.72 (m, 1H), 7.44 (d, J = 8.0 Hz, 2H), 7.67 (dd, J = 8.1 Hz, 1.7 Hz, 1H), 7.85 (d, J = 1.9 Hz, 1H), 7.92 (d, J = 8.6 Hz, 2H), 7.98 (d, J = 8.3 Hz, 1H), 8.26-8.34 (m, 1H) ppm | 632 |
| 11a | 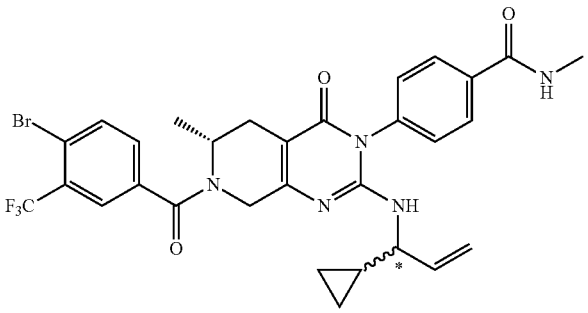 [SMILES: C=CC(Nc1nc2c(c(=O)n1-c1ccc(C(=O)NC)cc1)C[C@@H](C)N(C(=O)c1ccc(Br)c(C(F)(F)F)c1)C2)C1CC1] | (DMSO-d₆, 400 MHz, 80° C.): 0.17-0.31 (m, 2H), 0.32-0.48 (m, 2H), 0.93-1.05 (m, 1H), 1.20 (d, J = 6.6 Hz, 3H), 2.27-2.38 (m, 1H), 2.53-2.60 (m, 1H), 2.78-2.88 (m, 3H), 3.90-4.09 (m, 2H), 4.24-4.76 (m, 2H), 4.95-5.10 (m, 2H), 5.30-5.41 (m, 1H), 5.77-5.91 (m, 1H), 7.30-7.43 (m, 2H), 7.61-7.69 (m, 1H), 7.84 (s, 1H), 7.93-8.04 (m, 3H), 8.30-8.41 (m, 1H) ppm | 644 |
| 11b | 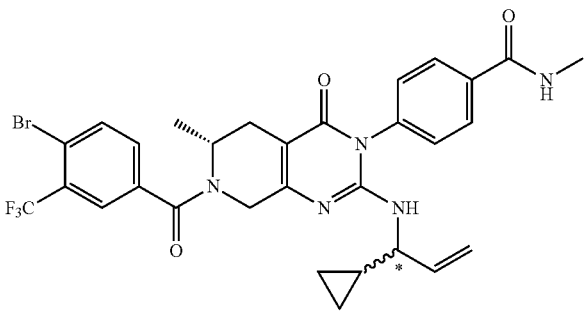 [SMILES: C=CC(Nc1nc2c(c(=O)n1-c1ccc(C(=O)NC)cc1)C[C@@H](C)N(C(=O)c1ccc(Br)c(C(F)(F)F)c1)C2)C1CC1] | (DMSO-d₆, 400 MHz, 80° C.): 0.16-0.31 (m, 2H), 0.31-0.48 (m, 2H), 0.93-1.05 (m, 1H), 1.19 (d, J = 6.7 Hz, 3H), 2.28-2.38 (m, 1H), 2.53-2.62 (m, 1H), 2.81-2.89 (m, 3H), 3.91-4.09 (m, 2H), 4.25-4.75 (m, 2H), 4.96-5.14 (m, 2H), 5.32-5.43 (m, 1H), 5.78-5.92 (m, 1H), 7.31-7.44 (m, 2H), 7.63-7.70 (m, 1H), 7.84 (s, 1H), 7.95-8.04 (m, 3H), 8.31-8.41 (m, 1H) ppm | 644 |
| 15 | 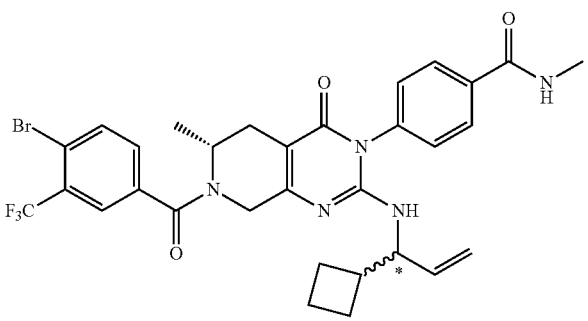 [SMILES: C=CC(Nc1nc2c(c(=O)n1-c1ccc(C(=O)NC)cc1)C[C@@H](C)N(C(=O)c1ccc(Br)c(C(F)(F)F)c1)C2)C1CCC1] | (DMSO-d₆, 400 MHz, 80° C.): 1.14-1.34 (m, 3H), 1.56-1.96 (m, 7H), 2.30-2.40 (m, 2H), 2.79-2.-88 (m, 3H), 3.96-4.12 (m, 1H), 4.27-4.84 (m, 3H), 4.95-5.15 (m, 3H), 5.64-5.77 (m, 1H), 7.30-7.41 (m, 2H), 7.63-7.70 (m, 1H), 7.83-7.88 (m, 1H), 7.95-8.06 (m, 3H), 8.35 (br s, 1H) ppm. | 658 |
| 16 | 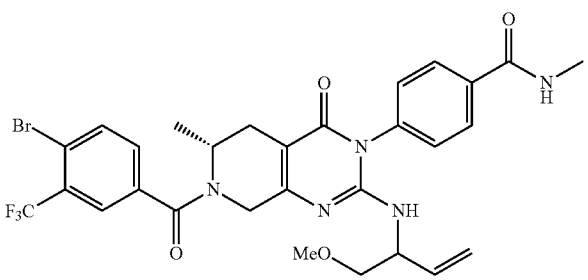 [SMILES: C=CC(COC)Nc1nc2c(c(=O)n1-c1ccc(C(=O)NC)cc1)C[C@@H](C)N(C(=O)c1ccc(Br)c(C(F)(F)F)c1)C2] | (DMSO-d₆, 400 MHz, 80° C.): 1.21 (d, J = 6.9 Hz, 3H), 2.36 (d, J = 16.6 Hz, 1H), 2.50-2.62 (m, 1H), 2.85 (d, J = 4.5 Hz, 3H), 3.20 (s, 3H), 3.31-3.42 (m, 2H), 3.95-4.13 (m, 1H), 4.29-4.71 (m, 2H), 4.72-4.83 (m, 1H), 5.03-5.17 (m, 2H), 5.24 (d, J = 8.3 Hz, 1H), 5.72-5.88 (m, 1H), 7.28-7.52 (m, 2H), 7.68 (dd, J = 6.9 Hz, 1.5 Hz, 1H), 7.86 (d, J = 1.5 Hz, 1H), 7.92-8.07 (m, 3H), 8.32-8.43 (m, 1H) ppm. | 648 |

Example 5

Compound 9

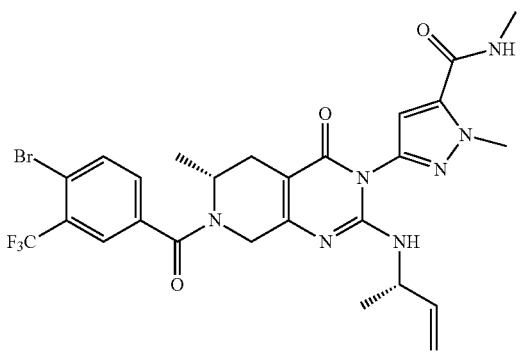 [SMILES: C=C[C@H](C)Nc1nc2c(c(=O)n1-c1cc(C(=O)NC)n(C)n1)C[C@@H](C)N(C(=O)c1ccc(Br)c(C(F)(F)F)c1)C2]

NEt$_3$ (0.68 mL, 4.90 mmol) was added to a solution of 3-amino-N,1-dimethyl-1H-pyrazole-5-carboxamide (0.66 g, 4.25 mmol) and ethyl (R)-1-(4-bromo-3-(trifluoromethyl) benzoyl)-5-isothiocyanato-2-methyl-1,2,3,6-tetrahydropyridine-4-carboxylate (1.56 g, 3.27 mmol) in anhydrous CH$_3$CN (25 mL) under N$_2$. The mixture was stirred at 80° C. for 18 h, evaporated to dryness and purified by chromatography on silica gel (0 to 6% CH$_3$OH in CH$_2$Cl$_2$) to give (R)-3-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N,1-dimethyl-1H-pyrazole-5-carboxamide (0.93 g, 49%) as a yellow solid. LC-MS: (C$_{22}$H$_{20}$BrF$_3$N$_6$O$_3$S) [M+H]$^+$: 585/587.

Thiophosgene (0.13 mL, 1.65 mmol) was added to a solution of (R)-3-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N,1-dimethyl-1H-pyrazole-5-carboxamide (965 mg, 1.65 mmol) in anhydrous dioxane (20 mL) under N$_2$ and stiffed at 110° C. for 1 h. The mixture was evaporated to dryness and purified by chromatography on silica gel (0 to 7% CH$_3$OH in CH$_2$Cl$_2$) to afford (R)-3-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N,1-dimethyl-1H-pyrazole-5-carboxamide (0.67 g, 69%) as a yellow solid. LC-MS: (C$_{22}$H$_{19}$BrClF$_3$N$_6$O$_3$) [M+H]$^+$: 589.

DIPEA (0.39 mL, 2.38 mmol) was added to a solution of (R)-3-(7-(4-bromo-3-(trifluoromethyl)benzoyl)-2-chloro-6-methyl-4-oxo-5,6,7,8-tetrahydropyrido[3,4-d]pyrimidin-3 (4H)-yl)-N,1-dimethyl-1H-pyrazole-5-carboxamide (200 mg, 0.34 mmol) and (2S)-but-3-en-2-amine hydrochloride (110 mg, 1.02 mmol) in anhydrous CH$_3$CN (4 mL) under N$_2$. The mixture was stirred at 110° C. for 2 h. After cooling to rt, the mixture was diluted with water. The resulting precipitate was collected by filtration and purified by chromatography on silica gel (0 to 10% CH$_3$OH in CH$_2$Cl$_2$) to afford 3-((R)-7-(4-bromo-3-(trifluoromethyl)benzoyl)-2-(((S)-but-3-en-2-yl)amino)-6-methyl-4-oxo-5,6,7,8-tetrahydropyrido[3,4-d]pyrimidin-3(4H)-yl)-N,1-dimethyl-1H-pyrazole-5-carboxamide (9) (93 mg, 44%) as a white solid. $^1$H-NMR (DMSO-d$_6$, 400 MHz, 80° C.): 1.18-1.20 (m, 6H), 2.31-2.35 (m, 1H), 2.52-2.58 (m, 1H), 2.80 (d, J=4.6 Hz, 3H), 3.97-4.05 (m, 1H), 4.11 (s, 3H), 4.49 (br s, 1H), 4.65-4.70 (m, 1H), 4.98-5.09 (m, 2H), 5.81-5.90 (m, 1H), 5.97 (d, J=7.6 Hz, 1H), 6.82 (s, 1H), 7.66 (dd, J=8.0 Hz, 2.0 Hz, 1H), 7.85 (d, J=2.0 Hz, 1H), 7.98 (d, J=8.0 Hz, 1H), 8.31-8.32 (m, 1H) ppm. LC-MS: (C$_{26}$H$_{27}$BrF$_3$N$_7$O$_3$) [M+H]$^+$: 622/624.

Example 6

Compound 12

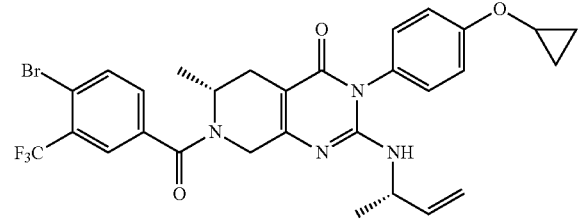 [SMILES: C=C[C@H](C)Nc1nc2c(c(=O)n1-c1ccc(OC3CC3)cc1)C[C@@H](C)N(C(=O)c1ccc(Br)c(C(F)(F)F)c1)C2]

A mixture of 4-fluoronitrobenzene (500 mg, 3.54 mmol), cyclopropanol (0.27 mL, 4.25 mmol) and K$_2$CO$_3$ (1.96 g, 14.16 mmol) in anhydrous DMF (10 mL) under N$_2$ was stirred at 100° C. for 4 d. After cooling to rt, the mixture was diluted with water and extracted with EA (3×). The combined organic phases were washed with brine and dried over Na$_2$SO$_4$. The solids were removed by filtration, and the filtrate was evaporated to dryness. The crude mixture was purified by chromatography on silica gel (0 to 10% EA in CyH) to give 1-cyclopropoxy-4-nitrobenzene (451 mg, 71%) as a yellow solid. $^1$H-NMR (DMSO-d$_6$, 400 MHz): 0.70-0.75 (m, 2H), 0.84-0.89 (m, 2H), 4.01-4.06 (m, 1H), 7.26 (d, J=9.6 Hz, 2H), 8.22 (d, J=9.6 Hz, 1H) ppm. LC-MS: (C$_9$H$_9$NO$_3$) [M+H]$^+$: 180.

Fe (768 mg, 13.76 mmol) was added to a solution of 1-cyclopropoxy-4-nitrobenzene (493 mg, 2.75 mmol) and NH$_4$Cl (736 mg, 13.76 mmol) in ethanol (2.5 mL) and water (2.5 mL). The mixture was stirred at 80° C. for 5 h. After cooling to rt, the mixture was filtered over Celite. The filtrate was diluted in EA, washed with brine and dried over Na$_2$SO$_4$. The solids were removed by filtration, and the filtrate was evaporated to dryness to give 4-cyclopropoxyaniline (341 mg, 83%), which was used without purification in the next step. $^1$H-NMR (DMSO-d$_6$, 400 MHz): 0.54-0.60 (m, 2H), 0.64-0.69 (m, 2H), 3.62-3.68 (m, 1H), 4.59 (s, 2H), 6.50 (d, J=8.8 Hz, 2H), 6.73 (d, J=8.8 Hz, 1H) ppm.

NEt$_3$ (0.95 mL, 0.50 mmol) was added to a solution of 4-cyclopropoxyaniline (75 mg, 0.50 mmol) and ethyl (R)-1-(4-bromo-3-(trifluoromethyl)benzoyl)-5-isothiocyanato-2-methyl-1,2,3,6-tetrahydropyridine-4-carboxylate (218 mg, 0.46 mmol) in anhydrous CH$_3$CN (3 mL) under N$_2$. The mixture was stirred at 80° C. for 4 h. The mixture was evaporated to dryness and purified by flash chromatography on silica gel (0 to 2% CH$_3$OH in CH$_2$Cl$_2$) to give (R)-7-(4-bromo-3-(trifluoromethyl)benzoyl)-3-(4-cyclopropoxyphenyl)-6-methyl-2-thioxo-2,3,5,6,7,8-hexahydropyrido[3,4-d]pyrimidin-4(1H)-one (157 mg, 59%) as a yellow solid. LC-MS: (C$_{25}$H$_{21}$BrF$_3$N$_3$O$_3$S) [M+H]$^+$: 580/582.

Thiophosgene (0.021 mL, 0.27 mmol) was added to a solution of (R)-7-(4-bromo-3-(trifluoromethyl)benzoyl)-3-(4-cyclopropoxyphenyl)-6-methyl-2-thioxo-2,3,5,6,7,8-hexahydropyrido[3,4-d]pyrimidin-4(1H)-one (157 mg, 0.27 mmol) in anhydrous dioxane (3.5 mL) under N$_2$. The mixture was stirred at 110° C. for 7 h, evaporated to dryness and purified by flash chromatography on silica gel (0 to 20% EA in CH$_2$Cl$_2$) to afford (R)-7-(4-bromo-3-(trifluoromethyl) benzoyl)-2-chloro-3-(4-cyclopropoxyphenyl)-6-methyl-5,6, 7,8-tetrahydropyrido[3,4-d]pyrimidin-4(3H)-one (88 mg, 56%) as a light-yellow oil. LC-MS: $(C_{25}H_{20}BrClF_3N_3O_3)$ [M+H]$^+$: 584.

DIPEA (0.17 mL, 1.06 mmol) was added to a solution of (R)-7-(4-bromo-3-(trifluoromethyl)benzoyl)-2-chloro-3-(4-cyclopropoxyphenyl)-6-methyl-5,6,7,8-tetrahydropyrido[3,4-d]pyrimidin-4(3H)-one (88 mg, 0.15 mmol) and (2S)-but-3-en-2-amine hydrochloride (49 mg, 0.45 mmol) in anhydrous CH$_3$CN (2 mL) under N$_2$ and stiffed at 110° C. for 3 days. After cooling to rt, the mixture was diluted with water. The resulting precipitate was collected by filtration and purified by flash chromatography on silica gel (0 to 1% CH$_3$OH in CH$_2$Cl$_2$) to give (R)-7-(4-bromo-3-(trifluoromethyl)benzoyl)-2-((S)-but-3-en-2-ylamino)-3-(4-cyclopropoxyphenyl)-6-methyl-5,6,7,8-tetrahydropyrido[3,4-d]pyrimidin-4(3H)-one (12) (47 mg, 50%) as a white solid. $^1$H-NMR (DMSO-d$_6$, 400 MHz, 80° C.): 0.74-0.77 (m, 2H), 0.82-0.89 (m, 2H), 1.16-1.26 (m, 6H), 2.33-2.40 (m, 2H), 2.52-2.72 (m, 1H), 3.91-3.96 (m, 1H), 4.02-4.10 (m, 1H), 4.52 (br s, 1H), 4.65-4.70 (m, 1H), 4.96-5.03 (m, 2H), 5.15-5.19 (m, 1H), 5.80-5.90 (m, 1H), 7.22-7.25 (m, 4H), 7.66-7.72 (m, 1H), 7.86-7.89 (m, 1H), 7.98-8.04 (m, 1H) ppm. LC-MS: $(C_{29}H_{28}BrF_3N_4O_3)$ [M+H]$^+$: 617/619.

Example 7

Compound 13

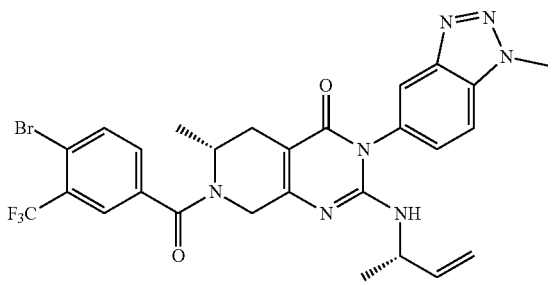 [SMILES: C=C[C@H](C)Nc1nc2c(c(=O)n1-c1ccc3c(c1)nnn3C)C[C@@H](C)N(C(=O)c1ccc(Br)c(C(F)(F)F)c1)C2]

NEt$_3$ (0.22 mL, 1.57 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (500 mg, 1.05 mmol) and 1-methyl-1H-1,2,3-benzotriazol-5-amine (186 mg, 1.26 mmol) in anhydrous CH$_3$CN (10 mL) under N$_2$. The mixture was stirred at 95° C. for 2 h. The mixture was evaporated to dryness and purified by chromatography on silica gel (0 to 10% CH$_3$OH in CH$_2$Cl$_2$) to afford (R)-7-(4-bromo-3-(trifluoromethyl)benzoyl)-6-methyl-3-(1-methyl-1H-benzo[d][1,2,3]triazol-5-yl)-2-thioxo-2,3,5,6,7,8-hexahydropyrido[3,4-d]pyrimidin-4(1H)-one (583 mg, 96%) as an orange solid. LC-MS: $C_{23}H_{18}BrF_3N_6O_2S$ [M+H]$^+$: 579/581.

Thiophosgene (0.11 mL, 1.22 mmol) was added to a solution of (R)-7-(4-bromo-3-(trifluoromethyl)benzoyl)-6-methyl-3-(1-methyl-1H-benzo[d][1,2,3]triazol-5-yl)-2-thioxo-2,3,5,6,7,8-hexahydropyrido[3,4-d]pyrimidin-4(1H)-one (590 mg, 1.02 mmol) in anhydrous dioxane (7 mL) under N$_2$. The mixture was stirred at 100° C. for 30 min. The mixture was then evaporated to dryness and purified by chromatography on silica gel (0 to 10% CH$_3$OH in CH$_2$Cl$_2$) to give (R)-7-(4-bromo-3-(trifluoromethyl)benzoyl)-2-chloro-6-methyl-3-(1-methyl-1H-benzo[d][1,2,3]triazol-5-yl)-5,6,7,8-tetrahydropyrido[3,4-d]pyrimidin-4(3H)-one (533 mg, 90%) as an orange solid. LC-MS: $C_{23}H_{17}BrClF_3N_6O_2$ [M+H]$^+$: 583.

DIPEA (0.4 mL, 2.41 mmol) was added to a solution of (R)-7-(4-bromo-3-(trifluoromethyl)benzoyl)-2-chloro-6-methyl-3-(1-methyl-1H-benzo[d][1,2,3]triazol-5-yl)-5,6,7,8-tetrahydropyrido[3,4-d]pyrimidin-4(3H)-one (200 mg, 0.34 mmol) and (2S)-but-3-en-2-amine hydrochloride (111 mg, 1.03 mmol) in anhydrous CH$_3$CN (6 mL) under N$_2$. The mixture was stirred at 100° C. for 2 days, and then evaporated to dryness. The resulting solid was triturated in CH$_3$CN and purified by chromatography on silica gel (0 to 10% CH$_3$OH in CH$_2$Cl$_2$) to give (R)-7-(4-bromo-3-(trifluoromethyl)benzoyl)-2-(((S)-but-3-en-2-yl)amino)-6-methyl-3-(1-methyl-1H-benzo[d][1,2,3]triazol-5-yl)-5,6,7,8-tetrahydropyrido[3,4-d]pyrimidin-4(3H)-one (13) (112 mg, 53%) as a white solid. $^1$H-NMR (DMSO-d$_6$, 400 MHz, 80° C.): 1.08-1.17 (m, 3H), 1.23 (d, J=6.8 Hz, 3H), 2.31-2.40 (m, 1H), 2.51-2.62 (m, 2H), 3.99-4.12 (m, 1H), 4.37 (s, 3H), 4.39-4.77 (m, 2H), 4.89-5.09 (m, 2H), 5.56 (d, J=8.0 Hz, 1H), 5.72-5.87 (m, 1H), 7.32-7.44 (m, 1H), 7.67 (dd, J=8.2 Hz, 1.9 Hz, 1H), 7.85 (d, J=1.6 Hz, 1H), 7.95-8.05 (m, 3H) ppm. LC-MS: $C_{27}H_{25}BrF_3N_7O_2$ [M+H]$^+$: 616/618.

Example 8

Compound 14

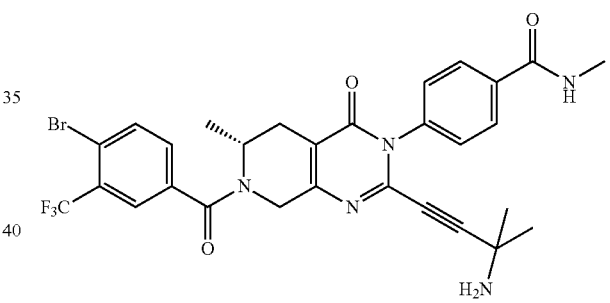

DIPEA (1.13 mL, 6.85 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (200 mg, 0.34 mmol) and 2-methyl-3-butyn-2-amine (285 mg, 0.36 mL, 3.43 mmol) in anhydrous CH$_3$CN (3.4 mL) under N$_2$. The mixture was stirred at 170° C. for 28 h. After cooling to rt, the mixture was diluted with EA and washed with water, HCl (aq., 1M) and brine (2×) and dried over Na$_2$SO$_4$. The solids were removed by filtration, and the filtrate was evaporated to dryness. The crude mixture was purified by prep-HPLC [15 to 100% CH$_3$CN in water (25 mM ammonium acetate)] then by chromatography on silica gel (0 to 5% CH$_3$OH in CH$_2$Cl$_2$) to give (R)-4-(2-(3-amino-3-methylbut-1-yn-1-yl)-7-(4-bromo-3-(trifluoromethyl)benzoyl)-6-methyl-4-oxo-5,6,7,8-tetrahydropyrido[3,4-d]pyrimidin-3(4H)-yl)-N-methylbenzamide (14) (43 mg) as a white solid. $^1$H-NMR (DMSO-d$_6$, 400 MHz, 25° C.): 1.10-1.32 (m, 9H), 2.24-2.36 (m, 1H), 2.52 (s, 1H), 2.80 (d, J=4.0 Hz, 3H), 4.07 (br s, 1H), 4.38 (br s, 1H), 4.63 (br s, 1H), 4.92 (br s, 1H), 5.41 (br s, 1H), 7.37 (d, J=8.4 Hz, 2H), 7.68 (br s, 1H), 7.87 (d, J=8.4 Hz, 3H), 8.02 (d, J=8.4 Hz, 1H), 8.50 (q, J=4.6 Hz, 1H) ppm. LC-MS: $C_{29}H_{27}BrF_3N_5O_3$ [M+H]$^+$: 630/632.

Example 9

Compound 17

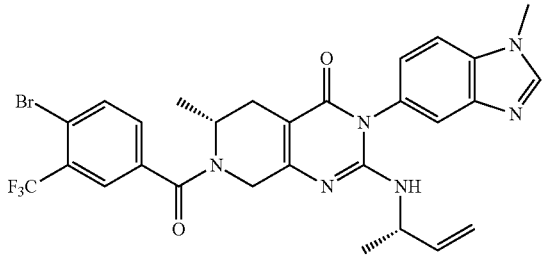 [SMILES: C=C[C@H](C)Nc1nc2c(c(=O)n1-c1ccc3c(c1)ncn3C)C[C@@H](C)N(C(=O)c1ccc(Br)c(C(F)(F)F)c1)C2]

Triethylamine (159 mg, 1.57 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (500 mg, 1.048 mmol) and 1-methyl-1H-1,3-benzodiazol-5-amine (185 mg, 1.26 mmol) in anhydrous $CH_3CN$ (10 mL) under $N_2$. The mixture was stirred at 95° C. for 1 h. The mixture was evaporated to dryness and purified by chromatography on silica gel (0 to 5% $CH_3OH$ in $CH_2Cl_2$) to afford (R)-7-(4-bromo-3-(trifluoromethyl)benzoyl)-6-methyl-3-(1-methyl-1H-benzo[d]imidazol-5-yl)-2-thioxo-2,3,5,6,7,8-hexahydropyrido[3,4-d]pyrimidin-4(1H)-one (414 mg, 68%) as a yellow solid. LC-MS: $C_{24}H_{19}BrF_3N_5O_2S$ [M+H]$^+$: 578.

Sulfuryl chloride (116 mg, 0.07 mL, 0.86 mmol) was added to a solution of (R)-7-(4-bromo-3-(trifluoromethyl)benzoyl)-6-methyl-3-(1-methyl-1H-benzo[d]imidazol-5-yl)-2-thioxo-2,3,5,6,7,8-hexahydropyrido[3,4-d]pyrimidin-4(1H)-one (250 mg, 0.43 mmol) in chloroform (4.5 mL) under $N_2$. The mixture was stirred for 5 min, and then evaporated to dryness to give (R)-7-(4-bromo-3-(trifluoromethyl)benzoyl)-2-chloro-6-methyl-3-(1-methyl-1H-benzo[d]imidazol-5-yl)-5,6,7,8-tetrahydropyrido[3,4-d]pyrimidin-4(3H)-one (249 mg, 99%) as a yellow solid, which was used as such in the next step. LC-MS: $C_{24}H_{18}BrClF_3N_5O_2$ [M+H]$^+$: 580.

Triethylamine (304 mg, 3.00 mmol) was added to a solution of (R)-7-(4-bromo-3-(trifluoromethyl)benzoyl)-2-chloro-6-methyl-3-(1-methyl-1H-benzo[d]imidazol-5-yl)-5,6,7,8-tetrahydropyrido[3,4-d]pyrimidin-4(3H)-one (249 mg, 0.43 mmol) and (S)-but-3-en-2-amine hydrochloride (276 mg, 2.58 mmol) in anhydrous $CH_3CN$ (7.50 mL) under $N_2$. The mixture was heated to 110° C. and stirred for 2 days. After cooling to rt, the mixture was evaporated to dryness. The residue was dissolved in EA and washed with sat. aq. $NH_4Cl$ and brine and dried over $Na_2SO_4$. The solids were removed by filtration. The filtrate was evaporated to dryness. The crude mixture was purified by silica gel chromatography (0 to 10% $CH_3OH$ in $CH_2Cl_2$) and HPLC (XBridge C18 [19 mm×250 mm, 5 um], 0 to 10% $CH_3CN$ in water (0.2% v/v formic acid)) to give (R)-7-(4-bromo-3-(trifluoromethyl)benzoyl)-2-(((S)-but-3-en-2-yl)amino)-6-methyl-3-(1-methyl-1H-benzo[d]imidazol-5-yl)-5,6,7,8-tetrahydropyrido[3,4-d]pyrimidin-4(3H)-one (17) (27 mg, 10%) as a white solid. $^1$H-NMR (DMSO, 400 MHz, 80° C.): 1.09-1.34 (m, 6H), 2.31-2.42 (m, 1H), 2.57-2.62 (m, 1H), 3.91-4.00 (m, 3H), 3.99-4.14 (m, 1H), 4.32-4.75 (m, 3H), 4.88-5.25 (m, 3H), 5.72-5.92 (m, 1H), 7.05-7.22 (m, 1H), 7.51-7.82 (m, 3H), 7.84-8.10 (m, 2H), 8.23-8.47 (m, 1H) ppm. LC-MS: $C_{28}H_{26}BrF_3N_6O_2$ [M+H]$^+$: 615.

Example 10

Compound 18

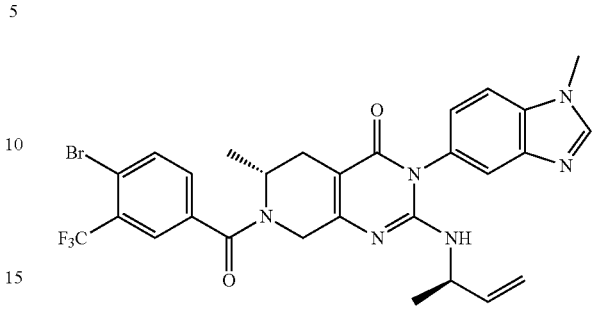

(R)-7-(4-bromo-3-(trifluoromethyl)benzoyl)-2-(((R)-but-3-en-2-yl)amino)-6-methyl-3-(1-methyl-1H-benzo[d]imidazol-5-yl)-5,6,7,8-tetrahydropyrido[3,4-d]pyrimidin-4(3H)-one (18) was synthesized using an analogous procedure to that described for (R)-7-(4-bromo-3-(trifluoromethyl)benzoyl)-2-(((S)-but-3-en-2-yl)amino)-6-methyl-3-(1-methyl-1H-benzo[d]imidazol-5-yl)-5,6,7,8-tetrahydropyrido[3,4-d]pyrimidin-4(3H)-one to afford a yellow solid (38 mg, 9%). $^1$H-NMR (DMSO-$d_6$, 400 MHz, 80° C.): 1.11 (d, J=6.5 Hz, 3H), 1.22 (d, J=6.7 HZ, 3H), 2.32-2.39 (m, 1H), 2.52-2.53 (m, 1H), 2.54-2.62 (m, 1H), 3.90 (s, 3H), 3.99-4.09 (m, 1H), 4.52 (br. s., 1H), 4.62-4.71 (m, 1H), 4.91-5.05 (m, 2H), 5.10-5.19 (m, 1H), 5.73-5.88 (m, 1H), 7.06-7.17 (m, 1H), 7.56 (d, J=16.8 Hz, 1H), 7.68 (dd, J=8.0 Hz, 1.7 Hz, 1H), 7.72 (d, J=8.5 Hz, 1H), 7.86 (d, J=1.6 Hz, 1H), 7.99 (d, J=8.0 Hz, 1H), 8.26 (s, 1H) ppm. LC-MS: $C_{28}H_{26}BrF_3N_6O_2$ [M+H]$^+$: 615.

Example 11

Compound 19

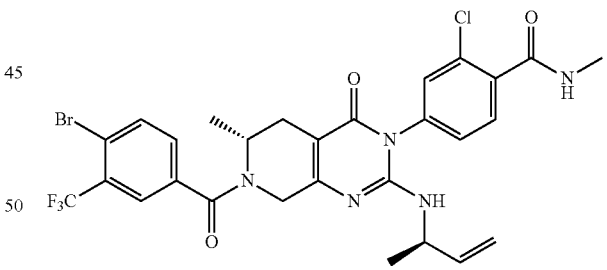

$NEt_3$ (0.57 mL, 4.08 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1.3 g, 2.72 mmol) and 4-amino-2-chloro-N-methylbenzamide (0.55 g, 3 mmol) in anhydrous $CH_3CN$ (20 mL) under $N_2$. The mixture was stirred at 80° C. for 22 h. The mixture was evaporated to dryness and purified by chromatography on silica gel (0 to 2.5% $CH_3OH$ in $CH_2Cl_2$) to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-2-chloro-N-methylbenzamide (660 mg, 39%) as a yellow solid. LC-MS: $C_{24}H_{19}BrF_3N_4O_3S$ [M+H]$^+$: 615.

Thiophosgene (0.164 mL, 2.14 mmol) was added to a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-2-chloro-N-methylbenzamide (660 mg, 1.07 mmol) in anhydrous dioxane (13 mL) under N$_2$. The mixture was stiffed at 110° C. for 22 h. The mixture was evaporated to dryness and purified by chromatography on silica gel (0 to 100% EA in CH$_2$Cl$_2$) to give (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-2-chloro-N-methylbenzamide (353 mg, 53%) as a beige solid. LC-MS: C$_{24}$H$_{18}$BrCl$_2$F$_3$N$_4$O$_2$ [M+H]$^+$: 619.

DIPEA (0.65 mL, 3.96 mmol) was added to a solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-2-chloro-N-methylbenzamide (350 mg, 0.57 mmol) and (2R)-but-3-en-2-amine hydrochloride (183 mg, 1.7 mmol) in anhydrous CH$_3$CN (6.5 mL) under N$_2$. The mixture was stirred at 110° C. for 22 h. After cooling to rt, the mixture was diluted with water and extracted with EA (3×). The combined organic phases were washed with brine and dried over Na$_2$SO$_4$. The solids were removed by filtration. The filtrate was evaporated to dryness. The crude mixture was purified by chromatography on silica gel (0 to 3% CH$_3$OH in CH$_2$Cl$_2$) to give 4-((R)-7-(4-bromo-3-(trifluoromethyl)benzoyl)-2-(((R)-but-3-en-2-yl)amino)-6-methyl-4-oxo-5,6,7,8-tetrahydropyrido[3,4-d]pyrimidin-3(4H)-yl)-2-chloro-N-methylbenzamide (19) (242 mg, 65%) as a yellow solid. $^1$H-NMR (DMSO-d$_6$, 400 MHz, 80° C.): 1.18 (m, 6H), 2.32-2.36 (m, 1H), 2.50-2.58 (m, 1H), 2.81 (d, J=4.7 Hz, 3H), 4.00-4.05 (m, 1H), 4.52 (br s, 2H), 4.67-4.72 (m, 1H), 4.98-5.08 (m, 2H), 5.68 (d, J=8.0 Hz, 1H) 5.81-5.90 (m, 1H), 7.30 (d, J=8.0 Hz, 1H), 7.47 (br s, 1H), 7.59 (d, J=8.0 Hz, 1H), 7.66 (dd, J=8.0 Hz, J=2.0 Hz, 1H), 7.84 (d, J=2.0 Hz, 1H), 7.98 (d, J=8.0 Hz, 1H), 8.18-8.22 (m, 1H) ppm. LC-MS: C$_{28}$H$_{26}$BrClF$_3$N$_5$O$_3$ [M+H]$^+$: 654.

Example 12

Compound 20

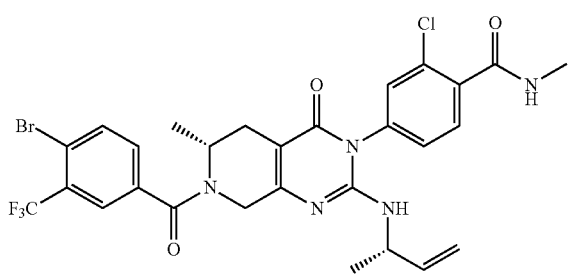 [SMILES: C=C[C@H](C)Nc1nc2c(c(=O)n1-c1ccc(C(=O)NC)c(Cl)c1)C[C@@H](C)N(C(=O)c1ccc(Br)c(C(F)(F)F)c1)C2]

4-((R)-7-(4-bromo-3-(trifluoromethyl)benzoyl)-2-(((S)-but-3-en-2-yl)amino)-6-methyl-4-oxo-5,6,7,8-tetrahydropyrido[3,4-d]pyrimidin-3(4H)-yl)-2-chloro-N-methylbenzamide (20) was synthesized using an analogous procedure to that described for 4-((R)-7-(4-bromo-3-(trifluoromethyl)benzoyl)-2-(((R)-but-3-en-2-yl)amino)-6-methyl-4-oxo-5,6,7,8-tetrahydropyrido[3,4-d]pyrimidin-3(4H)-yl)-2-chloro-N-methylbenzamide to afford a yellow solid (65 mg). $^1$H-NMR (DMSO-d$_6$, 400 MHz, 80° C.): 1.15-1.22 (m, 6H), 2.30-2.37 (m, 1H), 2.52-2.59 (m, 1H), 2.81 (d, J=4.5 Hz, 3H), 3.98-4.10 (m, 1H), 4.30-4.62 (m, 2H), 4.63-4.75 (m, 1H), 4.95-5.09 (m, 2H), 5.66-5.72 (m, 1H), 5.78-5.91 (m, 1H), 7.26-7.40 (m, 1H), 7.46 (s, 1H), 7.59 (d, J=7.8 Hz, 1H), 7.64-7.68 (m, 1H), 7.84 (s, 1H), 7.98 (d, J=7.8 Hz, 1H), 8.18-8.23 (m, 1H) ppm. LC-MS: C$_{28}$H$_{26}$BrClF$_3$N$_5$O$_3$ [M+H]$^+$: 652/654.

Example 13

Compound 21

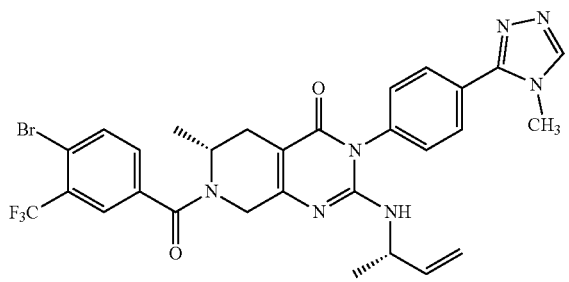

NEt$_3$ (0.61 mL, 4.37 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1.39 g, 2.91 mmol) and 4-(4-methyl-1,2,4-triazol-3-yl) phenylamine (0.56 g, 3.20 mmol) in anhydrous CH$_3$CN (20 mL) under N$_2$. The mixture was stiffed at 80° C. for 8 h. The mixture was evaporated to dryness and purified by chromatography on silica gel (0 to 10% CH$_3$OH in CH$_2$Cl$_2$) give (R)-7-(4-bromo-3-(trifluoromethyl)benzoyl)-6-methyl-3-(4-(4-methyl-4H-1,2,4-triazol-3-yl)phenyl)-2-thioxo-2,3,5,6,7,8-hexahydropyrido[3,4-d]pyrimidin-4(1H)-one (605 mg, 63%) as a yellow solid. LC-MS: C$_{25}$H$_{20}$BrF$_3$N$_6$O$_2$S [M+H]$^+$: 605.

CH$_3$I (0.09 mL, 1.45 mmol) and DBU (0.24 mL, 1.59 mmol) were added to a solution of (R)-7-(4-bromo-3-(trifluoromethyl)benzoyl)-6-methyl-3-(4-(4-methyl-4H-1,2,4-triazol-3-yl)phenyl)-2-thioxo-2,3,5,6,7,8-hexahydropyrido[3,4-d]pyrimidin-4(1H)-one (800 mg, 1.32 mmol) in anhydrous DMF (12 mL) at 0° C. The mixture was stirred at rt under N$_2$. The mixture was heated to 100° C. for 1 h and then diluted with water. The precipitate was isolated by filtration and washed with water to give (R)-7-(4-bromo-3-(trifluoromethyl)benzoyl)-6-methyl-3-(4-(4-methyl-4H-1,2,4-triazol-3-yl)phenyl)-2-(methylthio)-5,6,7,8-tetrahydropyrido[3,4-d]pyrimidin-4(3H)-one (818 mg, quant.) as a yellow solid, which was used without further purification in the next step. LC-MS: C$_{26}$H$_{22}$BrF$_3$N$_6$O$_2$S [M+H]$^+$: 619.

m-CPBA (1.02 mL, 1.58 mmol) was added to a solution of (R)-7-(4-bromo-3-(trifluoromethyl)benzoyl)-6-methyl-3-(4-(4-methyl-4H-1,2,4-triazol-3-yl)phenyl)-2-(methylthio)-5,6,7,8-tetrahydropyrido[3,4-d]pyrimidin-4(3H)-one (818 mg, 1.32 mmol) in anhydrous CH$_2$Cl$_2$ (85 mL) at 0° C. The mixture was stiffed at rt under N$_2$, and then diluted with water and CH$_2$Cl$_2$. The organic layer was removed, washed with brine and dried over Na$_2$SO$_4$. The solids were removed by filtration, and the filtrate was evaporated to dryness. The crude mixture was purified by chromatography on silica gel (0 to 15% CH$_3$OH in CH$_2$Cl$_2$) to give a mixture of (6R)-7-(4-bromo-3-(trifluoromethyl)benzoyl)-6-methyl-3-(4-(4-methyl-4H-1,2,4-triazol-3-yl)phenyl)-2-(methylsulfinyl)-5,6,7,8-tetrahydropyrido[3,4-d]pyrimidin-4(3H)-one (LC-MS: C$_{26}$H$_{22}$BrF$_3$N$_6$O$_3$S [M+H]$^+$: 635) and (R)-7-(4-bromo-3-(trifluoromethyl)benzoyl)-6-methyl-3-(4-(4-methyl-4H-1,2,4-triazol-3-yl)phenyl)-2-(methylsulfonyl)-5,6,7,8- tetrahydropyrido[3,4-d]pyrimidin-4(3H)-one (990 mg) as a beige solid, which was used without further purification in the next step. LC-MS: $C_{26}H_{22}BrF_3N_6O_4S$ [M+H]$^+$: 651.

In a round bottom flask equipped with a reflux condenser, a mixture of (6R)-7-(4-bromo-3-(trifluoromethyl)benzoyl)-6-methyl-3-(4-methyl-4H-1,2,4-triazol-3-yl)-2-(methylsulfinyl)-5,6,7,8-tetrahydropyrido[3,4-d]pyrimidin-4(3H)-one and (R)-7-(4-bromo-3-(trifluoromethyl)benzoyl)-6-methyl-3-(4-(4-methyl-4H-1,2,4-triazol-3-yl)phenyl)-2-(methylsulfonyl)-5,6,7,8-tetrahydropyrido[3,4-d]pyrimidin-4(3H)-one (840 mg, 1.32 mmol), (S)-but-3-en-2-amine hydrochloride (284.42 mg, 2.64 mmol), DIPEA (512.55 mg, 0.66 mL, 3.97 mmol) and DMAP (32.3 mg, 0.26 mmol) in anhydrous dioxane (12 mL) was stirred under $N_2$, at 100° C. for 20 h. The mixture was evaporated to dryness and purified by chromatography on silica gel (0 to 10% $CH_3OH$ in $CH_2Cl_2$) and then triturated in EtOH to give (R)-7-(4-bromo-3-(trifluoromethyl)benzoyl)-2-(((S)-but-3-en-2-yl)amino)-6-methyl-3-(4-methyl-4H-1,2,4-triazol-3-yl)-5,6,7,8-tetrahydropyrido[3,4-d]pyrimidin-4(3H)-one (69 mg, 8%) as a white solid. $^1$H-NMR (DMSO-d$_6$, 600 MHz, 80° C.): 1.17 (d, J=6.8 Hz, 3H), 1.20 (d, J=6.9 Hz, 3H), 2.32-2.36 (m, 1H), 2.50-2.59 (m, 1H), 3.81 (s, 3H), 4.01-4.06 (m, 1H), 4.51 (br s, 2H), 4.65-4.70 (m, 1H), 4.95-5.04 (m, 2H), 5.43 (dd, J=8.0 Hz, J=1.8 Hz, 1H), 5.79-5.87 (m, 1H), 7.45 (dd, J=8.0 Hz, J=1.6 Hz, 2H), 7.66 (dd, J=8.0 Hz, J=1.9 Hz, 1H), 7.84 (d, J=1.9 Hz, 1H), 7.93 (d, J=8.9 Hz, 2H), 7.97 (d, J=8.0 Hz, 1H), 8.53 (s, 1H) ppm. LC-MS: $C_{29}H_{27}BrF_3N_7O_2$ [M+H]$^+$: 642.

Example 14

Compound 22

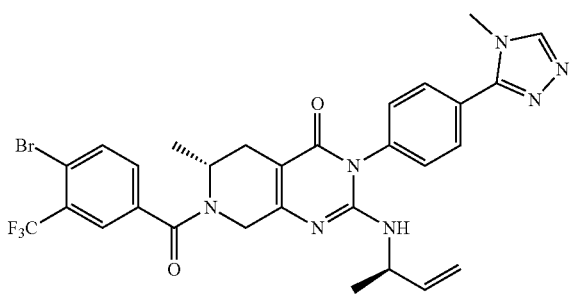 [SMILES: C=C[C@@H](C)Nc1nc2c(c(=O)n1-c1ccc(-c3nncn3C)cc1)C[C@@H](C)N(C(=O)c1ccc(Br)c(C(F)(F)F)c1)C2]

(R)-7-(4-bromo-3-(trifluoromethyl)benzoyl)-2-(((R)-but-3-en-2-yl)amino)-6-methyl-3-(4-methyl-4H-1,2,4-triazol-3-yl)-5,6,7,8-tetrahydropyrido[3,4-d]pyrimidin-4(3H)-one was synthesized using an analogous procedure to that described for (R)-7-(4-bromo-3-(trifluoromethyl)benzoyl)-2-(((S)-but-3-en-2-yl)amino)-6-methyl-3-(4-methyl-4H-1,2,4-triazol-3-yl)-5,6,7,8-tetrahydropyrido[3,4-d]pyrimidin-4(3H)-one to afford (R)-7-(4-bromo-3-(trifluoromethyl)benzoyl)-2-(((R)-but-3-en-2-yl)amino)-6-methyl-3-(4-(4-methyl-4H-1,2,4-triazol-3-yl)phenyl)-5,6,7,8-tetrahydropyrido[3,4-d]pyrimidin-4(3H)-one (22) (82 mg, 12%) as a white solid. $^1$H-NMR (DMSO-d$_6$, 400 MHz, 80° C.): 1.18-1.24 (m, 6H), 2.33-2.40 (m, 1H), 2.54-2.63 (m, 1H), 3.82 (s, 3H), 3.93-4.17 (m, 1H), 4.23-4.83 (m, 3H), 4.95-5.10 (m, 2H), 5.37-5.64 (m, 1H), 5.81-5.93 (m, 1H), 7.46 (d, J=8.0 Hz, 2H), 7.68 (dd, J=6.8 Hz, 1.4 Hz, 1H), 7.86 (d, J=1.4 Hz, 1H), 7.94 (d, J=8.8 Hz, 2H), 7.99 (d, J=8.1 Hz, 1H), 8.54 (s, 1H) ppm. LC-MS: $C_{29}H_{27}BrF_3N_7O_2$ [M+H]$^+$: 642.

Example 15

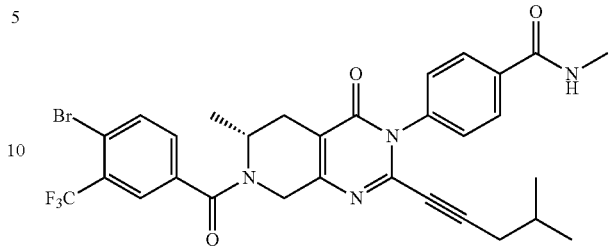

A solution of t-butyl (6R)-2-chloro-6-methyl-3-[4-(methylcarbamoyl)phenyl]-4-oxo-3H,4H,5H,6H,7H,8H-pyrido[3,4-d]pyrimidine-7-carboxylate (50 mg, 0.12 mmol), 4-methyl-1-pentyne (14.23 mg, 0.17 mmol) and Et$_3$N (1.2 mL) was stirred for 5 minutes at 0° C. Pd(dppf)Cl$_2$ (8.45 mg, 0.012 mmol) and CuI (2.2 mg, 0.012 mmol) were added. The mixture was heated to 60° C. for 24 h, and then diluted in EA and water. The layers were separated. The organic layer was washed with brine and dried over Na$_2$SO$_4$. The solids were removed by filtration. The filtrate was evaporated to dryness to give t-butyl (R)-6-methyl-3-(4-(methylcarbamoyl)phenyl)-2-(4-methylpent-1-yn-1-yl)-4-oxo-4,5,6,8-tetrahydropyrido[3,4-d]pyrimidine-7(3H)-carboxylate (crude) as a brown solid, which was used in the next step without further purification. LC-MS: $C_{27}H_{34}N_4O_4$ [M+H]$^+$: 479.

TFA (0.16 mL, 2.15 mmol) was added dropwise to a solution of t-butyl (R)-6-methyl-3-(4-(methylcarbamoyl)phenyl)-2-(4-methylpent-1-yn-1-yl)-4-oxo-4,5,6,8-tetrahydropyrido[3,4-d]pyrimidine-7(3H)-carboxylate (103 mg, 0.22 mmol) in anhydrous $CH_2Cl_2$ (6.4 mL) at rt for 4 h. The mixture was evaporated to dryness to give a dark solid. The solid was dissolved in EA:iPrOH (85:15), washed with sat. aq. NaHCO$_3$ and brine, and dried over Na$_2$SO$_4$. The solids were removed by filtration. The filtrate was evaporated to dryness to give (R)—N-methyl-4-(6-methyl-2-(4-methylpent-1-yn-1-yl)-4-oxo-5,6,7,8-tetrahydropyrido[3,4-d]pyrimidin-3(4H)-yl)benzamide (101 mg, quant., crude), which was used in the next step without further purification.

DIPEA (0.26 mL, 1.601 mmol) was added to a solution of (R)—N-methyl-4-(6-methyl-2-(4-methylpent-1-yn-1-yl)-4-oxo-5,6,7,8-tetrahydropyrido[3,4-d]pyrimidin-3(4H)-yl) benzamide (101 mg, 0.27 mmol), 4-bromo-3-(trifluoromethyl)benzoic acid (143.58 mg, 0.53 mmol) and HATU (203 mg, 0.53 mmol) in anhydrous DMF (2 mL) under $N_2$. The mixture was stirred at rt for 4 h. Water was added, and the aqueous layer was extracted with EA:iPrOH 85:1 (3×). The combined organic layers were dried over Na$_2$SO$_4$; the solids were removed by filtration, and the solvent of the filtrate was removed under reduced pressure. The crude product was purified by chromatography on silica gel ($CH_2Cl_2$:$CH_3OH$, 0 to 10%) to afford a yellow oil. The oil was purified by reverse phase chromatography (C18 column, $CH_3CN$:water+0.1% formic acid) to afford (R)-4-(7-(4-bromo-3-(trifluoromethyl)benzoyl)-6-methyl-2-(4-methylpent-1-yn-1-yl)-4-oxo-5,6,7,8-tetrahydropyrido[3,4-d]pyrimidin-3(4H)-yl)-N-methylbenzamide (23) as a white solid (15 mg, 9%). $^1$H-NMR (DMSO-d$_6$, 400 MHz, 80° C.): 0.64 (d, J=6.4 Hz, 6H), 1.20 (d, J=6.5 Hz, 3H), 1.45-1.47 (m, 1H), 2.08 (d, J=6.0 Hz, 2H), 2.42-2.49 (m, 1H), 2.62-2.68 (m, 1H), 2.82 (d, J=4.6 Hz, 3H), 4.14-4.24 (m, 1H), 4.37-4.82 (m, 2H), 7.45 (d, J=7.7 Hz, 2H), 7.66 (dd, J=8.1 Hz, 1.7 Hz, 1H), 7.85

(d, J=1.6 Hz, 1H), 7.92-8.01 (m, 3H), 8.25-8.32 (m, 1H) ppm. LC-MS: $C_{30}H_{28}BrF_3N_4O_3$ [M+H]$^+$: 629/631.

Example 16

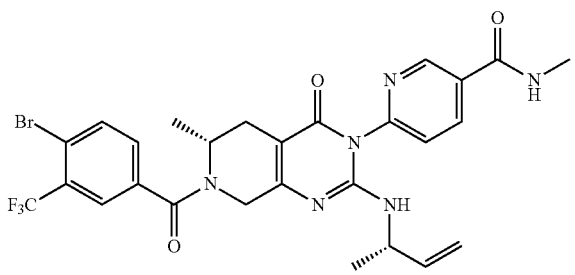 [SMILES: C=C[C@H](C)Nc1nc2c(c(=O)n1-c1ccc(C(=O)NC)cn1)C[C@@H](C)N(C(=O)c1ccc(Br)c(C(F)(F)F)c1)C2]

NaH (60% dispersion in oil, 170.95 mg, 4.27 mmol) was added to a solution of 6-amino-N-methylpyridine-3-carboxamide (349.97 mg, 2.32 mmol) in anhydrous DMF (10 mL) under $N_2$ cooled to 0° C. The mixture warmed to rt and stirred for 1 h. The mixture was cooled to 0° C., and a solution of (R)-1-(4-bromo-3-(trifluoromethyl)benzoyl)-5-isothiocyanato-2-methyl-1,2,3,6-tetrahydropyridine-4-carboxylate (850 mg, 1.78 mmol) in anhydrous DMF (10 mL) was added dropwise. The mixture was stirred at 0° C. for 1 h. The mixture was warmed to rt and stirred for 2 h. The mixture was poured into cold water and 1M HCl was added until the formation of an orange precipitate. The suspension was filtered. The solid was washed with water, then purified by chromatography on silica gel (0 to 10% $CH_3OH$ in $CH_2Cl_2$) to afford (R)-6-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylnicotinamide (140 mg, 13%) as a yellow solid. LC-MS: $C_{23}H_{19}BrF_3N_5O_3S$ [M+H]$^+$: 582/584.

Thiophosgene (0.024 mL, 0.27 mmol) was added to a solution of (R)-6-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylnicotinamide (130 mg, 0.22 mmol) in anhydrous dioxane (1.6 mL) under $N_2$. The mixture was heated at 100° C. for 30 min. The mixture was evaporated to dryness to give the crude mixture which was purified by chromatography on silica gel (0 to 10% $CH_3OH$ in $CH_2Cl_2$) to afford (R)-6-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylnicotinamide (65 mg, 50%) as an orange solid. LC-MS: $C_{23}H_{18}BrClF_3N_5O_3$ [M+H]$^+$: 584/586.

$Et_3N$ (0.108 mL, 0.78 mmol) was added to a solution of (R)-6-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylnicotinamide (65 mg, 0.11 mmol) and (S)-but-3-en-2-amine hydrochloride (35.87 mg, 0.33 mmol) in anhydrous $CH_3CN$ (1.4 mL). The mixture was stirred at 110° C. under $N_2$ for 2 h. The mixture was evaporated to dryness. The residue was dissolved in EA/iPrOH (85:15). washed with sat. aq. $NH_4Cl$ and brine, and dried over $Na_2SO_4$. The solids were removed by filtration. The filtrate was evaporated to dryness to give the crude product. The crude product was purified by chromatography on silica gel (0 to 10% $CH_3OH$ in $CH_2Cl_2$) to afford a white solid and then by SFC (isocratic $CH_3OH$:$CO_2$ (30:70)+$NH_3$) to afford 6-((R)-7-(4-bromo-3-(trifluoromethyl)benzoyl)-2-(((S)-but-3-en-2-yl)amino)-6-methyl-4-oxo-5,6,7,8-tetrahydropyrido[3,4-d]pyrimidin-3(4H)-yl)-N-methylnicotinamide (24) (16 mg, 23%) as a white solid. $^1$H-NMR (DMSO-d$_6$, 600 MHz, 80° C.): 1.15 (d, J=6.9 Hz, 3H), 1.20 (d, J=6.9 Hz, 3H), 2.31-2.35 (m, 1H), 2.53-2.58 (m, 1H), 2.87 (d, J=4.6 Hz, 3H), 4.02-4.06 (m, 1H), 4.48-4.55 (m, 1H), 4.69-4.74 (m, 1H), 4.97 (d, J=10.4 Hz, 1H), 5.06 (d, J=17.3 Hz, 1H), 5.77-5.87 (m, 2H), 7.55 (d, J=8.3 Hz, 2H), 7.67 (dd, J=8.2, 1.8 Hz, 1H), 7.85 (d, J=1.6 Hz, 1H), 7.98 (d, J=8.3 Hz, 1H), 8.37 (dd, J=8.2, 2.5 Hz, 1H), 8.54-8.55 (m, 1H), 9.03 (d, J=1.9 Hz, 1H) ppm. LC-MS: $C_{27}H_{26}BrF_3N_6O_3$ [M+H]$^+$: 619/621.

Example 17

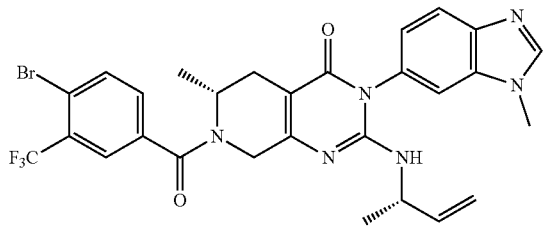 [SMILES: C=C[C@H](C)Nc1nc2c(c(=O)n1-c1ccc3ncn(C)c3c1)C[C@@H](C)N(C(=O)c1ccc(Br)c(C(F)(F)F)c1)C2]

(R)-7-(4-bromo-3-(trifluoromethyl)benzoyl)-2-(((S)-but-3-en-2-yl)amino)-6-methyl-3-(1-methyl-1H-benzo[d]imidazol-6-yl)-5,6,7,8-tetrahydropyrido[3,4-d]pyrimidin-4(3H)-one (25) (150 mg, 33%) was synthesized according to an analogous procedure to that described for (R)-7-(4-bromo-3-(trifluoromethyl)benzoyl)-2-(((S)-but-3-en-2-yl)amino)-6-methyl-3-(1-methyl-1H-benzo[d]imidazol-5-yl)-5,6,7,8-tetrahydropyrido[3,4-d]pyrimidin-4(3H)-one using 1-methyl-1H-benzo[d]imidazol-6-amine. $^1$H-NMR (DMSO-d$_6$, 400 MHz, 80° C.): 1.11 (d, J=6.6 Hz, 3H), 1.20 (d, J=6.9 Hz, 3H), 2.32-2.39 (m, 1H), 2.52-2.61 (m, 1H), 3.84 (s, 3H), 3.97-4.14 (m, 1H), 4.24-4.74 (m, 3H), 4.88-5.04 (m, 2H), 5.24 (d, J=8.3 Hz, 1H), 5.74-5.84 (m, 1H), 7.03 (dd, J=20.6, 8.0 Hz, 1H), 7.55 (d, J=26.6 Hz, 1H), 7.66 (dd, J=7.8 Hz, 1.0 Hz, 1H), 7.77 (d, J=8.5 Hz, 1H), 7.84 (s, 1H); 7.97 (d, J=8.1 Hz, 1H), 8.24 (s, 1H) ppm. LC-MS: $C_{28}H_{26}BrF_3N_6O_2$ [M+H]$^+$: 615/617.

Example 18

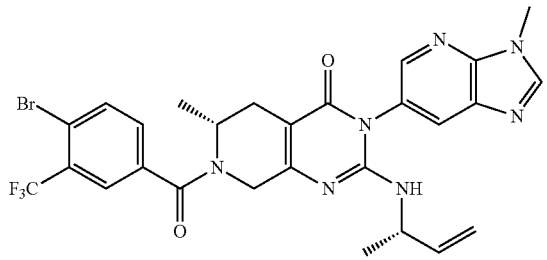 [SMILES: C=C[C@H](C)Nc1nc2c(c(=O)n1-c1cnc3c(c1)ncn3C)C[C@@H](C)N(C(=O)c1ccc(Br)c(C(F)(F)F)c1)C2]

3-methyl-3H-imidazo[4,5-b]pyridin-6-amine (0.34 g, 2.305 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 g, 2.095 mmol) and $Et_3N$ (2.039 mL, 14.67 mmol) in anhydrous $CH_3CN$ (8 mL) and under $N_2$. The mixture stiffed at 110° C. for 2 h. The mixture was evaporated to dryness and purified by chromatography on silica gel (from 0 to 100% EA in CyH, followed by 0 to 10% CH$_3$OH in CH$_2$Cl$_2$) to give (R)-7-(4-bromo-3-(trifluoromethyl)benzoyl)-6-methyl-3-(3-methyl-3H-imidazo[4,5-b]pyridin-6-yl)-2-thioxo-2,3,5,6,7,8-hexahydropyrido[3,4-d]pyrimidin-4(1H)-one (295 mg, 24%) as a yellow solid. LC-MS: C$_{23}$H$_{18}$BrF$_3$N$_6$O$_2$S [M+H]$^+$: 579/581.

SO$_2$Cl$_2$ (0.040 mL, 0.47 mmol) was added to a solution of (R)-7-(4-bromo-3-(trifluoromethyl)benzoyl)-6-methyl-3-(3-methyl-3H-imidazo[4,5-b]pyridin-6-yl)-2-thioxo-2,3,5,6,7,8-hexahydropyrido[3,4-d]pyrimidin-4(1H)-one (245 mg, 0.42 mmol) in CHCl$_3$ (3 mL) under N$_2$. The mixture was stiffed at rt for 1 h then was evaporated to dryness to afford (R)-7-(4-bromo-3-(trifluoromethyl)benzoyl)-2-chloro-6-methyl-3-(3-methyl-3H-imidazo[4,5-b]pyridin-6-yl)-5,6,7,8-tetrahydropyrido[3,4-d]pyrimidin-4(3H)-one, which was used in the next step without further purification.

DIPEA (0.59 mL, 3.54 mmol) was added to a solution of (R)-7-(4-bromo-3-(trifluoromethyl)benzoyl)-2-chloro-6-methyl-3-(3-methyl-3H-imidazo[4,5-b]pyridin-6-yl)-5,6,7,8-tetrahydropyrido[3,4-d]pyrimidin-4(3H)-one (294 mg, 0.50 mmol) and (2S)-but-3-en-2-amine hydrochloride (163 mg, 1.52 mmol) in anhydrous CH$_3$CN (3 mL) under N$_2$. The mixture was stirred at 110° C. for 3 d. The mixture was evaporated to dryness to afford the crude product which was purified by silica gel chromatography (0 to 10% CH$_3$OH in CH$_2$Cl$_2$) followed by reverse phase chromatography (C18 column, 5 to 100% CH$_3$CN in water+0.1% formic acid) to afford (R)-7-(4-bromo-3-(trifluoromethyl)benzoyl)-2-(((S)-but-3-en-2-yl)amino)-6-methyl-3-(3-methyl-3H-imidazo[4,5-b]pyridin-6-yl)-5,6,7,8-tetrahydropyrido[3,4-d]pyrimidin-4(3H)-one (26) (87 mg, 28%) as a white solid. $^1$H-NMR (DMSO-d$_6$, 400 MHz, 80° C.): 1.12 (d, J=6.9 Hz, 3H), 1.21 (d, J=6.9 Hz, 3H), 2.30-2.37 (m, 1H), 2.54-2.61 (m, 1H), 3.90 (s, 3H), 3.98-4.08 (m, 1H), 4.33-4.80 (m, 2H), 4.63-4.76 (m, 1H), 4.93 (dt, J=10.2 Hz, 1.0 Hz, 1H), 5.01 (d, J=10.2 Hz, 1H), 5.74-5.85 (m, 2H), 7.65 (dd, J=8.2 Hz, 1.5 Hz, 1H), 7.84 (d, J=1.5 Hz, 1H), 7.94-8.06 (m, 2H), 8.19 (d, J=16.8 Hz, 1H), 8.47 (s, 1H) ppm. LC-MS: C$_{27}$H$_{25}$BrF$_3$N$_7$O$_2$ [M+H]$^+$: 616/618.

Example 19

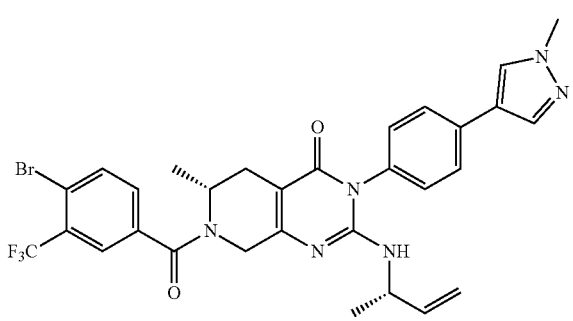 [SMILES: C=C[C@H](C)Nc1nc2c(c(=O)n1-c1ccc(-c3cnn(C)c3)cc1)C[C@@H](C)N(C(=O)c1ccc(Br)c(C(F)(F)F)c1)C2]

Et$_3$N (0.58 mL, 4.19 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 g, 2.095 mmol) and 4-(1-methyl-1H-pyrazol-4-yl)aniline (399.206 mg, 2.305 mmol) in anhydrous CH$_3$CN (20 mL) under N$_2$. The mixture was heated to 100° C. for 2 h, then evaporated to dryness to give the crude product, purified by chromatography on silica gel (0 to 10% CH$_3$OH in CH$_2$Cl$_2$) to afford (R)-7-(4-bromo-3-(trifluoromethyl)benzoyl)-6-methyl-3-(4-(1-methyl-1H-pyrazol-4-yl)phenyl)-2-thioxo-2,3,5,6,7,8-hexahydropyrido[3,4-d]pyrimidin-4(1H)-one (1.25 g, 99%) as an orange solid. LC-MS: C$_{26}$H$_{21}$BrF$_3$N$_5$O$_2$S [M+H]$^+$: 604/606.

Thiophosgene (0.08 mL, 0.83 mmol) was added to a solution of (R)-7-(4-bromo-3-(trifluoromethyl)benzoyl)-6-methyl-3-(4-(1-methyl-1H-pyrazol-4-yl)phenyl)-2-thioxo-2,3,5,6,7,8-hexahydropyrido[3,4-d]pyrimidin-4(1H)-one (500 mg, 0.83 mmol) in anhydrous dioxane (10 mL) under N$_2$. The mixture was stirred at 100° C. for 0.5 h, then evaporated to dryness to afford (R)-7-(4-bromo-3-(trifluoromethyl)benzoyl)-2-chloro-6-methyl-3-(4-(1-methyl-1H-pyrazol-4-yl)phenyl)-5,6,7,8-tetrahydropyrido[3,4-d]pyrimidin-4(3H)-one, which was directly used in the next step.

DIPEA (1.12 mL, 6.77 mmol) was added to a solution of (R)-7-(4-bromo-3-(trifluoromethyl)benzoyl)-2-chloro-6-methyl-3-(4-(1-methyl-1H-pyrazol-4-yl)phenyl)-5,6,7,8-tetrahydropyrido[3,4-d]pyrimidin-4(3H)-one (587 mg, 0.97 mmol) and (2S)-but-3-en-2-amine hydrochloride (312 mg, 2.9 mmol) in anhydrous CH$_3$CN (8 mL) under N$_2$. The mixture was stirred at 100° C. for 20 h. The mixture was evaporated to dryness to afford the crude product which was purified by chromatography on silica gel (0 to 10% CH$_3$OH in CH$_2$Cl$_2$), and then purified by reverse phase chromatography (C18 column) 5 to 100% CH$_3$CN in water (+0.1% formic acid) to afford (R)-7-(4-bromo-3-(trifluoromethyl)benzoyl)-2-(((S)-but-3-en-2-yl)amino)-6-methyl-3-(4-(1-methyl-1H-pyrazol-4-yl)phenyl)-5,6,7,8-tetrahydropyrido[3,4-d]pyrimidin-4(3H)-one (27) (127 mg, 20%) as a beige solid. $^1$H-NMR (DMSO-d$_6$, 400 MHz, 80° C.): 1.17 (d, J=6.9 Hz, 3H), 1.22 (d, J=6.7 Hz, 3H), 2.36 (d, J=16.6 Hz, 1H), 2.54-2.62 (m, 1H), 3.90 (s, 3H), 4.05 (d, J=19.1 Hz, 1H), 4.29-4.73 (m, 3H), 4.93-5.06 (m, 2H), 5.26 (d, J=7.8 Hz, 1H), 5.78-5.90 (m, 1H), 7.20-7.30 (m, 2H), 7.67 (dd, J=8.4 Hz, 1.8 Hz, 1H), 7.70-7.75 (m, 2H), 7.86 (d, J=1.8 Hz, 1H), 7.89 (s, 1H), 7.99 (d, J=8.2 Hz, 1H), 8.16 (s, 1H) ppm. LC-MS: C$_{30}$H$_{28}$BrF$_3$N$_6$O$_2$ [M+H]$^+$: 641/643.

Example 20

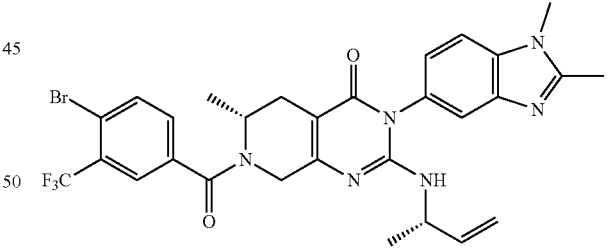

(R)-7-(4-bromo-3-(trifluoromethyl)benzoyl)-2-(((S)-but-3-en-2-yl)amino)-3-(1,2-dimethyl-1H-benzo[d]imidazol-5-yl)-6-methyl-5,6,7,8-tetrahydropyrido[3,4-d]pyrimidin-4(3H)-one (28) was obtained as a white solid (34 mg, 4%) using a procedure analogous to the preparation of compound 27. $^1$H-NMR (DMSO-d$_6$, 400 MHz, 80° C.): 1.11 (d, J=6.8 Hz, 3H), 1.22 (d, J=6.8 Hz, 3H), 2.32-2.40 (m, 1H), 2.57 (s, 3H), 2.55-2.60 (m, 1H), 3.79 (s, 3H), 4.02-4.07 (m, 1H), 4.34-4.66 (m, 3H), 4.98 (m, 3H), 5.79-5.85 (m, 1H), 6.89-7.10 (m, 1H), 7.41 (d, J=19.9 Hz, 1H), 7.62 (d, J=8.5 Hz, 1H), 7.67 (d, J=7.9, 1.4 Hz, 1H), 7.85 (d, J=1.4 Hz, 1H), 7.98 (d, J=8.3 Hz, 1H) ppm. LC-MS: C$_{29}$H$_{28}$BrF$_3$N$_6$O$_2$ [M+H]$^+$: 629/631.

Example 21

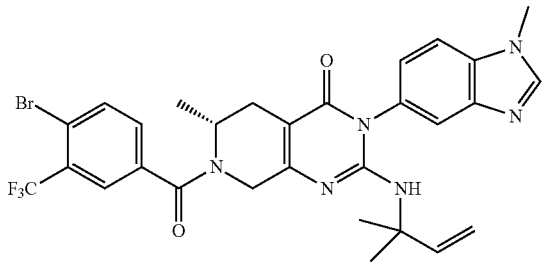 [SMILES: C=CC(C)(C)Nc1nc2c(c(=O)n1-c1ccc3c(c1)ncn3C)C[C@@H](C)N(C(=O)c1ccc(Br)c(C(F)(F)F)c1)C2]

(R)-7-(4-bromo-3-(trifluoromethyl)benzoyl)-6-methyl-3-(1-methyl-1H-benzo[d]imidazol-5-yl)-2-((2-methylbut-3-en-2-yl)amino)-5,6,7,8-tetrahydropyrido[3,4-d]pyrimidin-4(3H)-one (29) was made according to the procedure to make (R)-7-(4-bromo-3-(trifluoromethyl)benzoyl)-6-methyl-3-(1-methyl-1H-benzo[d]imidazol-5-yl)-2-thioxo-2,3,5,6,7,8-hexahydropyrido[3,4-d]pyrimidin-4(1H)-one using 2-methylbut-3-en-2-amine. The product was obtained as a yellow solid (17 mg, 3%). $^1$H-NMR (DMSO-$d_6$, 400 MHz, 80° C.): 1.22 (d, J=6.8 Hz, 3H), 1.35-1.40 (m, 6H), 2.30-2.40 (m, 1H), 2.53-2.64 (m, 1H), 3.91 (s, 3H), 3.96-4.09 (m, 1H), 4.27-4.78 (m, 3H), 4.88 (d, J=6.1 Hz, 1H), 4.92 (s, 1H), 6.03 (dd, J=17.3 Hz, 11.0 Hz, 1H), 7.08-7.27 (m, 1H), 7.57-7.65 (m, 1H), 7.65-7.70 (m, 1H), 7.76 (d, J=8.5 Hz, 1H), 7.86 (s, 1H), 7.99 (d, J=8.1 Hz, 1H), 8.28 (s, 1H) ppm. LC-MS: $C_{29}H_{28}BrF_3N_6O_2$ [M+H]$^+$: 629/631.

Example 22

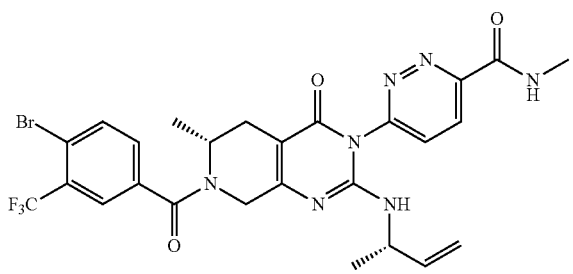

6-((R)-7-(4-bromo-3-(trifluoromethyl)benzoyl)-2-(((S)-but-3-en-2-yl)amino)-6-methyl-4-oxo-5,6,7,8-tetrahydropyrido[3,4-d]pyrimidin-3(4H)-yl)-N-methylpyridazine-3-carboxamide (30) (56 mg, 22%) was obtained as a white solid using a procedure analogous to that for the preparation of compound 26. $^1$H-NMR (DMSO-$d_6$, 400 MHz, 80° C.): 1.16 (d, J=7.0 Hz, 3H), 1.23 (d, J=6.9 Hz, 3H), 2.32-2.40 (m, 1H), 2.54-2.66 (m, 1H), 2.95 (d, J=4.8 Hz, 3H), 4.08 (d, J=19.6 Hz, 1H), 4.26-4.82 (m, 3H), 4.99 (d, J=10.4 Hz, 1H), 5.09 (d, J=17.3 Hz, 1H), 5.76-5.87 (m, 1H), 6.24 (d, J=6.8 Hz, 1H), 7.68 (dd, J=6.8 Hz, 1.4 Hz, 1H), 7.86 (d, J=1.4 Hz, 1H), 8.01 (dd, J=8.7 Hz, 4.6 Hz, 2H), 8.40 (d, J=8.7 Hz, 1H), 9.12 (d, J=4.6 Hz, 1H) ppm. LC-MS: $C_{26}H_{25}BrF_3N_7O_3$ [M+H]$^+$: 620/622.

Example 23

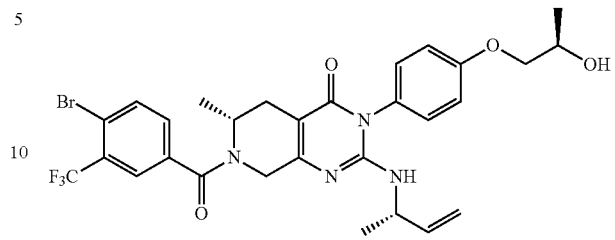

Ethyl L(-)-lactate (5 g, 42.33 mmol) in anhydrous CH$_2$Cl$_2$ (30 mL) was added to a solution of DBU (8.85 mL, 59.26 mmol) and triphenylmethyl chloride (11.8 g, 42.33 mmol) in anhydrous CH$_2$Cl$_2$ (30 mL) under N$_2$. The mixture was stirred at rt for 3 days. The mixture was diluted with cold water (20 mL), extracted with Et$_2$O (3×50 mL), washed with brine and dried over Na$_2$SO$_4$. The solids were removed by filtration, and the filtrate was evaporated to dryness to give the crude product which was purified by chromatography on silica gel (0 to 10% EA in CyH) to afford ethyl (S)-2-(trityloxy)propanoate (15.9 g, 99%) as a colorless oil. $^1$H-NMR (DMSO-$d_6$, 400 MHz): 0.98 (t, J=7.0 Hz, 3H), 1.22 (d, J=6.7 Hz, 3H), 3.62 (q, J=7.0 Hz, 2H), 4.01 (q, J=6.7 Hz, 1H), 7.24-7.29 (m, 3H), 7.30-7.35 (m, 6H), 7.37-7.41 (m, 6H) ppm.

LiAlH$_4$ (1M) in THF (42.33 mL, 42.33 mmol) was added, dropwise at −78° C. to a solution of ethyl (S)-2-(trityloxy)propanoate (15.26 g, 42.33 mmol) in anhydrous THF (200 mL) under N$_2$. The mixture was stirred at −78° C. for 4 h. The mixture was diluted with Et$_2$O (100 mL) and cooled to 0° C. Water (42 mL) was added slowly, then NaOH (42 mL, aq., 15%) followed by water (170 mL) was added. The mixture was stirred at rt for 15 mins, and MgSO$_4$ was added. The mixture was stirred for 15 mins. The salts were removed by filtration and washed with Et$_2$O, and the filtrate was evaporated to dryness to afford (S)-2-(trityloxy)propan-1-ol (9.3 g, 69%) as a white solid. $^1$H-NMR (DMSO-$d_6$, 400 MHz): 0.69 (d, J=6.1 Hz, 3H), 2.94-3.13 (m, 2H), 3.43-3.54 (m, 1H), 4.46-4.49 (m, 1H), 7.23-7.28 (m, 3H), 7.30-7.36 (m, 6H), 7.43-7.47 (m, 6H) ppm.

Cs$_2$CO$_3$ (697 mg, 2.14 mmol) was added to a solution of 4-fluoronitrobenzene (201 mg, 1.43 mmol) and (S)-2-(trityloxy)propan-1-ol (500 mg, 1.57 mmol) in anhydrous DMSO (6 mL) under N$_2$. The mixture was stirred at 50° C. for 4 h, then diluted with NaHCO$_3$ (20 mL) and extracted with EA (3×25 mL). The combined organic phases were washed with water and brine, and dried over Na$_2$SO$_4$. The solids were removed by filtration, and the filtrate was evaporated to dryness to give the crude product which was purified by chromatography on silica gel (0 to 20% EA in CyH) to afford (S)-(((1-(4-nitrophenoxy)propan-2-yl)oxy)methanetriyl)tribenzene (567 mg, 90%) as a white solid. $^1$H-NMR (DMSO-$d_6$, 400 MHz): 0.89 (d, J=6.2 Hz, 3H), 3.65-3.76 (m, 2H), 3.82-3.90 (m, 1H), 6.94-7.00 (m, 2H), 7.24-7.28 (m, 3H), 7.30-7.36 (m, 6H), 7.42-7.50 (m, 6H), 8.12-8.18 (m, 2H) ppm.

10% Pd/C (1.04 g, 0.98 mmol) was added to a solution of (S)-(((1-(4-nitrophenoxy)propan-2-yl)oxy)methanetriyl)tribenzene (4.3 g, 9.78 mmol) in EtOH (170 mL). The mixture was purged with N$_2$, then purged with H$_2$ and stiffed at rt for 3 days. The mixture was filtered over a pad of celite and evaporated to dryness to give (S)-4-(2-(trityloxy) propoxy)aniline (3.8 g, 95%) as a colorless oil. LC-MS: $C_{28}H_{27}NO_2$ [M+H]$^+$: 410.

(S)-4-(2-(trityloxy)propoxy)aniline (1.03 g, 2.51 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 g, 2.095 mmol) and Et$_3$N (2.0 mL, 4.19 mmol) in anhydrous CH$_3$CN (8 mL) under N$_2$. The mixture was stirred at 110° C. for 4 h. The mixture was evaporated to dryness and purified by flash chromatography on silica gel (0 to 100% EA in CyH) to afford (R)-7-(4-bromo-3-(trifluoromethyl)benzoyl)-6-methyl-2-thioxo-3-(4-((S)-2-(trityloxy)propoxy)phenyl)-2,3,5,6,7,8-hexahydropyrido[3,4-d]pyrimidin-4(1H)-one (1.20 g, 68%) as a yellow solid. LC-MS: $C_{44}H_{37}BrClF_3N_3O_4S$ [M+H]$^+$: 640/642.

Thiophosgene (0.08 mL, 0.89 mmol) was added to a solution of (R)-7-(4-bromo-3-(trifluoromethyl)benzoyl)-6-methyl-2-thioxo-3-(4-((S)-2-(trityloxy)propoxy)phenyl)-2,3,5,6,7,8-hexahydropyrido[3,4-d]pyrimidin-4(1H)-one (750 mg, 0.89 mmol) in anhydrous dioxane (10 mL) under N$_2$. The mixture was stirred at 110° C. for 1 h. The mixture was evaporated to dryness to afford (R)-7-(4-bromo-3-(trifluoromethyl)benzoyl)-2-chloro-3-(4-((S)-2-hydroxypropoxy)phenyl)-6-methyl-5,6,7,8-tetrahydropyrido[3,4-d]pyrimidin-4(3H)-one, which was directly used in the next step.

DIPEA (1 mL, 3.23 mmol) was added to a solution of (R)-7-(4-bromo-3-(trifluoromethyl)benzoyl)-2-chloro-3-(4-((S)-2-hydroxypropoxy)phenyl)-6-methyl-5,6,7,8-tetrahydropyrido[3,4-d]pyrimidin-4(3H)-one (534 mg, 0.89 mmol) and (2S)-but-3-en-2-amine hydrochloride (287 mg, 2.67 mmol) in anhydrous CH$_3$CN (5 mL) under N$_2$. The mixture was stirred at 110° C. for 16 h. The mixture was evaporated to dryness to afford the crude product which was purified by flash chromatography on silica gel (0% to 10% CH$_3$OH in CH$_2$Cl$_2$) to afford a yellow solid that was purified by reverse phase chromatography (C18 column) 5 to 100% CH$_3$CN in water (+0.1% formic acid) to afford (R)-7-(4-bromo-3-(trifluoromethyl)benzoyl)-2-(((S)-but-3-en-2-yl)amino)-3-(4-((S)-2-hydroxypropoxy)phenyl)-6-methyl-5,6,7,8-tetrahydropyrido[3,4-d]pyrimidin-4(3H)-one (31) (180 mg, 32%) as a white solid. $^1$H-NMR (DMSO-d$_6$, 400 MHz, 80° C.): 1.15 (d, J=6.6 Hz, 3H), 1.20 (d, J=6.3 Hz, 6H), 2.31-2.32 (m, 1H), 2.31-2.38 (m, 1H), 2.56-2.58 (m, 1H), 3.85-3.95 (m, 2H), 3.97-4.05 (m, 2H), 4.46-4.63 (m, 3H), 4.94-5.02 (m, 2H), 5.12 (d, J=6.3 Hz, 1H), 5.78-5.86 (m, 1H), 7.06-7.10 (m, 2H), 7.13-7.21 (m, 2H), 7.66 (dd, J=8.1, 2.3 Hz, 1H), 7.84 (d, J=1.9 Hz, 1H), 7.98 (d, J=8.5 Hz, 1H) ppm. LC-MS: $C_{29}H_{30}BrF_3N_4O_4$ [M+H]$^+$: 635/637.

Example 24

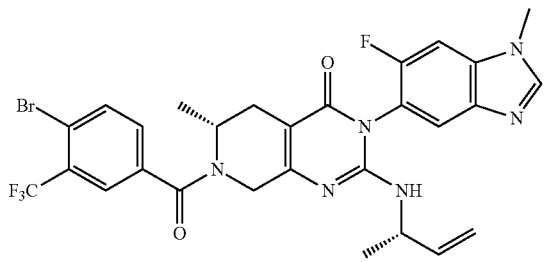 [SMILES: C=C[C@H](C)Nc1nc2c(c(=O)n1-c1cc3ncn(C)c3cc1F)C[C@@H](C)N(C(=O)c1ccc(Br)c(C(F)(F)F)c1)C2]

Pd$_2$(dba)$_3$ (199 mg, 0.22 mmol), XantPhos (126 mg, 0.22 mmol), benzophenone imine (593 mg, 3.27 mmol) and sodium t-butoxide (314 mg, 3.27 mmol) were added to a solution of 5-bromo-6-fluoro-1-methyl-1H-1,3-benzodiazole (500 mg, 2.18 mmol) in anhydrous 1,4-dioxane (10 mL) under N$_2$. The mixture was stirred at 100° C. for 1 h. The mixture was evaporated to dryness, then EA and water were added. The aqueous phase was extracted with EA (2×). The combined organic layers were washed with brine and dried over MgSO$_4$. The solids were removed by filtration, and the filtrate was evaporated to dryness to give the crude product which was purified by chromatography on silica gel (0 to 5% MeOH in DCM) to afford N-(6-fluoro-1-methyl-1H-benzo[d]imidazol-5-yl)-1,1-diphenylmethanimine (0.703 g, 98%) as a beige solid. LCMS: $C_{21}H_{16}FN_3$ [M+H]$^+$: 330.

A solution of HCl 1 N (3.19 mL, 3.19 mmol) was added to a solution of N-(6-fluoro-1-methyl-1H-benzo[d]imidazol-5-yl)-1,1-diphenylmethanimine (700 mg, 2.13 mmol) in THF (20 mL). The mixture was stirred at rt for 18 h., then THF was evaporated under reduced pressure. The resulting aqueous phase was extracted with Et$_2$O, basified with NaOH (1N) and EA was added. The aqueous layer was extracted with EA (2×). The combined organic layers were washed with brine and dried over MgSO$_4$. The solids were removed by filtration, and the filtrate was evaporated to dryness to afford 6-fluoro-1-methyl-1H-benzo[d]imidazol-5-amine (327 mg, 93%) as a beige solid. $^1$H-NMR (DMSO-d$_6$, 400 MHz): 3.71 (s, 3H), 4.75 (br. s., 2H), 6.97 (d, J=8.3 Hz, 1H), 7.28 (d, J=11.5 Hz, 1H), 7.93 (s, 1H) ppm.

(R)-7-(4-bromo-3-(trifluoromethyl)benzoyl)-2-(((S)-but-3-en-2-yl)amino)-3-(6-fluoro-1-methyl-1H-benzo[d]imidazol-5-yl)-6-methyl-5,6,7,8-tetrahydropyrido[3,4-d]pyrimidin-4(3H)-one (32) (149 mg, 24%) was obtained as a pale yellow solid and a mixture of atropoisomers using a procedure analogous to that for the preparation of compound 27. $^1$H-NMR (DMSO-d$_6$, 400 MHz, 80° C.): 1.11-1.18 (m, 3H), 1.21 (d, J=6.7 Hz, 3H), 2.30-2.39 (m, 1H), 2.53-2.63 (m, 1H), 3.88 (s, 3H), 3.98-4.13 (m, 1H), 4.27-4.76 (m, 3H), 4.90-5.11 (m, 2H), 5.72-5.90 (m, 2H), 7.61-7.71 (m, 3H), 7.86 (dd, J=7.8 Hz, 1.9 Hz, 1H), 7.98 (dd, J=8.6 Hz, 2.6 Hz, 1H), 8.26 (d, J=1.7 Hz, 1H) ppm LC-MS: $C_{28}H_{25}BrF_4N_6O_2$ [M+H]$^+$: 633/635.

The mixture of atropisomers was dissolved to 10 mg/mL in EtO and then purified by HPLC (isocratic EtOH) to afford the two pure compounds (32a) and (32b), respectively, 52 mg (8%) and 41 mg (7%) as white solids.

Atropoisomer 1 (32a): $^1$H-NMR (DMSO-d$_6$, 400 MHz, 80° C.): 1.16 (d, J=7.0 Hz, 3H), 1.21 (d, J=6.7 Hz, 3H), 2.30-2.39 (m, 1H), 2.53-2.63 (m, 1H), 3.88 (s, 3H), 3.98-4.13 (m, 1H), 4.27-4.76 (m, 3H), 4.93 (d, J=10.7 Hz, 1H), 5.00 (d, J=17.1 Hz, 1H), 5.72-5.90 (m, 2H), 7.61-7.71 (m, 3H), 7.86 (d, J=1.9 Hz, 1H), 7.98 (d, J=8.1 Hz, 1H), 8.26 (s, 1H) ppm. LCMS: $C_{28}H_{25}BrF_4N_6O_2$, [M+H]$^+$: 633/635.

Atropoisomer 2 (32b): $^1$H-NMR (DMSO-d$_6$, 400 MHz, 80° C.): 1.13 (d, J=6.9 Hz, 3H), 1.21 (d, J=6.7 Hz, 3H), 2.30-2.39 (m, 1H), 2.53-2.63 (m, 1H), 3.88 (s, 3H), 3.98-4.13 (m, 1H), 4.27-4.76 (m, 3H), 4.96 (d, J=10.4 Hz, 1H), 5.04 (d, J=17.5 Hz, 1H), 5.77-5.90 (m, 2H), 7.63 (d, J=6.4 Hz, 1H), 7.65-7.69 (m, 2H), 7.85 (d, J=1.6 Hz, 1H), 7.98 (d, J=8.4 Hz, 1H), 8.26 (s, 1H) ppm. LCMS: $C_{28}H_{25}BrF_4N_6O_2$, [M+H]$^+$: 633/635.

Example 25

Compounds 33-49

Compounds 33-54 were synthetized following the pathways and using the intermediates described herein and/or known in the art.

Tables A and B depicts the structures of Compounds 33-54, their analytical details and the method(s) used to prepare the intermediate used in the last step of the synthesis. Method A refers to the method depicted in Scheme 8, which provides the methylsulfoxide intermediate. Method B refers to the method depicted in Scheme 9, which provides to the chloro intermediate. Both intermediates are then subjected to leaving group displacement by an amine, as depicted in Scheme 2, where LG can be methylsulfoxide or chloro, respectively.

TABLE A

| No. | Name | LCMS [M + 1]+ | 1H NMR | Method |
|---|---|---|---|---|
| 33 | (6R)-7-[4-bromo-3-(trifluoromethyl)benzoyl]-6-methyl-2-[[(1S)-1-methylallyl]amino]-3-(1-methylindazol-5-yl)-6,8-dihydro-5H-pyrido[3,4-d]pyrimidin-4-one | 615/617 | (DMSO-$d_6$, 400 MHz, 80° C.): 1.13 (d, J = 6.5 Hz, 3H), 1.22 (d, J = 6.8 Hz, 3H), 2.32-2.39 (m, 1H), 2.53-2.61 (m, 1H), 4.00-4.10 (br. s., 1H), 4.11 (s, 3H), 4.33-4.74 (m, 3H), 4.94 (d, J = 10.7 Hz, 1H), 4.99 (d, J = 17.6 Hz, 1H), 5.33 (d, J = 7.9 Hz, 1H), 5.71-5.88 (m, 1H), 7.14-7.25 (m, 1H), 7.64-7.73 (m, 2H), 7.77 (d, J = 8.5 Hz, 1H), 7.85 (d, J = 1.9 Hz, 1H), 7.98 (d, J = 8.0 Hz, 1H), 8.11(s, 1H) ppm | B |
| 34 | (6R)-7-[4-bromo-3-(trifluoromethyl)benzoyyl]-3-(7-chloro-1-methyl-benzimidazol-5-yl)-6-methyl-2-[[(1S)-1-methylallyl]amino]-6,8-dihydro-5H-pyrido[3,4-d]pyrimidin-4-one | 649/651 | (DMSO-$d_6$, 400 MHz, 80° C.): 1.15 (d, J = 6.7 Hz, 3H), 1.22 (d, J = 6.8 Hz, 3H), 2.31-2.38 (m, 1H), 2.52-2.60 (m, 1H), 4.04 (d, J = 18.5 Hz, 1H), 4.15 (s, 3H), 4.34-4.74 (m, 3H), 4.92-5.06 (m, 2H), 5.58 (d, J = 8.3 Hz, 1H), 5.75-5.87 (m, 1H), 7.19 (d, J = 24.7 Hz, 1H), 7.54 (d, J = 19.2 Hz, 1H), 7.67 (dd, J = 7.9 Hz, 1.9 Hz, 1H), 7.85 (d, J = 1.7 Hz, 1H), 7.98 (d, J = 8.2 Hz, 1H), 8.29 (s, 1H) ppm | B |
| 35 | (6R)-7-[4-bromo-3-(trifluoromethyl)benzoyl]-6-methyl-2-[[(1S)-1-methylallyl]amino]-3-[1-(2,2,2-trifluoroethyl)benzimidazol-5-yl]-6,8-dihydro-5H-pyrido[3,4-d]pyrimidin-4-one | 683/685 | (DMSO-$d_6$, 400 MHz, 80° C.): 1.09-1.17 (m, 3H), 1.22 (d, J = 6.8 Hz, 3H), 2.30-2.39 (m, 1H), 2.53-2.57 (m, 1H), 4.05 (d, J = 18.9 Hz, 1H), 4.28-4.79 (m, 3H), 4.87-5.09 (m, 2H), 5.25-5.44 (m, 3H), 5.71-5.90 (m, 1H), 7.13-7.23 (m, 1H), 7.58-7.69 (m, 2H), 7.83-7.88 (m, 2H), 7.98 (d, J = 8.1 Hz, 1H), 8.38 (s, 1H) ppm. | B |
| 36 | (6R)-7-[4-bromo-3-(trifluoromethyl)benzoyl]-6-methyl-2-[[(1S)-1-methylallyl]amino]-3-(3-methyl-[1,2,4]triazolo[4,3-a]pyridin-7-yl)-6,8-dihydro-5H-pyrido[3,4-d]pyrimidin-4-one | 616/618 | (DMSO-$d_6$, 400 MHz, 80° C.): 1.18 (d, J = 6.4 Hz, 3H), 1.23 (d, J = 6.8 Hz, 3H), 2.32-2.40 (m, 1H), 2.52-2.61 (m, 1H), 2.75 (s, 3H), 4.01-4.09 (m, 1H), 4.29-4.82 (m, 3H), 4.99 (d, J = 10.6 Hz, 1H), 5.07 (d, J = 17.6 Hz, 1H), 5.77-5.90 (m, 1H), 6.17 (d, J = 7.9 Hz, 1H), 6.82 (d, J = 6.4 Hz, 1H), 7.67 (dd, J = 8.0 Hz, 1.6 Hz, 1H), 7.77 (s, 1H), 7.85 (d, J = 1.7 Hz, 1H), 8.0 (d, J = 8.2 Hz, 1H), 8.45 (dd, J = 7.3 Hz, 0.6 Hz, 1H) ppm. | B |
| 37 | (6R)-7-[4-bromo-3-(trifluoromethyl)benzoyl]-6-methyl-2-[[(1S)-1-methylallyl]amino]-3-[5-(1-methylpyrazol-4-yl)-2-pyridyl]-6,8-dihydro-5H-pyrido[3,4-d]pyrimidin-4-one | 642/644 | (DMSO-$d_6$, 400 MHz, 80° C.): 1.17 (d, J = 7.1 Hz, 3H), 1.21 (d, J = 6.7 Hz, 3H), 2.31-2.38 (m, 1H), 2.52-2.61 (m, 1H), 3.92 (s, 3H), 3.99-4.10 (m, 1H), 4.32-4.77 (m, 3H), 4.97 (d, J = 10.4 Hz, 1H), 5.06 (d, J = 17.7 Hz, 1H), 5.77-5.89 (m, 2H), 7.42 (d, J = 8.2 Hz, 1H), 7.67 (d, J = 8.1 Hz, 1.6 Hz, 1H), 7.85 (d, J = 1.8 Hz, 1H), 7.94-8.02 (m, 2H), 8.15 (dd, J = 8.1 Hz, 2.4 Hz, 1H), 8.28 (s, 1H), 8.85-8.86 (d, J = 2.2 Hz, 1H) ppm | B |
| 38 | (6R)-7-[4-bromo-3-(trifluoromethyl)benzoyl]-3-(1-cyclopropylbenzimidazol-5-yl)-6-methyl-2-[[(1S)-1-methylallyl]amino]-6,8-dihydro-5H-pyrido[3,4-d]pyrimidin-4-one | 641/643 | (DMSO-$d_6$, 400 MHz, 80° C.): 1.06-1.20 (m, 7H), 1.23 (d, J = 6.8 Hz, 3H), 2.36 (d, J = 16.5 Hz, 1H), 2.54-2.59 (m, 1H), 3.55-3.61 (m, 1H), 4.00-4.12 (m, 1H), 4.35-4.73 (m, 3H), 4.91-5.06 (m, 2H), 5.22 (d, J = 8.1 Hz, 1H), 5.76-5.87 (m, 1H), 7.14 (dd, J = 215 Hz, 8.1 Hz, 1H), 7.57 (d, J = 19.3 Hz, 1H), 7.68 (dd, J = 8.2 Hz, 1.6 Hz, 1H), 7.79 (d, J = 9.0 Hz, 1H), 7.86 (s, 1H), 7.99 (d, J = 7.8 Hz, 1H), 8.29 (s, 1H) ppm. | B |
| 39 | (6R)-7-[4-bromo-3-(trifluoromethyl)benzoyl]-3-[5-[(2R)-2-hydroxypropoxy]-2-pyridyl]-6-methyl-2-[[(1S)-1-methylallyl]amino]-6,8-dihydro-5H-pyrido[3,4-d]pyrimidin-4-one | 635/637 | (DMSO-$d_6$, 400 MHz, 80° C.): 1.15 (d, J = 6.8 Hz, 3H), 1.20 (d, J = 6.1 Hz, 6H), 2.34 (d, J = 16.0 Hz, 1H), 2.52-2.61 (m, 1H), 3.83-4.08 (m, 4H), 4.27-4.71 (m, 4H), 4.92-5.04(m, 2H), 5.11 (d, J = 8.3 Hz, 1H), 5.76-5.88 (m, 1H), 7.07-7.12 (m, 2H), 7.16 (br. s., 2H), 7.66 (dd, J = 8.1 Hz, 1.5 Hz, 1H), 7.84 (d, J = 1.6 Hz, 1H), 7.98 (d, J = 8.1 Hz, 1H) ppm | B |
| 40 | (6R)-7-[4-bromo-3-(trifluoromethyl)benzoyl]-6-methyl-2-[[(1S)-1-methylallyl]amino]-3-(1-methylimidazo[4,5-b]pyridin-5-yl)-6,8-dihydro-5H-pyrido[3,4-d]pyrimidin-4-one | 616/618 | (DMSO-$d_6$, 400 MHz, 80° C.): 1.13 (d, J = 7.0 Hz, 3H), 1.22 (d, J = 6.7 Hz, 3H), 2.35 (d, J = 17.2 Hz, 1H), 2.57 (dd, J = 16.3 Hz, 6.2 Hz, 1H), 3.95 (s, 3H), 4.06 (d, J 18.8 Hz, 1H), 4.33-4.76 (m, 3H), 4.95 (d, J = 11.1 Hz, 1H), 5.04 (d, J = 17.5 Hz, 1H), 5.63 (d, J = 8.3 Hz, 1H), 5.75-5.85 (m, 1H), 7.31 (d, J = 8.1 Hz, 1H), 7.68 (dd, J = 8.0 Hz, 1.6 Hz, 1H), 7.86 (d, J = 1.4 Hz, 1H), 7.98 (d, J = 8.2 Hz, 1H), 8.23 (d, J = 8.0 Hz, 1H), 8.51 (s, 1H) ppm | A |

TABLE A-continued

| No. | Name | LCMS [M + 1]+ | 1H NMR | Method |
|---|---|---|---|---|
| 41 | 5-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]-N-methyl-pyridine-2-carboxamide | 619/621 | (DMSO-d$_6$, 400 MHz, 80° C.): 1.15 (d, J = 6.7 Hz, 3H), 1.20 (d, J = 6.4 Hz, 3H), 2.27-2.36 (m, 1H), 2.52-2.59(m, 1H), 2.88 (d, J = 4.8 Hz, 3H), 4.03 (d, J = 18.1 Hz, 1H), 4.27-4.77 (m, 3H), 4.94-5.07 (m, 2H), 5.73-5.87 (m, 1H), 6.00 (d, J = 8.3 Hz, 1H), 7.65 (d, J = 6.5 Hz, 1H), 7.83 (s, 1H), 7.91 (d, J = 8.0 Hz, 1H), 7.97 (d, J = 8.0 Hz, 1H), 8.17 (d, J = 8.5 Hz, 1H), 8.50 (s, 1H), 8.59-8.69 (m, 1H) ppm. | B |
| 42 | 5-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]-3-chloro-N-methyl-pyridine-2-carboxamide | 653/655 | (DMSO-d$_6$, 400 MHz, 80° C.): 1.15-1.22 (m, 6H), 2.33 (d, J = 16.3 Hz, 1H), 2.50-2.58 (m, 1H), 2.82 (d, J = 5.0 Hz, 3H), 4.03 (d, J = 18.9 Hz, 1H), 4.30-4.77 (m, 3H), 4.98 (d, J = 10.4 Hz, 1H), 5.05 (d, J = 17.5 Hz, 1H), 5.77-5.88 (m, 1H), 6.26 (d, J = 8.5 Hz, 1H), 7.64 (dd, J = 8.0 Hz, 1.7H Hz, 1H), 7.82 (d, J = 1.2 Hz, 1H), 7.97 (d, J: 8.0 Hz, 1H), 8.06 (br. s., 1H), 8.41-8.47 (m, 2H) ppm. | B |
| 43 | 2-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]-N-methyl-pyrimidine-5-carboxamide | 620/622 | (DMSO-d$_6$, 400 MHz, 80° C.): 1.17 (dd, J = 14.0 Hz, 6.8 Hz, 6H), 2.26-2.34 (m, 1H), 2.54-2.70 (m, 1H), 2.87 (d, J = 4.5 Hz, 3H), 3.93-4.10 (m, 1H), 4.49 (br. s, 2H), 4.67-4.82 (m, 1H), 4.97 (d, J = 10.4 Hz, 1H), 5.06 (d, J = 17.3 Hz, 1H), 5.73-5.85 (m, 1H), 6.18 (d, J = 7.9 Hz, 1H), 7.61-7.70 (m, 1H), 7.84 (s, 1H), 7.96 (d, J = 8.1 Hz, 1H), 8.64-8.80 (m, 1H), 9.28 (s, 2H) ppm. | B |
| 44 | 4-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]-3-chloro-N-methyl-benzamide | 652/654 | (DMSO-d$_6$, 400 MHz, 80° C.): 1.16 (d, J = 7.2 Hz, 3H), 1.20 (d, J = 6.9 Hz, 3H), 2.31-2.37 (m, 1H), 2.52-2.62 (m, 1H), 2.85 (d, J = 4.6 Hz, 3H), 4.03 (d, J = 19.3 Hz, 1H), 4.27-4.76 (m, 3H) 4.96 (d, J = 10.3 Hz, 1H), 5.06 (d, J = 17.0 Hz, 1H), 5.75-5.89 (m, 2H), 7.54 (d, J = 8.5 Hz, 1H), 7.68 (dd, J = 8.3 Hz, 1.7 Hz, 1H), 7.87 (d, J = 1.6 Hz, 1H), 7.94 (dd, J = 8.2 Hz, 1.8 Hz, 1H), 7.98 (d, J = 8.2 Hz, 1H), 8.09 (d, J = 1.8 Hz, 1H), 8.43-8.53 (m, 1H) ppm | A |
| 45 | 4-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]-3-chloro-N-methyl-benzamide | 652/654 | (DMSO-d$_6$, 400 MHz, 80° C.): 1.16 (d, J = 7.2 Hz, 3H), 1.20 (d, J = 6.9 Hz, 3H), 2.31-2.37 (m, 1H), 2.52-2.60 (m, 1H), 2.85 (d, J = 4.6 Hz, 3H), 4.06 (d, J = 18.8 Hz, 1H), 4.27-4.76 (m, 3H) 4.97 (d, J = 10.3 Hz, 1H), 5.04 (d, J = 17.0 Hz, 1H), 5.75-5.89 (m, 2H), 7.50 (d, J = 8.1 Hz, 1H), 7.66 (dd, J = 8.0 Hz, 1.6 Hz, 1H), 7.84 (d, J = 1.6 Hz, 1H), 7.95 (dd, J = 8.2 Hz, 1.9 Hz, 1H), 7.98 (d, J = 8.2 Hz, 1H), 8.08 (d, J = 1.8 Hz, 1H), 8.43-8.53 (m, 1H) ppm | A |
| 46 | (6R)-7-[4-bromo-3-(trifluoromethyl)benzoyl]-6-methyl-2-[[(1S)-1-methylallyl]amino]-3-(1-methylimidazo[4,5-b]pyrazin-5-yl)-6,8-dihydro-5H-pyrido[3,4-d]pyrimidin-4-one | 617/619 | (DMSO-d$_6$, 400 MHz, 80° C.): 1.14 (d, J = 7.1 Hz, 3H), 1.22 (d, J = 6.9 Hz, 3H), 2.31-2.39 (m, 1H), 2.54-2.62 (m, 1H), 3.97 (s, 3H), 4.07 (d, J = 18.4 Hz, 1H), 4.32-4.81 (m, 3H), 4.97 (d, J = 10.2 Hz, 1H), 5.07 (d, J = 17.4 Hz, 1H), 5.74-5.86 (m, 1H), 6.13 (d, J = 8.2 Hz, 1H); 7.68 (dd, J = 8.0 Hz, 1.9 Hz, 1H), 7.89 (d, J = 1.9 Hz, 1H), 7.98 (d, J = 8.2 Hz, 1H), 8.46 (s, 1H), 8.84 (s, 1H) ppm | A |
| 47 | (6R)-7-[4-bromo-3-(trifluoromethyl)benzoyl]-3-(1,7-dimethylbenzimidazol-5-yl)-6-methyl-2-[[(1S)-1-methylallyl]amino]-6,8-dihydro-5H-pyrido[3,4-d]pyrimidin-4-one | 629/631 | (DMSO-d$_6$, 400 MHz, 80° C.): 1.13 (d, J = 6.7 Hz, 3H), 1.22 (d, J = 6.9 Hz, 3H), 2.35 (d, J = 15.5 Hz, 1H), 2.52-2.62 (m, 1H), 2.75 (s, 3H), 4.05 (d, J = 19.0 Hz, 1H), 4.10 (s, 3H), 4.35-4.73 (m, 3H), 4.92-5.04 (m, 2H), 5.14 (d, J = 9.6 Hz, 1H), 5.75-5.87 (m, 1H), 6.83 (d, J = 23.8 Hz, 1H), 7.36 (d, J = 19.0 Hz, 1H), 7.67 (dd, J = 8.1 Hz, 1.6 Hz, 1H), 7.86 (d, J = 1.9 Hz, 1H), 7.98 (d, J = 8.3 Hz, 1H), 8.14 (s, 1H) ppm | A |
| 48 | (6R)-7-[4-bromo-3-(trifluoromethyl)benzoyl]-3-(7-fluoro-1-methyl-benzimidazol-5-yl)-6-methyl-2-[[(1S)-1-methylallyl]amino]-6,8-dihydro-5H-pyrido[3,4-d]pyrimidin-4-one | 633/635 | (DMSO-d$_6$, 400 MHz, 80° C.): 1.14 (d, J = 6.9 Hz, 3H), 1.22 (d, J = 6.7 Hz, 3H), 2.31-2.39 (m, 1H), 2.52 -2.61 (m, 1H), 4.00-4.09 (m, 4H), 4.30-4.74 (m, 3H), 4.95 (d, J = 10.4 Hz, 1H), 5.02 (d, J = 17.4 Hz, 1H), 5.48 (d, J = 8.8 Hz, 1H), 5.76-5.88 (m, 1H), 6.95-7.10 (m, 1H), 7.42 (d, J = 17.6 Hz, 1H), 7.67 (dd, J = 8.1 Hz, 1.7 Hz, 1H), 7.85 (d, J = 1.7 Hz, 1H), 7.98 (d, J = 8.3 Hz, 1H), 8.26 (s, 1H) ppm. | B |

TABLE A-continued

| No. | Name | LCMS [M + 1]+ | 1H NMR | Method |
|---|---|---|---|---|
| 49 | (6R)-7-[4-bromo-3-(trifluoromethyl)benzoyl]-3-(7-fluoro-3-methyl-benzimidazol-5-yl)-6-methyl-2-[[(1S)-1-methylallyl]amino]-6,8-dihydro-5H-pyrido[3,4-d]pyrimidin-4-one | 633/ 635 | (DMSO-d$_6$, 400 MHz, 80° C.): 1.15 (d, J = 6.9 Hz, 3H), 1.22 (d, J = 6.7 Hz, 3H), 2.36 (d, J = 16.3 Hz, 1H), 2.53-2.62 (m, 1H), 3.87 (s, 3H), 4.05 (d, J = 18.6 Hz, 1H), 4.33-4.76 (m, 3H), 4.96 (d, J = 10.4 Hz, 1H), 5.02 (d, J = 17.6 Hz, 1H), 5.59 (d, J = 8.1 Hz, 1H), 5.76-5.90 (m, 1H), 6.89-7.04 (m, 1H), 7.46 (d, J = 27.7 Hz, 1H), 7.67 (dd, J = 8.0 Hz, 1.6 Hz, 1H), 7.85 (d, J = 1.5 Hz, 1H), 7.99 (d, J = 8.1 Hz, 1H), 8.30 (s, 1H) ppm. | B |
| 50 | 4-[(6R)-7-[4-ethynyl-3-(trifluoromethyl)benzoyl]-6-methyl-2-[[(1S)-1-methylallyl]amino]-4-oxo-6,8-dihydro-5H-pyrido[3,4-d]pyrimidin-3-yl]-N-methyl-benzamide | 564.2 | (DMSO-d6, 400 MHz, 80° C.): 1.15 (d, J = 6.9 Hz, 3H), 1.21 (d, J = 6.9 Hz, 3H), 2.28-2.40 (m, 1H), 2.52-2.61 (m, 1H), 2.84 (d, J = 4.3 Hz, 3H), 3.95-4.12 (m, 1H), 4.33-4.80 (m, 4H), 4.91-5.05 (m, 2H), 5.31 (d, J = 8.1 Hz, 1H), 5.74 -5.88 (m, 1H),7.36 (d, J = 7.9 Hz, 2H), 7.74 (d, J = 8.4 Hz, 1H), 7.78-7.85 (m, 2H), 8.0 (d, J = 8.8 Hz, 2H), 8.30-8.38 (m, 1H) | B |
| 51 | (6R)-7-[4-bromo-3-(trifluoromethyl)benzoyl]-3-(7-methoxy-1-methyl-benzimidazol-5-yl)-6-methyl-2-[[(1S)-1-methylallyl]amino]-6,8-dihydro-5H-pyrido[3,4-d]pyrimidin-4-one | 645/ 647 | (DMSO-d6, 400 MHz, 80° C.): 1.13 (d, J = 6.7 Hz, 3H); 1.21 (d, J = 6.4 Hz, 3H); 2.35 (d, J = 16.4 Hz, 1H) ; 2.52-2.61 (m, 1H); 3.90 (d, J = 5.4 Hz, 3H); 3.98-4.10 (m, 4H); 4.31-4.73 (m, 3H) ; 4.93 (d, J = 10.6 Hz, 1H); 5.00 (dd, J = 18.1 Hz, 4.9 Hz, 1H); 5.25 (d, J = 7.8 Hz, 1H); 5.74-5.69 (m, 1H) ; 6.65 (d, J = 24.5 Hz, 1H); 7.12 (d, J = 22.3 Hz, 1H); 7.65 (d, J = 8.5 Hz, 1H); 7.83 (d, J = 2.5 Hz, 1H); 7.97 (d, J = 8.2 Hz, 1H); 8.04 (s, 1H) | A |
| 52 | 2-[6-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]benzimidazol-1-yl]acetonitrile | 640/ 642 | (DMSO-D6, 400 MHZ, 80° C.): 1.12 (D, J = 6.4 HZ, 3H); 1.21 (D, J = 6.8 HZ, 3H); 2.34 (D, J = 16.4 HZ, 1H); 2.56 (DD, J = 16.4 HZ, 5.8 HZ, 1H); 4.04 (D, J = 16.4 HZ, 1H); 4.26-4.77 (M, 3H); 4.87-5.05 (M, 2H); 5.34 (D, J = 8.0 HZ, 1H); 5.66 (S, 2H); 5.73-5.85 (M, 1H); 7.21 (DD, J = 21.0 HZ, 8.1 HZ, 1H); 7.55-7.74 (M, 2H); 7.84 (M, 2H); 7.97 (D, J = 8.3 HZ, 1H); 8.38 (S, 1H) | A |
| 53 | 2-[5-[(6R)-7-[4-bromo-3-(trifluoromethyl)benzoyl]-6-methyl-2-[[(1S)-1-methylallyl]amino]-4-oxo-6,8-dihydro-5H-pyrido[3,4-d]pyrimidin-3-yl]benzimidazol-1-yl]acetonitrile | 640/ 642 | (DMSO-d6, 400 MHz, 80° C.): 1.11 (d, J = 6.9 Hz, 3H); 1.21 (d, J = 6.8 Hz, 3H); 2.36 (d, J = 16.4 Hz, 1H); 2.57 (dd, J = 16.5 Hz, 5.5 Hz, 1H); 4.06 (d, J = 18.4 Hz, 1H); 4.26-4.77 (m, 3H); 4.85-5.08 (m, 2H); 5.34 (d, J = 8.0 Hz, 1H); 5.60 (s, 2H); 5.73-5.84 (m, 1H); 7.14 (d, J = 19.5 Hz, 8.4 Hz, 1H); 7.62-7.77 (m, 2H); 7.80-7.90 (m, 2H); 7.97 (d, J = 8.1 Hz, 1H); 8.40 (s, 1H) | A |
| 54 | (6R)-7-[4-bromo-3-(trifluoromethyl)benzoyl]-6-methyl-2-[[(1S)-1-methylallyl]amino]-3-[6-(methylamino)-3-pyridyl]-6,8-dihydro-5H-pyrido[3,4-d]pyrimidin-4-one | 591/ 593 | (DMSO-d6, 600 MHz, 80° C.): 1.11-1.22 (m, 6H), 2.27-2.36 (m, 1H), 2.51-2.59 (m, 1H), 2.84 (d, J = 4.8 Hz, 3H), 3.91-4.05 (m, 1H), 4.27-4.70 (m, 3H), 4.91-5.07 (m, 2H), 5.58 (d, J = 7.8 Hz, 1H), 5.76-5.89 (m, 1H), 6.55 (d, J = 9.0 Hz, 1H), 6.57-6.64 (m, 1H), 7.13-7.26 (m, 1H), 7.61-7.67 (m, 1H), 7.74-7.86 (m, 2H), 7.96 (d, J = 8.1 Hz, 1H) | A |

TABLE B

| No. | Structure |
|---|---|
| 33 | 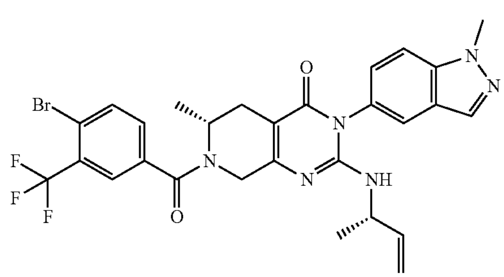 [SMILES: C=C[C@H](C)Nc1nc2c(c(=O)n1-c1ccc3c(cnn3C)c1)C[C@@H](C)N(C(=O)c1ccc(Br)c(C(F)(F)F)c1)C2] |
| 34 | |

TABLE B-continued

| No. | Structure |
|---|---|
| 35 | 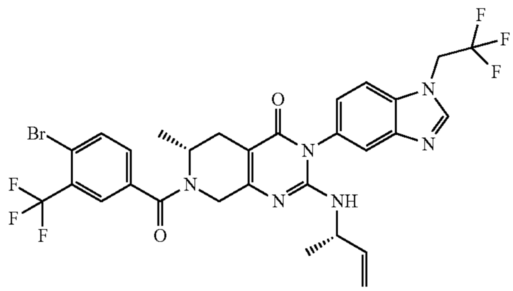 [SMILES: C=C[C@H](C)Nc1nc2c(c(=O)n1-c1ccc3c(c1)ncn3CC(F)(F)F)C[C@@H](C)N(C(=O)c1ccc(Br)c(C(F)(F)F)c1)C2] |
| 36 | 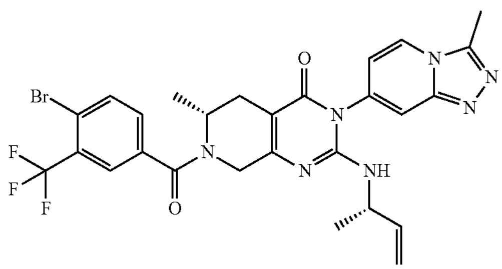 [SMILES: C=C[C@H](C)Nc1nc2c(c(=O)n1-c1ccn3c(C)nnc3c1)C[C@@H](C)N(C(=O)c1ccc(Br)c(C(F)(F)F)c1)C2] |
| 37 | 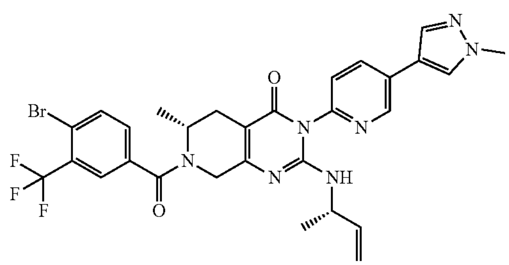 [SMILES: C=C[C@H](C)Nc1nc2c(c(=O)n1-c1ccc(-c3cnn(C)c3)cn1)C[C@@H](C)N(C(=O)c1ccc(Br)c(C(F)(F)F)c1)C2] |
| 38 | 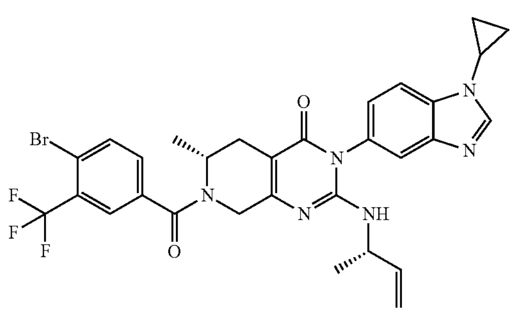 [SMILES: C=C[C@H](C)Nc1nc2c(c(=O)n1-c1ccc3c(c1)ncn3C1CC1)C[C@@H](C)N(C(=O)c1ccc(Br)c(C(F)(F)F)c1)C2] |
| 39 | 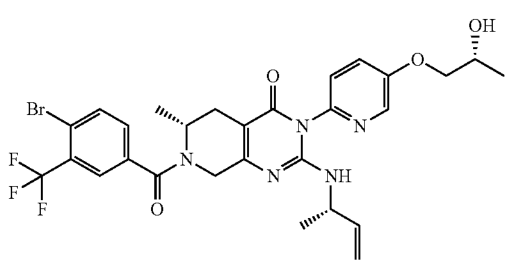 [SMILES: C=C[C@H](C)Nc1nc2c(c(=O)n1-c1ccc(OC[C@@H](C)O)cn1)C[C@@H](C)N(C(=O)c1ccc(Br)c(C(F)(F)F)c1)C2] |
| 40 | |
| 41 | |
| 42 | |
| 43 | |
| 44 | Atropoisomer of Compound 45 |

TABLE B-continued

| No. | Structure |
|-----|-----------|
| 45 | Atropoisomer of Compound 44 |
| 46 | 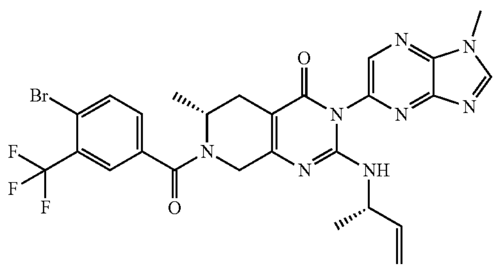 [SMILES: C=C[C@H](C)Nc1nc2c(c(=O)n1-c1cnc3c(ncn3C)n1)C[C@@H](C)N(C(=O)c1ccc(Br)c(C(F)(F)F)c1)C2] |
| 47 | 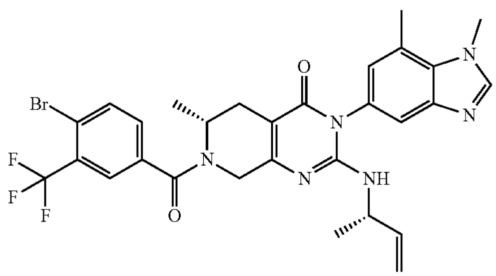 [SMILES: C=C[C@H](C)Nc1nc2c(c(=O)n1-c1cc(C)c3c(c1)ncn3C)C[C@@H](C)N(C(=O)c1ccc(Br)c(C(F)(F)F)c1)C2] |
| 48 | 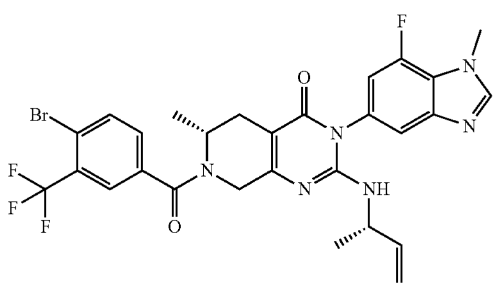 [SMILES: C=C[C@H](C)Nc1nc2c(c(=O)n1-c1cc(F)c3c(c1)ncn3C)C[C@@H](C)N(C(=O)c1ccc(Br)c(C(F)(F)F)c1)C2] |
| 49 | 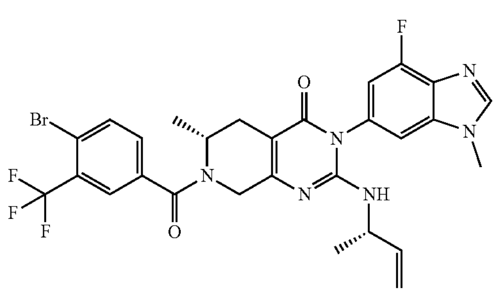 [SMILES: C=C[C@H](C)Nc1nc2c(c(=O)n1-c1cc(F)c3ncn(C)c3c1)C[C@@H](C)N(C(=O)c1ccc(Br)c(C(F)(F)F)c1)C2] |
| 50 | |
| 51 | |
| 52 | |
| 53 | |
| 54 | |

Example 26

Intermediates I1 to I7

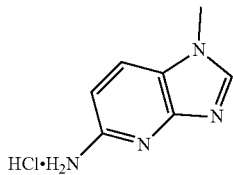

NaHMDS 2M in THF (1.5 eq., 24.42 mL, 48.84 mmol) was added dropwise to a solution of 5-chloro-1H-imidazo[4,5-b]pyridine1 (1 eq., 5 g, 32.56 mmol) in anhydrous THF (162 mL) at 0° C. MeI (3 eq., 6.081 mL, 97.68 mmol) was added and the mixture was stirred at rt for 1 h. Sat. aq. NH$_4$Cl was added to the mixture and the THF was evaporated under vacuum. The aqueous phase was extracted with DCM (3×). The combined organic layers were washed with brine and dried over MgSO$_4$. The solids were removed by filtration and the filtrate was evaporated to dryness to give the crude mixture as a brown solid. The solid was purified by flash chromatography on silica gel (from 0 to 10% of MeOH in DCM) to afford 5-chloro-1-methyl-1H-imidazo[4,5-b]pyridine (3.65 g, 67%) as a colorless oil. $^1$H-NMR (DMSO-d$_6$, 400 MHz): 3.88 (s, 3H), 7.37 (d, J=8.2 Hz, 1H), 8.13 (d, J=8.4 Hz, 1H), 8.50 (s, 1H) ppm.

Pd$_2$(dba)$_3$ (0.1 eq., 0.55 g, 0.6 mmol), (+/−)-BINAP (0.2 eq., 0.74 g, 1.19 mmol), benzophenone imine (1.5 eq., 1.502 mL, 8.95 mmol) and Cs$_2$CO$_3$ (2.5 eq., 4.86 g, 14.92 mmol) were added to a solution of 5-chloro-1-methyl-1H-imidazo[4.5-b]pyridine (I eq., 1 g. 5.97 mmol) in DME (50 mL). The mixture was purged with N$_2$ and stirred at 120° C. for 18 h. The mixture was evaporated to dryness to give the crude product which was purified by flash chromatography on silica gel (from 0 to 100% of EA in CyH, then from 0 to 10% of MeOH in DCM) to give N-(1-methyl-1H-imidazo[4,5-b]pyridin-5-yl)-1.1-diphenylmethanimine (1.49 g, 80%) as a beige solid. $^1$H-NMR (DMSO-d$_6$, 400 MHz): 3.77 (s, 3H), 6.60 (d, J=8.2 Hz, 1H), 7.13-7.18 (m, 2H), 7.23-7.29 (m, 3H), 7.46-7.52 (m, 2H), 7.54-7.60 (m, 1H), 7.67-7.73 (m, 2H), 7.80 (d, J=8.2 Hz, 1H), 8.23 (s, 1H) ppm.

HCl 1M (1.5 eq., 8.64 mL, 8.64 mmol) was added to a solution of N—(O-methyl-1H-imidazo[4,5-b]pyridin-5-yl)-1.1-diphenylmethanimine (1 eq., 1.8 g, 5.76 mmol) in THF (55 mL). The mixture was stirred at rt for 18 h. The THF was evaporated under vacuum and the resulting aqueous phase was extracted with Et$_2$O (3×20 mL). The aqueous phase was evaporated to dryness to give 1-methyl-1H-imidazo[4,5-b]pyridin-5-amine hydrochloride (1.05 g. 99%) as a beige solid. LCMS: C$_7$H$_8$N$_4$. [M+H]$^+$: 149.

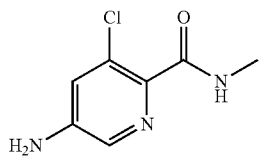

5-amino-3-chloropyridine-2-carboxylate1 (1 eq., 1 g, 5.36 mmol) was added to a solution of MeNH$_2$ 2M in THF (14.93 eq., 40 mL, 80 mmol). The mixture was stirred at 130° C. for 16 h. The mixture was evaporated to dryness and was purified by flash chromatography on silica gel (from 0 to 10% of MeOH in DCM) to afford 5-amino-3-chloro-N-methylpicolinamide (553 mg, 53%) as a beige solid. $^1$H-NMR (DMSO-d$_6$, 400 MHz): 2.72 (d, J=4.7 Hz, 3H), 6.09 (s, 2H), 6.98 (d, J=2.3 Hz, 1H), 7.86 (d, J=2.3 Hz, 1H), 8.19-8.26 (m, 1H) ppm.

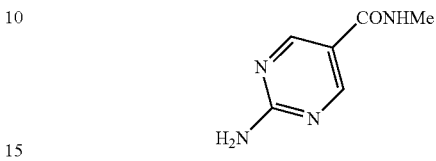

LiOH·H$_2$O (2.6 eq., 2.85 g, 67.91 mmol) was added to a suspension of methyl 2-aminopyrimidine-5-carboxylate (1 eq., 4 g, 26.12 mmol) in MeOH (80 mL) and H$_2$O (8 mL). The mixture was stirred at 60° C. for 1 h and then concentrated to remove the MeOH. The solution was diluted with water (10 mL) and acidified with HCl 1N until pH=4. The precipitate was filtered, washed with water and co-evaporated with EtOH to give 2-aminopyrimidine-5-carboxylic acid (2.65 g, 73%) as a white solid. $^1$H-NMR (DMSO-d$_6$, 400 MHz): 7.45 (s, 2H), 8.63 (s, 2H), 12.60-12.81 (br. s. 1H) ppm. LCMS: C$_5$H$_5$N$_3$O$_2$, [M+H]$^+$: 140.

T$_3$P (50% in DMF, 1.6 eq., 6.69 mL, 11.50 mmol) was added to a solution of 2-aminopyrimidine-5-carboxylic acid (1 eq., 1 g, 7.19 mmol) in anhydrous DMF (12 mL). The mixture was stiffed at rt for 1 h. and MeNH$_2$ (2M in THF, 5 eq., 17.97 mL, 35.94 mmol) was then added. The mixture was heated to 60° C. for 16 h. After full conversion of the starting material, the mixture was evaporated to dryness to give the crude mixture which was purified by flash chromatography (from 0% to 100% of MeOH/NH$_4$OH (9:1) in DCM) to afford a sticky oil. The corresponding oil was triturated in CH$_2$Cl$_2$ to afford 2-amino-N-methylpyrimidine-5-carboxamide (0.70 g, 64%) as a white solid. $^1$H-NMR (DMSO-d$_6$, 400 MHz): 2.73 (d, J=4.5 Hz, 3H), 7.15 (s, 2H), 8.19-8.26 (m, 1H), 8.63 (s, 2H) ppm. LCMS: C$_6$H$_8$N$_4$O$_2$, [M+H]$^+$: 153.

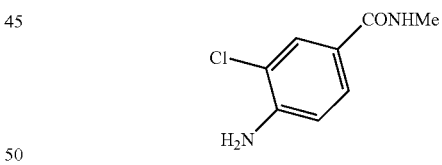

Methylammonium chloride (2.5 eq., 19.68 g, 291.409 mmol) was added to a solution of 4-amino-3-chlorobenzoic acid (1 eq., 20 g, 116.56 mmol), HATU (1.2 eq., 53.19 g, 139.88 mmol) and DIPEA (6 eq., 121.82 mL, 699.38 mmol) in anhydrous DCM (400 mL) under N$_2$. The mixture was stirred at rt for 16 h. The mixture was evaporated to dryness and the crude product was diluted in EA (200 mL) and sat. NaHCO$_3$ (200 mL). The layers were separated and the aqueous layer was extracted with EA (2×200 mL). The combined organic phases were washed with, water (5×) and brine (2×)m and dried over Na$_2$SO$_4$. The solids were removed by filtration. The filtrate was evaporated to dryness to give an orange oil which was purified by flash chromatography on silica gel (from 0 to 2% of MeOH in DCM) to afford 4-amino-3-chloro-N-methylbenzamide (11.4 g, 53%) as a yellow solid. $^1$H-NMR (DMSO-d$_6$, 400 MHz): 2.73 (d, J=4.5 Hz, 3H), 5.83 (s, 2H), 6.79 (d, J=8.4 Hz, 1H), 7.54 (dd, J=8.4 Hz, 1.5 Hz, 1H), 7.72 (d, J=1.5 Hz, 1H), 8.04-8.15 (m, 1H) ppm. LCMS: $C_8H_9ClN_2O$, $[M+H]^+$: 185/187.

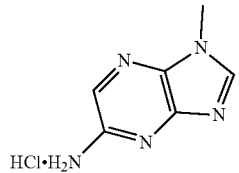

MeI (1 eq., 1.49 mL, 23.99 mmol) and LiHMDS (1 M in THF, 1 eq., 23.99 mL, 23.99 mmol) were added to a solution of 5-bromo-3-chloropyrazin-2-amine (1 eq., 5 g, 23.99 mmol) in anhydrous DMF (150 mL) at 0° C. The mixture was stirred at rt for 2 h. Water and EA were then added. The aqueous phase was extracted with EA (3×). The combined organic layers were washed with water (2×) and brine (2×). and dried over $Na_2SO_4$. The solids were removed by filtration. The filtrate was evaporated to dryness to give the crude product which was purified by flash chromatography on silica gel (from 0 to 50% of EA in cyclohexane) to afford 5-bromo-3-chloro-N-methylpyrazin-2-amine (2.72 g, 51%) as a colorless oil. $^1$H-NMR (DMSO-$d_6$, 400 MHz): 2.85 (d, J=4.5 Hz, 3H), 7.25-7.31 (m, 1H), 8.18 (s, 1H) ppm.

A solution of 5-bromo-3-chloro-N-methylpyrazin-2-amine (1 eq., 2.5 g, 11.24 mmol) in $NH_4OH$ (33% in water. 50 eq., 72.93 mL, 561.87 mmol) was stirred at 120° C. for 2 days. The mixture was evaporated to dryness to give the crude product which was washed with $CH_2Cl_2$ (3×) to give 5-bromo-$N^2$-methylpyrazine-2,3-diamine (2.36 g, 99%) as a beige powder. LCMS: $C_5H_7BrN_4$, $[M+H]^+$: 203/205.

A solution of 5-bromo-$N^2$-methylpyrazine-2,3-diamine (1 eq., 5.11 g, 25.17 mmol) and p-TsOH (0.12 eq., 0.51 g, 2.97 mmol) in triethyl orthoformate (24.39 eq., 102.2 mL, 613.74 mmol) was stirred and heated at 130° C. for 2 h. The mixture was cooled to 0° C. The resulting solid was filtered to give 5-bromo-1-methyl-1H-imidazo[4.5-b]pyrazine (4.73 g. 88%) as a brown solid. $^1$H-NMR (DMSO-$d_6$, 400 MHz): 3.87 (s, 3H), 8.59 (s, 1H), 8.80 (s, 1H) ppm. LCMS: $C_6H_5BrN_4$, $[M+H]^+$: 213/215.

$Pd_2(dba)_3$ (0.1 eq., 0.64 g, 0.704 mmol), (+/−)-BINAP (0.2 eq., 0.88 g, 1.408 mmol), benzophenone imine (1.5 eq., 1.77 mL, 10.56 mmol) and $Cs_2CO_3$ (2.5 eq., 5.74 g, 17.602 mmol) were added to a solution of 5-bromo-1-methyl-1H-imidazo[4,5-b]pyrazine (1 eq., 1.5 g, 7.041 mmol) in DME (59 mL). The mixture was purged with $N_2$ (3×) and then stirred at 120° C. for 18 h. The mixture was evaporated to dryness to give the crude product which was purified by flash chromatography on silica gel (from 0 to 100% of EA in CyH, then from 0 to 10% of MeOH in DCM) to afford N-(1-methyl-1H-imidazo[4.5-b]pyrazin-5-yl)-1.1-diphenyl-methanimine (2.11 g. 96%). $^1$H-NMR (DMSO-$d_6$, 400 MHz): 3.78 (s, 3H), 7.16-7.21 (m, 2H), 7.28-7.32 (m, 3H), 7.49-7.64 (m, 3H), 7.71-7.76 (m, 2H), 7.84 (s, 1H), 8.54 (s, 1H) ppm.

HCl 1 N (1.5 eq., 10.1 mL, 10.1 mmol) was added to a solution of N-(1-methyl-1H-imidazo[4.5-b]pyrazin-5-yl)-1.1-diphenylmethanimine (I eq., 2.11 g. 6.73 mmol) in THF (60 mL). The mixture was stirred at rt for 18 h and then the THF was evaporated under vacuum. The resulting aqueous phase was extracted with $Et_2O$. The aqueous phase was evaporated to dryness to give 1-methyl-1H-imidazo[4.5-b] pyrazin-5-amine hydrochloride (1.15 g, 92%) as an orange solid. $^1$H-NMR (DMSO-$d_6$, 400 MHz): 3.90 (s, 3H), 7.96 (s, 1H), 9.23 (s, 1H) ppm.

Intermediate I6

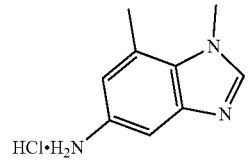

Tetrabutylammonium hydrogen sulfate (0.1 eq., 1.47 g, 4.33 mmol) and dimethyl sulfate (1.1 eq., 4.51 mL, 47.609 mmol) were added to a solution of 4-bromo-2-methyl-6-nitroaniline (1 eq., 10 g. 43.28 mmol) in toluene (80 mL) and a solution of NaOH 50% (24 eq., 80 mL, 1040 mmol). The mixture was stirred at rt for 2 h and then water was added. The organic layers were separated. washed with water and brine, and dried over $Na_2SO_4$. The solids were removed by filtration. The filtrate was evaporated to dryness to give a red solid which was triturated with n-pentane to afford 4-bromo-N,2-dimethyl-6-nitroaniline (10.2 g. 96%) as a red solid. $^1$H-NMR (DMSO-$d_6$, 400 MHz): 2.26 (s, 3H), 2.70 (d. J=5.2 Hz, 3H), 6.45-6.54 (m, 1H), 7.48 (d, J=2.0 Hz, 1H), 7.77 (d, J=2.4 Hz, 1H) ppm. LCMS: $C_8H_9BrN_2O_2$. $[M+H]^+$: 245/247.

Fe (5 eq., 5.7 g, 102.009 mmol) was added to a solution of 4-bromo-N,2-dimethyl-6-nitroaniline (1 eq., 5 g. 20.402 mmol) and AcOH (10 eq., 11.69 mL, 204.018 mmol) in EtOH (130 mL) and water (70 mL). The mixture was stirred at 80° C. for 2 h. The mixture was filtered through a pad of celite and washed with EtOAc. The filtrate was concentrated to removed EtOH and then sat. aq. $NaHCO_3$ was added. The aqueous phase was extracted with EtOAc (3×). The combined organics layers were washed with brine and dried over $Na_2SO_4$. The solids were removed by filtration. The filtrate was evaporated to dryness to give 4-bromo-N1,6-dimethyl-benzene-1.2-diamine (5.54 g) as a crude product and a brown oil. A solution of 4-bromo-N1,6-dimethylbenzene-1, 2-diamine (1 eq., 4.5 g, 20.92 mmol) and p-TsOH (0.1 eq., 0.36 g, 2.092 mmol) in trimethyl orthoformate (25 eq., 57.22 mL, 523.027 mmol) was heated at 80° C. for 1 h. The mixture was evaporated to dryness and purified by flash chromatography on silica gel (from 0 to 100% of EA in CyH, then, from 0 to 10% of MeOH in DCM) to afford 5-bromo-1,7-dimethyl-1H-benzo[d]imidazole (3.59 g. 72%) as a beige solid. $^1$H-NMR (DMSO-$d_6$, 400 MHz); 2.69 (s, 3H); 4.03 (s, 3H), 7.10-7.15 (m, 1H), 7.60-7.65 (m, 1H), 8.11 (s, 1H) ppm. LCMS: $C_6H_9BrN_2$. $[M+H]^+$: 225/227.

$Pd_2(dba)_3$ (0.1 eq., 1.38 g, 1.51 mmol), (+/−)-BINAP (0.2 eq., 1.88 g, 3.021 mmol), benzophenone imine (1.5 eq., 3.802 mL, 22.66 mmol) and $Cs_2CO_3$ (2.5 eq., 12.304 g. 37.76 mmol) were added to a solution of 5-bromo-1,7-dimethyl-1H-benzo[d]imidazole (1 eq., 3.4 g, 15.105 mmol) in DME (126 mL). The mixture was purged with $N_2$ and stirred at 100° C. for 24 h. The mixture was filtered through a pad of celite. The filtrate was evaporated to dryness and purified by flash chromatography on silica gel (from 0 to 100% of EA in CyH, then from 0 to 10% of MeOH in DCM) to afford N-(1,7-dimethyl-1H-benzo[d]imidazol-5-yl)-1.1-diphenylmethanimine (4.08 g, 83%) as an orange oil. $^1$H-NMR (DMSO-$d_6$, 400 MHz): 2.56 (s, 3H), 3.94 (s, 3H), 6.48 (br. s., 1H), 6.65 (d. J=1.9 Hz, 1H), 7.13-7.20 (m, 2H), 7.25-7.34 (m, 3H), 7.42-7.54 (m, 3H), 7.62-7.69 (m, 2H), 7.90 (s, 1H) ppm. LCMS: C₂₂H₁₉N₃, [M+H]⁺: 326.

HCl 1N (1.5 eq., 19.96 mL, 19.96 mmol) was added to a solution of N-(1,7-dimethyl-1H-benzo[d]imidazol-5-yl)-1.1-diphenylmethanimine (1 eq., 4.33 g. 13.306 mmol) in THF (125 mL). The mixture was stirred at rt for 2 days. The THF was evaporated under vacuum. The resulting aqueous phase was extracted with Et₂O (2×) and AcOEt (2×). The aqueous phase was evaporated to dryness to give 1.7-dimethyl-1H-benzo[d]imidazol-5-amine hydrochloride (2.96 g, 99%) as a beige solid. LCMS: C₉H₁₁N₃, [M+H]⁺: 162.

Intermediate I7

MeI (1.5 eq., 1.74 mL, 27.904 mmol) and isopropylmagnesium chloride 2M in THF (1.5 eq., 13.95 mL, 27.904 mmol) were added to a solution of 5-bromo-7-fluoro-1H-1, 3-benzodiazole (1 eq., 4 g, 18.602 mmol) in anhydrous THF (160 mL) at 0° C. The mixture was stirred for 5 min and then heated at 50° C. for 18 h. Sat. aq. NaHCO₃ was added to the mixture. The aqueous layer was extracted with EA (3×). The combined organic layers were washed with brine and dried over Na₂SO₄. The solids were removed by filtration. The filtrate was evaporated to dryness and purified by flash chromatography on silica gel (from 0 to 10% of MeOH in DCM) to afford a mixture of 5-bromo-7-fluoro-1-methyl-1H-benzo[d]imidazole/6-bromo-4-fluoro-1-methyl-1H-benzo[d]imidazole (1.85 g, 43%. 2/2'3:1) as a brown solid. ¹H-NMR (DMSO-d₆, 400 MHz): 2.26 (s, 3H), 2.70 (d, J=5.2 Hz, 3H), 6.45-6.54 (m, 1H), 7.48 (d, J=2.0 Hz, 1H), 7.77 (d, J=2.4 Hz, 1H) ppm. LCMS: C₈H₆BrN₂, [M+H]⁺: 229/231.

Pd₂(dba)₃ (0.1 eq., 0.68 g, 0.74 mmol). (+/−)-BINAP (0.2 eq., 0.92 g. 1.48 mmol), benzophenone imine (1.5 eq., 1.87 mL, 11.13 mmol) and Cs₂CO₃ (2.5 eq., 6.045 g, 18.55 mmol) were added to a solution of 5-bromo-7-fluoro-1-methyl-1H-benzo[d]imidazole/6-bromo-4-fluoro-1-methyl-1H-benzo[d]imidazole (1 eq., 1.7 g. 7.42 mmol) in DME (62 mL). The mixture was purged with N₂ (3×) and stirred at 100° C. for 35 h. The mixture was filtered through a pad of celite. The filtrate was evaporated to dryness and purified by flash chromatography on silica gel (from 0 to 100% of EA in CyH. then from 0 to 10% of MeOH in DCM) to afford N-(7-fluoro-1-methyl-1H-benzo[d]imidazol-5-yl)-1.1-diphenylmethanimine/N-(4-fluoro-1-methyl-1H-benzo[d]imidazol-6-yl)-1.1-diphenylmethanimine (4.08 g, 83%. in a ratio 3:1) as a yellow solid. LCMS: C₂₁H₁₆FN₃. [M+H]⁺: 330.

HCl 1N (1.5 eq., 12.3 mL, 12.3 mmol) was added to a solution of N-(7-fluoro-1-methyl-1H-benzo[d]imidazol-5-yl)-1,1-diphenylmethanimine/N-(4-fluoro-1-methyl-1H-benzo[d]imidazol-6-yl)-1,1-diphenylmethanimine (1 eq., 2.7 g. 8.02 mmol) in THF (80 mL). The mixture was stirred at rt for 2 days and the THF was evaporated under vacuum. The aqueous phase was extracted with Et₂O (2×) and then evaporated to dryness to give 7-fluoro-1-methyl-1H-benzo[d]imidazol-5-amine hydrochloride/4-fluoro-1-methyl-1H-benzo[d]imidazol-6-amine hydrochloride (1.60 g. 99% in a ratio of 3:1) as a beige solid. LCMS: C₈H₈FN₃, [M+H]⁺: 166.

Intermediate I8

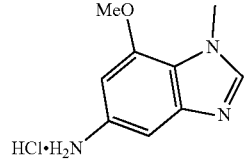

NBS (1.05 eq., 11.11 g, 62.44 mmol) was added to a solution of 2-methoxy-6-nitroaniline (1 eq., 10 g, 59.47 mmol) in DCM (350 mL). The mixture was stirred at rt for 1 h. The mixture was evaporated to dryness to give the crude product as a brown solid. EA was added. The organic layer was washed with water (5×) and brine (2×) and dried over Na₂SO₄. The solids were removed by filtration, and the filtrate was evaporated to dryness to give 4-bromo-2-methoxy-6-nitroaniline (14.6 g, 99%) as an orange solid. ¹H-NMR (DMSO-d₆, 400 MHz): 3.90 (s, 3H), 7.19 (d, J=2.0 Hz, 1H), 7.24 (br. s., 2H), 7.71 (d, J=2.0 Hz, 1H) ppm.

Tetrabutylammonium hydrogen sulfate (0.1 eq., 2.019 g, 5.95 mmol) and dimethyl sulfate (1.1 eq., 6.203 mL, 65.408 mmol) were added to a solution of 4-bromo-2-methoxy-6-nitroaniline (1 eq., 14.69 g, 59.46 mmol) in PhMe (110 mL) and NaOH 50% in water (35 eq., 109 mL, 2088 mmol). The mixture was stirred at rt for 1 h and then filtered. The resulting solid was triturated into n-pentane to give a red solid. The corresponding solid was purified by normal flash chromatography on silica gel (from 0 to 50% of EA in PE) to afford 4-bromo-2-methoxy-N-methyl-6-nitroaniline (7.5 g, 48%) as an orange solid. ¹H-NMR (DMSO-d₆, 400 MHz): 2.89 (d, J=5.3 Hz, 3H), 3.87 (s, 3H), 7.18 (d, J=2.1 Hz, 1H), 7.20-7.27 (m, 1H), 7.59 (d, J=2.1 Hz, 1H) ppm.

Fe (5 eq., 7.49 g, 134.061 mmol) was added to a solution of 4-bromo-2-methoxy-N-methyl-6-nitroaniline (1 eq., 7 g, 26.81 mmol) and AcOH (10 eq., 15.36 mL, 268.12 mmol) in EtOH (185 mL) and water (100 mL). The mixture was stirred at 80° C. for 1 h and then filtered through a pad of celite. The filtrate was evaporated to dryness to give the crude product which was purified by flash chromatography on silica gel (from 0 to 100% of EA in PE, and then from 0 to 10% of MeOH in DCM) to give 4-bromo-6-methoxy-N1-methylbenzene-1,2-diamine (3.5 g, 52%) as a yellow oil. ¹H-NMR (DMSO-d₆, 400 MHz): 2.52 (m, 3H), 3.20-3.42 (br s., 1H), 3.71 (s, 3H), 4.80-5.00 (br s., 2H), 6.35 (d, J=2.1 Hz, 1H), 6.47 (d, J=2.1 Hz, 1H) ppm.

A solution of 4-bromo-6-methoxy-N1-methylbenzene-1, 2-diamine (1 eq., 3.2 g, 13.85 mmol) and p-TsOH (0.1 eq., 0.24 g, 1.38 mmol) in trimethyl orthoformate (56 mL) was stirred and heated at 80° C. for 1 h. The mixture was evaporated to dryness to give the crude product which was purified by flash chromatography on silica gel (from 0 to 100% of EA in PE, then, from 0 to 10% of MeOH in DCM) to give 5-bromo-7-methoxy-1-methyl-1H-benzo[d]imidazole (2.95 g, 88%) as a red solid. ¹H-NMR (DMSO-d₆, 400 MHz): 3.92 (s, 3H), 3.96 (s, 3H), 6.91 (d, J=1.2 Hz, 1H), 7.41 (d, J=1.2 Hz, 1H), 8.08 (s, 1H) ppm.

Pd₂(dba)₃ (0.1 eq., 1.083 g, 1.18 mmol), (+/−)-BINAP (0.2 eq., 1.47 g, 2.36 mmol), benzophenone imine (1.5 eq., 2.98 mL, 17.73 mmol) and Cs₂CO₃ (4 eq., 15.407 g, 47.29 mmol) were added to a solution of 5-bromo-7-methoxy-1-methyl-1H-benzo[d]imidazole (1 eq., 2.85 g, 11.82 mmol) in DME (24 mL). The mixture was purged with N₂ (3×) and then stirred at 100° C. for 20 h. The mixture was evaporated to dryness and purified by flash chromatography (from 0 to 100% of EA in PE, then from 0 to 10% of MeOH in DCM) to give N-(7-methoxy-1-methyl-1H-benzo[d]imidazol-5-yl)-1,1-diphenylmethanimine (4.0 g, 99%) as a brown oil. ¹H-NMR (DMSO-d₆, 400 MHz): 3.71 (s, 3H), 3.87 (s, 3H), 6.25 (d, J=1.3 Hz, 1H), 6.46 (d, J=1.5 Hz, 1H), 7.15-7.21 (m, 2H), 7.28-7.34 (m, 3H), 7.43-7.55 (m, 3H), 7.65-7.70 (m, 2H), 7.89 (s, 1H) ppm.

HCl 1 N (1.5 eq., 19.77 mL, 19.77 mmol) was added to a solution of N-(7-methoxy-1-methyl-1H-benzo[d]imidazol-5-yl)-1,1-diphenylmethanimine (1 eq., 4.5 g, 13.18 mmol) in THF (125 mL). The mixture was stirred at rt for 18 h. THF was evaporated under vacuum and the resulting aqueous phase was extracted with Et₂O (2×). The aqueous phase was evaporated to dryness to give 7-methoxy-1-methyl-1H-benzo[d]imidazol-5-amine hydrochloride (2.8 g, 100%) as a beige solid. ¹H-NMR (DMSO-d₆, 400 MHz): 4.11 (s, 3H), 6.97 (d, J=1.3 Hz, 1H), 7.20 (d, J=1.3 Hz, 1H), 9.45 (s, 1H) ppm.

Intermediate I9

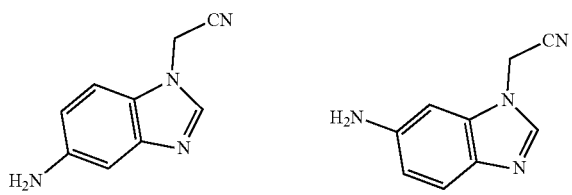 [SMILES: N#CCn1cnc2cc(N)ccc21 ; N#CCn1cnc2ccc(N)cc21]

K₂CO₃ (1.2 eq., 1.017 g, 7.36 mmol) was added to a solution of 5-nitrobenzimidazole (1 eq., 1 g, 6.13 mmol) in MeCN (10 mL). The mixture was stirred at rt for 0.5 h. Bromoacetonitrile (1.1 eq., 0.47 mL, 6.74 mmol) was added and the mixture was stirred at 70° C. for 16 h. The mixture was allowed to cool to rt and then evaporated to dryness. The crude mixture was purified by flash chromatography on silica gel (from 0% to 10% of MeOH in DCM) to give a 1:1 mixture of 2-(5-nitro-1H-benzo[d]imidazol-1-yl)acetonitrile and 2-(6-nitro-1H-benzo[d]imidazol-1-yl)acetonitrile (1.19 g, 96%) as an orange solid. LCMS: C₉H₆N₄O₂ [M+H]⁺: 203.

Iron (5 eq., 1.64 g, 29.43 mmol) was added to a solution of a 1:1 mixture of 2-(5-nitro-1H-benzo[d]imidazol-1-yl)acetonitrile and 2-(6-nitro-1H-benzo[d]imidazol-1-yl)acetonitrile (1 eq., 1.19 g, 5.89 mmol) and AcOH (10 eq., 3.37 mL, 58.86 mmol) in EtOH (10 mL) and water (10 mL). The mixture was stirred at 70° C. for 30 min and then filtered through celite pad. The pad was rinsed with EA (3×50 mL). The filtrate was evaporated to dryness. The mixture was purified by flash chromatography on silica gel (from 0% to 10% of MeOH in DCM) to give a 1:1 mixture of 2-(5-amino-1H-benzo[d]imidazol-1-yl)acetonitrile and 2-(6-amino-1H-benzo[d]imidazol-1-yl)acetonitrile (0.92 g, 91%) as an orange oil. LCMS: C₉H₈N₄ [M+H]⁺: 173.

Example 27

Additional Compounds

Additional compounds shown below and including those described herein, can be prepared using similar materials and methods described herein, such as those described herein.

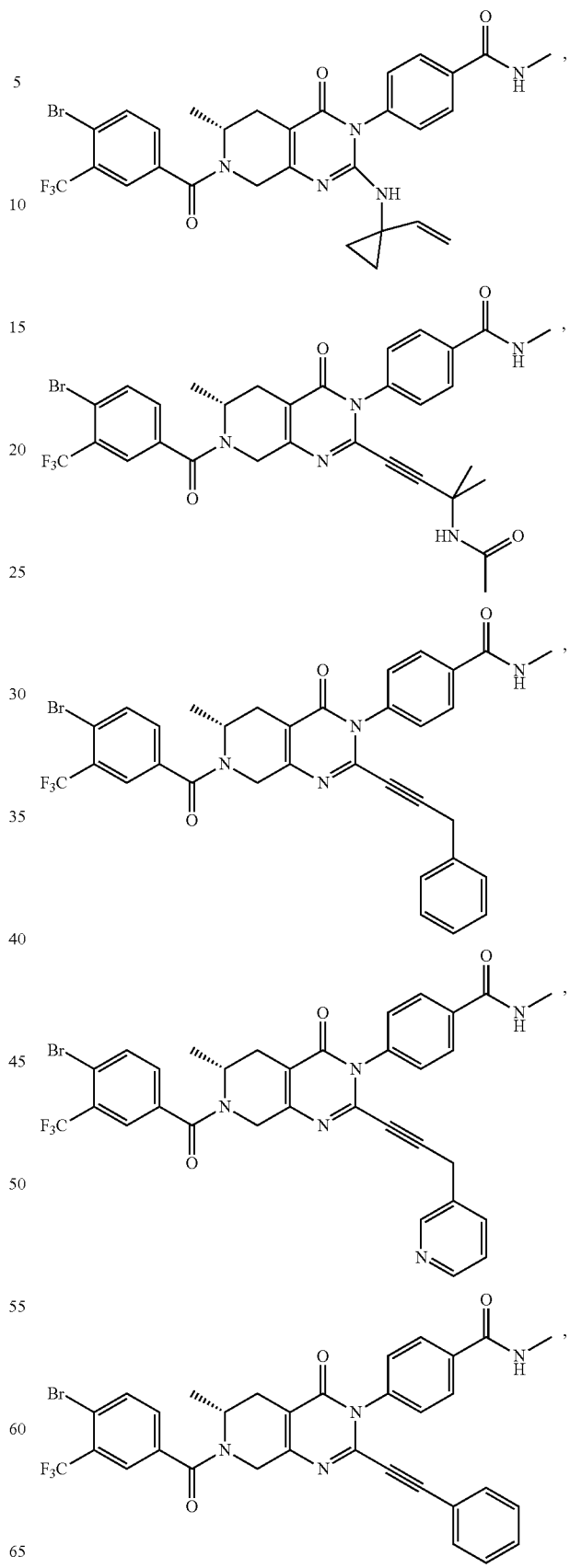

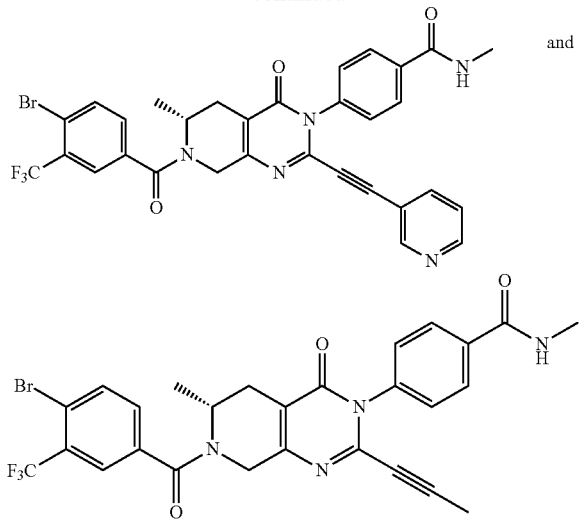

and (including pharmaceutically acceptable salts of any of the foregoing).

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using CellTiter-Glo 2.0 (Promega).

On day 0, HepG2.117 cells (which are maintained in routine cell culture with doxycycline present in the medium at a final concentration of 1 μg/mL) are seeded in 96-well plates (white with clear bottom) at a density of $2.0 \times 10^4$ cells/well (0.1 mL/well) in medium without doxycycline to induce pgRNA transcription and subsequent formation of HBV particles. The cells are incubated at 37° C. and 5% $CO_2$.

On day 1, medium is removed from each well, the test articles are diluted in culture medium without doxycycline and 100 μL was added to cell culture wells (9 concentrations, 4-fold dilution). For each plate, 6 untreated (merely DMSO) wells are included. The final concentration of DMSO in the culture medium is 2%. Each plate is prepared in duplicate (one for HBV DNA extraction, one for CellTiter-Glo 2.0 measurement). The cells are incubated at 37° C. and 5% $CO_2$ for 3 days.

On day 4, cell viability is assessed using CellTiter-Glo 2.0 and cell lysates are prepared for HBV DNA extraction and subsequent quantification by qPCR.

HBV DNA quantification by qPCR

Medium is removed from each well and 100 μL of 0.33% NP-40 in $H_2O$ was added to each well. Plates are sealed, incubated at 4° C. for 5 mins, vortexed extensively and centrifuged briefly. Next, 35 μL of lysate is added to 65 μL QuickExtract DNA Extraction Solution (Epicentre) in a PCR plate for each well. PCR plate is incubated at 65° C. for 6 mins, 98° C. for 2 mins and finally cooled to 4° C. HBV DNA is then quantified by qPCR with HBV-specific primers and probes as specified in Table 2 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 2

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 1) |
|  | HBV-reverse | GACAAACGGGCAACATACCTT (SEQ ID NO: 2) |
| HBV Probe | HBV probe | FAM/CCTCTKCAT/ZEN/CCTG CTGCTATGCCTCATC/3IABkFQ/ (SEQ ID NO: 3) |

A DNA standard is prepared by dilution of an IDT gBlock corresponding to the amplicon with concentrations ranging from 10^2 to 10^8 copies/input (i.e., per 4 μL) and used to generate a standard curve by plotting Cq values vs. HBV DNA standard concentration. The quantity of HBV DNA in each sample is determined by interpolating from the standard curve.

Cell Viability

Using the other plates, the cell viability is quantified by CellTiter-Glo 2.0 according to the manufacturer's manual. In brief, 100 μL of reagent solution is added to the culture plates and shaken for 2'. The plates are incubated at rt for 10 min and luminescence signal is subsequently measured on a VarioSkan Lux (ThermoFisher) plate reader.

Data Analysis

Cell viability is calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir is required due to the excellent dynamic window of this assay. The $CC_{50}$, $EC_{50}$ and $EC_{90}$ values were determined by dose-response curves fitted using non-linear regression.

As shown in Table 3, compounds of Formula (I) are active against HBV, where 'A' indicates an $EC_{50} \leq 50$ nM, 'B' indicates an $EC_{50} > 50$ nM and ≤500 nM, 'C' indicates an $EC_{50} > 500$ nM and ≤5000 nM, and 'D' indicates an $EC_{50} > 5000$ nM. Cell viability assessments indicated a large window between effective antiviral concentrations and cytotoxic compound concentrations.

TABLE 3

| Compound | $EC_{50}$ (nM) | $CC_{50}$ (nM) |
|---|---|---|
| 1 | A | >500 |
| 2a | A | >500 |
| 2b | A | >500 |
| 3a | A | >500 |
| 3b | A | >500 |
| 4a | A | >500 |
| 5 | A | >50000 |
| 6 | A | >500 |
| 7 | A | 7346 |
| 8 | A | 7329 |
| 9 | A | >50000 |
| 10a | A | >50000 |
| 10b | A | >50000 |
| 11a | A | >50000 |
| 11b | A | >50000 |
| 12 | A | >50000 |

TABLE 3-continued

| Compound | EC$_{50}$ (nM) | CC$_{50}$ (nM) |
|---|---|---|
| 13 | A | 48014 |
| 14 | B | >500 |
| 15 | A | >500 |
| 16 | A | >500 |
| 17 | A | >500 |
| 18 | A | >500 |
| 19 | A | >500 |
| 20 | A | 2950 |
| 21 | A | >500 |
| 22 | A | >50000 |
| 23 | B | 11728 |
| 24 | A | >500 |
| 25 | A | 29655 |
| 26 | A | >500 |
| 27 | A | 22847 |
| 28 | A | 30465 |
| 29 | A | 30503 |
| 30 | A | >50000 |
| 31 | A | 29614 |
| 32a | A | 29539 |
| 32b | A | 21891 |
| 33 | A | >50000 |
| 34 | A | 11574 |
| 35 | A | 28508 |
| 36 | A | >50000 |
| 37 | A | >50000 |
| 38 | A | 24280 |
| 39 | A | 28084 |
| 40 | A | >50000 |
| 41 | A | >50000 |
| 42 | A | >50000 |
| 43 | A | >50000 |
| 44 | A | >50000 |
| 45 | A | 30096 |
| 46 | A | >50000 |
| 47 | A | 23711 |
| 48 | A | 25993 |
| 49 | A | 23043 |
| 50 | A | >50000 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

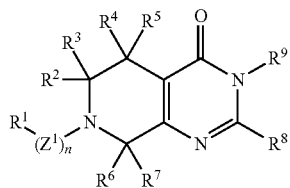

wherein:

n is 0 or 1;

$Z^1$ is —C(=O)— or —NH—C(=O)—;

$R^1$ is selected from the group consisting of an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^2$ and $R^3$ are independently selected from the group consisting of hydrogen, an optionally substituted $C_{1-4}$ alkyl, an optionally substituted $C_{2-4}$ alkenyl, an optionally substituted $C_{2-4}$ alkynyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^4$ and $R^5$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^6$ and $R^7$ are independently selected from the group consisting of hydrogen, an unsubstituted $C_{1-4}$ alkyl and an unsubstituted $C_{1-4}$ haloalkyl;

$R^8$ is —$NR^{10A}R^{10B}$ or an optionally substituted $C_{2-12}$ alkynyl, wherein the $C_{2-12}$ alkynyl is optionally substituted with one or more substituents selected from the group consisting of amino, —NH—C(=O)(an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl an unsubstituted 4-6 membered monocyclic heterocyclyl, an optionally substituted aryl and an optionally substituted 5-6 membered monocyclic heteroaryl;

$R^9$ is a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl is substituted with one or more substituents selected from the group consisting of halogen, an unsubstituted $C_{1-4}$ alkyl, a cyano-substituted $C_{1-4}$ alkyl, an unsubstituted $C_{1-4}$ haloalkyl, an unsubstituted $C_{1-4}$ alkoxy, a hydroxy-substituted $C_{1-4}$ alkoxy, an optionally substituted monocyclic $C_{3-6}$ cycloalkyl, an optionally substituted monocyclic heteroaryl, an optionally substituted monocyclic heterocyclyl, amino, a mono-substituted amine, a di-substituted amine and —C(=O)$NHR^{11}$;

$R^{10A}$ is hydrogen, an unsubstituted $C_{1-6}$ alkyl, a monocyclic $C_{3-6}$ cycloalkyl optionally substituted with one or two halogens, an optionally substituted 5-6 membered monocyclic heteroaryl, an optionally substituted 4-6 membered monocyclic heterocyclyl or an optionally substituted monocyclic $C_{3-6}$ cycloalkyl($C_{1-4}$ alkyl);

$R^{10B}$ is an optionally substituted $C_{2-8}$ alkenyl, wherein the $C_{2-8}$ alkenyl is optionally substituted with one or more substituents selected from the group consisting of amino, hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl and an unsubstituted 4-6 membered monocyclic heterocyclyl;

wherein when $R^{10A}$ is an optionally substituted monocyclic $C_{3-6}$ cycloalkyl($C_{1-4}$ alkyl), then $R^{10B}$ cannot be an unsubstituted $C_{2-6}$ alkenyl; and $R^{11}$ is hydrogen, an unsubstituted $C_{1-6}$ alkyl, an optionally substituted $C_{2-6}$ alkenyl, an optionally substituted $C_{1-6}$ alkynyl or an optionally substituted $C_{3-6}$ monocyclic cycloalkyl.

2. The compound of claim 1, wherein $Z^1$ is —C(=O)—.

3. The compound of claim 1, wherein $R^1$ is an optionally substituted aryl.

4. The compound of claim 3, wherein $R^1$ is an optionally substituted phenyl.

5. The compound of claim 4, wherein $R^1$ is selected from the group consisting of:

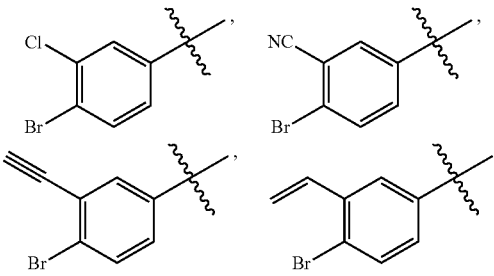

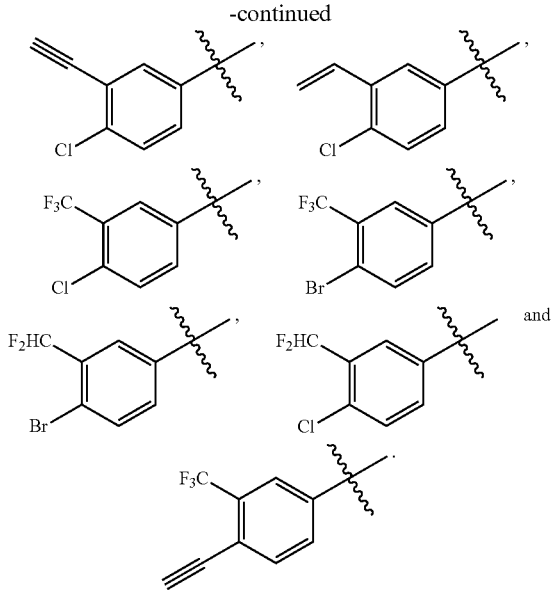

6. The compound of claim 5, wherein $R^1$ is

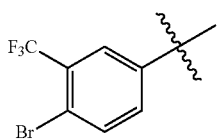

7. The compound of claim 6, wherein $R^9$ is a substituted phenyl, wherein the phenyl is substituted with —C(=O)NHR$^{11}$; and R$^{11}$ can be an unsubstituted $C_{1-6}$ alkyl.

8. The compound of claim 1, wherein $R^2$ is hydrogen; $R^3$ is an unsubstituted $C_{1-4}$ alkyl; $R^4$ is hydrogen; $R^5$ is hydrogen; $R^6$ is hydrogen; and $R^7$ is hydrogen; or wherein $R^2$ is an unsubstituted $C_{1-4}$ alkyl; $R^3$ is hydrogen; $R^4$ is hydrogen; $R^5$ is hydrogen; $R^6$ is hydrogen; and $R^7$ is hydrogen.

9. The compound of claim 1, wherein $R^8$ is —NR$^{10A}$R$^{10B}$; and R$^{10A}$ is hydrogen.

10. The compound of claim 9, wherein R$^{10B}$ is a substituted $C_{2-8}$ alkenyl.

11. The compound of claim 9, wherein R$^{10B}$ is selected from the group consisting of

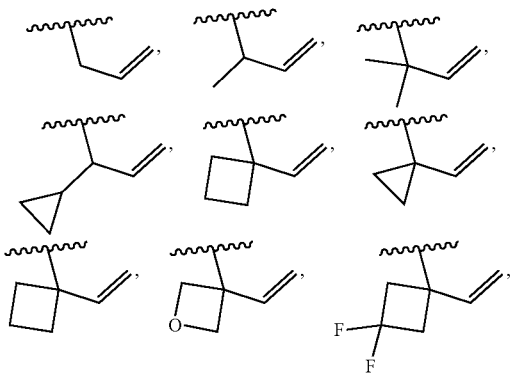

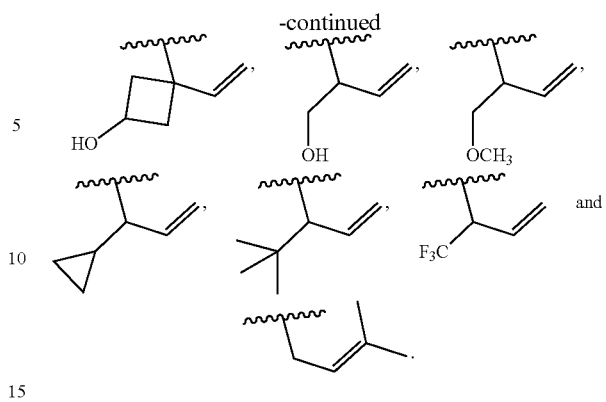

12. The compound of claim 9, wherein R$^{10B}$ is an unsubstituted $C_{2-8}$ alkenyl.

13. The compound of claim 1, wherein $R^8$ is an unsubstituted $C_{2-12}$ alkynyl; or $R^8$ is a substituted $C_{2-12}$ alkynyl substituted with one or more substituents selected from the group consisting of amino, —NH—C(=O)(an unsubstituted $C_{1-4}$ alkyl), hydroxy, an unsubstituted $C_{1-4}$ alkoxy, an unsubstituted $C_{1-4}$ haloalkyl, an unsubstituted $C_{3-4}$ monocyclic cycloalkyl, a fluoro-substituted $C_{3-4}$ monocyclic cycloalkyl, a hydroxy-substituted $C_{3-4}$ monocyclic cycloalkyl, an unsubstituted 4-6 membered monocyclic heterocyclyl, an optionally substituted aryl and an optionally substituted 5-6 membered monocyclic heteroaryl.

14. The compound of claim 1, wherein $R^9$ is a substituted phenyl.

15. The compound of claim 14, wherein $R^9$ is substituted with —C(=O)NHR$^{11}$; and R$^{11}$ is an unsubstituted $C_{1-6}$ alkyl.

16. The compound of claim 15, wherein $R^9$ is substituted with an optionally substituted monocyclic heteroaryl or an optionally substituted monocyclic heterocyclyl.

17. The compound of claim 15, wherein $R^9$ is substituted with a substituent selected from the group consisting of halogen, an unsubstituted $C_{1-4}$ alkyl, a cyano-substituted $C_{1-4}$ alkyl, an optionally substituted monocyclic $C_{3-6}$ cycloalkyl, an unsubstituted $C_{1-4}$ haloalkyl, an unsubstituted $C_{1-4}$ alkoxy, a hydroxy-substituted $C_{1-4}$ alkoxy, amino, a mono-substituted amine and a di-substituted amine.

18. The compound of claim 1, wherein $R^9$ is a substituted monocyclic heteroaryl or a substituted fused-bicyclic heteroaryl.

19. The compound of claim 1 selected from the group consisting of:

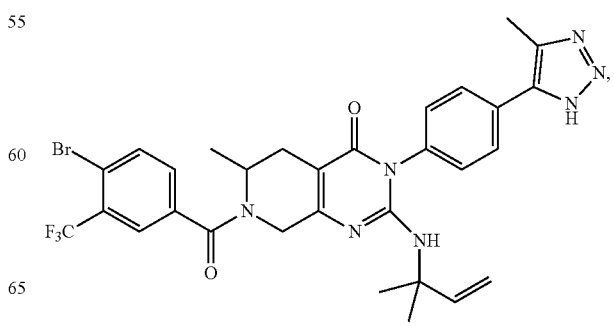

157
-continued
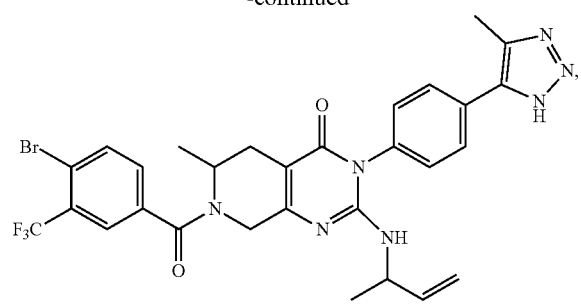
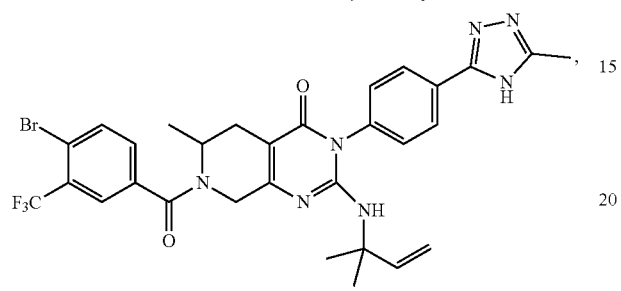
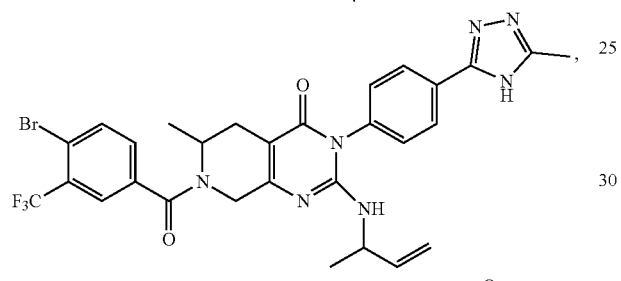
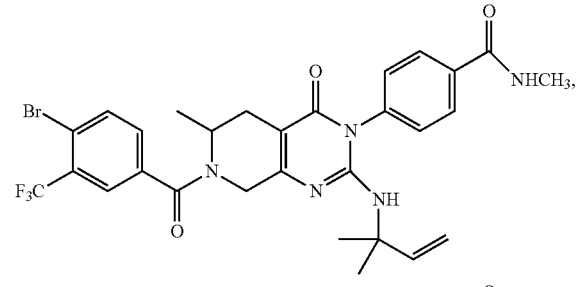
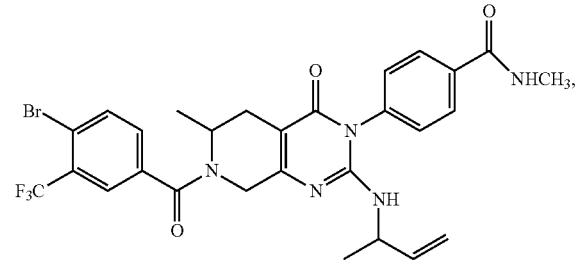
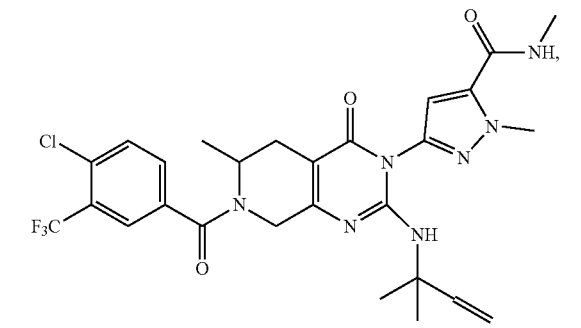
158
-continued
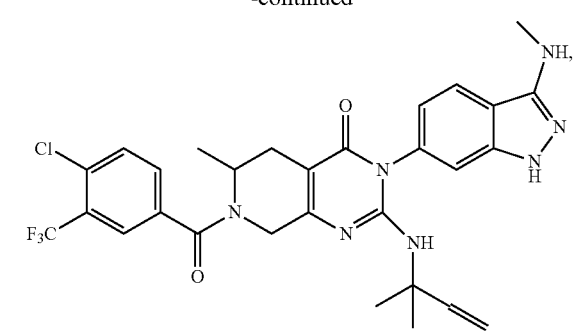
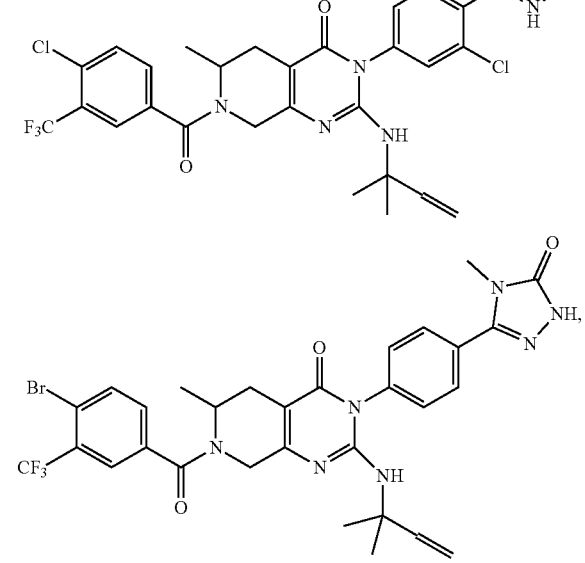
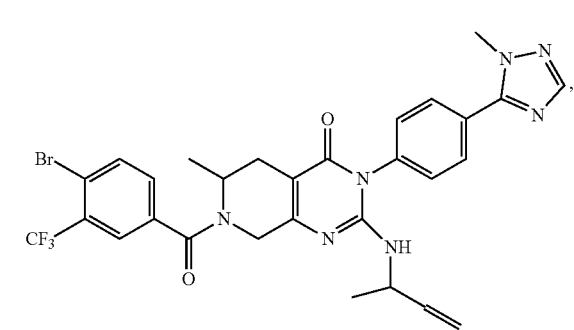
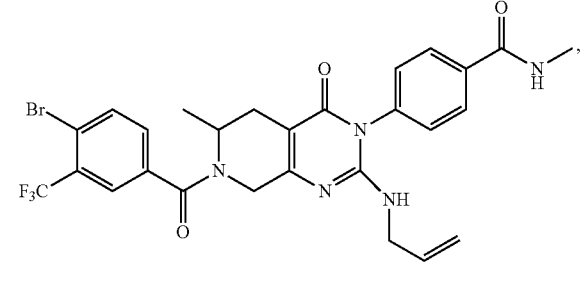

159
-continued
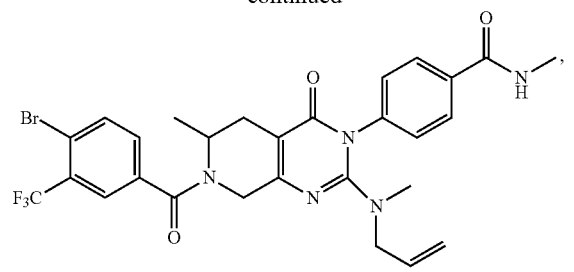
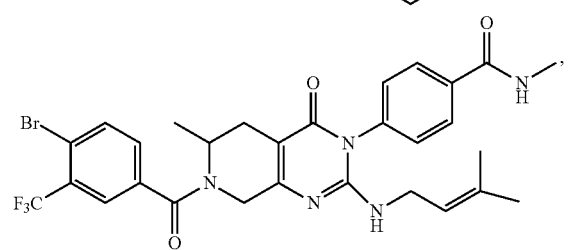
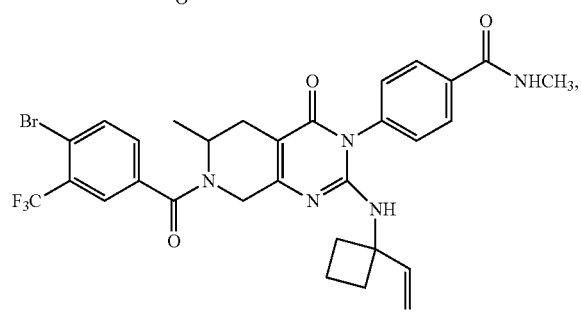
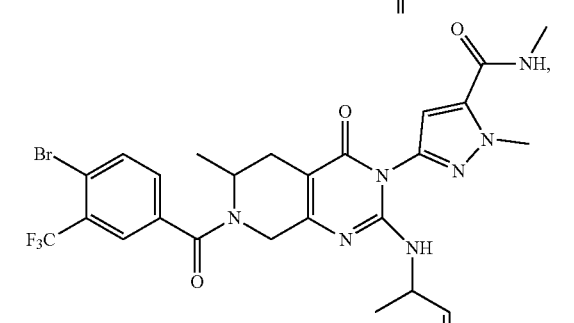
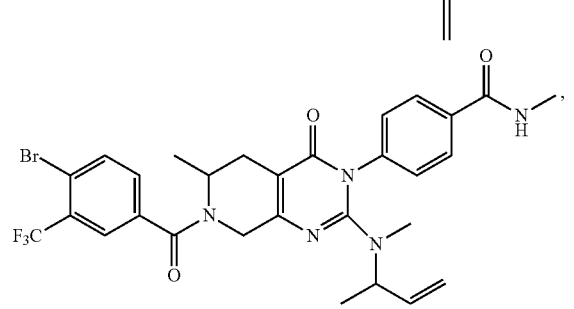
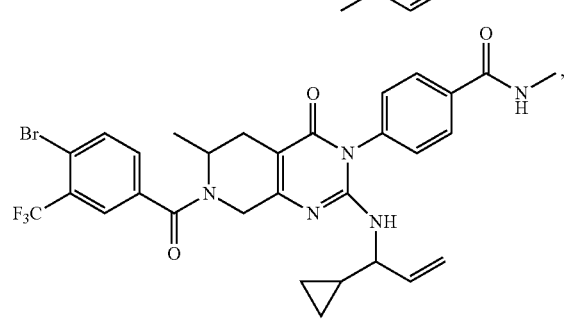
160
-continued
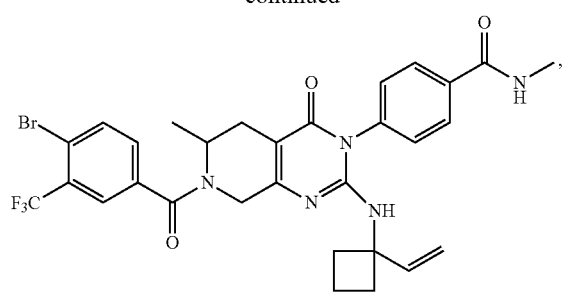
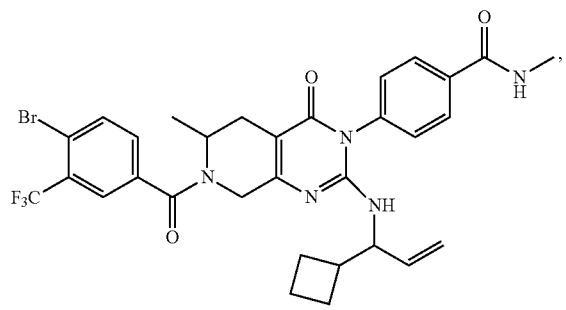
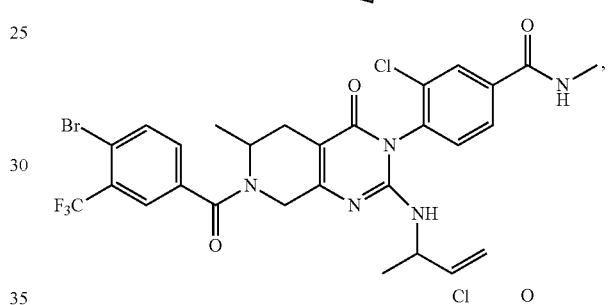
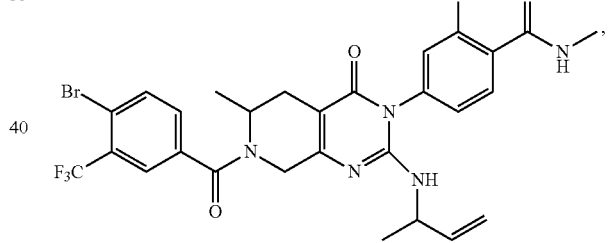
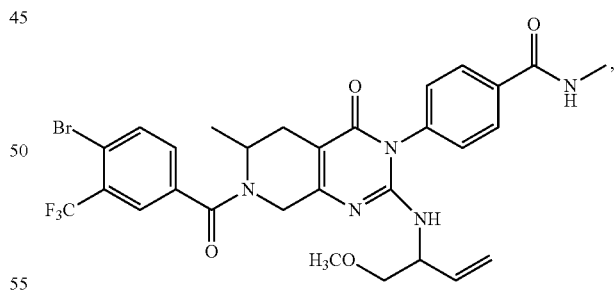
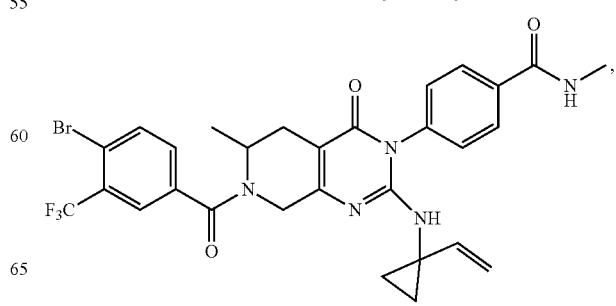

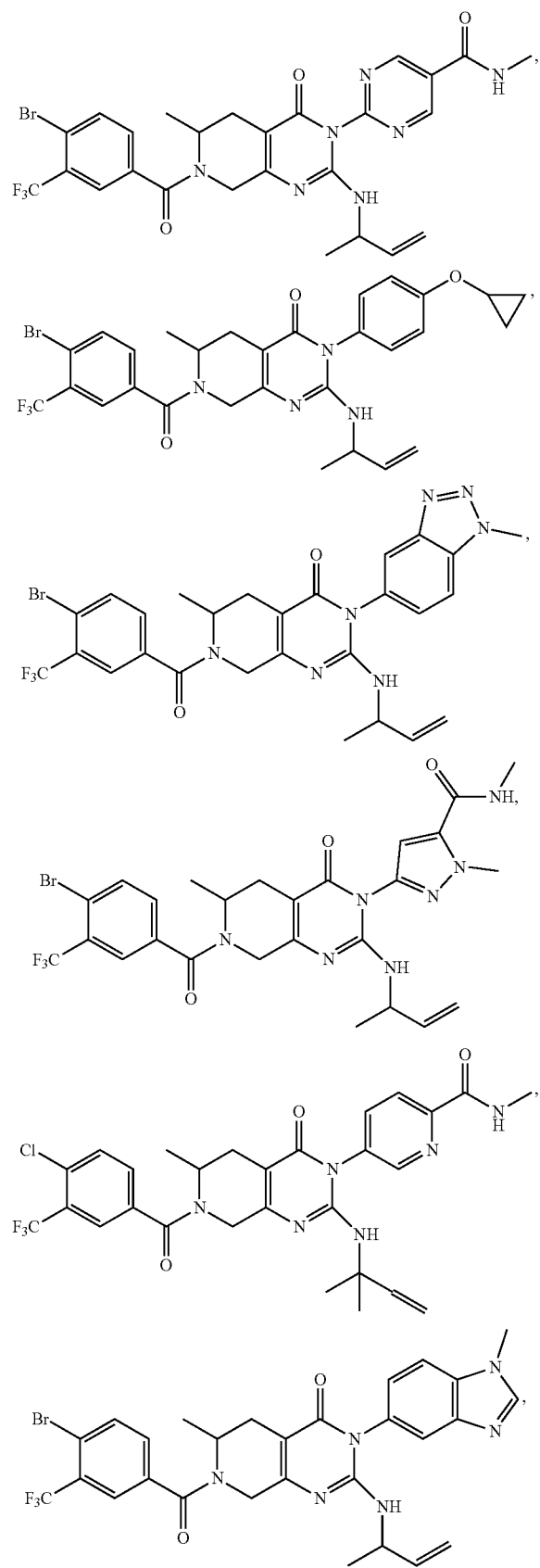
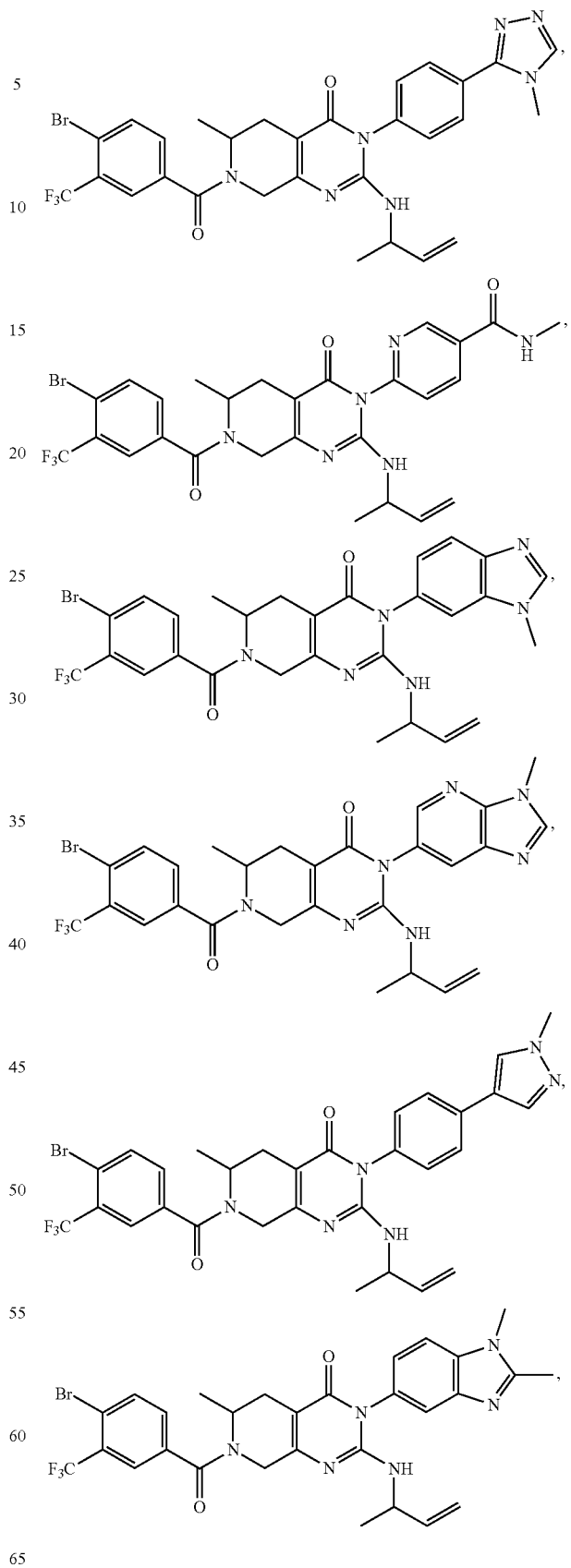

163
-continued
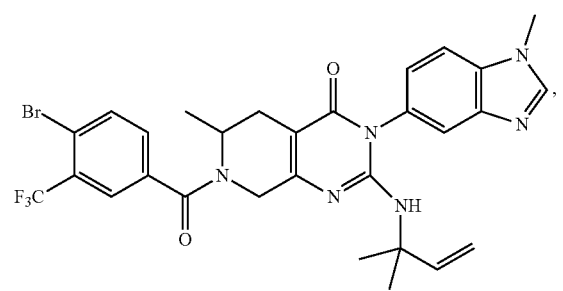
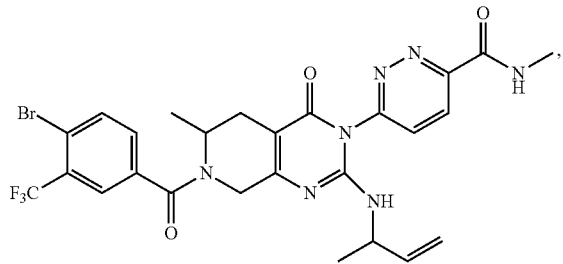
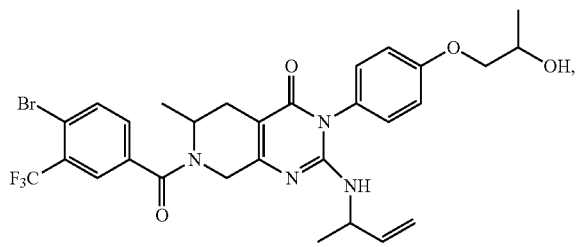
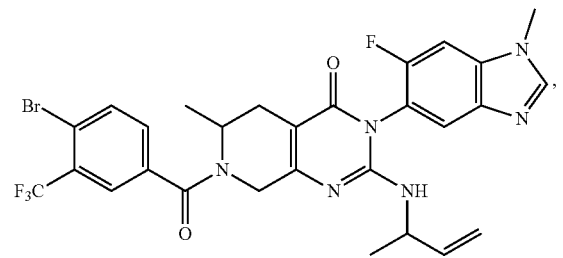
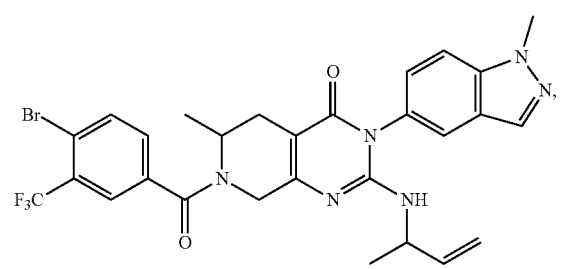
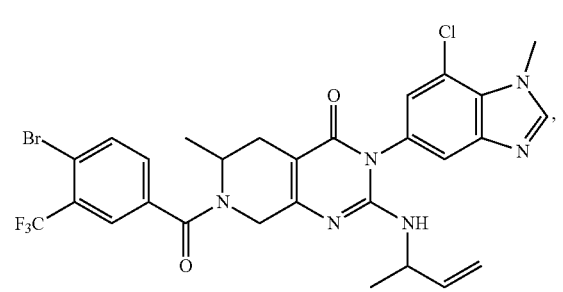
164
-continued
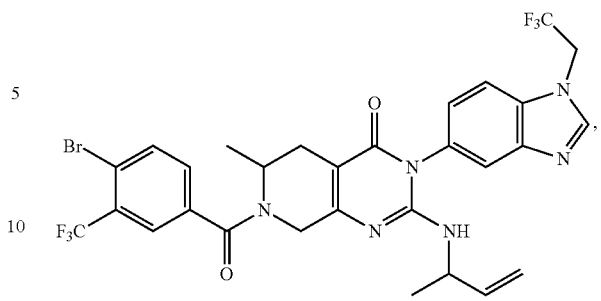
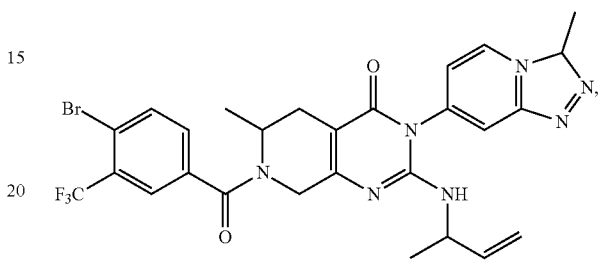
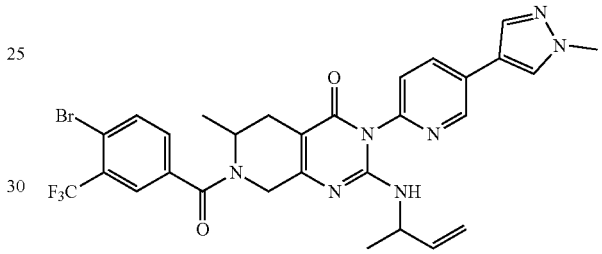
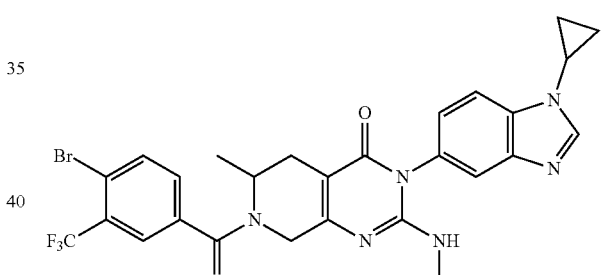
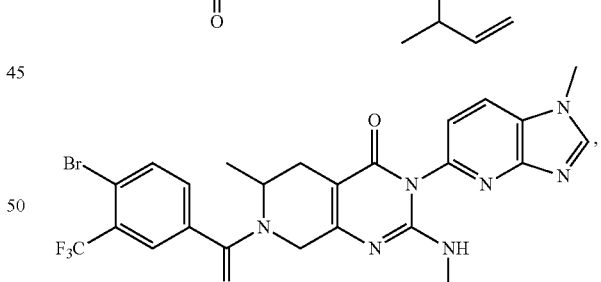
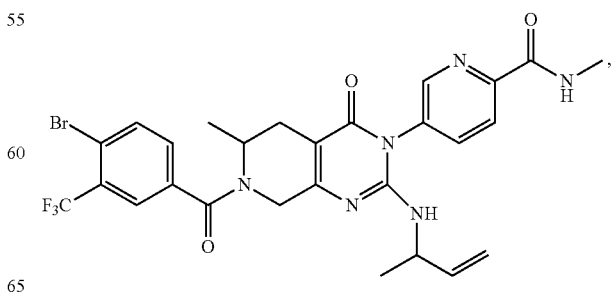

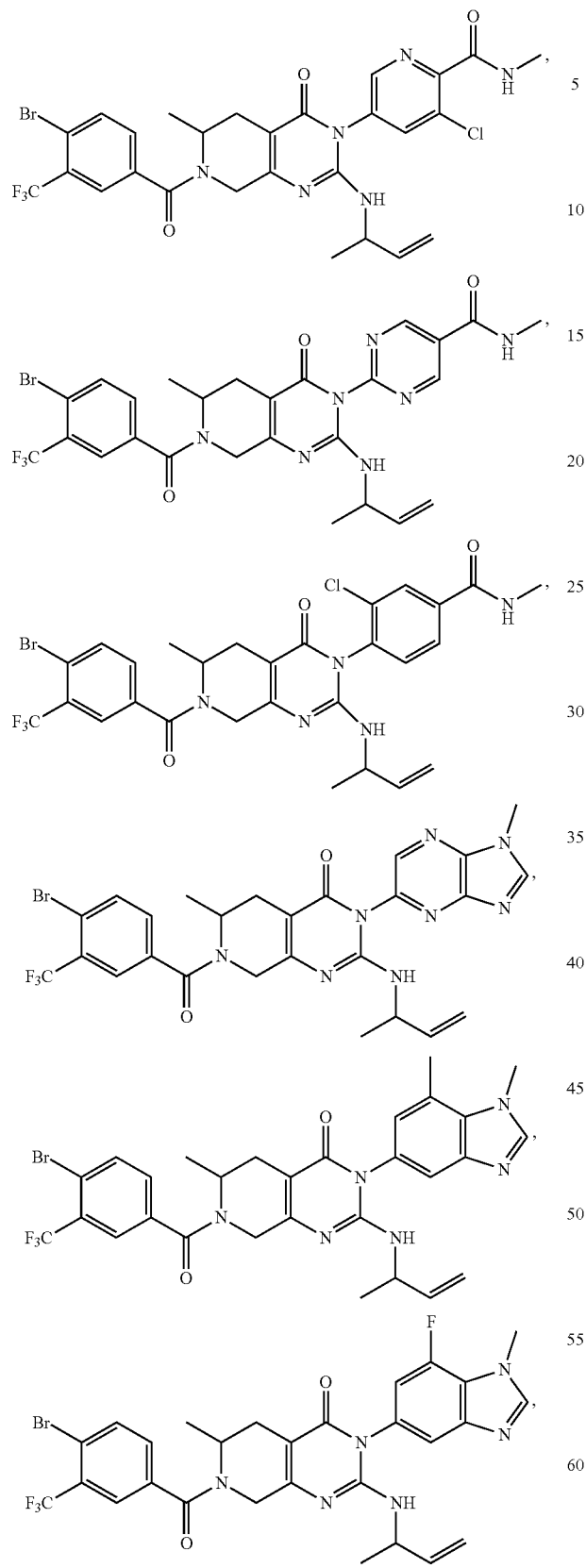
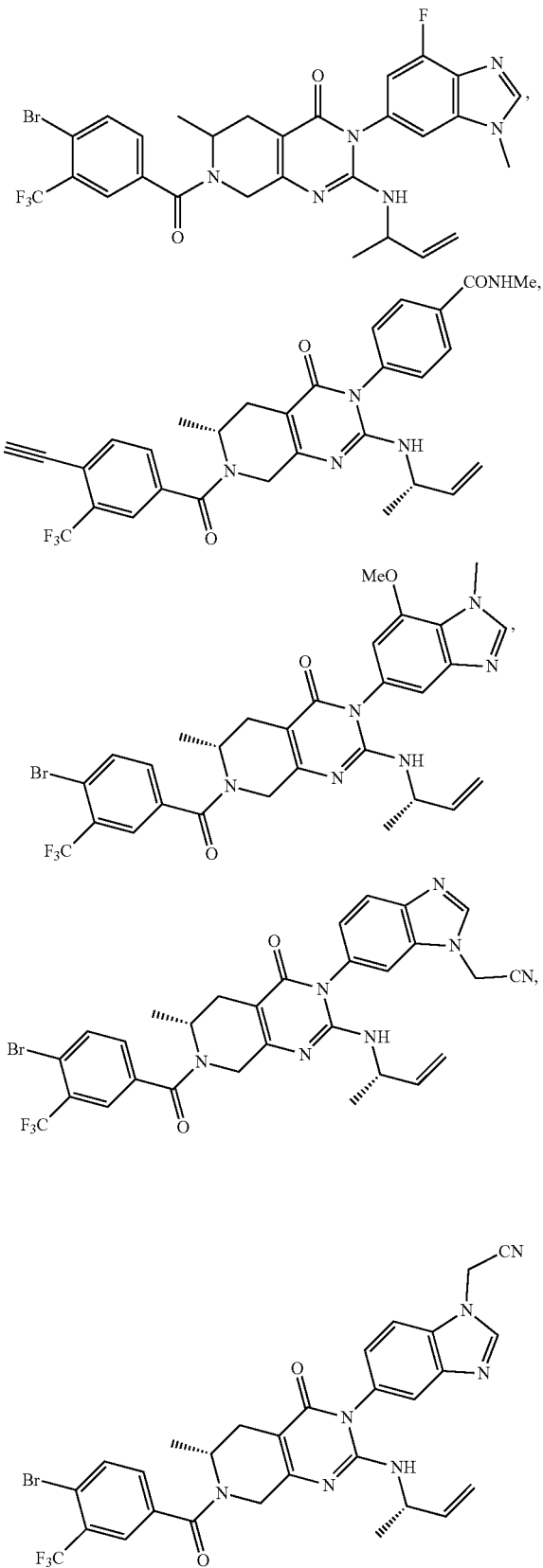

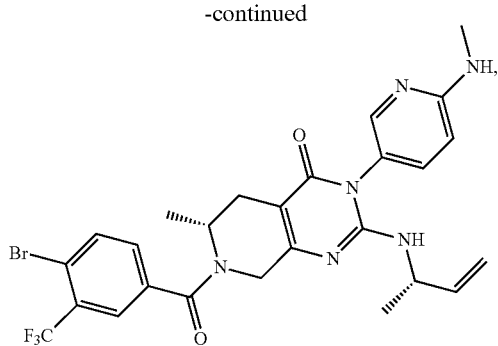
or a pharmaceutically acceptable salt of any of the foregoing.
20. The compound of claim 1 selected from the group consisting of:
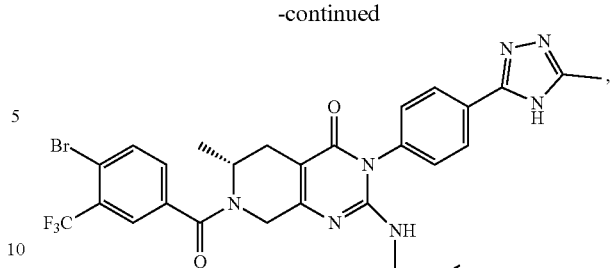
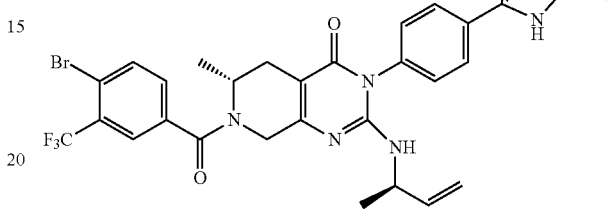
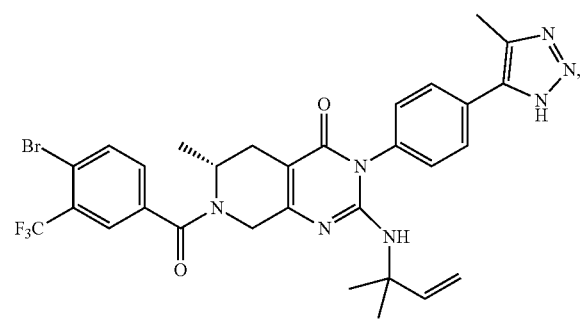
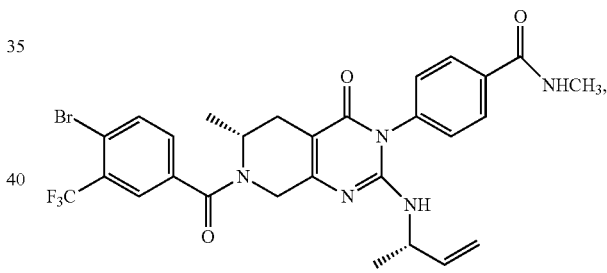
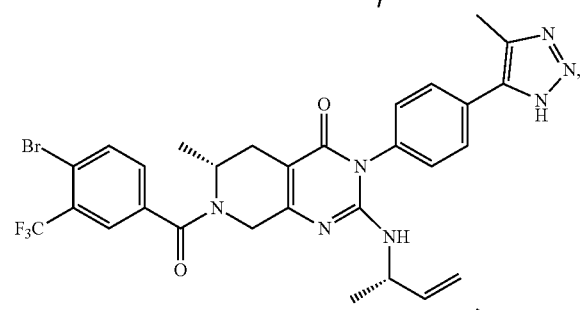
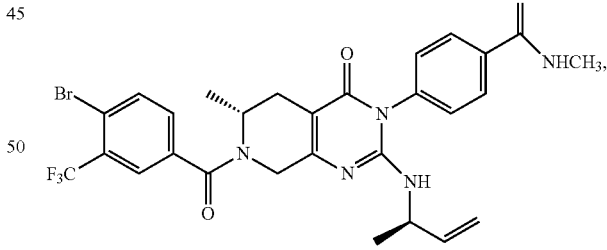
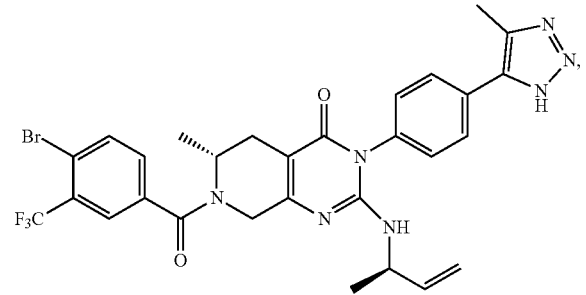
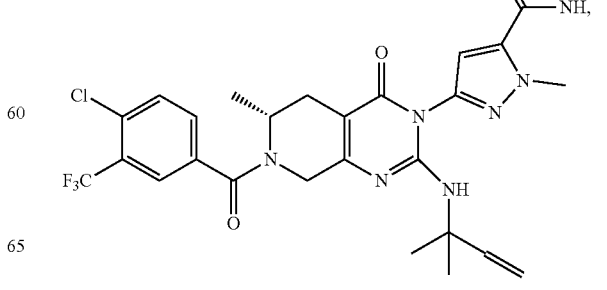

169
-continued
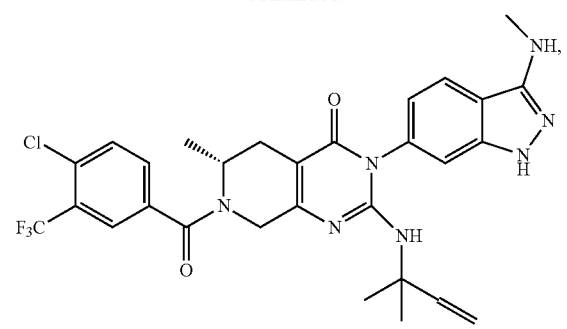
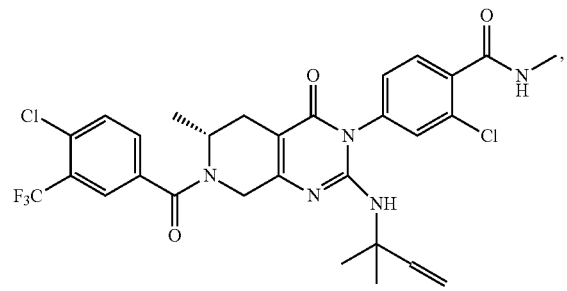
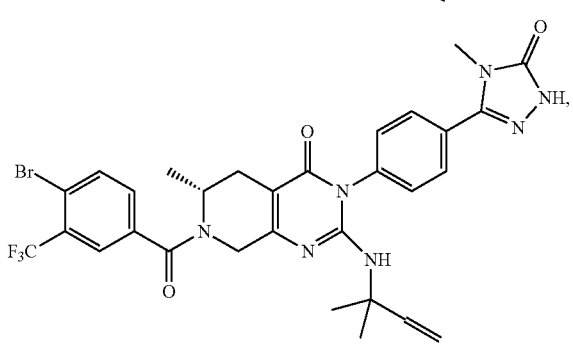
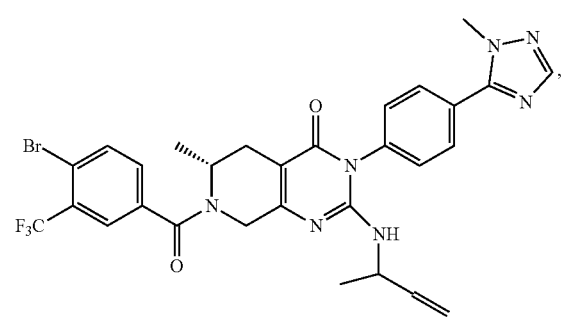
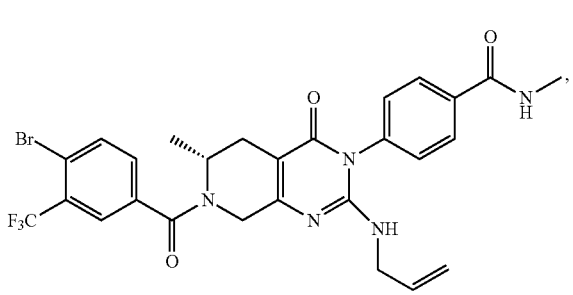
170
-continued
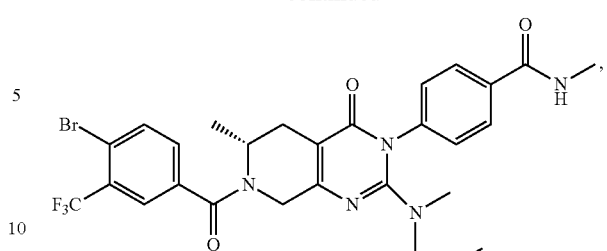
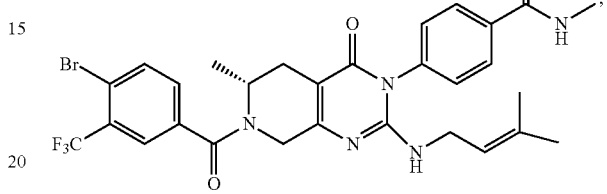
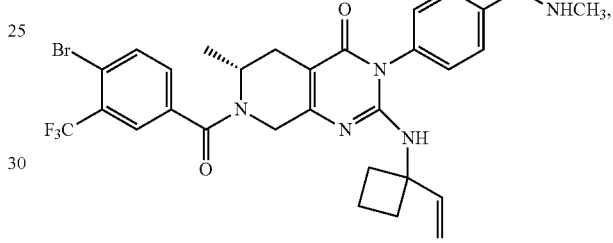
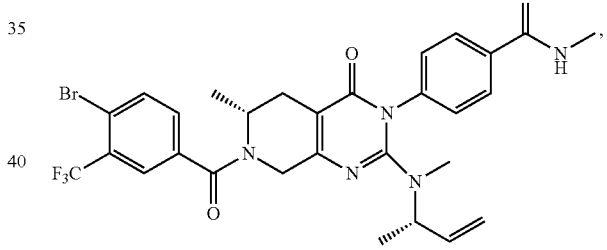
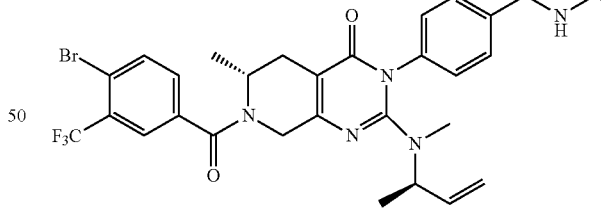
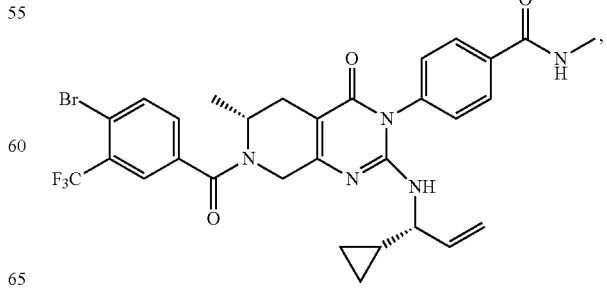

171
-continued
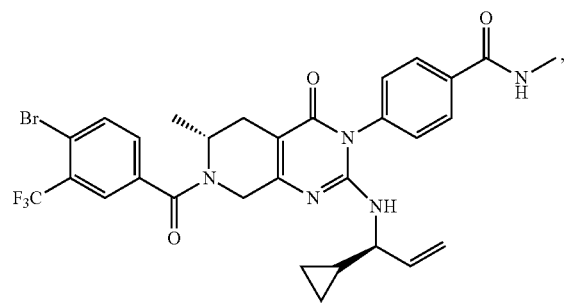
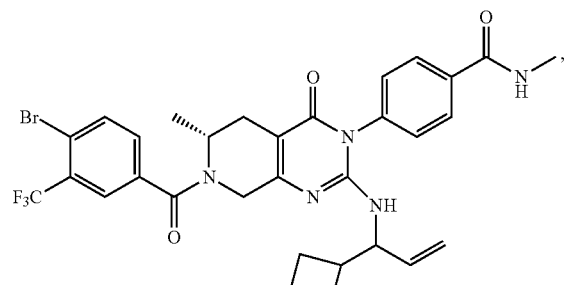
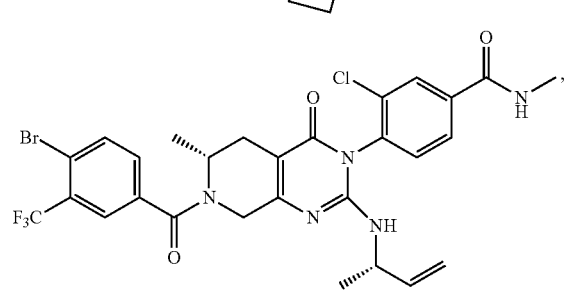
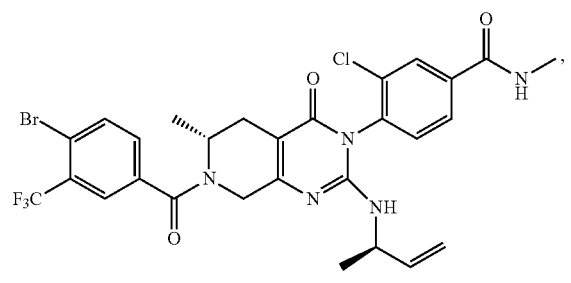
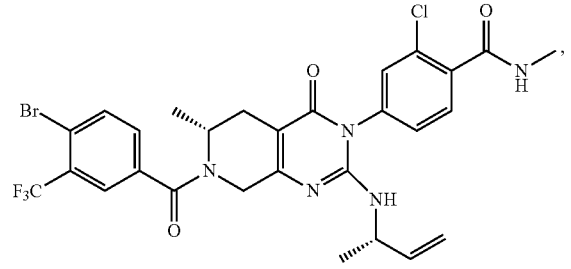
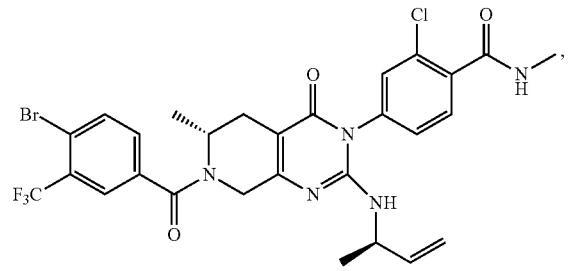 [SMILES: C=C[C@@H](C)Nc1nc2c(c(=O)n1-c1ccc(C(=O)NC)c(Cl)c1)C[C@@H](C)N(C(=O)c1ccc(Br)c(C(F)(F)F)c1)C2]
172
-continued
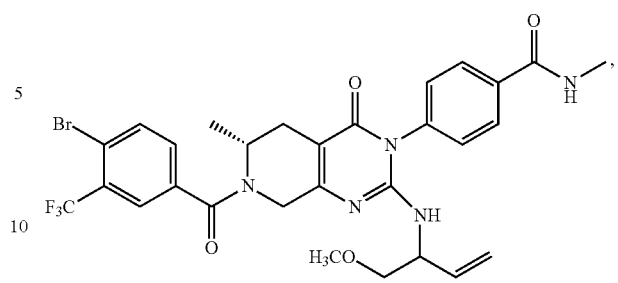
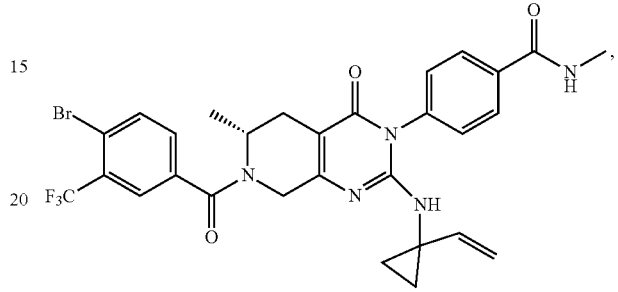
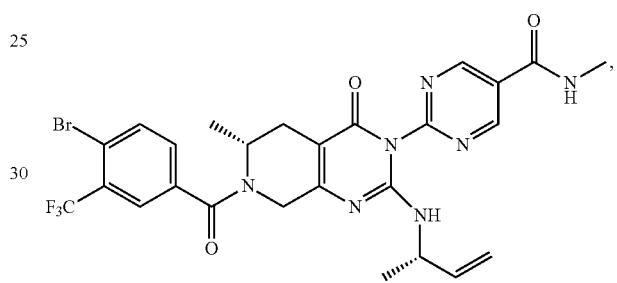
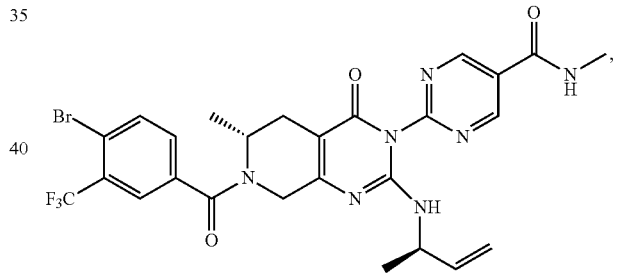
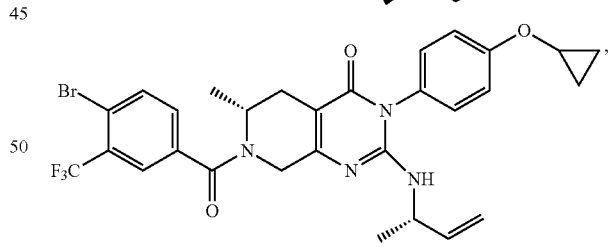
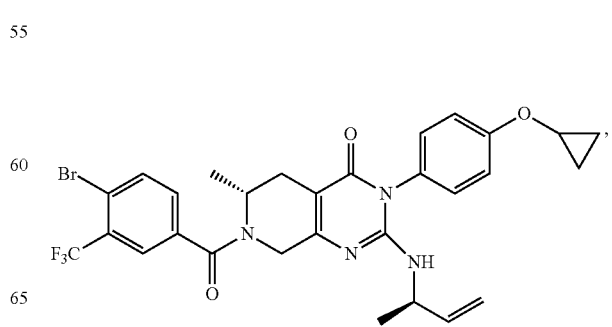

173
-continued
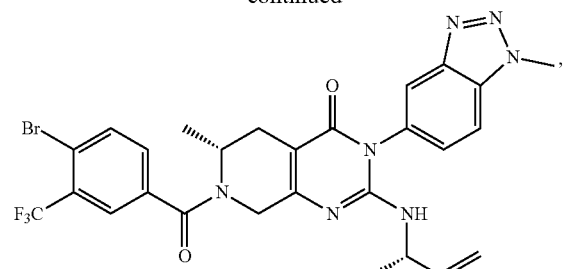
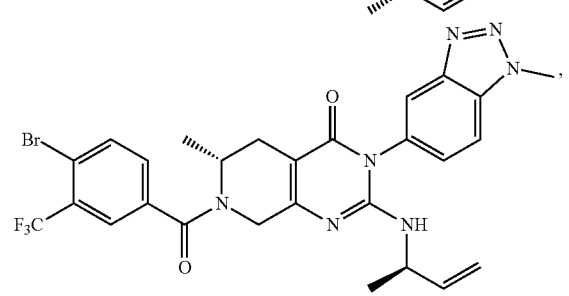
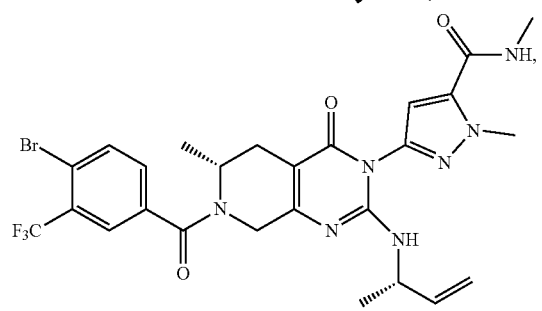
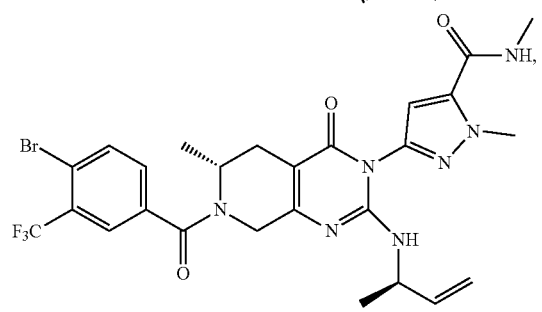
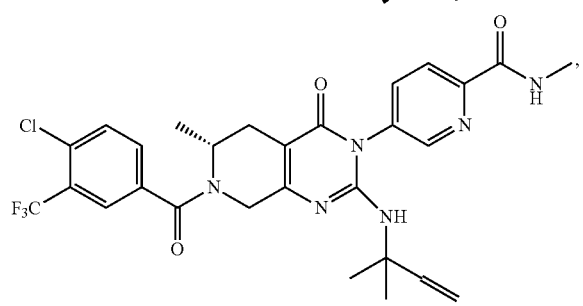
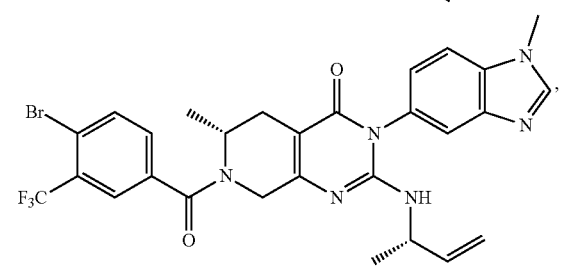
174
-continued
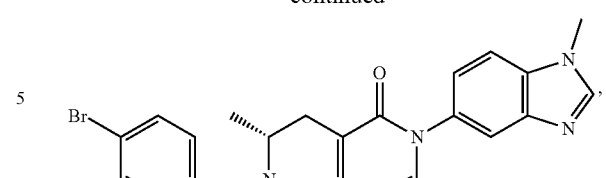
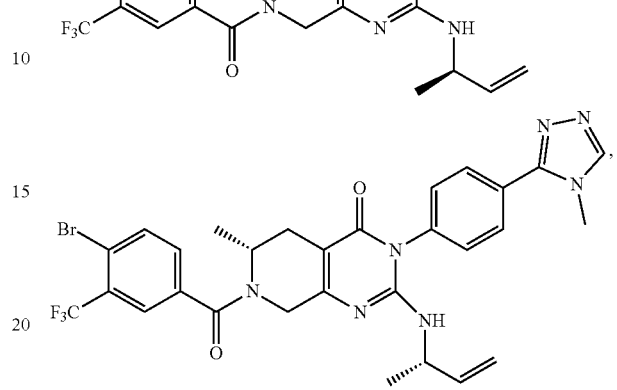
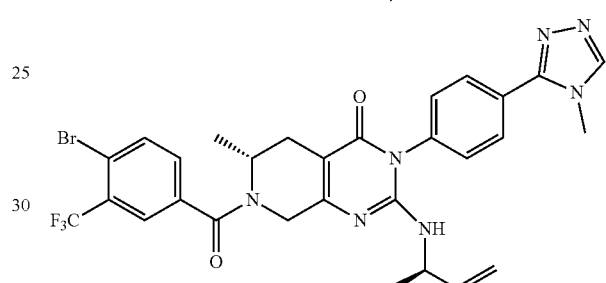
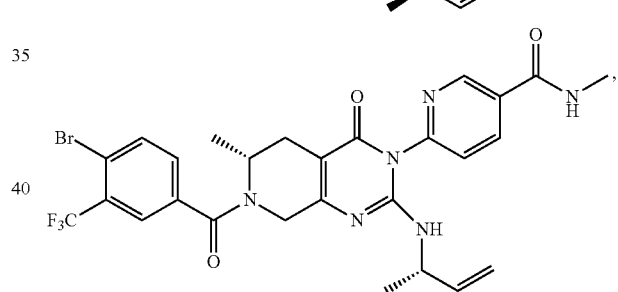
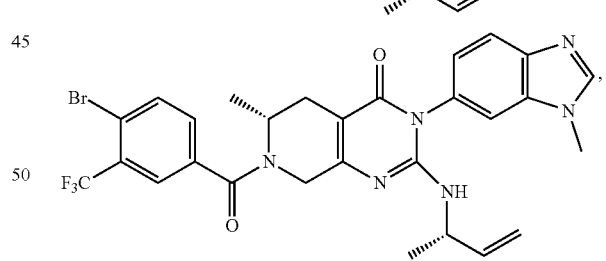
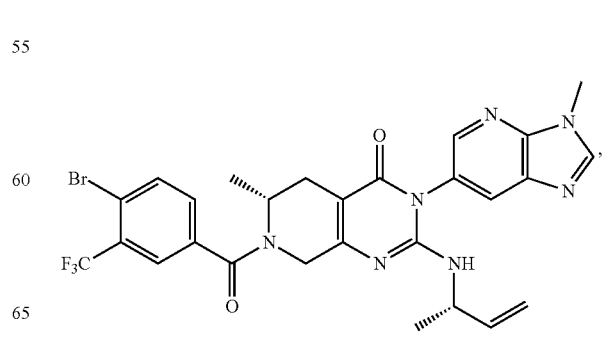

175
-continued
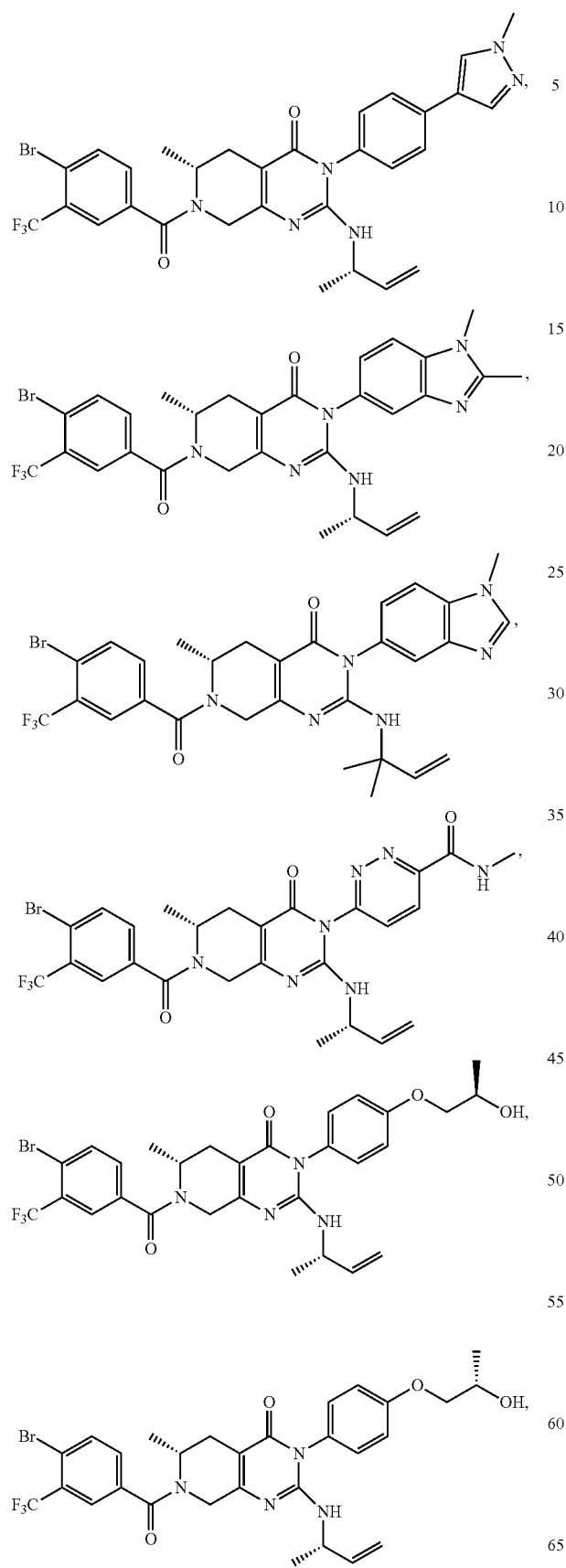
176
-continued
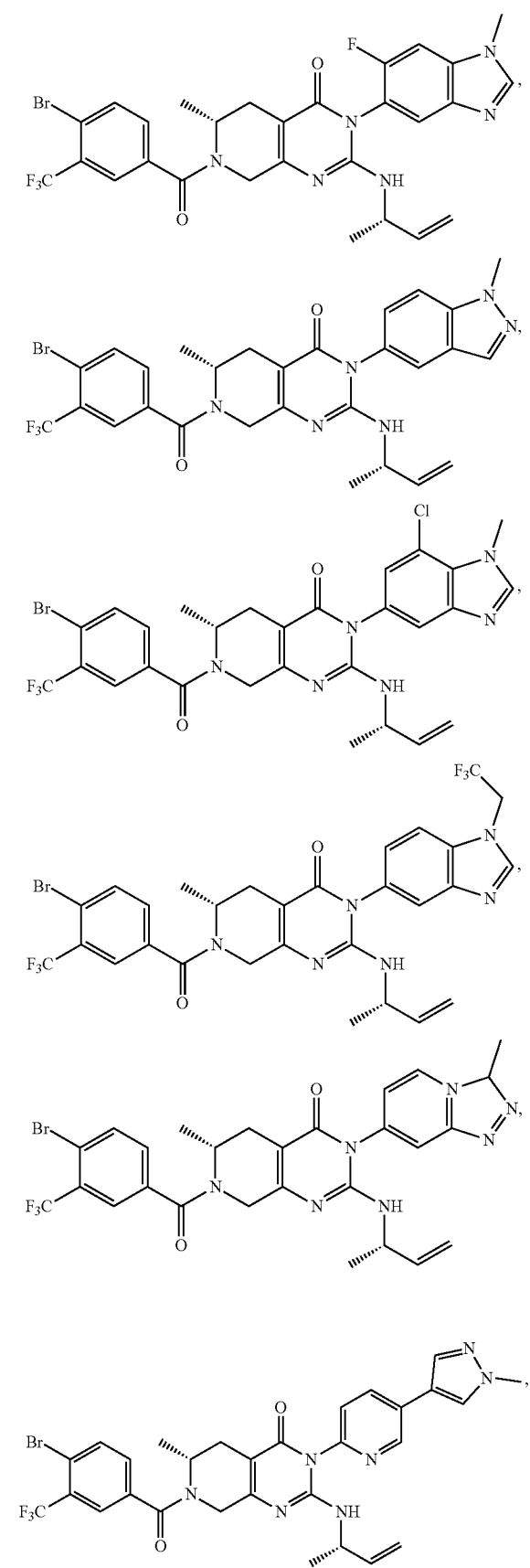

177
-continued
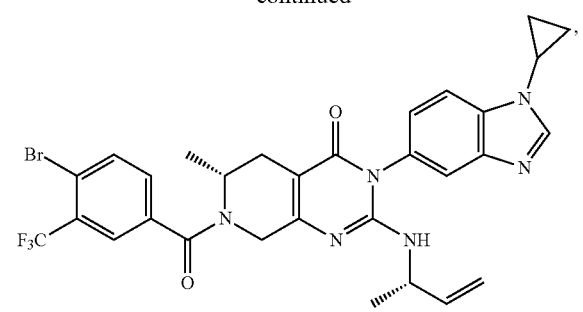
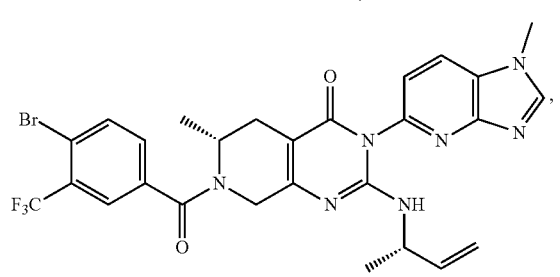
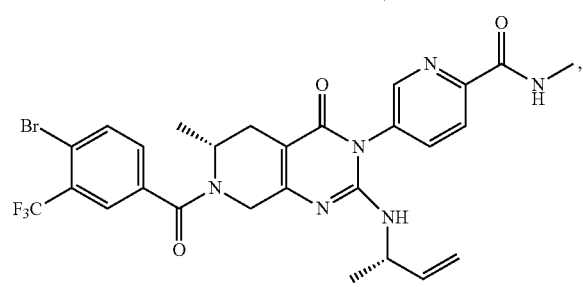
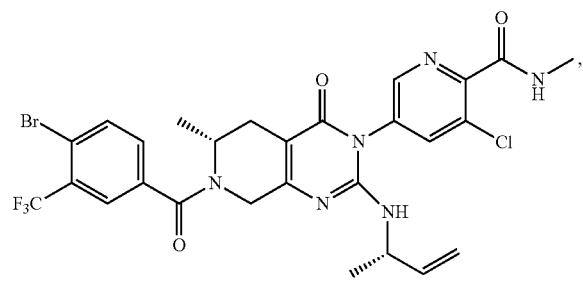
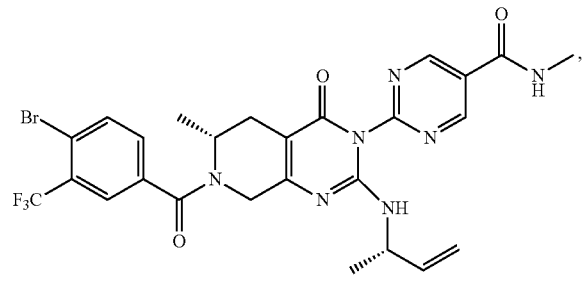
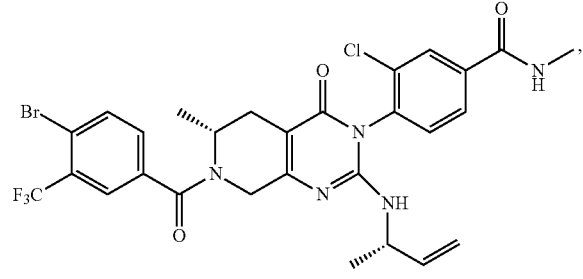
178
-continued
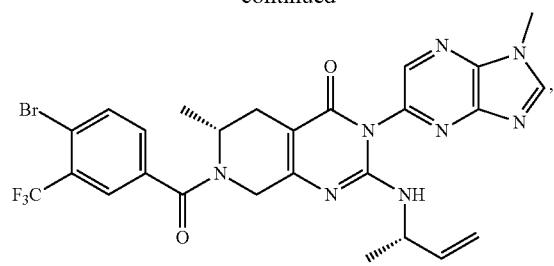
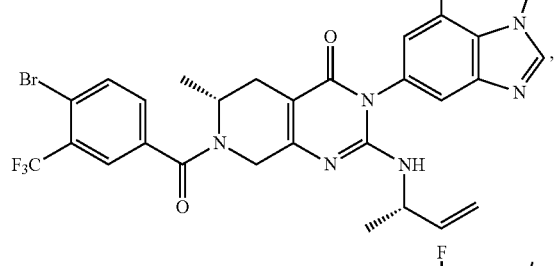
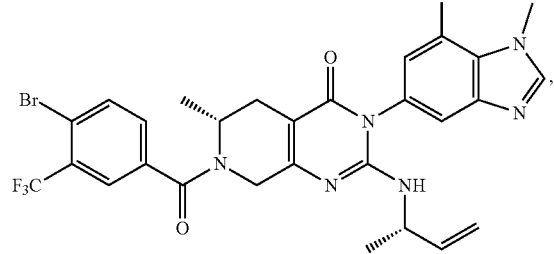
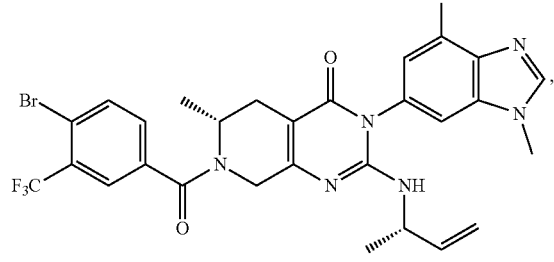
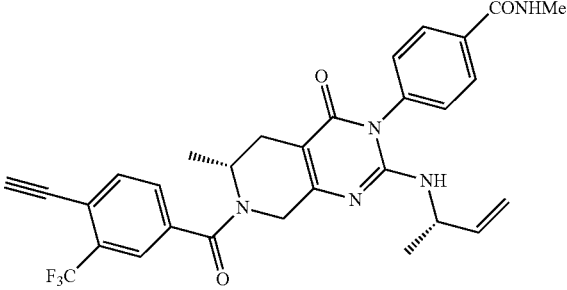
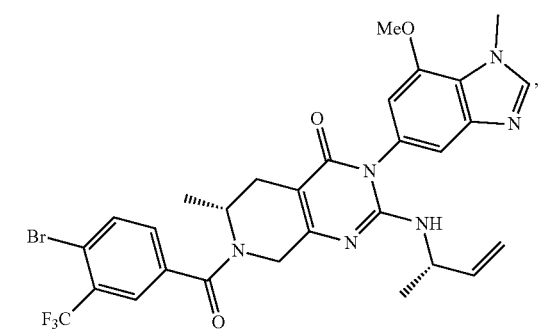

-continued

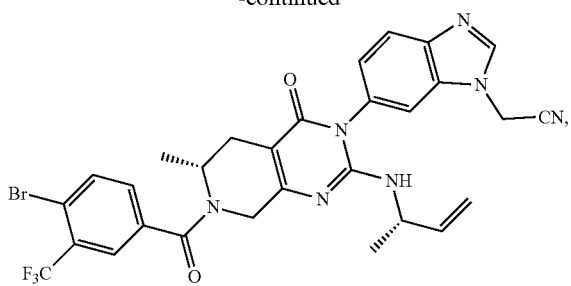

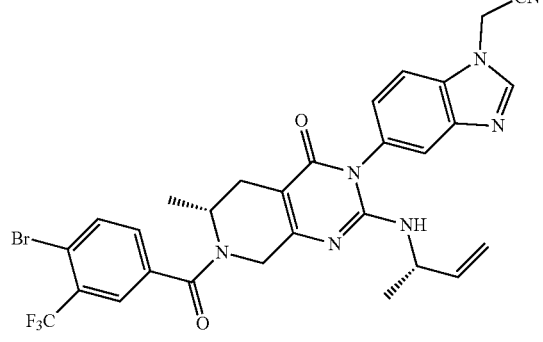

and

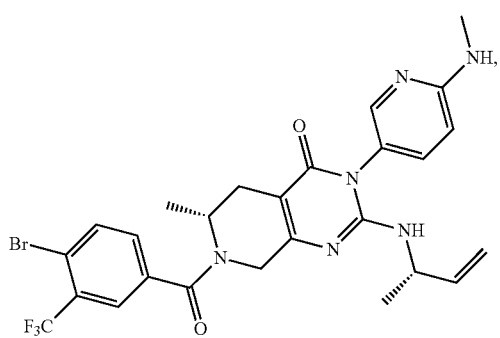

or a pharmaceutically acceptable salt of any of the foregoing.

21. The compound of claim 1, wherein the compound is

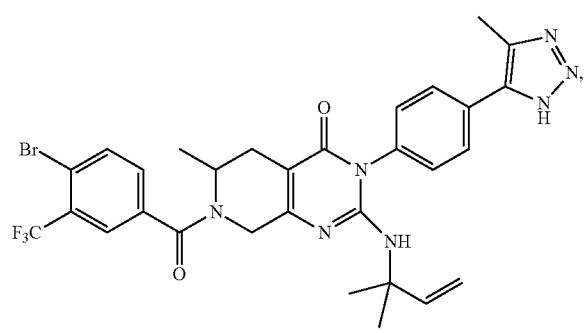 [SMILES: C=CC(C)(C)Nc1nc2c(c(=O)n1-c1ccc(-c3[nH]nnc3C)cc1)CC(C)N(C(=O)c1ccc(Br)c(C(F)(F)F)c1)C2]

or a pharmaceutically acceptable salt thereof.

22. The compound of claim 1, wherein the compound is

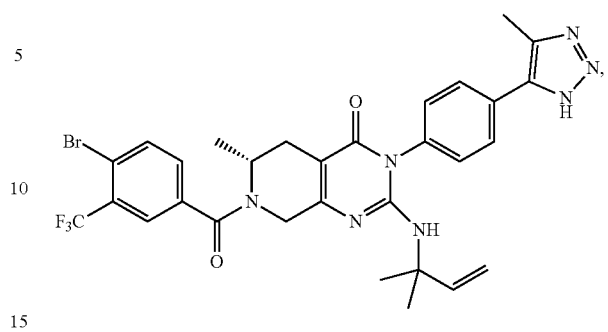

or a pharmaceutically acceptable salt thereof.

23. The compound of claim 1, wherein the compound is

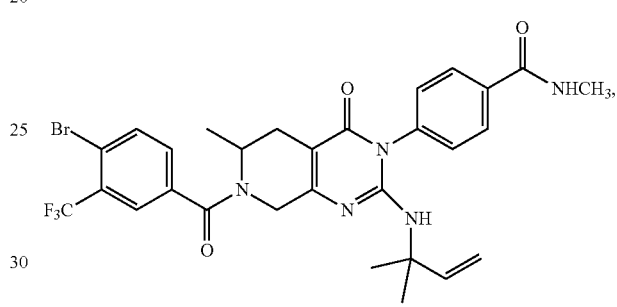

or a pharmaceutically acceptable salt thereof.

24. The compound of claim 1, wherein the compound is

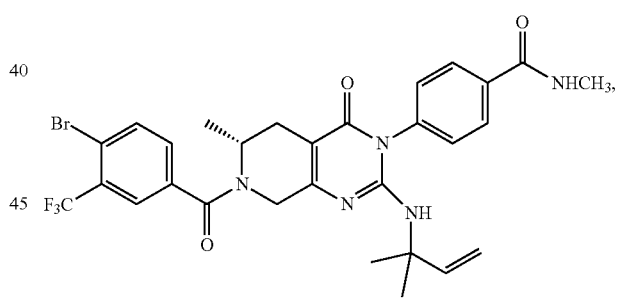

or a pharmaceutically acceptable salt thereof.

25. The compound of claim 1, wherein the compound is

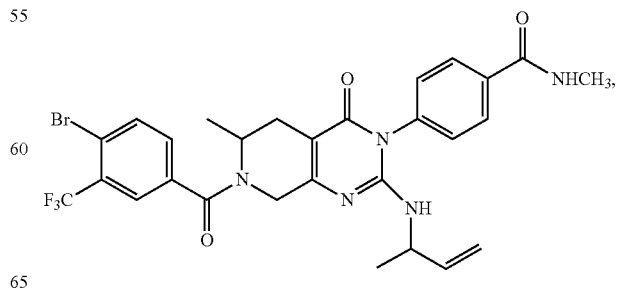

or a pharmaceutically acceptable salt thereof.

26. The compound of claim 1, wherein the compound is

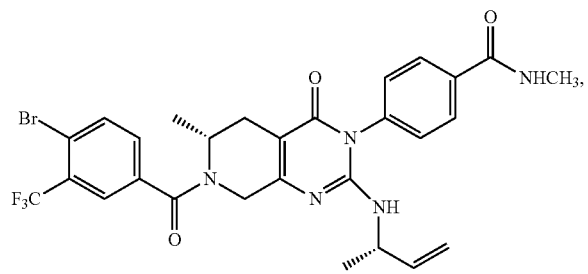 [SMILES: C=C[C@H](C)Nc1nc2c(c(=O)n1-c1ccc(C(=O)NC)cc1)C[C@@H](C)N(C(=O)c1ccc(Br)c(C(F)(F)F)c1)C2]

or a pharmaceutically acceptable salt thereof.

27. The compound of claim 1, wherein the compound is

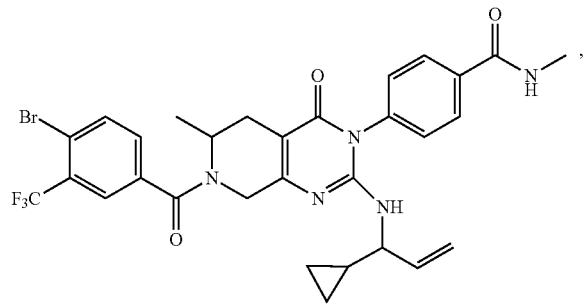 [SMILES: C=CC(Nc1nc2c(c(=O)n1-c1ccc(C(=O)NC)cc1)CC(C)N(C(=O)c1ccc(Br)c(C(F)(F)F)c1)C2)C1CC1]

or a pharmaceutically acceptable salt thereof.

28. The compound of claim 1, wherein the compound is

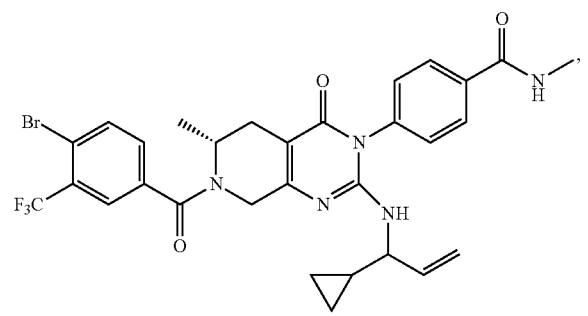 [SMILES: C=CC(Nc1nc2c(c(=O)n1-c1ccc(C(=O)NC)cc1)C[C@@H](C)N(C(=O)c1ccc(Br)c(C(F)(F)F)c1)C2)C1CC1]

or a pharmaceutically acceptable salt thereof.

29. The compound of claim 1, wherein the compound is

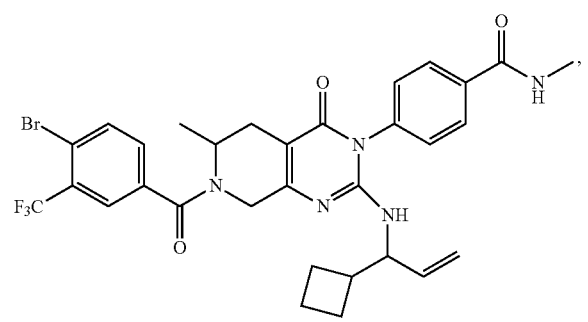 [SMILES: C=CC(Nc1nc2c(c(=O)n1-c1ccc(C(=O)NC)cc1)CC(C)N(C(=O)c1ccc(Br)c(C(F)(F)F)c1)C2)C1CCC1]

or a pharmaceutically acceptable salt thereof.

30. The compound of claim 1, wherein the compound is

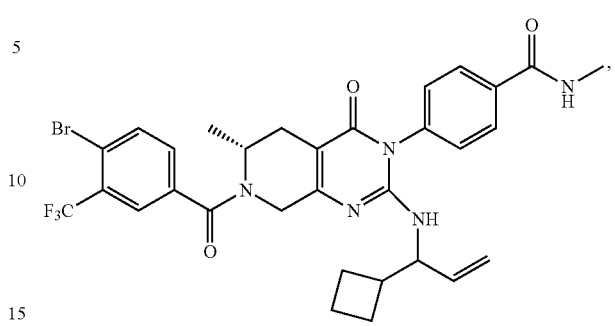

or a pharmaceutically acceptable salt thereof.

31. The compound of claim 1, wherein the compound is

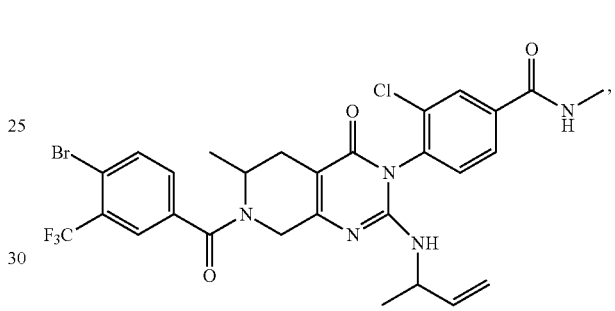

or a pharmaceutically acceptable salt thereof.

32. The compound of claim 1, wherein the compound is

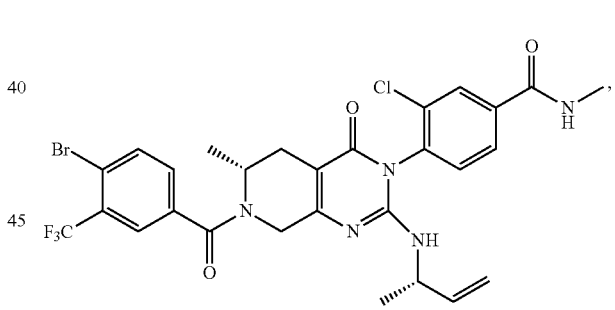

or a pharmaceutically acceptable salt thereof.

33. The compound of claim 1, wherein the compound is

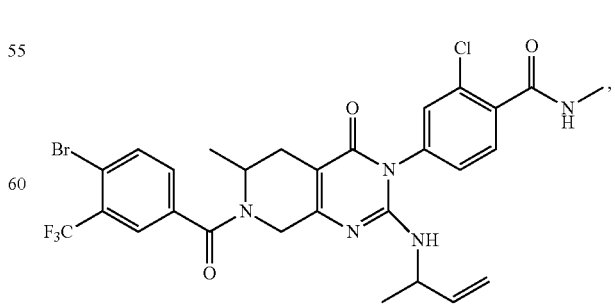

or a pharmaceutically acceptable salt thereof.

34. The compound of claim 1, wherein the compound is

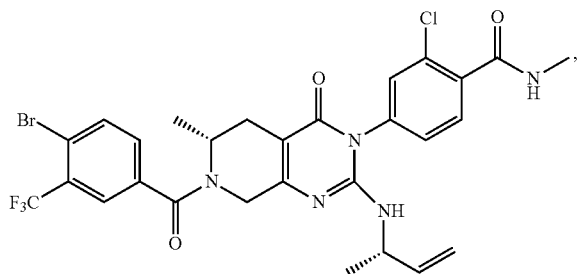 [SMILES: C=CC(C)Nc1nc2c(c(=O)n1-c1ccc(C(=O)NC)c(Cl)c1)CC(C)N(C(=O)c1ccc(Br)c(C(F)(F)F)c1)C2]

or a pharmaceutically acceptable salt thereof.

35. The compound of claim 1, wherein the compound is

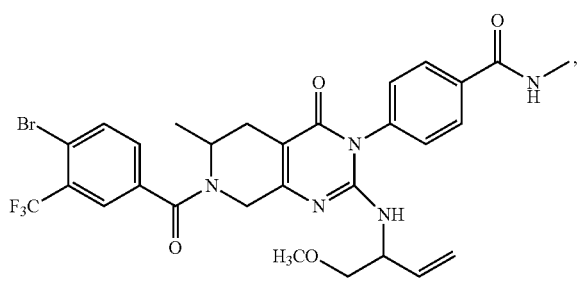 [SMILES: C=CC(COC)Nc1nc2c(c(=O)n1-c1ccc(C(=O)NC)cc1)CC(C)N(C(=O)c1ccc(Br)c(C(F)(F)F)c1)C2]

or a pharmaceutically acceptable salt thereof.

36. The compound of claim 1, wherein the compound is

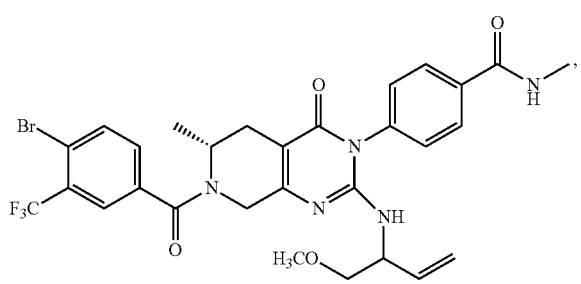 [SMILES: C=CC(COC)Nc1nc2c(c(=O)n1-c1ccc(C(=O)NC)cc1)C[C@@H](C)N(C(=O)c1ccc(Br)c(C(F)(F)F)c1)C2]

or a pharmaceutically acceptable salt thereof.

37. The compound of claim 1, wherein the compound is

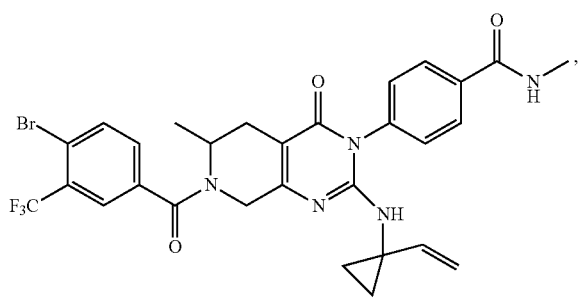 [SMILES: C=CC1(Nc2nc3c(c(=O)n2-c2ccc(C(=O)NC)cc2)CC(C)N(C(=O)c2ccc(Br)c(C(F)(F)F)c2)C3)CC1]

or a pharmaceutically acceptable salt thereof.

38. The compound of claim 1, wherein the compound is

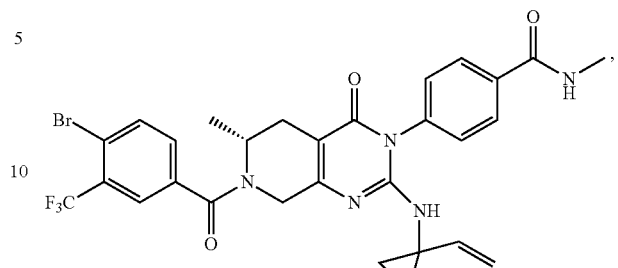

or a pharmaceutically acceptable salt thereof.

39. The compound of claim 1, wherein the compound is

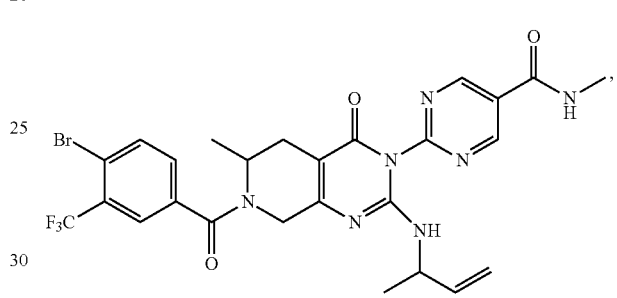

or a pharmaceutically acceptable salt thereof.

40. The compound of claim 1, wherein the compound is

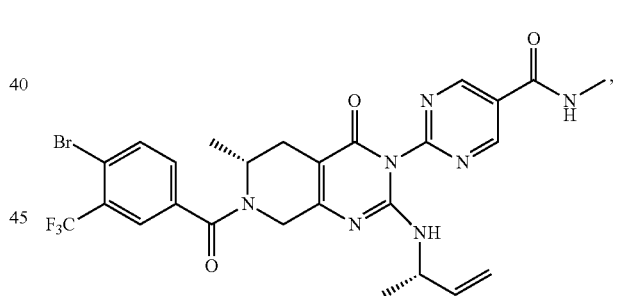

or a pharmaceutically acceptable salt thereof.

41. The compound of claim 1, wherein the compound is

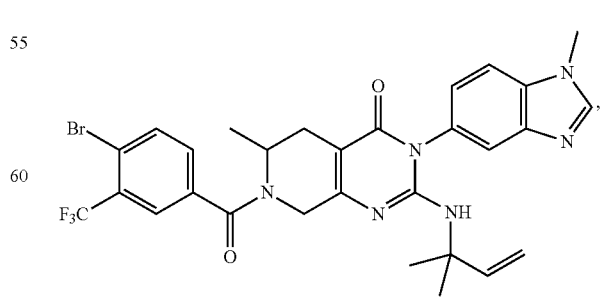

or a pharmaceutically acceptable salt thereof.

42. The compound of claim 1, wherein the compound is

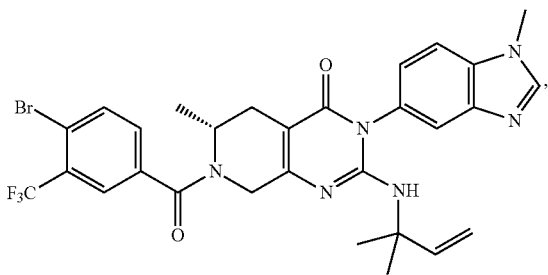 [SMILES: C=CC(C)(C)Nc1nc2c(c(=O)n1-c1ccc3c(c1)ncn3C)C[C@@H](C)N(C(=O)c1ccc(Br)c(C(F)(F)F)c1)C2]

or a pharmaceutically acceptable salt thereof.

43. A pharmaceutical composition comprising an effective amount of a compound of claim 1, or a pharmaceutically acceptable salt thereof, and excipient.

44. A method for treating hepatitis B in a subject comprising administering to the subject in need thereof an effective amount of a compound of claim 1, or a pharmaceutically acceptable salt thereof, suffering from hepatitis B.

45. A method for treating hepatitis D in a subject comprising administering to the subject in need thereof an effective amount of a compound of claim 1, or a pharmaceutically acceptable salt thereof, suffering from hepatitis D.

46. The method of claim 44, further comprising administering an additional agent selected from the group consisting of an interferon, a nucleoside analog, a nucleotide analog, a sequence specific oligonucleotide, a nucleic acid polymer, an entry inhibitor and a small molecule immunomodulator.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: HBV forward primer

<400> SEQUENCE: 1
gtgtctgcgg cgttttatca                                         20

<210> SEQ ID NO 2
<211> LENGTH: 21
<212> TYPE: DNA
<213> ORGANISM: Artificial Sequence
<220> FEATURE:
<223> OTHER INFORMATION: HBV reverse primer

<400> SEQUENCE: 2
gacaaacggg caacatacct t                                       21

<210> SEQ ID NO 3
<211> LENGTH: 28
<212> TYPE: DNA
<213> ORGANISM: Artificial Sequence
<220> FEATURE:
<223> OTHER INFORMATION: HBV probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
```

```
<221> NAME/KEY: modified_base
<222> LOCATION: (28)...(0)
<223> OTHER INFORMATION: N=C-3IABkFQ

<400> SEQUENCE: 3
nctctkcanc ctgctgctat gcctcatn                                    28
```